US012479902B2

(12) United States Patent
Deniger et al.

(10) Patent No.: US 12,479,902 B2
(45) Date of Patent: Nov. 25, 2025

(54) T CELL RECEPTORS RECOGNIZING R175H OR Y220C MUTATION IN P53

(71) Applicant: The United States of America, as represented by the Secretary, Department of Health and Human Services, Bethesda, MD (US)

(72) Inventors: Drew C. Deniger, Houston, TX (US); Parisa Malekzadeh, Norfolk, VA (US); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 884 days.

(21) Appl. No.: 17/620,942

(22) PCT Filed: Jun. 26, 2020

(86) PCT No.: PCT/US2020/039785
§ 371 (c)(1),
(2) Date: Dec. 20, 2021

(87) PCT Pub. No.: WO2020/264269
PCT Pub. Date: Dec. 30, 2020

(65) Prior Publication Data

US 2022/0332785 A1 Oct. 20, 2022

Related U.S. Application Data

(60) Provisional application No. 62/867,619, filed on Jun. 27, 2019.

(51) Int. Cl.

| | |
|---|---|
| ***C07K 14/725*** | (2006.01) |
| ***A61K 38/00*** | (2006.01) |
| ***A61K 40/11*** | (2025.01) |
| ***A61K 40/32*** | (2025.01) |
| ***A61K 40/42*** | (2025.01) |
| ***G01N 33/574*** | (2006.01) |

(52) U.S. Cl.
CPC .......... *C07K 14/7051* (2013.01); *A61K 40/11* (2025.01); *A61K 40/32* (2025.01); *A61K 40/4201* (2025.01); *G01N 33/5748* (2013.01); *A61K 38/00* (2013.01); *G01N 2333/4748* (2013.01); *G01N 2333/7051* (2013.01)

(58) Field of Classification Search
CPC .............................. C07K 14/705; A61K 40/11
See application file for complete search history.

(56) References Cited

U.S. PATENT DOCUMENTS

| | | | |
|---|---|---|---|
| 8,034,334 | B2 | 10/2011 | Dudley et al. |
| 8,383,099 | B2 | 2/2013 | Dudley et al. |
| 10,174,098 | B2 | 1/2019 | Hinrichs et al. |
| 2012/0244133 | A1 | 9/2012 | Rosenberg et al. |
| 2017/0166622 | A1 | 6/2017 | Baeuerle et al. |

FOREIGN PATENT DOCUMENTS

| | | | |
|---|---|---|---|
| EA | 201792420 | A1 | 4/2018 |
| WO | WO 2019/067242 | A1 | 9/2018 |
| WO | WO 2019/067243 | A1 | 9/2018 |
| WO | WO 2022/236050 | A1 | 11/2022 |
| WO | WO 2024/206274 | A2 | 10/2024 |

OTHER PUBLICATIONS

Berry et al., "Substitution of Cysteine for Selenocysteine in Type I Iodothyronine Deiodinase Reduces the Catalytic Efficiency of the Protein but Enhances its Translation", *Endocrinology*, 131(4): 1848-1852 (1992).
Bonifant et al., "Toxicity and management in CAR T-cell therapy", *Molecular Therapy—Oncolytics*, 3: 16011, pp. 1-7 (2016).
Brunner et al., "Cytotoxic T cells: Double-barreled shot guns", *Nature Medicine*, 5(1): 20 (1999).
Chmielewski et al., "Antigen-specific T-cell activation independently of the MHC: chimeric antigen receptor-redirected T cells", *Frontiers in Immunology*, 4:371, pp. 1-7 (2013).
Cordoba et al., "The large ectodomains of CD45 and CD148 regulate their segregation from and inhibition of ligated T-cell receptor", *Blood*, 121(21): 4295-4302 (2013).
Gasser et al., "Antibody production with yeasts and filamentous fungi: on the road to large scale?", *Biotechnology Letters*, 29: 201-2012 (2007).
Grupp et al., "Chimeric Antigen Receptor-Modified T Cells for Acute Lymphoid Leukemia", *The New England Journal of Medicine*, 368(16): 1509-1518 (2013).
Holler et al., "Quantitative Analysis of the Contribution of TCR/pepMHC Affinity and CD8 to T Cell Activation", *Immunity*, 18: 255-264 (2003).
Jain et al., "Barriers to Drug Delivery in Solid Tumors", *Scientific American*, 271(1): 58-65 (1994).
Jones et al., "Lentiviral Vector Design for Optimal T Cell Receptor Gene Expression in the Transduction of Peripheral Blood Lymphocytes and Tumor-Infiltrating Lymphocytes", *Human Gene Therapy*, 20:630-640 (2009).

(Continued)

*Primary Examiner* — Christopher M Babic
*Assistant Examiner* — Jennifer S Spence
(74) *Attorney, Agent, or Firm* — Leydig, Voit & Mayer

(57) ABSTRACT

Disclosed are isolated or purified T cell receptors (TCRs) having antigenic specificity for human $p53^{R175H}$ or human $p53^{Y220C}$. Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

35 Claims, 24 Drawing Sheets

Specification includes a Sequence Listing.

(56) References Cited

OTHER PUBLICATIONS

Lo et al., Supplemental Materials for "Immunologic Recognition of a Shared p53 Mutated Neoantigen in a Patient with Metastatic Colorectal Cancer", *Cancer Immunology Research*, 7(4): 534-543 (2019).
Muller et al., "Spliceosomal Peptide P140 for Immunotherapy of Systemic Lupus Erythematosus", *Arthritis & Rheumatism*, 58(12) 3873-3883 (2008).
Sachs et al., "Impact of Cysteine Residues on MHC Binding Predictions and Recognition by Tumor-Reactive T Cells", *The Journal of Immunology*, 205(2): 539-549 (2020).
Wu et al., "T cell receptors employ diverse strategies to target a p53 cancer neoantigen", *Journal of Biological Chemistry*, 298(3): 101684, pp. 1-10 (2022).
"Human TCR alpha chain variable region, SEQ ID 383", retrieved from EBI accession No. GSP:BGE48275, published on May 16, 2019.
Boyd et al., "Measurement and clinical monitoring of human lymphocyte clonality by massively parallel VDJ pyrosequencing", *Science Translational Medicine*, vol. 1, Issue 12, p. 12ra23 (2009).
Cafri et al., "Memory T cells targeting oncogenic mutations detected in peripheral blood of epithelial cancer patients", *Nature Communications*, vol. 10, Issue 1, Article No. 449, pp. 1-9 (2019).
Cancer Genome Atlas Research Network, "Integrated genomic analyses of ovarian carcinoma", *Nature*, 474:7353, pp. 609-615 (2011).
Cohen et al., "Isolation of neoantigen-specific T cells from tumor and peripheral lymphocytes", *Journal of Clinical Investigation*, vol. 125, No. 10, pp. 3981-3991 (2015).
Deniger et al., "A Pilot Trial of the Combination of Vemurafenib with Adoptive Cell Therapy in Patients with Metastatic Melanoma", *Clinical Cancer Research*, vol. 23, Issue 2, pp. 351-362 (2017).
Deniger et al., "T-cell Responses to TP53 "Hotspot" Mutations and Unique Neoantigens Expressed by Human Ovarian Cancers", *Clinical Cancer Research*, vol. 24, Issue 22, pp. 5562-5573 (2018).
Dudley et al., "Generation of Tumor-Infiltrating Lymphocyte Cultures for Use in Adoptive Transfer Therapy for Melanoma Patients", *Journal of Immunotherapy*, vol. 26, pp. 332-342 (2003).
Freed-Pastor et al., "Mutant p53: one name, many proteins", *Genes Development*, vol. 26, Issue 12, pp. 1268-1286 (2012).
Gonzales et al., "Racial-Ethnic Disparities in Late-Stage Colorectal Cancer Among Hispanics and Hon-Hispanic Whites of New Mexico", *Hispanic Health Care International*, vol. 15, Issue 4, pp. 180-188 (2017).
Howie et al., "High-throughput pairing of T cell receptor α and β sequences", *Science Translational Medicine*, vol. 7, No. 301, p. 301ra131 (2015).
International Searching Authority, International Search Report and Written Opinion issued in International Application No. PCT/US2020/039785, mailed on Nov. 30, 2020.
Lo et al., "Immunologic Recognition of a Shared p53 Mutated Neoantigen in a Patient with Metastatic Colorectal Cancer", *Cancer Immunology Research*, vol. 7, Issue 4, pp. 534-543 (2019).
Lundegaard et al., Accurate approximation method for prediction of class I MHC affinities for peptides of length 8, 10 and 11 using prediction tools trained on 9mers *Bioinformatics*, vol. 24, Issue 11, pp. 1397-1398 (2008).
Malekzadeh et al., "Neoantigen screening identifies broad TP53 mutant immunogenicity in patients with epithelial cancers", *Journal of Clinical Investigation*, vol. 129, No. 3, pp. 1109-1114 (2019).
Malekzadeh et al., "Antigen Experienced T Cells from Peripheral Blood Recognize p53 Neoantigens," *Clinical Cancer Research*, vol. 26, pp. 1267-1276 (2020).
Olivier et al., "TP53 Mutations in Human Cancers: Origins, Consequences, and Clinical Use", *Cold Spring Harbor Perspectives in Biology*, vol. 2, Issue 1, pp. 1-17 (2010).
Parrales et al., "Targeting Oncogenic Mutant p53 for Cancer Therapy", *Frontiers in Oncology*, vol. 5, Article 288, pp. 1-13 (2015).
Pasetto et al., "Tumor- and neoantigen-reactive T-cell receptors can be identified based on their frequency in fresh tumor", *Cancer Immunology Research*, vol. 4, Issue 9, pp. 734-743 (2016).
Riddell et al., "The use of anti-CD3 and anti-CD28 monoclonal antibodies to clone and expand human antigen-specific T cells", *Journal of Immunological Methods*, vol. 128, Issue 2, pp. 189-201 (1990).
Tran et al., "Immunogenicity of somatic mutations in human gastrointestinal cancers", *Science*, 350:6266, pp. 1387-1390 (2015).
Wu et al., "Structural basis for oligoclonal T cell recognition of a shared p53 cancer neoantigen", *Nature Communications*, vol. 11, Issue 1, pp. 1-12 (2020).
Wu et al., "Supplementary Information: Structural basis for oligoclonal T cell recognition of a shared p53 cancer neoantigen", *Nature Communications*, vol. 11, Issue 1, pp. 1-17 (2020).
Xu et al., "Heterogeneity of Li-Fraumeni syndrome links to unequal gain-of-function effects of p53 mutations", *Scientific Reports*, 4:4223, pp. 1-5 (2014).
Zhao et al., "Molecularly targeted therapies for p-53-mutant cancers", *Cellular and Molecular Life Sciences*, vol. 74, pp. 4171-4187 (2017).
Kim et al., "Adoptive Cellular Therapy with Autologous Tumor-Infiltrating Lymphocytes and T-cell Receptor-Engineered T Cells Targeting Common p53 Neoantigens in Human Solid Tumors", *Cancer Immunology Research*, 10(8): 932-946 (2022).
Murphy et al., eds., *Janeway's Immunobiology*, 7th Ed., New York: Garland Science (2008), pp. 157-158 (Section 4-10).

```
CLUSTAL O(1.2.4) multiple sequence alignment          41/41

SP|P04637|P53_HUMAN    MEEPQSDPSVEPPLSQETFSDLWKLLPENNVLSPLPSQAMDDLMLSPDDIEQWFTEDPGP 60
SP|P04637-2|P53_HUMAN MEEPQSDPSVEPPLSQETFSDLWKLLPENNVLSPLPSQAMDDLMLSPDDIEQWFTEDPGP 60
SP|P04637-3|P53_HUMAN MEEPQSDPSVEPPLSQETFSDLWKLLPENNVLSPLPSQAMDDLMLSPDDIEQWFTEDPGP 60
SP|P04637-4|P53_HUMAN ---------------------------------------MDDLMLSPDDIEQWFTEDPGP 21
SP|P04637-5|P53_HUMAN ---------------------------------------MDDLMLSPDDIEQWFTEDPGP 21
SP|P04637-6|P53_HUMAN ---------------------------------------MDDLMLSPDDIEQWFTEDPGP 21
SP|P04637-7|P53_HUMAN ------------------------------------------------------------
SP|P04637-8|P53_HUMAN ------------------------------------------------------------
SP|P04637-9|P53_HUMAN ------------------------------------------------------------

SP|P04637|P53_HUMAN    DEAPRMPEAAPPVAPAPAAPTPAAPAPAPSWPLSSSVPSQKTYQGSYGFRLGFLHSGTAK 120
SP|P04637-2|P53_HUMAN DEAPRMPEAAPPVAPAPAAPTPAAPAPAPSWPLSSSVPSQKTYQGSYGFRLGFLHSGTAK 120
SP|P04637-3|P53_HUMAN DEAPRMPEAAPPVAPAPAAPTPAAPAPAPSWPLSSSVPSQKTYQGSYGFRLGFLHSGTAK 120
SP|P04637-4|P53_HUMAN DEAPRMPEAAPPVAPAPAAPTPAAPAPAPSWPLSSSVPSQKTYQGSYGFRLGFLHSGTAK 81
SP|P04637-5|P53_HUMAN DEAPRMPEAAPPVAPAPAAPTPAAPAPAPSWPLSSSVPSQKTYQGSYGFRLGFLHSGTAK 81
SP|P04637-6|P53_HUMAN DEAPRMPEAAPPVAPAPAAPTPAAPAPAPSWPLSSSVPSQKTYQGSYGFRLGFLHSGTAK 81
SP|P04637-7|P53_HUMAN ------------------------------------------------------------
SP|P04637-8|P53_HUMAN ------------------------------------------------------------
SP|P04637-9|P53_HUMAN ------------------------------------------------------------

SP|P04637|P53_HUMAN    SVTCTYSPALNKMFCQLAKTCPVQLWVDSTPPPGTRVRAMAIYKQSQHMTEVVRRCPHHE 180
SP|P04637-2|P53_HUMAN SVTCTYSPALNKMFCQLAKTCPVQLWVDSTPPPGTRVRAMAIYKQSQHMTEVVRRCPHHE 180
SP|P04637-3|P53_HUMAN SVTCTYSPALNKMFCQLAKTCPVQLWVDSTPPPGTRVRAMAIYKQSQHMTEVVRRCPHHE 180
SP|P04637-4|P53_HUMAN SVTCTYSPALNKMFCQLAKTCPVQLWVDSTPPPGTRVRAMAIYKQSQHMTEVVRRCPHHE 141
SP|P04637-5|P53_HUMAN SVTCTYSPALNKMFCQLAKTCPVQLWVDSTPPPGTRVRAMAIYKQSQHMTEVVRRCPHHE 141
SP|P04637-6|P53_HUMAN SVTCTYSPALNKMFCQLAKTCPVQLWVDSTPPPGTRVRAMAIYKQSQHMTEVVRRCPHHE 141
SP|P04637-7|P53_HUMAN ------------MFCQLAKTCPVQLWVDSTPPPGTRVRAMAIYKQSQHMTEVVRRCPHHE 48
SP|P04637-8|P53_HUMAN ------------MFCQLAKTCPVQLWVDSTPPPGTRVRAMAIYKQSQHMTEVVRRCPHHE 48
SP|P04637-9|P53_HUMAN ------------MFCQLAKTCPVQLWVDSTPPPGTRVRAMAIYKQSQHMTEVVRRCPHHE 48
                                  ************************************************

SP|P04637|P53_HUMAN    RCSDSDGLAPPQHLIRVEGNLRVEYLDDRNTFRHSVVVPYEPPEVGSDCTTIHYNYMCNS 240
SP|P04637-2|P53_HUMAN RCSDSDGLAPPQHLIRVEGNLRVEYLDDRNTFRHSVVVPYEPPEVGSDCTTIHYNYMCNS 240
SP|P04637-3|P53_HUMAN RCSDSDGLAPPQHLIRVEGNLRVEYLDDRNTFRHSVVVPYEPPEVGSDCTTIHYNYMCNS 240
SP|P04637-4|P53_HUMAN RCSDSDGLAPPQHLIRVEGNLRVEYLDDRNTFRHSVVVPYEPPEVGSDCTTIHYNYMCNS 201
SP|P04637-5|P53_HUMAN RCSDSDGLAPPQHLIRVEGNLRVEYLDDRNTFRHSVVVPYEPPEVGSDCTTIHYNYMCNS 201
SP|P04637-6|P53_HUMAN RCSDSDGLAPPQHLIRVEGNLRVEYLDDRNTFRHSVVVPYEPPEVGSDCTTIHYNYMCNS 201
SP|P04637-7|P53_HUMAN RCSDSDGLAPPQHLIRVEGNLRVEYLDDRNTFRHSVVVPYEPPEVGSDCTTIHYNYMCNS 108
SP|P04637-8|P53_HUMAN RCSDSDGLAPPQHLIRVEGNLRVEYLDDRNTFRHSVVVPYEPPEVGSDCTTIHYNYMCNS 108
SP|P04637-9|P53_HUMAN RCSDSDGLAPPQHLIRVEGNLRVEYLDDRNTFRHSVVVPYEPPEVGSDCTTIHYNYMCNS 108
                      ************************************************************

SP|P04637|P53_HUMAN    SCMGGMNRRPILTIITLEDSSGNLLGRNSFEVRVCACPGRDRRTEEENLRKKGEPHHELP 300
SP|P04637-2|P53_HUMAN SCMGGMNRRPILTIITLEDSSGNLLGRNSFEVRVCACPGRDRRTEEENLRKKGEPHHELP 300
SP|P04637-3|P53_HUMAN SCMGGMNRRPILTIITLEDSSGNLLGRNSFEVRVCACPGRDRRTEEENLRKKGEPHHELP 300
SP|P04637-4|P53_HUMAN SCMGGMNRRPILTIITLEDSSGNLLGRNSFEVRVCACPGRDRRTEEENLRKKGEPHHELP 261
SP|P04637-5|P53_HUMAN SCMGGMNRRPILTIITLEDSSGNLLGRNSFEVRVCACPGRDRRTEEENLRKKGEPHHELP 261
SP|P04637-6|P53_HUMAN SCMGGMNRRPILTIITLEDSSGNLLGRNSFEVRVCACPGRDRRTEEENLRKKGEPHHELP 261
SP|P04637-7|P53_HUMAN SCMGGMNRRPILTIITLEDSSGNLLGRNSFEVRVCACPGRDRRTEEENLRKKGEPHHELP 168
SP|P04637-8|P53_HUMAN SCMGGMNRRPILTIITLEDSSGNLLGRNSFEVRVCACPGRDRRTEEENLRKKGEPHHELP 168
SP|P04637-9|P53_HUMAN SCMGGMNRRPILTIITLEDSSGNLLGRNSFEVRVCACPGRDRRTEEENLRKKGEPHHELP 168
                      ************************************************************

SP|P04637|P53_HUMAN    PGSTKRALPNNTSSSPQPKKKPLDGEYFTLQIRGRERFEMFRELNEALELKDAQAGKEPG 360
SP|P04637-2|P53_HUMAN PGSTKRALPNNTSSSPQPKKKPLDGEYFTLQDQTSFQKENC------------------- 341
SP|P04637-3|P53_HUMAN PGSTKRALPNNTSSSPQPKKKPLDGEYFTLQMLLDLRWCYFLINSS-------------- 346
SP|P04637-4|P53_HUMAN PGSTKRALPNNTSSSPQPKKKPLDGEYFTLQIRGRERFEMFRELNEALELKDAQAGKEPG 321
SP|P04637-5|P53_HUMAN PGSTKRALPNNTSSSPQPKKKPLDGEYFTLQDQTSFQKENC------------------- 302
SP|P04637-6|P53_HUMAN PGSTKRALPNNTSSSPQPKKKPLDGEYFTLQMLLDLRWCYFLINSS-------------- 307
SP|P04637-7|P53_HUMAN PGSTKRALPNNTSSSPQPKKKPLDGEYFTLQIRGRERFEMFRELNEALELKDAQAGKEPG 228
SP|P04637-8|P53_HUMAN PGSTKRALPNNTSSSPQPKKKPLDGEYFTLQDQTSFQKENC------------------- 209
SP|P04637-9|P53_HUMAN PGSTKRALPNNTSSSPQPKKKPLDGEYFTLQMLLDLRWCYFLINSS-------------- 214
                      *******************************     :

SP|P04637|P53_HUMAN    GSRAHSSHLKSKKGQSTSRHKKLMFKTEGPDSD 393
SP|P04637-2|P53_HUMAN ---------------------------------
SP|P04637-3|P53_HUMAN ---------------------------------
SP|P04637-4|P53_HUMAN GSRAHSSHLKSKKGQSTSRHKKLMFKTEGPDSD 354
SP|P04637-5|P53_HUMAN ---------------------------------
SP|P04637-6|P53_HUMAN ---------------------------------
SP|P04637-7|P53_HUMAN GSRAHSSHLKSKKGQSTSRHKKLMFKTEGPDSD 261
SP|P04637-8|P53_HUMAN ---------------------------------
SP|P04637-9|P53_HUMAN ---------------------------------
```

FIG. 8

```
L36092|TRBV7-9*01|Homo      MGTSLLCWMALCLLGADHADTGVSQNPRHKITKRGQNVTFRCDPISEHNRLYWYRQTLGQ  60
AF009663|TRBV7-9*03|Homo    MGTSLLCWMALCLLGADHADTGVSQDPRHKITKRGQNVTFRCDPISEHNRLYWYRQTLGQ  60
                            *************************:**********************************

L36092|TRBV7-9*01|Homo      GPEFLTYFQNEAQLEKSRLLSDRFSAERPKGSFSTLEIQRTEQGDSAMYLCASSL       115
AF009663|TRBV7-9*03|Homo    GPEFLTYFQNEAQLEKSRLLSDRFSAERPKGSFSTLEIQRTEQGDSAMYLCASSL       115
                            *******************************************************
```

FIG. 9

T CELL RECEPTORS RECOGNIZING R175H OR Y220C MUTATION IN P53

CROSS REFERENCE TO RELATED APPLICATIONS

This patent application is the U.S. national stage of PCT/US2020/039785, filed Jun. 26, 2020, which claims the benefit of U.S. Provisional Patent Application No. 62/867,619, filed Jun. 27, 2019, each of which is incorporated by reference in its entirety herein.

STATEMENT REGARDING FEDERALLY SPONSORED RESEARCH OR DEVELOPMENT

This invention was made with Government support under project number BC010985 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 357,822Byte ASCII (Text) file named "757482_ST25.txt," dated Nov. 30, 2021.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified T cell receptor (TCR) having antigenic specificity for a human $p53^{R175H}$ or human $p53^{Y220C}$ amino acid sequence, wherein the TCR comprises the amino acid sequences of: (1) all of SEQ ID NOs: 3-8; (2) all of SEQ ID NOs: 14-19; (3) all of SEQ ID NOs: 25-30; (4) all of SEQ ID NOs: 36-41; (5) all of SEQ ID NOs: 47-52; (6) all of SEQ ID NOs: 58-63; (7) all of SEQ ID NOs: 69-74; (8) all of SEQ ID NOs: 80-85; or (9) all of SEQ ID NOs: 131-136.

In an embodiment of the invention, the TCR has antigenic specificity for a human $p53^{R175H}$ or human $p53^{Y220C}$ amino acid sequence, wherein the human $p53^{R175H}$ amino acid sequence is SEQ ID NO: 2 or SEQ ID NO: 96.

In an embodiment of the invention, the TCR has antigenic specificity for a human $p53^{R175H}$ or human $p53^{Y220C}$ amino acid sequence, wherein the human $p53^{Y220C}$ amino acid sequence is SEQ ID NO: 113.

In an embodiment of the invention, the TCR does not have antigenic specificity for the wild-type human p53 amino acid sequence of SEQ ID NO: 95.

In an embodiment of the invention, the TCR does not have antigenic specificity for the wild-type human p53 amino acid sequence of SEQ ID NO: 112.

Further embodiments of the invention provide related polypeptides and proteins, as well as related nucleic acids, recombinant expression vectors, host cells, populations of cells, and pharmaceutical compositions relating to the TCRs of the invention.

An embodiment of the invention provides an isolated or purified nucleic acid comprising, from 5' to 3', a first nucleic acid sequence and a second nucleotide sequence, wherein the first and second nucleotide sequence, respectively, encode the amino sequences of SEQ ID NOs: 9 and 10; 10 and 9; 20 and 21; 21 and 20; 31 and 32; 32 and 31; 42 and 43; 43 and 42; 53 and 54; 54 and 53; 64 and 65; 65 and 64; 75 and 76; 76 and 75; 86 and 87; 87 and 86; 137 and 138; 138 and 137; 142 and 143; 143 and 142; 144 and 145; 145 and 144; 146 and 147; 147 and 146; 148 and 149; 149 and 148; 150 and 151; 151 and 150; 152 and 153; 153 and 152; 154 and 155; 155 and 154; 156 and 157; 157 and 156; 159 and 158; 158 and 159; 178 and 10; 10 and 178; 181 and 21; 21 and 181; 184 and 32; 32 and 184; 187 and 43; 43 and 187; 190 and 54; 54 and 190; 193 and 65; 65 and 193; 196 and 76; 76 and 196; 199 and 87; 87 and 199; 137 and 202; 202 and 137; 9 and 205; 205 and 9; 20 and 207; 207 and 20; 31 and 209; 209 and 31; 42 and 211; 211 and 42; 53 and 213; 213 and 53; 64 and 215; 215 and 64; 75 and 217; 217 and 75; 86 and 219; 219 and 86; 137 and 221; 221 and 137; 223 and 202; 202 and 223; 223 and 221; 221 and 223; 20 and 226; 226 and 20; 181 and 226; or 226 and 181.

An embodiment of the invention provides an isolated or purified nucleic acid comprising, from 5' to 3', a first nucleic acid sequence and a second nucleotide sequence, wherein the first and second nucleotide sequence, respectively, encode the amino sequences of SEQ ID NOs: 11 and 12; 12 and 11; 22 and 23; 23 and 22; 33 and 34; 34 and 33; 44 and 45; 45 and 44; 55 and 56; 56 and 55; 66 and 67; 67 and 66; 77 and 78; 78 and 77; 88 and 89; 89 and 88; 139 and 140; 140 and 139; 160 and 161; 161 and 160; 162 and 163; 163 and 162; 164 and 165; 165 and 164; 166 and 167; 167 and 166; 168 and 169; 169 and 168; 170 and 171; 171 and 170; 172 and 173; 173 and 172; 174 and 175; 175 and 174; 176 and 177; 177 and 176; 179 and 12; 12 and 179; 182 and 23; 23 and 182; 185 and 34; 34 and 185; 188 and 45; 45 and 188; 191 and 56; 56 and 191; 194 and 67; 67 and 194; 197 and 78; 78 and 197; 200 and 89; 89 and 200; 139 and 203; 203 and 139; 11 and 206; 206 and 11; 22 and 208; 208 and 22; 33 and 210; 210 and 33; 44 and 212; 212 and 44; 55 and 214; 214 and 55; 66 and 216; 216 and 66; 77 and 218; 218 and 77; 88 and 220; 220 and 88; 139 and 222; 222 and 139; 224 and 203; 203 and 224; 224 and 222; 222 and 224; 22 and 227; 227 and 22; 182 and 227; or 227 and 182.

In an embodiment of the invention, the isolated or purified nucleic acid further comprises a third nucleotide acid sequence interposed between the first and second nucleotide sequence, wherein the third nucleotide sequence encodes a cleavable linker peptide.

In an embodiment of the invention, the cleavable linker peptide comprises the amino acid sequence of SEQ ID NO: 94.

In an embodiment of the invention, the isolated or purified nucleic acid encodes an amino acid sequence selected from the group consisting of: SEQ ID NO: 13, 24, 35, 46, 57, 68, 79, 90, 141, 180, 183, 186, 189, 192, 195, 198, 201, 204, 225, 228, and 229.

In an embodiment of the invention, the recombinant expression vector is a transposon or a lentiviral vector.

Another embodiment of the invention provides an isolated or purified TCR, polypeptide, or protein encoded by any of the nucleic acids or vectors described herein.

Another embodiment of the invention provides an isolated or purified TCR, polypeptide, or protein that results from expression of any of the nucleic acids or vectors described herein in a cell.

Another embodiment of the invention provides a method of producing a host cell expressing a TCR that has antigenic specificity for the peptide of SEQ ID NO: 2, 96 or 113, the method comprising contacting a cell with any of the vectors described herein under conditions that allow introduction of the vector into the cell.

Another embodiment of the invention provides an isolated or purified host cell comprising any of the nucleic acids or recombinant expression vectors described herein.

In an embodiment of the invention, the host cell is a human lymphocyte.

In an embodiment of the invention, the host cell is selected from the group consisting of a T cell, a natural killer T (NKT) cell, an invariant natural killer T (iNKT) cell, and a natural killer (NK) cell.

Another embodiment of the invention provides a method of producing any of the TCRs, polypeptides, or proteins described herein, the method comprising culturing any of the host cells or populations of host cells described herein, so that the TCR, polypeptide, or protein is produced.

Another embodiment of the invention provides any of the TCRs, polypeptides, proteins, nucleic acids, recombinant expression vectors, host cells, populations of cells, or pharmaceutical compositions described herein, for use in inducing an immune response against a cancer in a mammal. In one embodiment, the invention provides a method of inducing an immune response against a cancer in a mammal comprising administering any of the TCRs, polypeptides, proteins, nucleic acids, recombinant expression vectors, host cells, populations of cells, or pharmaceutical compositions described herein.

Still further embodiments of the invention provide methods of detecting the presence of cancer in a mammal and methods of treating or preventing cancer in a mammal. In one embodiment, the invention provides a method of treating or preventing cancer in a mammal comprising administering any of the TCRs, polypeptides, proteins, nucleic acids, recombinant expression vectors, host cells, populations of cells, or pharmaceutical compositions described herein. In an embodiment, the cancer is cholangiocarcinoma, melanoma, colon cancer, rectal cancer, ovarian cancer, endometrial cancer, non-small cell lung cancer (NSCLC), glioblastoma, uterine cervical cancer, head and neck cancer, breast cancer, pancreatic cancer, or bladder cancer.

In an embodiment of the invention, the cancer is known to comprise an R175H or a Y220C mutation in human p53.

BRIEF DESCRIPTION OF THE SEVERAL VIEWS OF THE DRAWINGS

FIG. 8 shows an alignment of the amino acid sequences of the nine p53 splice variants. SP|P04637|P53_HUMAN (SEQ ID NO: 1); SP|P04637-2|P53_HUMAN (SEQ ID NO: 114); SP|P04637-3|P53_HUMAN (SEQ ID NO: 115); SP|P04637-4|P53_HUMAN (SEQ ID NO: 116); SP|P04637-5|P53_HUMAN (SEQ ID NO: 117); SP|P04637-6|P53_HUMAN (SEQ ID NO: 118); SP|P04637-7|P53_HUMAN (SEQ ID NO: 119); SP|P04637-8|P53_HUMAN (SEQ ID NO: 120); and SP|P04637-9|P53_HUMAN (SEQ ID NO: 121).

FIG. 9 shows an alignment of the amino acid sequences of portions of the sequence of TRBV7-9*03 with that of TRBV7-9*01. "L36092|TRBV7-9*01|Homo" is SEQ ID NO: 129. "AF009663|TRBV7-9*03|Homo" is SEQ ID NO: 130.

DETAILED DESCRIPTION OF THE INVENTION

Figure 1A:
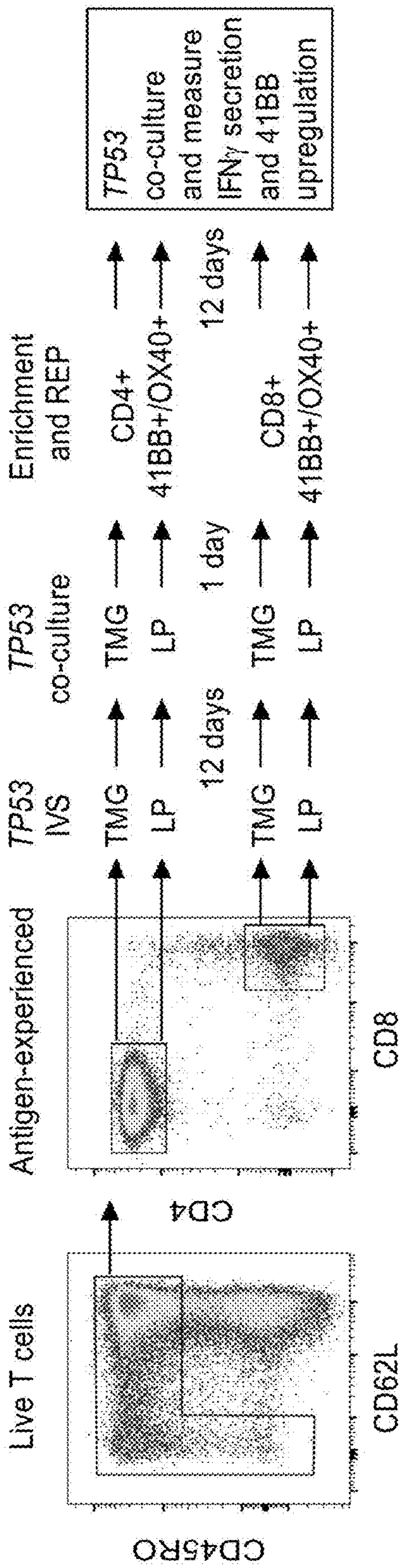
FIG. 1A is a schematic showing an experimental design wherein the parent gate was lymphocytes→single cells→live (PI negative)→$CD3^+$ (T cells).

Tumor Protein P53 (also referred to as "TP53" or "p53") acts as a tumor suppressor by, for example, regulating cell division. The p53 protein is located in the nucleus of the cell, where it binds directly to DNA. When DNA becomes damaged, the p53 protein is involved in determining whether the DNA will be repaired or the damaged cell will undergo apoptosis. If the DNA can be repaired, p53 activates other genes to fix the damage. If the DNA cannot be repaired, the p53 protein prevents the cell from dividing and signals it to undergo apoptosis. By stopping cells with mutated or damaged DNA from dividing, p53 helps prevent the development of tumors. WT (normal) full-length p53 comprises the amino acid sequence of SEQ ID NO: 1.

Mutations in the p53 protein may reduce or eliminate the p53 protein's tumor suppressor function. Alternatively or additionally, a p53 mutation may be a gain-of-function mutation by interfering with WT p53 in a dominant negative fashion. Mutated p53 protein may be expressed in any of a variety of human cancers such as, for example, cholangiocarcinoma, melanoma, colon cancer, rectal cancer, ovarian cancer, endometrial cancer, non-small cell lung cancer (NSCLC), glioblastoma, uterine cervical cancer, head and neck cancer, breast cancer, pancreatic cancer, or bladder cancer.

An embodiment of the invention provides an isolated or purified T cell receptor (TCR) having antigenic specificity for mutated human p53 (hereinafter, "mutated p53"). Hereinafter, references to a "TCR" also refer to functional portions and functional variants of the TCR, unless specified otherwise. Mutations of p53 are defined herein by reference to the amino acid sequence of full-length, WT p53 (SEQ ID NO: 1). Mutations of p53 are described herein by reference to the amino acid residue present at a particular position, followed by the position number, followed by the amino acid with which that residue has been replaced in the particular mutation under discussion. A p53 amino acid sequence (e.g., a p53 peptide) may comprise fewer than all of the amino acid residues of the full-length, WT p53 protein. Accordingly, the position numbers are defined herein by reference to the WT full-length p53 protein (namely, SEQ ID NO: 1) with the understanding that the actual position of the corresponding residue in a particular example of a p53 amino acid sequence may be different. Because the positions are as defined by SEQ ID NO: 1, the term "R175" refers to the arginine present at position 175 of SEQ ID NO: 1, "R175H" indicates that the arginine present at position 175 of SEQ ID NO: 1 is replaced by histidine, while "Y220C" indicates that the tyrosine present at position 220 of SEQ ID NO: 1 has been replaced with cysteine. For example, when a particular example of a p53 amino acid sequence is, e.g., YKQSQHMTEVVR<u>R</u>CPHHERCSDSDG (SEQ ID NO: 110) (an exemplary WT p53 peptide corresponding to contiguous amino acid residues 163 to 187 of SEQ ID NO: 1), "R175H" refers to a substitution of the underlined arginine in SEQ ID NO: 110 with histidine, even though the actual position of the underlined arginine in SEQ ID NO: 110 is 13. Human p53 amino acid sequences with the R175H mutation are hereinafter referred to as "R175H" or "$p53^{R175H}$." Human p53 amino acid sequences with the Y220C mutation are hereinafter referred to as "Y220C" or "$p53^{Y220C}$." As used herein, "mutated p53" refers to human $p53^{R175H}$ or human $p53^{Y220C}$.

P53 has nine known splice variants. The p53 mutations described herein are conserved over all nine p53 splice variants. An alignment of the nine p53 splice variants is shown in FIG. 8. Accordingly, the inventive TCRs may have antigenic specificity for any mutated p53 amino acid sequence described herein encoded by any of the nine p53 splice variants. Because the positions are as defined by SEQ ID NO: 1, then the actual positions of the amino acid sequence of a particular splice variant of p53 are defined relative to the corresponding positions of SEQ ID NO: 1, and the positions as defined by SEQ ID NO: 1 may be different than the actual positions in a particular splice variant. Thus, for example, mutations refer to a replacement of an amino acid residue in the amino acid sequence of a particular splice variant of p53 corresponding to the indicated position of the 393-amino acid sequence of SEQ ID NO: 1 with the understanding that the actual positions in the splice variant may be different.

In an embodiment of the invention, the TCR has antigenic specificity for human p53 with a mutation at position 175, as defined by SEQ ID NO: 1. The p53 mutation at position 175 may be any missense mutation. Accordingly, the mutation at position 175 may be a substitution of the native (WT) arginine residue present at position 175 with any amino acid residue other than arginine. In an embodiment of the invention, the TCR has antigenic specificity for human p53 with the R175H mutation. For example, the inventive TCR may have antigenic specificity for one or more mutated p53 amino acid sequences selected from the group consisting of: EVVR<u>H</u>CPHHER (SEQ ID NO: 2), HMTEVVR<u>H</u>C (SEQ ID NO: 96), KQSQHMTEVVR<u>H</u>CPH (SEQ ID NO: 100), QSQHMTEVVR<u>H</u>CPHH (SEQ ID NO: 101), SQHMTEVVR<u>H</u>CPHHE (SEQ ID NO: 102), QHMTEVVR<u>H</u>CPHHER (SEQ ID NO: 103), HMTEVVR<u>H</u>CPHHERC (SEQ ID NO: 104), MTEVVR<u>H</u>CPHHERCS (SEQ ID NO: 105), TEVVR<u>H</u>CPHHERCSD (SEQ ID NO: 106), EVVR<u>H</u>CPHHERCSDS (SEQ ID NO: 107), VVR<u>H</u>CPHHERCSDSD (SEQ ID NO: 108),

VRHCPHHERCSDSDG (SEQ ID NO: 109), YKQSQHMTEVVRHCPHHERCSDSDG (SEQ ID NO: 111).

In an embodiment of the invention, the TCR has antigenic specificity for human p53 with a mutation at position 220, as defined by SEQ ID NO: 1. The p53 mutation at position 220 may be any missense mutation. Accordingly, the mutation at position 220 may be a substitution of the native (WT) tyrosine residue present at position 220 with any amino acid residue other than tyrosine. In an embodiment of the invention, the TCR has antigenic specificity for human p53 with the Y220C mutation. For example, the inventive TCR may have antigenic specificity for the mutated p53 amino acid sequence of VVPCEPPEV (SEQ ID NO: 113).

In an embodiment of the invention, the inventive TCRs may be able to recognize mutated p53 in an HLA (human leukocyte antigen)-molecule-dependent manner. "HLA-molecule-dependent manner," as used herein, means that the TCR elicits an immune response upon binding to mutated p53 within the context of an HLA molecule, which HLA molecule is expressed by the patient from which the TCR was isolated. The inventive TCRs may be able to recognize mutated p53 that is presented by the applicable HLA molecule and may bind to the HLA molecule in addition to mutated p53.

In an embodiment of the invention, the inventive TCRs are able to recognize R175H presented by an HLA Class II molecule. In this regard, the TCR may elicit an immune response upon binding to R175H within the context of an HLA Class II molecule. The inventive TCRs are able to recognize R175H that is presented by an HLA Class II molecule and may bind to the HLA Class II molecule in addition to R175H.

In an embodiment of the invention, the HLA Class II molecule is an HLA-DR heterodimer. The HLA-DR heterodimer is a cell surface receptor including an α chain and a β chain. The HLA-DR α chain is encoded by the HLA-DRA gene. In an embodiment, the alpha chain of the HLA Class II molecule is expressed by the HLA-DRA1*01:01:01 allele. The HLA-DR β chain is encoded by the HLA-DRB1 gene, the HLA-DRB3 gene, HLA-DRB4 gene, or the HLA-DRB5 gene. Examples of molecules encoded by the HLA-DRB1 gene may include, but are not limited to, HLA-DR1, HLA-DR2, HLA-DR3, HLA-DR4, HLA-DR5, HLA-DR6, HLA-DR7, HLA-DR8, HLA-DR9, HLA-DR10, HLA-DR11, HLA-DR12, HLA-DR13, HLA-DR14, HLA-DR15, HLA-DR16, and HLA-DR17. The HLA-DRB3 gene encodes HLA-DR52. The HLA-DRB4 gene encodes HLA-DR53. The HLA-DRB5 gene encodes HLA-DR51. In an embodiment of the invention, the HLA Class II molecule is an HLA-DRB1:HLA-DRA heterodimer. The beta chain of the HLA Class II molecule may be expressed by the HLA-DRB1*13:01, HLA-DRB1*13:02, HLA-DRB1*13:03, HLA-DRB1*13:04, HLA-DRB1*13:05, HLA-DRB1*13:06, HLA-DRB1*13:07, HLA-DRB1*13:08, HLA-DRB1*13:09, or HLA-DRB1*13:10 allele. In an especially preferred embodiment, the beta chain of the HLA Class II molecule is expressed by the HLA-DRB1*13:01 allele.

In an embodiment of the invention, one of the inventive TCRs is able to recognize Y220C presented by an HLA Class I molecule. In this regard, the TCR may elicit an immune response upon binding to Y220C within the context of an HLA Class I molecule. The inventive TCR is able to recognize Y220C that is presented by an HLA Class I molecule and may bind to the HLA Class I molecule in addition to Y220C.

In an embodiment of the invention, the HLA Class I molecule is an HLA-A molecule. The HLA-A molecule is a heterodimer of an α chain and β2 microglobulin. The HLA-A α chain may be encoded by an HLA-A gene. β2 microglobulin binds non-covalently to the alpha1, alpha2 and alpha3 domains of the alpha chain to build the HLA-A complex. The HLA-A molecule may be any HLA-A molecule. In an embodiment of the invention, the HLA Class I molecule is an HLA-A2 molecule. The HLA-A2 molecule may be any HLA-A2 molecule. Examples of HLA-A2 molecules may include, but are not limited to, HLA-A*02:01, HLA-A*02:02, HLA-A*02:03, HLA-A*02:05, HLA-A*02:06, HLA-A*02:07, or HLA-A*02:11. Preferably, the HLA Class I molecule is an HLA-A*02:01 molecule.

The TCRs of the invention may provide any one or more of many advantages, including when expressed by cells used for adoptive cell transfer. Mutated p53 is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, the inventive TCRs may, advantageously, successfully treat or prevent mutated p53-positive cancers that do not respond to other types of treatment such as, for example, chemotherapy, surgery, or radiation. Additionally, the inventive TCRs may provide highly avid recognition of mutated p53, which may provide the ability to recognize unmanipulated tumor cells (e.g., tumor cells that have not been treated with interferon (IFN)-γ, transfected with a vector encoding one or both of mutated p53 and the applicable HLA molecule, pulsed with a p53 peptide with the p53 mutation, or a combination thereof). Roughly half of all tumors harbor a mutation in p53, about half of which will be a missense mutation. The R175H mutation is expressed by about 4.5% of all cancers, and the HLA-DRB1*13:01 allele is expressed by about 15% of the U.S. population. The Y220C mutation occurs in about 1.5% of all cancers, and the HLA-A*02:01 allele is expressed by about 40% to about 50% of the U.S. population. The R175H and Y220C mutations arise in many cancer histologies, suggesting that a diverse group of patients could benefit from the inventive TCRs.

Accordingly, the inventive TCRs may increase the number of patients who may be eligible for treatment with immunotherapy.

The phrase "antigenic specificity," as used herein, means that the TCR can specifically bind to and immunologically recognize mutated p53 with high avidity. For example, a TCR may be considered to have "antigenic specificity" for mutated p53 if about $1\times10^4$ to about $1\times10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative, applicable HLA molecule positive target cells pulsed with a low concentration of mutated p53 peptide (e.g., about 0.05 ng/mL to about 5 ng/mL, 0.05 ng/mL, 0.1 ng/mL, 0.5 ng/mL, 1 ng/mL, 5 ng/mL, or a range defined by any two of the foregoing values) or (b) antigen-negative, applicable HLA molecule positive target cells into which a nucleotide sequence encoding mutated p53 has been introduced such that the target cell expresses mutated p53. Cells expressing the inventive TCRs may also secrete IFN-γ upon co-culture with antigen-negative, applicable HLA molecule positive target cells pulsed with higher concentrations of mutated p53 peptide.

Alternatively or additionally, a TCR may be considered to have "antigenic specificity" for mutated p53 if T cells expressing the TCR secrete at least twice as much IFN-γ upon co-culture with (a) antigen-negative, applicable HLA molecule positive target cells pulsed with a low concentration of mutated p53 peptide or (b) antigen-negative, applicable HLA molecule positive target cells into which a nucleotide sequence encoding mutated p53 has been introduced such that the target cell expresses mutated p53 as compared to the amount of IFN-γ expressed by a negative control. The negative control may be, for example, (i) T cells expressing the TCR, co-cultured with (a) antigen-negative, applicable HLA molecule positive target cells pulsed with the same concentration of an irrelevant peptide (e.g., some other peptide with a different sequence from the mutated p53 peptide) or (b) antigen-negative, applicable HLA molecule positive target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative, applicable HLA molecule positive target cells pulsed with the same concentration of mutated p53 peptide or (b) antigen-negative, applicable HLA molecule positive target cells into which a nucleotide sequence encoding mutated p53 has been introduced such that the target cell expresses mutated p53. IFN-γ secretion may be measured by methods known in the art such as, for example, enzyme-linked immunosorbent assay (ELISA).

Alternatively or additionally, a TCR may be considered to have "antigenic specificity" for mutated p53 if at least twice as many of the numbers of T cells expressing the TCR secrete IFN-γ upon co-culture with (a) antigen-negative, applicable HLA molecule positive target cells pulsed with a low concentration of mutated p53 peptide or (b) antigen-negative, applicable HLA molecule positive target cells into which a nucleotide sequence encoding mutated p53 has been introduced such that the target cell expresses mutated p53 as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, enzyme-linked immunospot (ELISOT) assay.

Alternatively or additionally, a TCR may be considered to have "antigenic specificity" for mutated p53 if at least twice as many spots are detected by ELISPOT for the T cells expressing the TCR upon co-culture with (a) antigen-negative, applicable HLA molecule positive target cells pulsed with a low concentration of mutated p53 peptide or (b) antigen-negative, applicable HLA molecule positive target cells into which a nucleotide sequence encoding mutated p53 has been introduced such that the target cell expresses mutated p53 as compared to the number of spots detected by ELISPOT for negative control T cells co-cultured with the same target cells. The concentration of peptide and the negative control may be as described herein with respect to other aspects of the invention.

Alternatively or additionally, a TCR may be considered to have "antigenic specificity" for mutated p53 if greater than about 50 spots are detected by ELISPOT for the T cells expressing the TCR upon co-culture with (a) antigen-negative, applicable HLA molecule positive target cells pulsed with a low concentration of mutated p53 peptide or (b) antigen-negative, applicable HLA molecule positive target cells into which a nucleotide sequence encoding mutated p53 has been introduced such that the target cell expresses mutated p53. The concentration of peptide may be as described herein with respect to other aspects of the invention.

Alternatively or additionally, a TCR may be considered to have "antigenic specificity" for mutated p53 if T cells expressing the TCR upregulate expression of one or both of 4-1BB and OX40 as measured by, for example, flow cytometry after stimulation with target cells expressing mutated p53.

An embodiment of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for mutated p53.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising an α chain CDR1 (CDR1α), an α chain CDR2 (CDR2α), and an α chain CDR3 (CDR3α), and a second polypeptide chain comprising a β chain CDR1 (CDR1β), a β chain CDR2 (CDR2β), and a β chain CDR3 (CDR3β). In an embodiment of the invention, the TCR comprises the amino acid sequences of: (1) all of SEQ ID NOs: 3-8; (2) all of SEQ ID NOs: 14-19; (3) all of SEQ ID NOs: 25-30; (4) all of SEQ ID NOs: 36-41; (5) all of SEQ ID NOs: 47-52; (6) all of SEQ ID NOs: 58-63; (7) all of SEQ ID NOs: 69-74; (8) all of SEQ ID NOs: 80-85; or (9) all of SEQ ID NOs: 131-136. Each one of the foregoing nine collections of amino acid sequences in this paragraph sets forth the six CDR regions of each of nine different TCRs having antigenic specificity for mutated human p53. The six amino acid sequences in each collection correspond to the CDR1α, CDR2α, CDR3α, CDR1β, CDR2β, and CDR3β of a TCR, respectively.

In an embodiment of the invention, the TCR comprises an α chain variable region amino acid sequence and a β chain variable region amino acid sequence, which together comprise one of the collections of CDRs set forth above. In this regard, the TCR can, e.g., comprise the amino acid sequences of any one of SEQ ID NOs: 9, 10, 20, 21, 31, 32, 42, 43, 53, 54, 64, 65, 75, 76, 86, 87, 137, 138, 142-159, 178, 181, 184, 187, 190, 193, 196, 199, 202, 205, 207, 209, 211, 213, 215, 217, 219, 221, 223, and 226. For example, the TCR can comprise: (1) both of SEQ ID NOs: 9 and 10; (2) both of SEQ ID NOs: 20 and 21; (3) both of SEQ ID NOs: 31 and 32; (4) both of SEQ ID NOs: 42 and 43; (5) both of SEQ ID NOs: 53 and 54; (6) both of SEQ ID NOs: 64 and 65; (7) both of SEQ ID NOs: 75 and 76; (8) both of SEQ ID NOs: 86 and 87; (9) both of SEQ ID NOs: 137 and 138; (10) both of SEQ ID NOs: 142 and 143; (11) both of SEQ ID NOs: 144 and 145; (12) both of SEQ ID NOs: 146 and 147; (13) both of SEQ ID NOs: 148 and 149; (14) both of SEQ ID NOs: 150 and 151; (15) both of SEQ ID NOs: 152 and 153; (16) both of SEQ ID NOs: 154 and 155; (17) both of SEQ ID NOs: 156 and 157; (18) both of SEQ ID NOs: 159 and 158; (19) both of SEQ ID NOs: 178 and 10; (20) both of SEQ ID NOs: 181 and 21; (21) both of SEQ ID NOs: 184 and 32; (22) both of SEQ ID NOs: 187 and 43; (23) both of SEQ ID NOs: 190 and 54; (24) both of SEQ ID NOs: 193 and 65; (25) both of SEQ ID NOs: 196 and 76; (26) both of SEQ ID NOs: 199 and 87; (27) both of SEQ ID NOs: 137 and 202; (28) both of SEQ ID NOs: 9 and 205; (29) both of SEQ ID NOs: 20 and 207; (30) both of SEQ ID NOs: 31 and 209; (31) both of SEQ ID NOs: 42 and 211; (32) both of SEQ ID NOs: 53 and 213; (33) both of SEQ ID NOs: 64 and 215; (34) both of SEQ ID NOs: 75 and 217; (35) both of SEQ ID NOs: 86 and 219; (36) both of SEQ ID NOs: 137 and 221; (37) both of SEQ ID NOs: 223 and 202; (38) both of SEQ ID NOs: 223 and 221; (39) both of SEQ ID NOs: 20 and 226; or (40) both of SEQ ID NOs: 181 and 226. Each one of the foregoing collections of amino acid sequences in this paragraph sets forth the two variable regions of each of the different TCRs having antigenic specificity for mutated human p53. The two amino acid sequences in each collection correspond to the variable region of the α chain and the variable region of the β chain of a TCR, respectively.

The inventive TCRs may further comprise a constant region. The constant region may be derived from any suitable species such as, e.g., human or mouse. In an embodiment of the invention, the TCRs further comprise a murine constant region. As used herein, the term "murine" or "human," when referring to a TCR or any component of a TCR described herein (e.g., complementarity determining region (CDR), variable region, constant region, alpha chain, and/or beta chain), means a TCR (or component thereof) which is derived from a mouse or a human, respectively, i.e., a TCR (or component thereof) that originated from or was, at one time, expressed by a mouse T cell or a human T cell, respectively. In an embodiment of the invention, the TCR may comprise a murine α chain constant region and a murine β chain constant region. The murine α chain constant region may be modified or unmodified. A modified murine α chain constant region may be, e.g., cysteine-substituted, LVL-modified, or both cysteine-substituted and LVL-modified, as described, for example, in U.S. Pat. No. 10,174,098. The murine β chain constant region may be modified or unmodified. A modified murine β chain constant region may be, e.g., cysteine-substituted, as described, for example, in U.S. Pat. No. 10,174,098. In an embodiment of the invention, the TCR comprises a cysteine-substituted, LVL-modified murine α chain constant region comprising the amino acid sequence of SEQ ID NO: 91 or 92. In an embodiment of the invention, the TCR comprises a cysteine-substituted murine β chain constant region comprising the amino acid sequence of SEQ ID NO: 93.

In an embodiment of the invention, the inventive TCR can comprise an α chain of a TCR and a β chain of a TCR. The α chain of the TCR may comprise a variable region of an α chain and a constant region of an α chain. An α chain of this type can be paired with any β chain of a TCR. The β chain may comprise a variable region of a β chain and a constant region of a β chain.

In some embodiments, the amino acid sequence of any of the α chains and/or β chains disclosed herein further comprises the amino acid sequence RAKR (SEQ ID NO: 230) at the C-terminal end.

In an embodiment of the invention, the TCR comprises the amino acid sequences of any one of SEQ ID NOs 11, 12, 22, 23, 33, 34, 44, 45, 55, 56, 66, 67, 77, 78, 88, 89, 139, 140, 160-177, 179, 182, 185, 188, 191, 194, 197, 200, 203, 206, 208, 210, 212, 214, 216, 218, 220, 222, 224, and 227. For example, the TCR can comprise: (1) both of SEQ ID NOs: 11 and 12; (2) both of SEQ ID NOs: 22 and 23; (3) both of SEQ ID NOs: 33 and 34; (4) both of SEQ ID NOs: 44 and 45; (5) both of SEQ ID NOs: 55 and 56; (6) both of SEQ ID NOs: 66 and 67; (7) both of SEQ ID NOs: 77 and 78; (8) both of SEQ ID NOs: 88 and 89; (9) both of SEQ ID NOs: 139 and 140; (10) both of SEQ ID NOs: 160 and 161; (11) both of SEQ ID NOs: 162 and 163; (12) both of SEQ ID NOs: 164 and 165; (13) both of SEQ ID NOs: 166 and 167; (14) both of SEQ ID NOs: 168 and 169; (15) both of SEQ ID NOs: 170 and 171; (16) both of SEQ ID NOs: 172 and 173; (17) both of SEQ ID NOs: 174 and 175; (18) both of SEQ ID NOs: 176 and 177; (19) both of SEQ ID NOs: 179 and 12; (20) both of SEQ ID NOs: 182 and 23; (21) both of SEQ ID NOs: 185 and 34; (22) both of SEQ ID NOs: 188 and 45; (23) both of SEQ ID NOs: 191 and 56; (24) both of SEQ ID NOs: 194 and 67; (25) both of SEQ ID NOs: 197 and 78; (26) both of SEQ ID NOs: 200 and 89; (27) both of SEQ ID NOs: 139 and 203; (28) both of SEQ ID NOs: 11 and 206; (29) both of SEQ ID NOs: 22 and 208; (30) both of SEQ ID NOs: 33 and 210; (31) both of SEQ ID NOs: 44 and 212; (32) both of SEQ ID NOs: 55 and 214; (33) both of SEQ ID NOs: 66 and 216; (34) both of SEQ ID NOs: 77 and 218; (35) both of SEQ ID NOs: 88 and 220; (36) both of SEQ ID NOs: 139 and 222; (37) both of SEQ ID NOs: 224 and 203; (38) both of SEQ ID NOs: 224 and 222; (39) both of SEQ ID NOs: 22 and 227; or (40) both of SEQ ID NOs: 182 and 227. Each one of the foregoing collections of amino acid sequences in this paragraph sets forth the α chain and β chain of each of different TCRs having antigenic specificity for mutated human p53. The two amino acid sequences in each collection correspond to the α chain and the β chain of a TCR, respectively.

Included in the scope of the invention are functional variants of the inventive TCRs described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to mutated p53 for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, at least about 50%, at least about 75%, at least about 80%, at least about 90%, at least about 95%, at least about 96%, at least about 97%, at least about 98%, at least about 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein.

Also provided by the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to mutated p53. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to mutated p53 (e.g., in an applicable HLA molecule-dependent manner), or detect, treat, or prevent cancer, to a similar extent, the same extent, or to a higher extent, as the parent TCR. In reference to the parent TCR, the functional portion can comprise, for instance, about 10%, about 25%, about 30%, about 50%, about 68%, about 80%, about 90%, about 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to mutated p53; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the invention. In an embodiment of the invention, the polypeptide can comprise a functional portion comprising the amino acid sequences of: (1) all of SEQ ID NOs: 3-8; (2) all of SEQ ID NOs: 14-19; (3) all of SEQ ID NOs: 25-30; (4) all of SEQ ID NOs: 36-41; (5) all of SEQ ID NOs: 47-52; (6) all of SEQ ID NOs: 58-63; (7) all of SEQ ID NOs: 69-74; (8) all of SEQ ID NOs: 80-85; or (9) all of SEQ ID NOs: 131-136.

In an embodiment of the invention, the inventive polypeptide can comprise, for instance, the variable region of the inventive TCR comprising a combination of the CDR regions set forth above. In this regard, the polypeptide can comprise, e.g., the amino acid sequences of: (1) both of SEQ ID NOs: 9 and 10; (2) both of SEQ ID NOs: 20 and 21; (3) both of SEQ ID NOs: 31 and 32; (4) both of SEQ ID NOs: 42 and 43; (5) both of SEQ ID NOs: 53 and 54; (6) both of SEQ ID NOs: 64 and 65; (7) both of SEQ ID NOs: 75 and 76; (8) both of SEQ ID NOs: 86 and 87; (9) both of SEQ ID NOs: 137 and 138; (10) both of SEQ ID NOs: 142 and 143; (11) both of SEQ ID NOs: 144 and 145; (12) both of SEQ ID NOs: 146 and 147; (13) both of SEQ ID NOs: 148 and 149; (14) both of SEQ ID NOs: 150 and 151; (15) both of SEQ ID NOs: 152 and 153; (16) both of SEQ ID NOs: 154 and 155; (17) both of SEQ ID NOs: 156 and 157; (18) both of SEQ ID NOs: 159 and 158; (19) both of SEQ ID NOs: 178 and 10; (20) both of SEQ ID NOs: 181 and 21; (21) both of SEQ ID NOs: 184 and 32; (22) both of SEQ ID NOs: 187 and 43; (23) both of SEQ ID NOs: 190 and 54; (24) both of SEQ ID NOs: 193 and 65; (25) both of SEQ ID NOs: 196 and 76; (26) both of SEQ ID NOs: 199 and 87; (27) both of SEQ ID NOs: 137 and 202; (28) both of SEQ ID NOs: 9 and 205; (29) both of SEQ ID NOs: 20 and 207; (30) both of SEQ ID NOs: 31 and 209; (31) both of SEQ ID NOs: 42 and 211; (32) both of SEQ ID NOs: 53 and 213; (33) both of SEQ ID NOs: 64 and 215; (34) both of SEQ ID NOs: 75 and 217; (35) both of SEQ ID NOs: 86 and 219; (36) both of SEQ ID NOs: 137 and 221; (37) both of SEQ ID NOs: 223 and 202; (38) both of SEQ ID NOs: 223 and 221; (39) both of SEQ ID NOs: 20 and 226; or (40) both of SEQ ID NOs: 181 and 226.

In an embodiment of the invention, the inventive polypeptide can further comprise the constant region of the inventive TCR set forth above. In this regard, the polypeptide can comprise, e.g., the amino acid sequence of (i) one of SEQ ID NOs 91-93 or (ii) SEQ ID NO: 93 and one of SEQ ID NOs: 91 and 92.

In an embodiment of the invention, the inventive polypeptide may comprise an α chain and a β chain of the inventive TCR. In this regard, the polypeptide can comprise, e.g., the amino acid sequences of: (1) both of SEQ ID NOs: 11 and 12; (2) both of SEQ ID NOs: 22 and 23; (3) both of SEQ ID NOs: 33 and 34; (4) both of SEQ ID NOs: 44 and 45; (5) both of SEQ ID NOs: 55 and 56; (6) both of SEQ ID NOs: 66 and 67; (7) both of SEQ ID NOs: 77 and 78; (8) both of SEQ ID NOs: 88 and 89; (9) both of SEQ ID NOs: 139 and 140; (10) both of SEQ ID NOs: 160 and 161; (11) both of SEQ ID NOs: 162 and 163; (12) both of SEQ ID NOs: 164 and 165; (13) both of SEQ ID NOs: 166 and 167; (14) both of SEQ ID NOs: 168 and 169; (15) both of SEQ ID NOs: 170 and 171; (16) both of SEQ ID NOs: 172 and 173; (17) both of SEQ ID NOs: 174 and 175; (18) both of SEQ ID NOs: 176 and 177; (19) both of SEQ ID NOs: 179 and 12; (20) both of SEQ ID NOs: 182 and 23; (21) both of SEQ ID NOs: 185 and 34; (22) both of SEQ ID NOs: 188 and 45; (23) both of SEQ ID NOs: 191 and 56; (24) both of SEQ ID NOs: 194 and 67; (25) both of SEQ ID NOs: 197 and 78; (26) both of SEQ ID NOs: 200 and 89; (27) both of SEQ ID NOs: 139 and 203; (28) both of SEQ ID NOs: 11 and 206; (29) both of SEQ ID NOs: 22 and 208; (30) both of SEQ ID NOs: 33 and 210; (31) both of SEQ ID NOs: 44 and 212; (32) both of SEQ ID NOs: 55 and 214; (33) both of SEQ ID NOs: 66 and 216; (34) both of SEQ ID NOs: 77 and 218; (35) both of SEQ ID NOs: 88 and 220; (36) both of SEQ ID NOs: 139 and 222; (37) both of SEQ ID NOs: 224 and 203; (38) both of SEQ ID NOs: 224 and 222; (39) both of SEQ ID NOs: 22 and 227; or (40) both of SEQ ID NOs: 182 and 227.

The invention further provides a protein comprising at least one of the polypeptides described herein. By "protein" is meant a molecule comprising one or more polypeptide chains. In an embodiment, the protein of the invention can comprise: (1) a first polypeptide chain comprising the amino acid sequences of all of SEQ ID NOs: 3-5 and a second polypeptide chain comprising the amino acid sequences of all of SEQ ID NOs: 6-8; (2) a first polypeptide chain comprising the amino acid sequences of all of SEQ ID NOs: 14-16 and a second polypeptide chain comprising the amino acid sequences of all of SEQ ID NOs: 17-19; (3) a first polypeptide chain comprising the amino acid sequences of all of SEQ ID NOs: 25-27 and a second polypeptide chain comprising the amino acid sequences of all of SEQ ID NOs: 28-30; (4) a first polypeptide chain comprising the amino acid sequences of all of SEQ ID NOs: 36-38 and a second polypeptide chain comprising the amino acid sequences of all of SEQ ID NOs: 39-41; (5) a first polypeptide chain comprising the amino acid sequences of all of SEQ ID NOs: 47-49 and a second polypeptide chain comprising the amino acid sequences of all of SEQ ID NOs: 50-52; (6) a first polypeptide chain comprising the amino acid sequences of all of SEQ ID NOs: 58-60 and a second polypeptide chain comprising the amino acid sequences of all of SEQ ID NOs: 61-63; (7) a first polypeptide chain comprising the amino acid sequences of all of SEQ ID NOs: 69-71 and a second polypeptide chain comprising the amino acid sequences of all of SEQ ID NOs: 72-74; (8) a first polypeptide chain comprising the amino acid sequences of all of SEQ ID NOs: 80-82 and a second polypeptide chain comprising the amino acid sequences of all of SEQ ID NOs: 83-85; or (9) a first polypeptide chain comprising the amino acid sequences of all of SEQ ID NOs: 131-133 and a second polypeptide chain comprising the amino acid sequences of all of SEQ ID NOs: 134-136.

In an embodiment of the invention, the protein comprises: (1) a first polypeptide chain comprising the amino acid sequence of SEQ ID NO: 9 and a second polypeptide chain comprising the amino acid sequence of SEQ ID NO: 10; (2) a first polypeptide chain comprising the amino acid sequence of SEQ ID NO: 20 and a second polypeptide chain comprising the amino acid sequence of SEQ ID NO: 21; (3) a first polypeptide chain comprising the amino acid sequence of SEQ ID NO: 31 and a second polypeptide chain comprising the amino acid sequence of SEQ ID NO: 32; (4) a first polypeptide chain comprising the amino acid sequence of SEQ ID NO: 42 and a second polypeptide chain comprising the amino acid sequence of SEQ ID NO: 43; (5) a first polypeptide chain comprising the amino acid sequence of SEQ ID NO: 53 and a second polypeptide chain comprising the amino acid sequence of SEQ ID NO: 54; (6) a first polypeptide chain comprising the amino acid sequence of SEQ ID NO: 64 and a second polypeptide chain comprising the amino acid sequence of SEQ ID NO: 65; (7) a first polypeptide chain comprising the amino acid sequence of SEQ ID NO: 75 and a second polypeptide chain comprising the amino acid sequence of SEQ ID NO: 76; (8) a first polypeptide chain comprising the amino acid sequence of SEQ ID NO: 86 and a second polypeptide chain comprising the amino acid sequence of SEQ ID NO: 87; (9) a first polypeptide chain comprising the amino acid sequence of SEQ ID NO: 137 and a second polypeptide chain comprising the amino acid sequence of SEQ ID NO: 138; (10) a first polypeptide chain comprising the amino acid sequence of SEQ ID NO: 142 and a second polypeptide chain comprising the amino acid sequence of SEQ ID NO: 143; (11) a first polypeptide chain comprising the amino acid sequence of SEQ ID NO: 144 and a second polypeptide chain comprising the amino acid sequence of SEQ ID NO: 145; (12) a first polypeptide chain comprising the amino acid sequence of SEQ ID NO: 146 and a second polypeptide chain comprising the amino acid sequence of SEQ ID NO: 147; (13) a first polypeptide chain comprising the amino acid sequence of SEQ ID NO: 148 and a second polypeptide chain comprising the amino acid sequence of SEQ ID NO: 149; (14) a first polypeptide chain comprising the amino acid sequence of SEQ ID NO: 150 and a second polypeptide chain comprising the amino acid sequence of SEQ ID NO: 151; (15) a first polypeptide chain comprising the amino acid sequence of SEQ ID NO: 152 and a second polypeptide chain comprising the amino acid sequence of SEQ ID NO: 153; (16) a first polypeptide chain comprising the amino acid sequence of SEQ ID NO: 154 and a second polypeptide chain comprising the amino acid sequence of SEQ ID NO: 155; (17) a first polypeptide chain comprising the amino acid sequence of SEQ ID NO: 156 and a second polypeptide chain comprising the amino acid sequence of SEQ ID NO: 157; (18) a first polypeptide chain comprising the amino acid sequence of SEQ ID NO: 158 and a second polypeptide chain comprising the amino acid sequence of SEQ ID NO: 159; (19) a first polypeptide chain comprising the amino acid sequence of SEQ ID NO: 178 and a second polypeptide chain comprising the amino acid sequence of SEQ ID NO: 10; (20) a first polypeptide chain comprising the amino acid sequence of SEQ ID NO: 181 and a second polypeptide chain comprising the amino acid sequence of SEQ ID NO: 21; (21) a first polypeptide chain comprising the amino acid sequence of SEQ ID NO: 184 and a second polypeptide chain comprising the amino acid sequence of SEQ ID NO: 32; (22) a first polypeptide chain comprising the amino acid sequence of SEQ ID NO: 187 and a second polypeptide chain comprising the amino acid sequence of SEQ ID NO: 43; (23) a first polypeptide chain comprising the amino acid sequence of SEQ ID NO: 190 and a second polypeptide chain comprising the amino acid sequence of SEQ ID NO: 54; (24) a first polypeptide chain comprising the amino acid sequence of SEQ ID NO: 193 and a second polypeptide chain comprising the amino acid sequence of SEQ ID NO: 65; (25) a first polypeptide chain comprising the amino acid sequence of SEQ ID NO: 196 and a second polypeptide chain comprising the amino acid sequence of SEQ ID NO: 76; (26) a first polypeptide chain comprising the amino acid sequence of SEQ ID NO: 199 and a second polypeptide chain comprising the amino acid sequence of SEQ ID NO: 87; (27) a first polypeptide chain comprising the amino acid sequence of SEQ ID NO: 137 and a second polypeptide chain comprising the amino acid sequence of SEQ ID NO: 202; (28) a first polypeptide chain comprising the amino acid sequence of SEQ ID NO: 9 and a second polypeptide chain comprising the amino acid sequence of SEQ ID NO: 205; (29) a first polypeptide chain comprising the amino acid sequence of SEQ ID NO: 20 and a second polypeptide chain comprising the amino acid sequence of SEQ ID NO: 207; (30) a first polypeptide chain comprising the amino acid sequence of SEQ ID NO: 31 and a second polypeptide chain comprising the amino acid sequence of SEQ ID NO: 209; (31) a first polypeptide chain comprising the amino acid sequence of SEQ ID NO: 42 and a second polypeptide chain comprising the amino acid sequence of SEQ ID NO: 211; (32) a first polypeptide chain comprising the amino acid sequence of SEQ ID NO: 53 and a second polypeptide chain comprising the amino acid sequence of SEQ ID NO: 213; (33) a first polypeptide chain comprising the amino acid sequence of SEQ ID NO: 64 and a second polypeptide chain comprising the amino acid sequence of SEQ ID NO: 215; (34) a first polypeptide chain comprising the amino acid sequence of SEQ ID NO: 75 and a second polypeptide chain comprising the amino acid sequence of SEQ ID NO: 217; (35) a first polypeptide chain comprising the amino acid sequence of SEQ ID NO: 86 and a second polypeptide chain comprising the amino acid sequence of SEQ ID NO: 219; (36) a first polypeptide chain comprising the amino acid sequence of SEQ ID NO: 137 and a second polypeptide chain comprising the amino acid sequence of SEQ ID NO: 221; (37) a first polypeptide chain comprising the amino acid sequence of SEQ ID NO: 223 and a second polypeptide chain comprising the amino acid sequence of SEQ ID NO: 202; (38) a first polypeptide chain comprising the amino acid sequence of SEQ ID NO: 223 and a second polypeptide chain comprising the amino acid sequence of SEQ ID NO: 221; (39) a first polypeptide chain comprising the amino acid sequence of SEQ ID NO: 20 and a second polypeptide chain comprising the amino acid sequence of SEQ ID NO: 226; or (40) a first polypeptide chain comprising the amino acid sequence of SEQ ID NO: 181 and a second polypeptide chain comprising the amino acid sequence of SEQ ID NO: 226.

In an embodiment of the invention, the protein comprises: (1) a first polypeptide chain comprising the amino acid sequence of SEQ ID NO: 11 and a second polypeptide chain comprising the amino acid sequence of SEQ ID NO: 12; (2) a first polypeptide chain comprising the amino acid sequence of SEQ ID NO: 22 and a second polypeptide chain comprising the amino acid sequence of SEQ ID NO: 23; (3) a first polypeptide chain comprising the amino acid sequence of SEQ ID NO: 33 and a second polypeptide chain comprising the amino acid sequence of SEQ ID NO: 34; (4) a first polypeptide chain comprising the amino acid sequence of SEQ ID NO: 44 and a second polypeptide chain comprising the amino acid sequence of SEQ ID NO: 45; (5) a first polypeptide chain comprising the amino acid sequence of SEQ ID NO: 55 and a second polypeptide chain comprising the amino acid sequence of SEQ ID NO: 56; (6) a first polypeptide chain comprising the amino acid sequence of SEQ ID NO: 66 and a second polypeptide chain comprising the amino acid sequence of SEQ ID NO: 67; (7) a first polypeptide chain comprising the amino acid sequence of SEQ ID NO: 77 and a second polypeptide chain comprising the amino acid sequence of SEQ ID NO: 78; (8) a first polypeptide chain comprising the amino acid sequence of SEQ ID NO: 88 and a second polypeptide chain comprising the amino acid sequence of SEQ ID NO: 89; (9) a first polypeptide chain comprising the amino acid sequence of SEQ ID NO: 139 and a second polypeptide chain comprising the amino acid sequence of SEQ ID NO: 140; (10) a first polypeptide chain comprising the amino acid sequence of SEQ ID NO: 160 and a second polypeptide chain comprising the amino acid sequence of SEQ ID NO: 161; (11) a first polypeptide chain comprising the amino acid sequence of SEQ ID NO: 162 and a second polypeptide chain comprising the amino acid sequence of SEQ ID NO: 163; (12) a first polypeptide chain comprising the amino acid sequence of SEQ ID NO: 164 and a second polypeptide chain comprising the amino acid sequence of SEQ ID NO: 165; (13) a first polypeptide chain comprising the amino acid sequence of SEQ ID NO: 166 and a second polypeptide chain comprising the amino acid sequence of SEQ ID NO: 167; (14) a first polypeptide chain comprising the amino acid sequence of SEQ ID NO: 168 and a second polypeptide chain comprising the amino acid sequence of SEQ ID NO: 169; (15) a first polypeptide chain comprising the amino acid sequence of SEQ ID NO: 170 and a second polypeptide chain comprising the amino acid sequence of SEQ ID NO: 171; (16) a first polypeptide chain comprising the amino acid sequence of SEQ ID NO: 172 and a second polypeptide chain comprising the amino acid sequence of SEQ ID NO: 173; (17) a first polypeptide chain comprising the amino acid sequence of SEQ ID NO: 174 and a second polypeptide chain comprising the amino acid sequence of SEQ ID NO: 175; (18) a first polypeptide chain comprising the amino acid sequence of SEQ ID NO: 176 and a second polypeptide chain comprising the amino acid sequence of SEQ ID NO: 177; (19) a first polypeptide chain comprising the amino acid sequence of SEQ ID NO: 179 and a second polypeptide chain comprising the amino acid sequence of SEQ ID NO: 12; (20) a first polypeptide chain comprising the amino acid sequence of SEQ ID NO: 182 and a second polypeptide chain comprising the amino acid sequence of SEQ ID NO: 23; (21) a first polypeptide chain comprising the amino acid sequence of SEQ ID NO: 185 and a second polypeptide chain comprising the amino acid sequence of SEQ ID NO: 34; (22) a first polypeptide chain comprising the amino acid sequence of SEQ ID NO: 188 and a second polypeptide chain comprising the amino acid sequence of SEQ ID NO: 45; (23) a first polypeptide chain comprising the amino acid sequence of SEQ ID NO: 191 and a second polypeptide chain comprising the amino acid sequence of SEQ ID NO: 56; (24) a first polypeptide chain comprising the amino acid sequence of SEQ ID NO: 194 and a second polypeptide chain comprising the amino acid sequence of SEQ ID NO: 67; (25) a first polypeptide chain comprising the amino acid sequence of SEQ ID NO: 197 and a second polypeptide chain comprising the amino acid sequence of SEQ ID NO: 78; (26) a first polypeptide chain comprising the amino acid sequence of SEQ ID NO: 200 and a second polypeptide chain comprising the amino acid sequence of SEQ ID NO: 89; (27) a first polypeptide chain comprising the amino acid sequence of SEQ ID NO: 139 and a second polypeptide chain comprising the amino acid sequence of SEQ ID NO: 203; (28) a first polypeptide chain comprising the amino acid sequence of SEQ ID NO: 11 and a second polypeptide chain comprising the amino acid sequence of SEQ ID NO: 206; (29) a first polypeptide chain comprising the amino acid sequence of SEQ ID NO: 22 and a second polypeptide chain comprising the amino acid sequence of SEQ ID NO: 208; (30) a first polypeptide chain comprising the amino acid sequence of SEQ ID NO: 33 and a second polypeptide chain comprising the amino acid sequence of SEQ ID NO: 210; (31) a first polypeptide chain comprising the amino acid sequence of SEQ ID NO: 44 and a second polypeptide chain comprising the amino acid sequence of SEQ ID NO: 212; (32) a first polypeptide chain comprising the amino acid sequence of SEQ ID NO: 55 and a second polypeptide chain comprising the amino acid sequence of SEQ ID NO: 214; (33) a first polypeptide chain comprising the amino acid sequence of SEQ ID NO: 66 and a second polypeptide chain comprising the amino acid sequence of SEQ ID NO: 216; (34) a first polypeptide chain comprising the amino acid sequence of SEQ ID NO: 77 and a second polypeptide chain comprising the amino acid sequence of SEQ ID NO: 218; (35) a first polypeptide chain comprising the amino acid sequence of SEQ ID NO: 88 and a second polypeptide chain comprising the amino acid sequence of SEQ ID NO: 220; (36) a first polypeptide chain comprising the amino acid sequence of SEQ ID NO: 139 and a second polypeptide chain comprising the amino acid sequence of SEQ ID NO: 222; (37) a first polypeptide chain comprising the amino acid sequence of SEQ ID NO: 224 and a second polypeptide chain comprising the amino acid sequence of SEQ ID NO: 203; or (38) a first polypeptide chain comprising the amino acid sequence of SEQ ID NO: 224 and a second polypeptide chain comprising the amino acid sequence of SEQ ID NO: 222; (39) a first polypeptide chain comprising the amino acid sequence of SEQ ID NO: 22 and a second polypeptide chain comprising the amino acid sequence of SEQ ID NO: 227; or (40) a first polypeptide chain comprising the amino acid sequence of SEQ ID NO: 182 and a second polypeptide chain comprising the amino acid sequence of SEQ ID NO: 227.

The protein of the invention may be a TCR. Alternatively, if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. For example, the linker peptide may comprise the amino acid sequence of SEQ ID NO: 94. Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

In some embodiments, the TCR, polypeptide or protein disclosed herein comprises an α chain and/or a β chain, as disclosed herein, comprising a signal peptide. In some embodiments, the sequence of the signal peptide of any of the α chains and/or β chains disclosed herein comprises an alanine or histidine residue substituted for the wild-type residue at position 2.

In some embodiments, the TCR, polypeptide or protein disclosed herein comprises a mature version of an α chain and/or a β chain, as disclosed herein, that lacks a signal peptide.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fc, Fab, or $F(ab)_2'$ fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

The TCRs, polypeptides, and proteins of the invention can be of any length, i.e., can comprise any number of amino acids, provided that the TCRs, polypeptides, or proteins retain their biological activity, e.g., the ability to specifically bind to mutated p53; detect cancer in a mammal; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention can be, e.g., glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual,* 4$^{th}$ ed., Cold Spring Harbor Press, Cold Spring Harbor, NY (2012). Alternatively, the TCRs, polypeptides, and/or proteins described herein can be commercially synthesized by companies, such as Synpep (Dublin, CA), Peptide Technologies Corp. (Gaithersburg, MD), and Multiple Peptide Systems (San Diego, CA). In this respect, the inventive TCRs, polypeptides, and proteins can be synthetic, recombinant, isolated, and/or purified.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

In an embodiment of the invention, the nucleic acid comprises a codon-optimized nucleotide sequence encoding any of the TCRs, polypeptides, or proteins described herein. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the $\alpha$ chain, the $\beta$ chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the transposon/transposase series, pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a transposon vector or a viral vector, e.g., a retroviral vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColEl, 2μ, plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter, e.g., a human elongation factor-1α promoter, or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.,* 26:332-42 (2003); and Riddell et al., *J. Immunol. Methods,* 128:189-201 (1990). In an embodiment, expansion of the numbers of T cells is carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, at least about 60%, at least about 70%, at least about 80%, at least about 90%, at least about 95%, or can be about 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agent, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy,* 22$^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., mutated p53), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1\times10^6$ to about $1\times10^{12}$ cells or more. In certain embodiments, fewer than $1\times10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are ideal sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to mutated p53 or to detect, treat, or prevent cancer.

It is contemplated that the inventive pharmaceutical compositions, TCRs, polypeptides, proteins, nucleic acids, recombinant expression vectors, host cells, or populations of cells can be used in methods of treating or preventing cancer.

Without being bound to a particular theory, the inventive TCRs are believed to bind specifically to mutated p53, such that the TCR (or related inventive polypeptide or protein), when expressed by a cell, is able to mediate an immune response against a target cell expressing mutated p53. In this regard, an embodiment of the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof. Alternatively or additionally, "prevention" may encompass preventing or delaying the recurrence of cancer, or a symptom or condition thereof.

Also provided by an embodiment of the invention is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including, e.g., any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. In a preferred embodiment, the cancer is a cancer which expresses mutated p53. The cancer may express p53 with a mutation at one or both of positions 175 and 220, as defined by SEQ ID NO: 1. The cancer may express p53 with one or both of the following human p53 mutations: R175H and Y220C. Preferably, the cancer is an epithelial cancer or cholangiocarcinoma, melanoma, colon cancer, rectal cancer, ovarian cancer, endometrial cancer, non-small cell lung cancer (NSCLC), glioblastoma, uterine cervical cancer, head and neck cancer, breast cancer, pancreatic cancer, or bladder cancer.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLES

The following materials and methods were employed in the experiments described in Examples 1-7.

Subjects and Samples

Leukapheresis products and tumor samples were obtained from individuals with metastatic epithelial cancers enrolled on National Institute of Health protocol NCT01174121, which was approved by the institutional-review board (IRB) of National Cancer Institute (NCI). Patients were chosen on basis of availability of pre-treatment leukapheresis and TIL screening results and had received prior therapies (surgery, chemotherapy, radiation therapy) per standard of care (Malekzadeh et al., *J Clin. Invest.* 129(3):1109-14 (2019); Deniger et al., *Clin. Cancer Res.,* 24(22):5562-73 (2018)). Ficoll-Hypaque was used to isolated PBL from leukapheresis and cells were cryopreserved for further use. All patients studied had a confirmed TP53 mutation by whole-exome sequencing in line with clinical protocols as previously described (Malekzadeh et al., *J. Clin. Invest.* 129(3):1109-14 (2019)).

Antibodies and FACS

Fluorescently labeled antibodies flow cytometry are detailed in Table 1. Analytical flow cytometry was performed on FACS CANTO II system (BD Biosciences, San Jose, CA) with analysis by FLOWJO software (TreeStar, Ashland, OR). All cells were gated by lymphocytes and live cells by exclusion of cells stained with propidium iodide (PI). Cells were sorted for IVS and 4-1BB/OX40 on a FACS ARIA II cell sorter (BD Biosciences). 4-1BB$^+$ and/or OX40$^+$ cells were sorted separately through CD3$^+$CD4$^+$CD8$^-$ (CD4) and CD3$^+$CD4$^-$CD8+ (CD8) gates. Co-cultures were sorted by SH800S cell sorter (Sony Biotechnology) for single-cell PCR to identify TCR genes.

TABLE 1

| Antigen | Catalog # | Clone | Fluorochrome | Vendor |
|---|---|---|---|---|
| CD3 | 560176 | SK7 | APC-H7 | BD Pharminogen |
| CD3 | 349201 | SK7 | FITC | BD Biosciences |
| CD3 | 130-093-387 | OKT3 | purified | Miltenyi Biotec |
| CD4 | 555347 | RPA-T4 | PE | BD Pharminogen |
| CD4 | 340133 | SK3 | FITC | BD Biosciences |
| CD4 | 317438 | OKT4 | BV605 | BioLegend |
| CD8 | 557746 | RPA-T8 | PE-Cy7 | BD Pharminogen |
| CD134 | 555837 | ACT35 | FITC | BD Pharminogen |
| CD137 | 550890 | 4B4-1 | APC | BD Pharminogen |
| CD62L | 555544 | DREG-56 | PE | BD Pharminogen |
| CD45RO | 559865 | UCHL1 | APC | BD Pharminogen |
| TCRb | MA5-17652 | H57-597 | FITC | eBioscience/ ThermoFisher |
| TCRb | 560656 | H57-597 | APC | eBioscience/ ThermoFisher |
| Live/Dead | P4864 | n/a | Propidium Iodide | Sigma-Aldrich |

TP53 "Hotspot" Mutation Screening Reagents

The WT (TMG-WT-TP53) and mutated TP53 (TMG-MUT-TP53) TMG constructs were generated for TIL screening as previously described (Malekzadeh et al., *J. Clin. Invest.* 129(3):1109-14 (2019)). In brief, each TP53 "hotspot" mutation (R175H, Y220C, G245S, G245D, R248L, R248Q, R248W, R249S, R273C, R273H, R273L and R282W) was composed into a minigene with mutated codon in the middle and 12 normal codons upstream and downstream and the minigenes were concatenated into a TMG. A similar sequence corresponding to WT sequences was also derived. TMGs were synthesized as DNA and cloned in frame to LAMP signal sequence and DC-LAMP localization sequence then in vitro transcribed to mRNA using mMESSAGE mMACHINE T7 Ultra Kit according to manufacturer's instructions (Thermo-Fisher; Waltham, MA). In addition, WT and mutated peptides were synthesized for $p53^{R175H}$, $p53^{R248W}$ and $p53^{Y220C}$ and purified to >95% by high-performance liquid chromatography (Genscript; Piscataway, NJ). All peptides were reconstituted in DMSO.

Antigen Presenting Cells

Monocyte-derived immature dendritic cells (DCs) were generated by adherence method (Tran et al., *Science,* 350 (6266):1387-90 (2015)). Briefly, PBL were plated in AIM-V media (Life Technologies, Waltham, MA) containing DNase (Genentech Inc., San Francisco, CA) and incubated for 1.5-2 hours at 37° C. Non-adherent cells were removed and used fresh or cryopreserved. Adherent cells were washed in AIM-V, incubated one hour at 37° C. and media was exchanged to DC media (RPMI-1640, 2 mM L-glutamine, with 5% human serum, 100 U/mL penicillin, 100 μg/mL streptomycin, amphotericin B, 800 IU/mL granulocyte-macrophage colony-stimulating factor (GM-CSF) and 200 U/mL interleukin-4 (IL-4) (Peprotech, Rocky Hill, NJ)). Cells were fed every 2-3 days and harvested on days 5-6.

IVS, Mutant TP53 Co-Culture, 4-1BB/OX40 Enrichment and REP

To perform the antigen experienced sort, pre-treatment PBL were processed as previously described (Cafri et al., *Nat. Commun.,* 10(1):449 (2019)). Cryopreserved apheresis samples were thawed, washed, set to 5-10×10$^6$ cells/ml with AIM-V media containing DNase and 1.75-2×10$^8$ viable cells were plated per T175 flasks (Corning Inc., Corning, NY) and incubated at 37° C., 5% $CO_2$ for 90 minutes. After 90 minutes the non-adherent monocyte-depleted PBL were harvested, centrifuged, and incubated overnight at 37° C. and 5% $CO_2$ in 50/50 media (AIM-V media, RPMI-1640 media (Lonza, Walkersville, MD), 5% human AB serum, 100 U/mL penicillin and 100 μg/mL streptomycin (Life Technologies), 2 mM L-glutamine (Life Technologies), 10 μg/mL gentamicin (Quality Biological Inc., Gaithersburg, MD), 12.5 mM HEPES (Life Technologies)). Adherent monocytes were differentiated into immature DCs as described above. After resting the non-adherent cells overnight, the cells were harvested, and 1-2×10$^8$ cells were resuspended in 50 μl of staining buffer (PBS, 0.5% BSA, 2 mM EDTA) with CD3, CD8, CD4, CD62L, CD45RO antibodies. Cells were incubated for 30 minutes at 4° C. and washed twice before acquisition. To determine the sorting population, gating was performed on live cells (propidium iodide negative), single cells, CD3$^+$ T cells then antigen experienced cells (CD62L$^-$CD45RO$^+$, CD62L$^+$CD45RO$^+$, CD62L$^-$CD45RO$^-$), which were further subdivided into CD4$^+$ or CD8$^+$. The CD8$^+$ and CD4$^+$ antigen experienced memory T cells were sorted separately, collected, counted and resuspended in 50/50 media containing concentration of 60 ng/mL interleukin-21 (IL-21). Autologous DCs were electroporated 18-24 hours in advance with TMG-MUT-TP53 or pulsed for 2-4 hours the day of the FACS sort with patient-specific mutant p53-LP. Target cells (DCs) were washed in 50/50 media twice and resuspended in 50/50 media with no cytokines. In vitro stimulation (IVS) was performed with a 1:3 to 1:6 ratio (DC:T cell) co-culture in a final concentration of 30 ng/ml IL-21 after the addition of the DCs. Following 14 days of growth and 3 feedings with IL-21 and interleukin-2 (IL-2; aldesleukin) as previously described (Cafri et al., *Nat. Commun.,* 10(1):449 (2019)), autologous DCs were again electroporated or pulsed with TMG-MUT-TP53 or mutated long peptide (LP), respectively, and co-cultured IVS cultures for 18-24 hours at 37° C. and 5% $CO_2$. In parallel, IVS cultures were co-cultured with DCs electroporated with irrelevant TMG or pulsed with DMSO for negative controls during the 4-1BB/OX40 enrichment sort. Following co-culture, the cells were harvested and resuspended in 50 μl of staining buffer (PBS, 0.5% BSA, 2 mM EDTA) containing CD3, CD4, CD8, 4-1BB and OX40 antibodies, incubated for 30 minutes at 4° C. and washed twice before acquisition. The sorted 4-1B$^+$/OX40$^+$ enriched T cells were expanded by REP using irradiated PBL feeders, 30 ng/mL OKT3 antibody (Miltenyi Biotec, Bergisch Gladbach, Germany) and 3,000 IU/mL IL-2 in 50/50 media. The rapidly expanded (REP) cultures were fed 3 times and were tested for reactivity or cryopreserved on day 14.

Co-Culture

Screening of IVS and enriched T cells was accomplished through same strategy used to screen TIL fragments (Malekzadeh et al., *J. Clin. Invest.* 129(3):1109-14 (2019)). Briefly, autologous DCs were electroporated with TMG ($10^5$ cells/well) and rested overnight or pulsed with peptide or DMSO ($8\times10^4$ cells/well) for 2-4 hours. Target cells were washed twice and resuspended in 50/50 media and co-cultured with $2\times10^4$ T cells in interferon-γ (IFNγ) Enzyme-Linked ImmunoSpot (ELISPOT) plates (EMD Millipore, Burlington, MA). Phorbol 12-myristate 13-acetate (PMA) and ionomycin (Thermo Fisher) were used as a positive control and media only was a negative control. The co-cultured cells were removed, stained and analyzed by flow cytometry as above whilst the ELISPOT plate was processed according to manufacturer's instructions. Tumor cell lines were grown for at least a week from cryopreserved stocks before co-culture and their generation is described elsewhere (Malekzadeh et al., *J. Clin. Invest.* 129(3):1109-14 (2019)). Tumor cells were co-cultured at 1:1 ratio with T cells ($2\times10^5$ total cells) overnight in round-bottom 96 well plates. Following harvesting of co-culture supernatant to assess IFNγ secretion by enzyme linked immunosorbent assay (ELISA; ThermoFisher), the co-cultured cells were and analyzed by flow cytometry.

Minimal Peptide Assay and HLA Restriction Mapping

A similar method previously described was used to identify minimal peptides and determine HLA restrictions (Malekzadeh et al., *J. Clin. Invest.* 129(3):1109-14 (2019)). In short, NetMHC peptide binding affinity algorithm (v3.4) was used (Lundegaard et al., *Bioinformatics,* 24(11): 1397-8 (2008)) to predict neoepitopes for HLA Class-I alleles. Candidate 9-11 amino acid were co-cultured as described above. To investigate the $CD4^+$ minimal neoantigens, 15 amino acid peptides overlapping 14 amino acids were co-cultured as described above. To determine the HLA restrictions, COST tumor cells were plated at $2.5\times10^4$ cells/well in RPMI-1640, 2 mM L-glutamine and 10% fetal bovine serum in flat-bottom 96 well plates and incubated overnight at 37° C. Patient specific individual HLA Class-I alleles (300 ng/well) or both HLA Class-II α and β chains (150 ng/well each) in DNA plasmids (pcDNA3.1 backbone) were transfected with LIPOFECTAMINE 2000 transfection reagent according to manufacturer's instructions (ThermoFisher). When TMGs were co-transfected with HLA, the concentration of HLAs reduced to 150 ng/well for Class-I and to 100 ng/well for Class-II. The WT TMGs used for these experiments was the TMG-MUT-TP53 reverted to WT only at the position of interest, e.g., R175H. Following 24-hour incubation, transfection media was removed, peptides or DMSO were pulsed for 2-4 hours in 50/50 media, wells were washed twice with 50/50 media and $10^5$ T cells were incubated overnight. Co-culture supernatants were analyzed for IFNγ secretion by ELISA and cells were stained for upregulation of 4-1BB and analyzed by flow cytometry.

TCRB Sequencing

TCRB survey sequencing was performed from genomic DNA by Adaptive Biotechnologies (Seattle, WA). A minimum $5\times10^4$ cells were sent for sequencing. Analysis of productive TCR rearrangements was performed using IMMUNOSEQ ANALYZER 3.0 tool (Adaptive Biotechnologies).

TCR Identification and Reconstruction

TCRs were identified by sorting co-cultures of T cells and DCs expressing p53 neoantigens into single wells followed by single cell reverse transcriptase polymerase chain reaction (RT-PCR) of TCR genes similar to previous studies (Pasetto et al., *Cancer Immunol. Res.*, doi 10.1158/2326-6066.CIR-16-0001 (2016); Deniger et al., *Clin. Cancer Res.,* 23(2): 351-62 (2017)). The PCR products were kept separate for TCRα and TCRβ and were analyzed by Sanger sequencing. These partial TCR sequences were analyzed with IMGT/V-Quest (imgt.org/IMGT) and IGBLAST (ncbi.nlm-.nih.gov/igblast) websites which identified the exact CDR3 and J or D/J regions and the most likely TRAV and TRBV family. The human full-length variable sequences were fused to murine constant chains as was done in other studies (Deniger et al., *Clin. Cancer Res.,* 23(2): 351-62 (2017); Cohen et al., J. Clin. Invest., 125(10): 3981-91 (2015). The murinized TCRα and TCRβ genes were linked with a RAKR-SGSG (SEQ ID NO: 128) and P2A ribosomal slip sequence to result in stoichiometric expression of the TCR chains in a single cistron. This sequence was synthesized and cloned into MSGV1 vector for generation of transient retroviral supernatants.

TCR Transduction

PBL donors were adjusted to $3\times10^6$ cells/ml in 50/50 media supplemented 50 ng/ml soluble OKT3 and 300 IU/ml IL-2 and were activated on low adherence plates for two days prior to retroviral transduction. The pMSGV1 plasmid encoding mutation-specific TCR (1.5 μg/well) and the envelope-encoding plasmid RD114 (0.75 μg/well) were co-transfected into $10^6$ HEK293GP cells/well of a 6-well poly-D-lysine-coated plate using LIPOFECTAMINE 2000 transfection reagent (Life Technologies). Retroviral supernatants were collected two days after transfection, diluted 1:1 with DMEM media, and centrifuged onto non-tissue culture-treated 6-well plate coated with RETRONECTIN reagent (10 μg/well, Takara, Rockville, MD) at 2000×g for 2 hours at 32° C. Supernatants were aspirated and $2\times10^6$ stimulated T-cells at $5\times10^5$ cells/mL were added to each well in 50/50 media with 300 IU/mL IL-2. The T cells were centrifuged onto the RETRONECTIN reagent coated plates for 10 min at 300×g. The media was exchanged 3-4 days later with 300 IU/mL IL-2 and transduced cells were assayed 10-14 days post-transduction.

Example 1

This example demonstrates the IVS of antigen experienced peripheral blood T cells with TP53 mutations.

Antigen experienced T cells from PBL were evaluated in 7 colon, 1 rectal and 1 ovarian cancer patients with a TP53 mutated tumor (Table 2). Patients 4217 ($p53^{R175H}$), 4213 ($p53^{R248Q}$), 4257 ($p53^{R248W}$) and 4254 ($p53^{R273H}$) did not have TIL responses to p53 neoantigens. In contrast, TIL were reactive to the autologous TP53 mutation in patients 4141 ($p53^{R175H}$), 4285 ($p53^{R175H}$), 4149 ($p53^{Y220C}$), 4266 ($p53^{R248W}$) and 4273 ($p53^{R248W}$) (Malekzadeh et al., *J. Clin. Invest.* 129(3):1109-14 (2019); Deniger et al., *Clin. Cancer Res.,* 24(22):5562-73 (2018)). Cryopreserved aphereses (prior to any ACT) were used to sort antigen experienced $CD4^+$ or $CD8^+$ T cells from PBL (FIG. 1A left). Sorted $CD4^+$ or $CD8^+$ T cells were in vitro stimulated with DCs expressing mutated TP53-TMG mRNA (TP53-TMG-IVS) or pulsed with patient-specific mutated p53-LP (p53-LP-IVS). After 12 days of culture in the presence of IL-21 and IL-2, in vitro stimulated $CD4^+$ and $CD8^+$ memory cells were co-cultured with DCs electroporated with mutated TP53-TMG mRNA, in the case of TP53-TMG-IVS, or co-cultured with patient-specific mutated p53-LP, in the case of p53-LP-IVS, and sorted the following day based on expression of T cell activation markers 4-1BB and/or OX40 (FIG. 1A middle). The cell yields after TP53-TMG-IVS and p53-LP-IVS were comparable for both $CD4^+$ and $CD8^+$ T cells ranging from $0.9\times10^7$-$18.3\times10^7$ cells from $0.3\times10^7$-$15.6\times10^7$ starting T cells (Table 3). A portion of $CD4^+$4-$1BB^+$/$OX40^+$ and $CD8^+$4-$1BB^+$/$OX40^+$ T cells were sorted from all populations for completeness and symmetry of the experiment, which ranged from $2\times10^2$-$1.7\times10^5$ cells and 0.1%-6.9% from the parent CD4 or CD8 gate (Table 3). The sorted T cells underwent a REP and were analyzed after 14 days of rapid expansion. The final cell yields ranged from $7\times10^6$-$4.2\times10^8$ T cells, which were likely influenced by the input cell numbers into the REP (Table 3).

TABLE 2

| Patient # | Age/ Sex | Cancer type | p53 amino acid substitution | p53 neoepitope HLA restriction | TIL response | PBL response |
|---|---|---|---|---|---|---|
| 4141 | 52M | Colon | R175H | A*02:01 | CD8 | CD8 |
| 4217 | 51M | Colon | R175H | n/a | — | — |
| 4285 | 46M | Colon | R175H | DRB1*13:01 | CD4 | CD4 |
| 4149 | 36F | Ovarian | Y220C | Class-II | CD4 | CD4 |
| 4213 | 65M | Colon | R248Q | n/a | — | — |
| 4257 | 65M | Colon | R248W | n/a | — | — |
| 4266 | 41F | Colon | R248W | A*68:01 | CD8 | CD8 |
| 4273 | 49M | Rectal | R248W | DPB1*02:01 | CD4 | CD4 |
| 4254 | 55F | Colon | R273H | n/a | — | — |

TABLE 3

T-cell yields after IVS, 4-1BB/OX40 enrichment and rapid expansion in patients with a p53 neoantigen-reactive culture. The numbers of cells to start the IVS depended upon the frequencies of CD4 and CD8 antigen experienced T cells in the PBL. The percentage of 4-1BB/OX40 T cells sorted was based on control gating to eliminate as many non-specific T cells as possible and is likely an underestimate of the percentage of reactive T cells in the population. All enriched cells were placed in a REP.

| Patient # | p53 a.a. sub | T cell type | IVS | # cells to start IVS ($\times10^6$) | # cells after IVS ($\times10^6$) | %4-1BB/ OX40 sorted | # cells to start REP ($\times10^6$) | # cells after REP ($\times10^6$) |
|---|---|---|---|---|---|---|---|---|
| 4141 | R175H | CD4 | p53-LP | 13.2 | 12.6 | 0.9 | 0.0146 | 15.9 |
| | | | TP53-TMG | 15.6 | 18.3 | 2.3 | 0.0179 | 42.2 |
| | | CD8 | p53-LP | 1 | 9.1 | 0.1 | 0.0002 | 12.9 |
| | | | TP53-TMG | 1.5 | 7.9 | 4.9 | 0.1185 | 44.2 |
| 4285 | R175H | CD4 | p53-LP | 5 | 31 | 2.0 | 0.0360 | 360 |
| | | | TP53-TMG | 5 | 36 | 2.2 | 0.0428 | 420 |
| | | CD8 | p53-LP | 1.5 | 10 | 2.4 | 0.0192 | 34 |
| | | | TP53-TMG | 1.5 | 19 | 0.2 | 0.0788 | 10 |
| 4149 | Y220C | CD4 | p53-LP | 1 | 14 | 0.7 | 0.0127 | 19.3 |
| | | | TP53-TMG | 1 | 5.7 | 0.1 | 0.0002 | 7.1 |
| | | CD8 | p53-LP | 1 | 6.6 | 0.2 | 0.0040 | 45.4 |
| | | | TP53-TMG | 1 | 7.2 | 0.1 | 0.0011 | 48.4 |
| 4266 | R248W | CD4 | p53-LP | 5 | 0.9 | 0.1 | 0.0041 | 305 |
| | | | TP53-TMG | 7.8 | 11.5 | 0.1 | 0.0351 | 294 |
| | | CD8 | p53-LP | 0.3 | 0.5 | 0.2 | 0.0010 | 136.8 |
| | | | TP53-TMG | 0.4 | 13.3 | 0.1 | 0.0123 | 131.2 |
| 4273 | R248W | CD4 | p53-LP | 8.4 | 1.6 | 1.1 | 0.0642 | 15.1 |
| | | | TP53-TMG | 8.4 | 3.3 | 2.2 | 0.1719 | 68.6 |
| | | CD8 | p53-LP | 0.4 | 3.9 | 6.9 | 0.0084 | 66.6 |
| | | | TP53-TMG | 0.8 | 5.6 | 2.9 | 0.0419 | 44.8 |

Example 2

This example demonstrates that TP53 mutation-reactive T cells were present in PBL of patients with intratumoral TIL responses to p53 neoantigens.

Figure 1C:
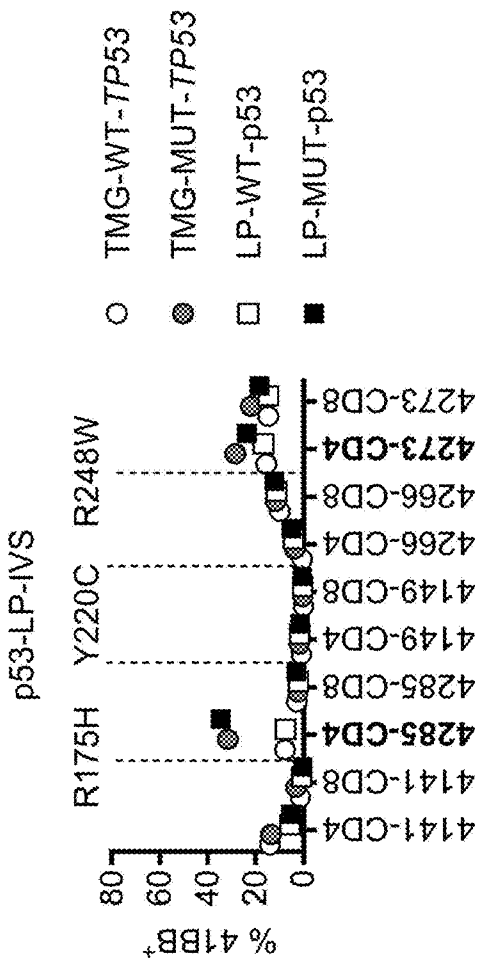
FIGS. 1B-1C are graphs showing the percentage of 4-1BB positive cells detected after IVS (TP53-TMG-IVS (B) or p53-LP-IVS (C)) and 4-1BB/OX40 enrichment. Cultures deemed positive are bolded. Responses to mutated TP53 (TMG (closed circles); LP (closed squares)) and the wild type (WT) counterparts (TMG (open circles); LP (open squares)) are shown.
Figure 1B:
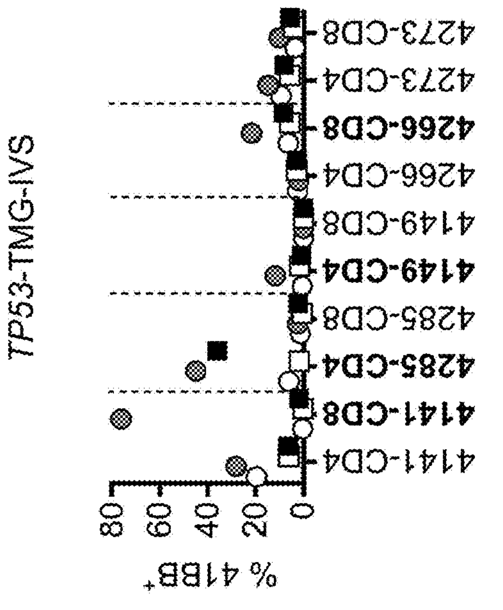
Figure 1D:
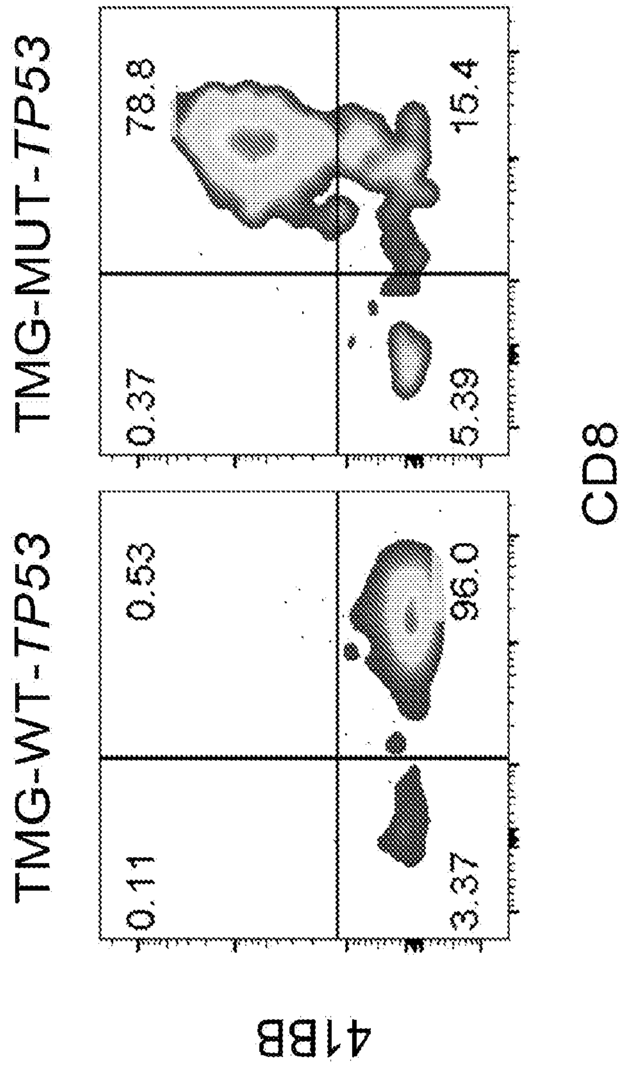
FIG. 1D shows representative flow cytometry plots from the 4141-CD8 TP53-TMG-IVS culture following co-culture with autologous antigen presenting cells electroporated with WT or mutated (MUT) TP53 tandem minigenes (TMG).
Figure 1E:
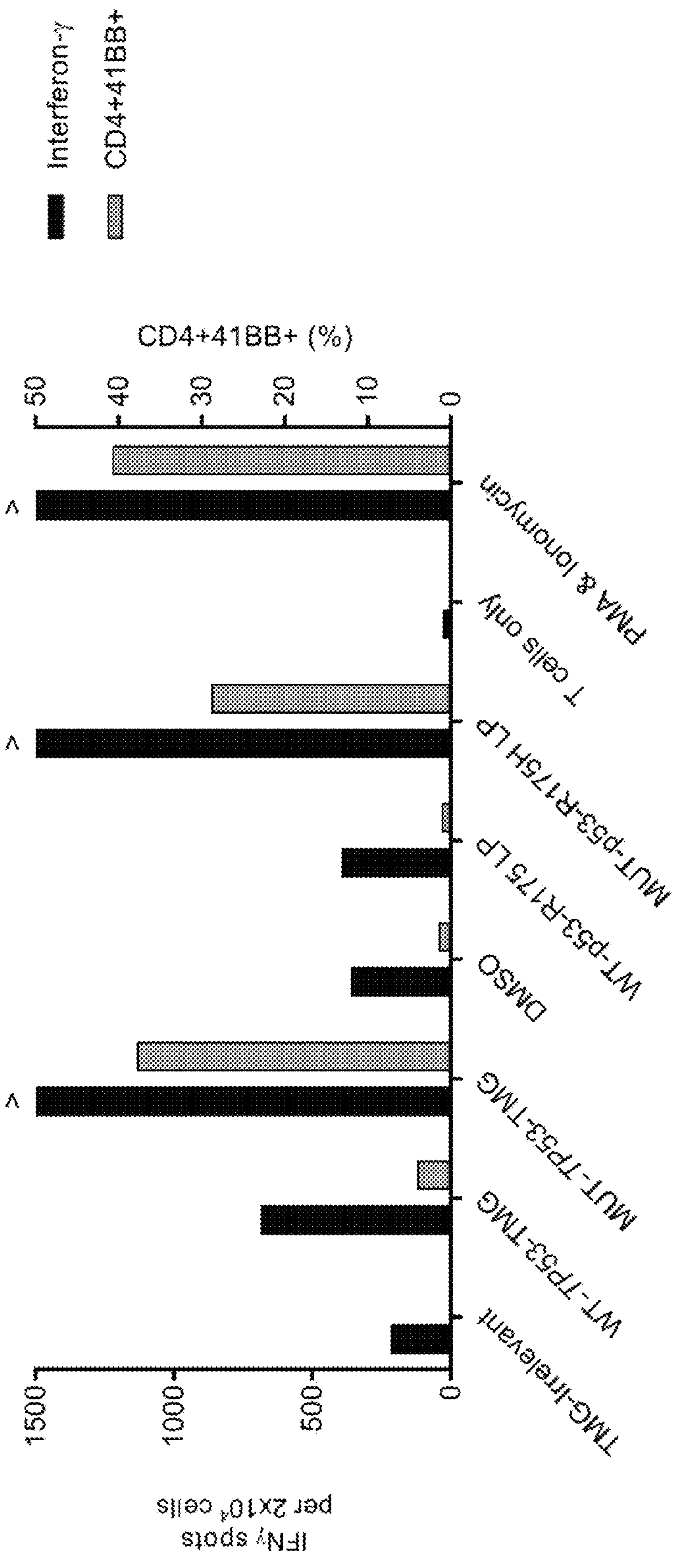
FIG. 1E shows the interferon-gamma secretion (left axis) or upregulation of 4-1BB (right axis) measured after antigen experienced CD4 T cells were sorted and in vitro stimulated with immature dendritic cells electroporated with mutated TP53-TMG. The culture was then co-cultured with immature dendritic cells electroporated with mutated TP53-TMG and the following day 4-1BB+ and/or OX40+ cells were sorted and expanded by rapid expansion protocol. After 12-14 days of expansion the culture (4285-CD4 TP53-TMG-IVS) was tested for specificity to p53-R175H neoantigen by interferon-gamma ELISPOT (left axis) or upregulation of 4-1BB by flow cytometry (right axis).
Figure 1F:
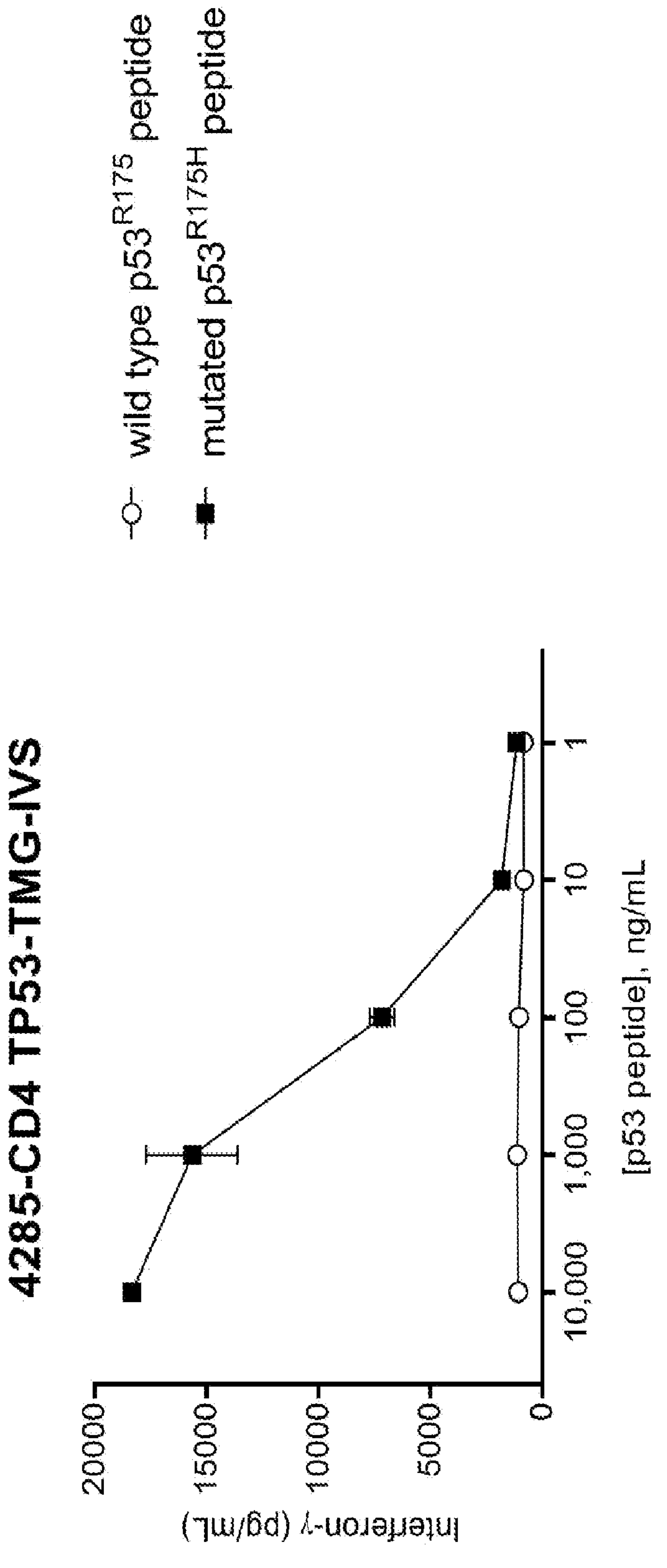
FIG. 1F is a graph showing interferon-γ secretion as measured by ELISA into 4285-CD4 TP53-TMG-IVS and peptide pulsed autologous antigen presenting cell co-culture supernatants. The 4285-CD4 TP53-TMG-IVS culture was co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3 technical replicates).

An analytical screen was performed on the cultures of Example 1 after IVS, 4-1BB/OX40 enrichment and REP where reactivities were evaluated by cell surface marker 4-1BB upregulation via flow cytometry and IFNγ secretion using an ELISPOT assay (FIG. 1A right). Peripheral blood T cells were not reactive to p53 neoantigens in patients 4213, 4217, 4254, and 4257, which corroborated the TIL screening results (Table 2). These patients may not have had an immunogenic combination of HLA and p53 neoepitope. In contrast, TP53 mutation specific T cells were identified in antigen experienced T cells from PBL of 5 patients (4141 and 4285: $p53^{R175H}$, 4149: $p53^{Y220C}$, 4266 and 4273: $p53^{R248W}$) who had intratumoral T-cell responses to mutated TP53 by TIL (FIGS. 1B-1C and Table 2) (Malekzadeh et al., *J. Clin. Invest.* 129(3):1109-14 (2019)). TP53-TMG-IVS resulted in p53 neoantigen-specific T cells in 4141-CD8, 4285-CD4, 4149-CD4 and 4266-CD8 cultures (FIG. 1B), and p53-LP-IVS resulted in p53 neoantigen-specific T cells in 4285-CD4 and 4273-CD4 cultures (FIG. 1C). The specificity of the responses to mutated TP53 (FIGS. 1B-1C closed shapes) was exemplified by the lack of response to the WT counterpart (FIGS. 1B-1C open shapes). The highest frequency of TP53 mutation-reactive cells was 78% in the 4141-CD8 TP53-TMG-IVS culture against $p53^{R175H}$ (FIG. 1D). The 4285-CD4 TP53-TMG-IVS culture exemplified a positive IFNγ secretion screening result as T cells were reactive to the mutant TMG-MUT-TP53 and $p53^{R175H}$ LP but not against WT TMG-MUT-TP53, irrelevant TMG, DMSO (peptide vehicle) or WT $p53^{R175}$ LP (FIG. 1E). The $p53^{R175H}$ LP had the amino acid sequence YKQSQHMTE-VVRHCPHHERCSDSDG (SEQ ID NO: 111). The WT $p53^{R175}$ LP had the amino acid sequence YKQSQHMTE-VVRRCPHHERCSDSDG (SEQ ID NO: 110). Selected cultures were deemed reactive based on 4-1BB upregulation and/or IFNγ secretion and were studied further (Tables 4A-4B). The 4285-CD4 TP53-TMG-IVS culture showed specific recognition of the cognate $p53^{R175H}$ LP with peptide concentrations down to 10 ng/mL (FIG. 1F). Thus, through IVS and 4-1BB/OX40 enrichment, highly specific CD8⁺ and CD4⁺ T cells targeting public TP53 mutations could be identified.

TABLE 4A

| | p53 amino | | | Interferon-gamma ELISPOT | | | | | | CD8− 4-1BB+ | | | | | |
|---|---|---|---|---|---|---|---|---|---|---|---|---|---|---|---|
| Patient # | acid substitution | T cell population | IVS | TMG #s | TMG FC | call | PEP #s | PEP FC | call | TMG % | TMG FC | call | PEP % | PEP FC | call |
| 4141 | R175H | CD4 | p53-LP | >1000 | <2 | no | >1000 | <2 | no | 13.6 | 0.9 | no | 5.28 | 1.0 | no |
| 4141 | R175H | CD4 | TP53-TMG | >1000 | <2 | no | >1000 | <2 | no | 28.3 | 1.8 | no | 6.56 | 0.8 | no |
| 4141 | R175H | CD8 | p53-LP | 66 | 1.8 | no | 95 | 0.7 | no | 19.7 | 7.1 | yes | 6.72 | 1.5 | no |
| 4141 | R175H | CD8 | TP53-TMG | >1000 | >69 | yes | 617 | 19.3 | yes | 1.29 | 5.6 | yes | 1.94 | 4.5 | Yes |
| 4285 | R175H | CD4 | p53-LP | >1000 | <2 | no | >1000 | <2 | no | 24.0 | 20.5 | yes | 22.93 | 5.5 | no |
| 4285 | R175H | CD4 | TP53-TMG | >1000 | >5 | yes | >1000 | >3 | yes | 37.6 | 151.2 | yes | 27.43 | 19.7 | yes |
| 4285 | R175H | CD8 | p53-LP | 0 | 0.0 | no | 0 | 0.0 | no | 0.72 | 2.4 | no | 0.37 | 1.3 | no |
| 4285 | R175H | CD8 | TP53-TMG | 456 | 2.9 | yes | 304 | 1.8 | no | 0.32 | 3.9 | no | 0.2 | 1.6 | no |
| 4149 | Y220C | CD4 | p53-LP | >1000 | <2 | no | >1000 | <2 | no | 0.88 | 1.8 | no | 0.51 | 1.5 | no |
| 4149 | Y220C | CD4 | TP53-TMG | 794 | 23.7 | yes | 0 | 0.0 | no | 11.25 | 18.3 | yes | 0.15 | 1.2 | no |
| 4149 | Y220C | CD8 | p53-LP | >1000 | <2 | no | >1000 | <2 | no | 0.13 | 1.7 | no | 0.2 | 1.6 | no |
| 4149 | Y220C | CD8 | TP53-TMG | 0 | <2 | no | 216 | <2 | no | 0.023 | 2.2 | no | 0.026 | 2.4 | no |
| 4266 | R248W | CD4 | p53-LP | 570 | >2 | yes | >1000 | <2 | no | 2.34 | 2.5 | yes | 0.78 | 1.2 | no |
| 4266 | R248W | CD4 | TP53-TMG | 390 | 2.6 | yes | >1000 | <2 | no | 1.84 | 7.1 | yes | 0.15 | 1.1 | no |
| 4266 | R248W | CD8 | p53-LP | 576 | >2 | no | >1000 | <2 | no | 0.942 | 14.9 | no | 0.34 | 1.6 | no |
| 4266 | R248W | CD8 | TP53-TMG | 668 | >3 | yes | 0 | <2 | no | 1.2 | 14.3 | no | 0.46 | 1.7 | no |
| 4273 | R248W | CD4 | p53-LP | >1000 | >2 | yes | >1000 | <2 | no | 9.3 | 4.2 | yes | 4.81 | 2.1 | yes |
| 4273 | R248W | CD4 | TP53-TMG | >1000 | >2 | no | >1000 | <2 | no | 4.24 | 5.2 | yes | 0.91 | 1.5 | no |
| 4273 | R248W | CD8 | p53-LP | 251 | 2.0 | yes | 151 | 1.3 | no | 0.577 | 8.1 | no | 0.24 | 1.8 | no |
| 4273 | R248W | CD8 | TP53-TMG | 343 | 4.3 | yes | 51 | 1.2 | no | 1.04 | >2 | no | 0.67 | 3.2 | no |

TABLE 4B

| | p53 amino | | | CD8+ 4-1BB+ | | | | | | |
|---|---|---|---|---|---|---|---|---|---|---|
| Patient # | acid substitution | T cell population | IVS | TMG % | TMG FC | call | PEP % | PEP FC | call | Selected |
| 4141 | R175H | CD4 | p53-LP | 0 | 0.0 | no | 0.19 | 0.8 | no | no |
| 4141 | R175H | CD4 | TP53-TMG | 0.25 | 0.3 | no | 0.21 | 1.4 | no | no |
| 4141 | R175H | CD8 | p53-LP | 3.35 | 2.7 | Yes | 0.48 | 1.0 | no | no |
| 4141 | R175H | CD8 | TP53-TMG | 76.3 | 165.9 | Yes | 1.89 | 8.2 | Yes | Yes |

TABLE 4B-continued

| Patient # | p53 amino acid substitution | T cell population | IVS | CD8+ 4-1BB+ TMG % | TMG FC | call | PEP % | PEP FC | call | Selected |
|---|---|---|---|---|---|---|---|---|---|---|
| 4285 | R175H | CD4 | p53-LP | 0.14 | >2 | no | 0.047 | 2.0 | no | Yes |
| 4285 | R175H | CD4 | TP53-TMG | 0.26 | >2 | no | 0 | 0.0 | no | Yes |
| 4285 | R175H | CD8 | p53-LP | 0.71 | 1.8 | no | 0.49 | 1.3 | no | no |
| 4285 | R175H | CD8 | TP53-TMG | 2.47 | 16.4 | yes | 1.59 | 3.1 | yes | no |
| 4149 | Y220C | CD4 | p53-LP | 0 | 0.0 | no | 0 | 0.0 | no | no |
| 4149 | Y220C | CD4 | TP53-TMG | 0 | 0.0 | no | 0 | 0.0 | 0 | Yes |
| 4149 | Y220C | CD8 | p53-LP | 0.06 | 1.2 | no | 0.03 | 1.1 | no | no |
| 4149 | Y220C | CD8 | TP53-TMG | 0.042 | 1.5 | no | 0.017 | 1.2 | no | no |
| 4266 | R248W | CD4 | p53-LP | 0.012 | 1.3 | no | 0 | 0.0 | no | no |
| 4266 | R248W | CD4 | TP53-TMG | 0.013 | >2 | no | 0 | 0.0 | no | no |
| 4266 | R248W | CD8 | p53-LP | 10.92 | 13.4 | yes | 0.2 | 1.0 | no | no |
| 4266 | R248W | CD8 | TP53-TMG | 20.85 | 22.9 | yes | 0.52 | 1.1 | no | Yes |
| 4273 | R248W | CD4 | p53-LP | 0.03 | >2 | no | 0.0 | 0.0 | no | Yes |
| 4273 | R248W | CD4 | TP53-TMG | 0.01 | >2 | no | 0.0 | >2 | no | no |
| 4273 | R248W | CD8 | p53-LP | 7.77 | 6.8 | yes | 3.00 | 1.5 | no | no |
| 4273 | R248W | CD8 | TP53-TMG | 3.14 | 29.5 | yes | 0.9 | 2.0 | no | no |

Example 3

This example demonstrates that TCRB tracking demonstrated enrichment of p53 neoantigen-reactive T cells from PBL.

Figure 2A:
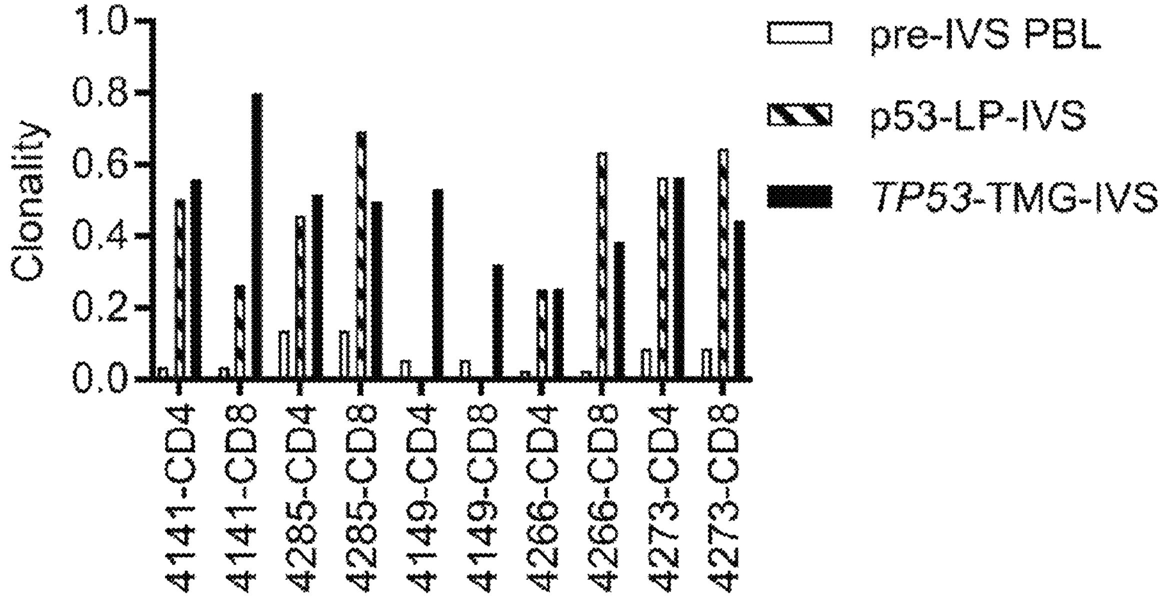
FIG. 2A is a graph showing clonality of the total populations, which is a normalized estimate of sample diversity where numbers closer to 1 are less diverse. TCRB sequencing was performed on PBL prior to or after expansion with IVS and 4-1BB/OX40 enrichment with either LP or TMG. The cultures with verified p53 neoantigen responses are highlighted with an asterisk.
Figure 2B:
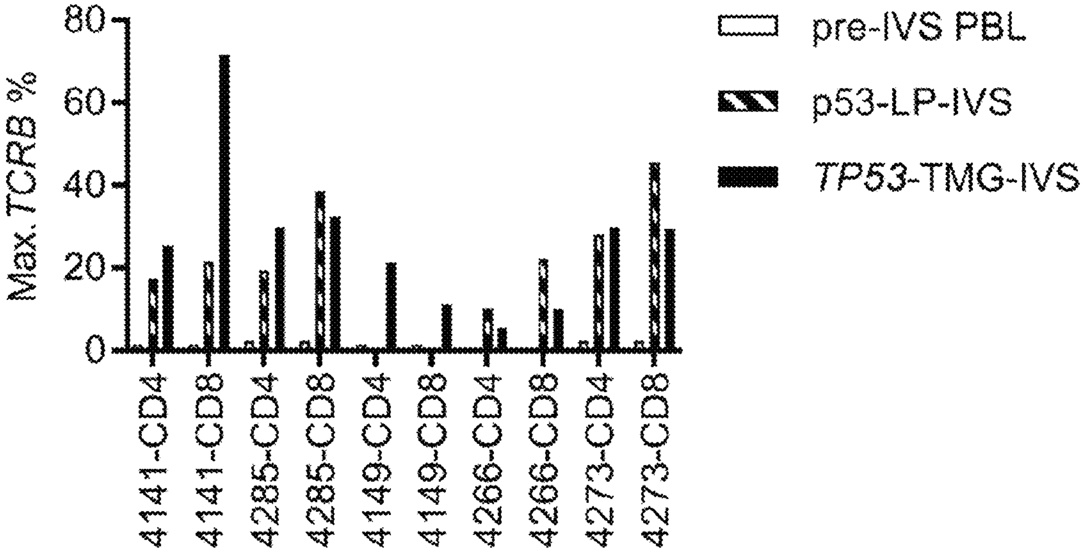
FIG. 2B is a graph showing the maximum productive unique CDR3B frequency from each population. TCRB sequencing was performed on PBL prior to or after expansion with IVS and 4-1BB/OX40 enrichment with either LP or TMG. The cultures with verified p53 neoantigen responses are highlighted with an asterisk.
Figure 2C:
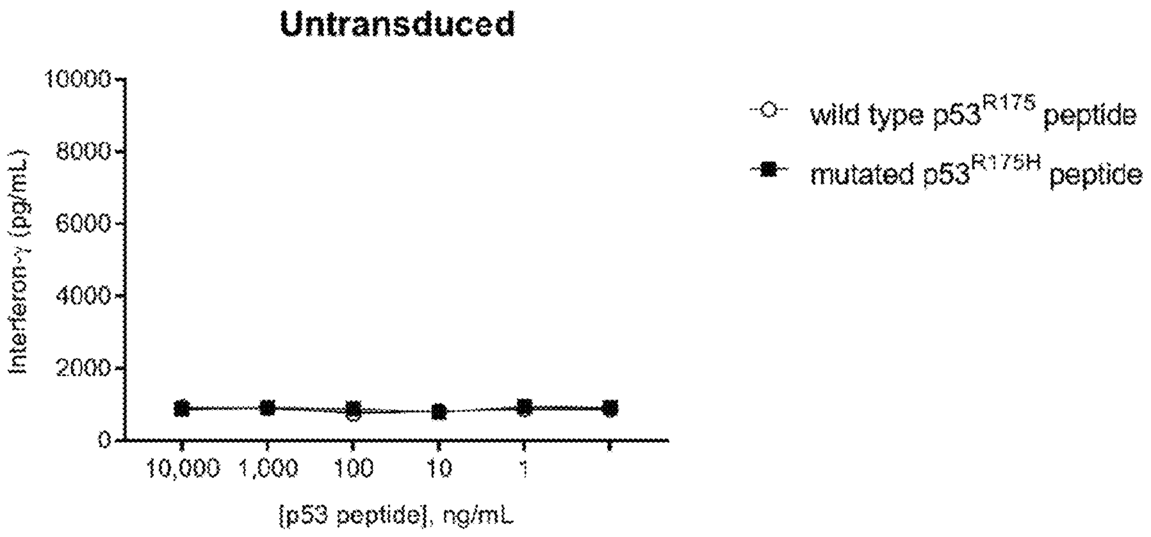
FIG. 2C is a graph showing the results of an experiment in which untransduced T cells (a negative control for TCR transduced T cells) were co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3).
Figure 2D:
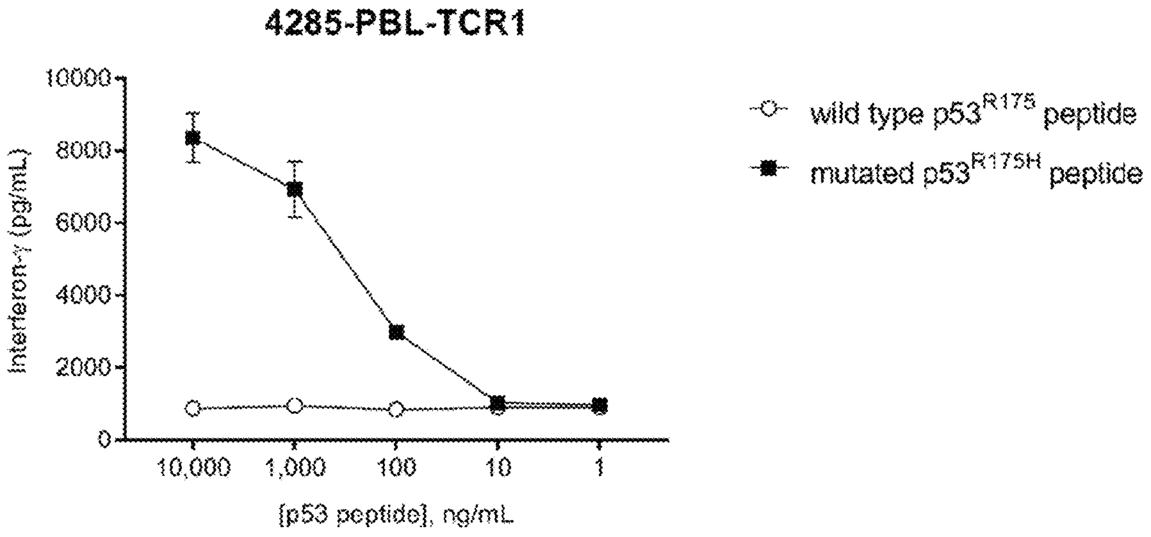
FIG. 2D is a graph showing the results of an experiment in which T cells transduced with 4285-PBL-TCR1 were co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3).
Figure 2E:
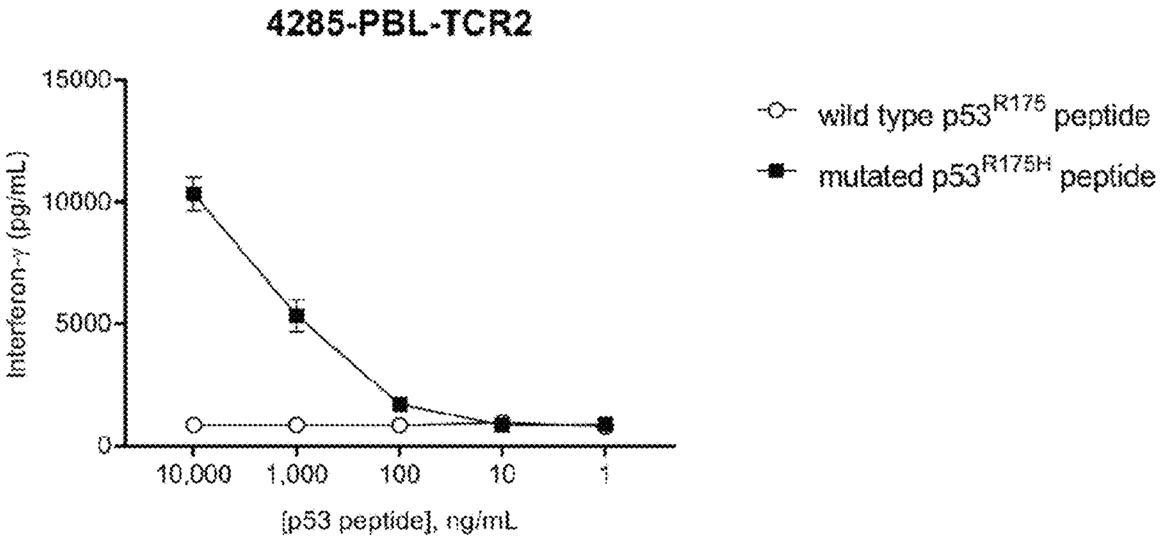
FIG. 2E is a graph showing the results of an experiment in which T cells transduced with 4285-PBL-TCR2 were co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3).
Figure 2F:
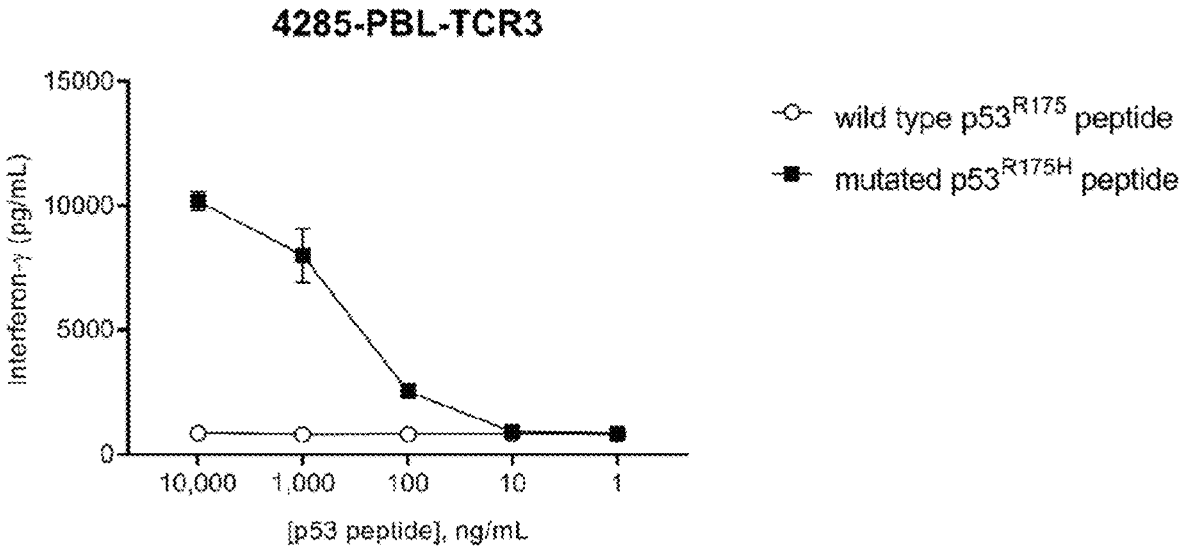
FIG. 2F is a graph showing the results of an experiment in which T cells transduced with 4285-PBL-TCR3 were co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3).
Figure 2G:
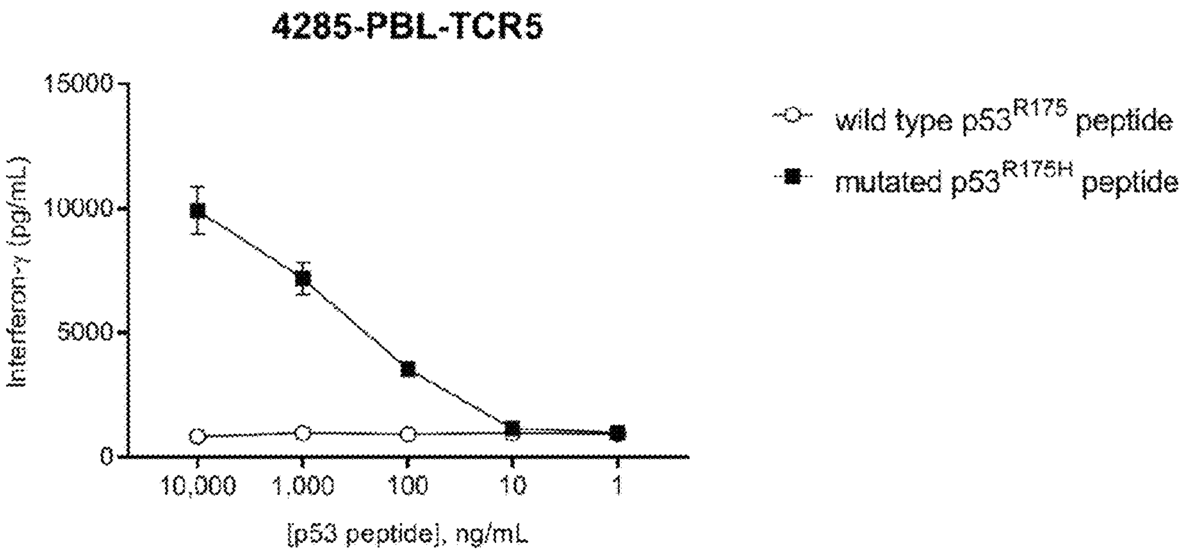
FIG. 2G is a graph showing the results of an experiment in which T cells transduced with 4285-PBL-TCR5 were co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3).
Figure 2H:
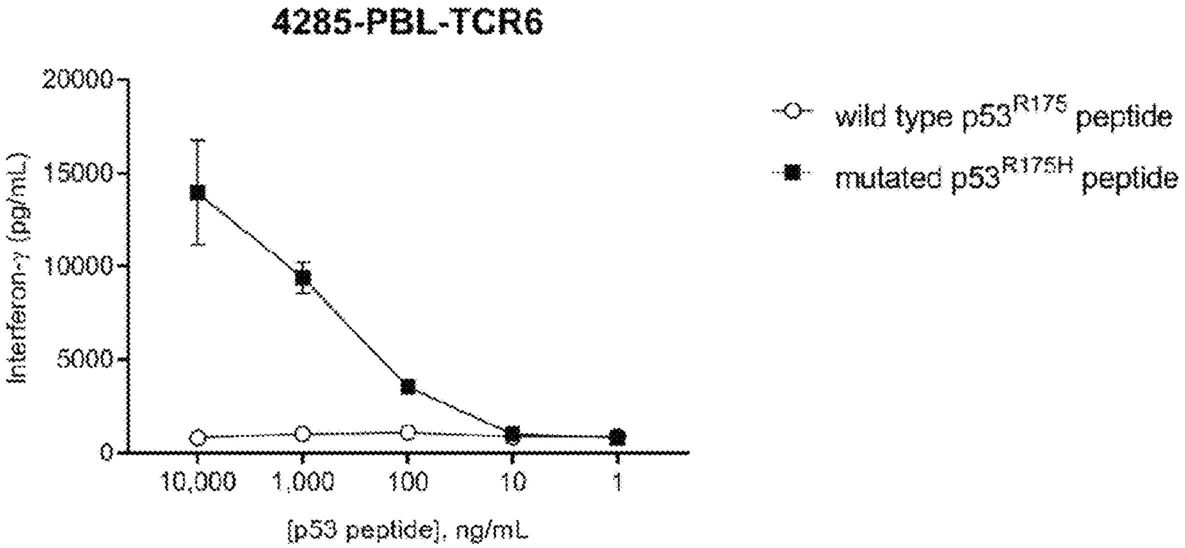
FIG. 2H is a graph showing the results of an experiment in which T cells transduced with 4285-PBL-TCR6 were co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3).
Figure 2I:
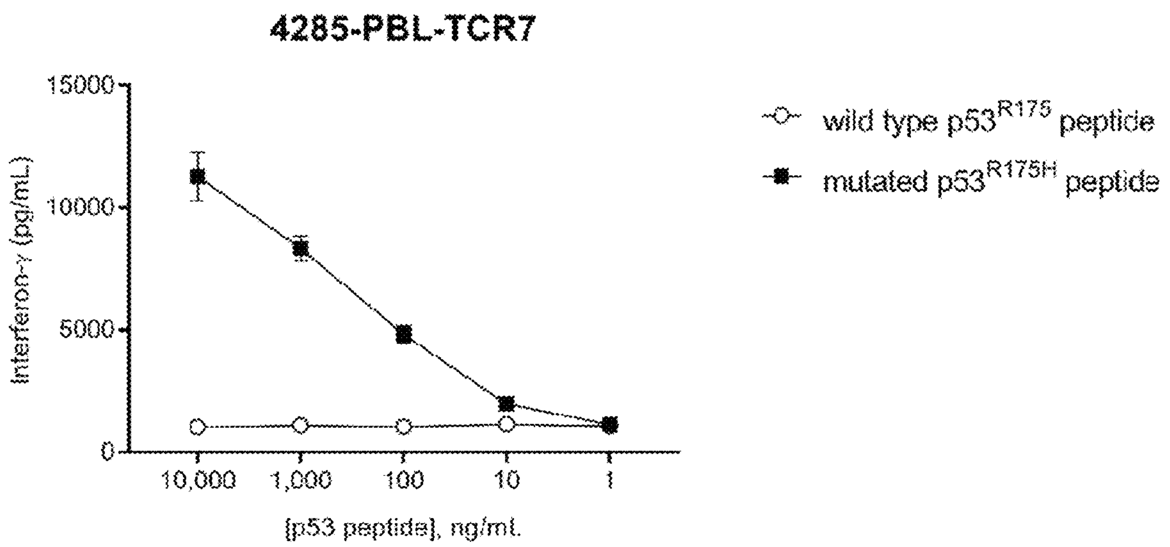
FIG. 2I is a graph showing the results of an experiment in which T cells transduced with 4285-PBL-TCR7 were co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3).
Figure 2J:
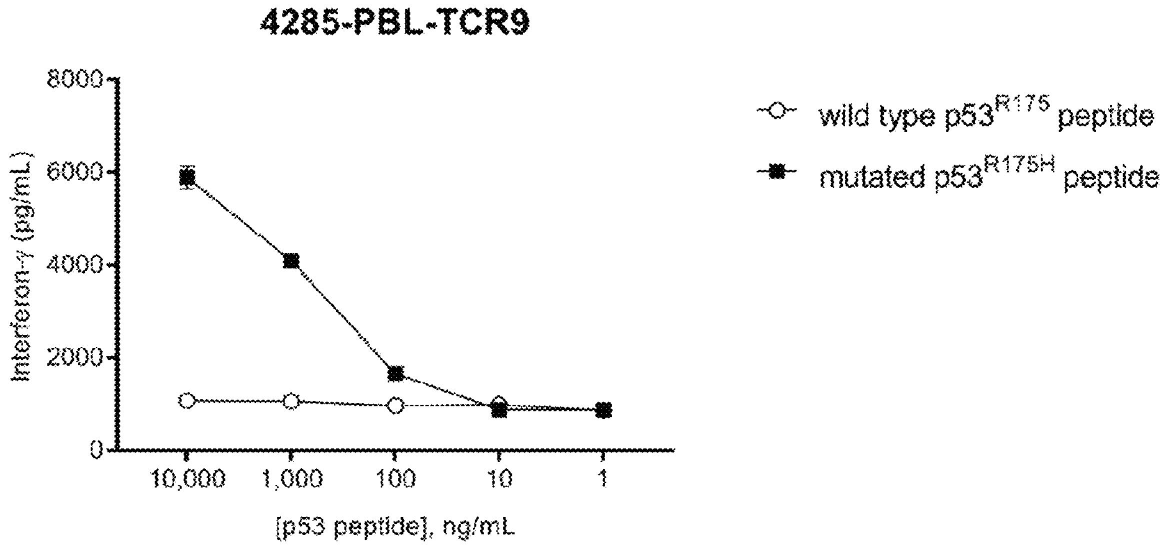
FIG. 2J is a graph showing the results of an experiment in which T cells transduced with 4285-PBL-TCR9 were co-cultured with immature dendritic cells pulsed with decreasing concentrations of either WT (open circles) or mutated (closed squares) p53-R175 peptides of 25 amino acid length. After overnight incubation, the co-culture supernatants were analyzed by ELISA for interferon-gamma secretion. Data are mean±SEM (n=3).

It was desired to further characterize the TCR diversity for each patient's TP53 mutation reactive T-cell population and determine whether the IVS and 4-1BB/OX40 enrichment altered the T-cell repertoire. To accomplish this, TCRB deep sequencing (Pasetto et al., *Cancer Immunol. Res.,* 4(9):734-43 (2016)) was performed and productive T cell clonotype frequencies were measured based on unique CDR3B sequences and overall sample clonality, which is a normalized measurement of the population diversity where more oligoclonal samples approach 1 (Boyd et al., *Sci. Transl. Med.,* 1(12):12ra23) (2009); Howie et al., *Sci. Transl. Med.,* 7(301):301ra131 (2015)). TCRB clonality significantly increased in TP53-TMG-IVS and p53-LP-IVS cultures generated from all patient PBL samples relative to the pre-IVS PBL (FIG. 2A). Similarly, the most frequent unique TCRB clonotype in each TP53-TMG-IVS and p53-LP-IVS sample was of higher frequency than in the pre-IVS PBL (FIG. 2B). The ranking of p53 neoantigen-reactive TCRB sequences ranged from 1-167 in the final p53-LP-IVS or TP53-TMG-IVS cultures but were not detected or rank 5,020 in the original PBL (Table 5). The increased clonality or maximum TCRB clonotype frequencies were not restricted to cultures with T-cell responses to p53 neoantigens (FIGS. 2A-2B; asterisks denoted positive cultures). This suggested that there was T-cell repertoire skewing through the IVS and 4-1BB/OX40 enrichment but assessments of top frequency and clonality were not sufficient to predict a culture's response to mutated TP53.

TABLE 5

TrCRB tracking of p53 neoantigen-reactive cells before and after IVS, co-cu ture, 4-1BB/QX40 sorting and REP. Adadptive Biotechnologies TCRB survey sequencing was performed with at least 50,000 cells.

| Patient # | p53 amino acid substitution | CDR3B | pre-IVS PBL Rank | pre-IVS PBL % | post-IVS, 4-1BB/QX40 enrichment and REP Rank | post-IVS, 4-1BB/QX40 enrichment and REP % |
|---|---|---|---|---|---|---|
| 4141 | R175H | CASSIQQGADTQYF (SEQ ID NQ: 122) | n/a | <0.001 | 1 | 71.553 |
| 4285 | R175H | CASGLVGFNQPQHF (SEQID NQ: 8) | n/a | <0.001 | 3 | 10.861 |
| | | CASLQFNEQFF (SEQ ID NQ: 19) | n/a | <0.001 | 9 | 2.317 |
| | | CASSEYQSQSNEQFF (SEQ ID NQ: 30) | n/a | <0.001 | 1 | 29.844 |
| | | CASSIN RYTEAFF (SEQ ID NQ: 123) | n/a | <0.001 | 6 | 4.944 |
| | | CASSIRTEAFF (SEQ ID NQ: 41) | n/a | <0.001 | 15 | 0.941 |
| | | CASSPFVVIGQINEQYF (SEQ ID NQ: 52) | n/a | <0.001 | 34 | 0.223 |
| | | CASSYAGLAAPREQFF (SEQ ID NQ: 63) | n/a | <0.001 | 10 | 1.676 |
| | | CASSYPSMDRDRYGYTF (SEQ ID NQ: 124) | n/a | <0.001 | 72 | 0.048 |
| | | CATRTGNEAFF (SEQ ID NQ: 74) | n/a | <0.001 | 23 | 0.435 |

TABLE 5-continued

TrCRB tracking of p53 neoantigen-reactive cells before and after IVS, co-cu ture, 4-1BB/QX40 sorting and REP. Adadptive Biotechnologies TCRB survey sequencing was performed with at least 50,000 cells.

| Patient # | p53 amino acid substitution | CDR3B | pre-IVS PBL Rank | pre-IVS PBL % | post-IVS, 4-1BB/QX40 enrichment and REP Rank | post-IVS, 4-1BB/QX40 enrichment and REP % |
|---|---|---|---|---|---|---|
| 4266 | R248W | CASNLGGGSTDTQYF (SEQ ID NQ: 125) | n/a | <0.001 | 3 | 7.450 |
| | | CASSFGSGSTDTQYF (SEQ ID NQ: 126) | n/a | <0.001 | 11 | 2.578 |
| 4273 | R248W | CASSSRDYEQYF (SEQ ID NQ: 127) | 5020 | 0.002 | 167 | 0.017 |

Example 4

This example demonstrates the isolation of p53 neoantigen-reactive TCRs and tracking by TCRB sequencing.

TCRs were then identified from the p53 neoantigen-reactive IVS populations for potential therapeutic and research use and to track the TCRB clonotypes during the culture period to evaluate the extent of TP53 mutation-reactive T-cell enrichment. The TCRs were identified following a co-culture of reactive IVS cultures with the cognate p53 neoantigen (TMG or LP), sorting 4-1BB$^+$ T cells and single-cell RT-PCR of TCR alpha and beta genes, similar to previous studies (Pasetto et al., *Cancer Immunol. Res.*, 4(9):734-43 (2016)). TCR pairs were reconstructed, cloned into retroviral vectors and transduced into donor PBL. The second amino acid residue was changed to alanine (A) to have a stronger kozak sequence for highly efficient translation. The TCR α chain constant regions were replaced with a cysteine-substituted, LVL-modified murine α chain constant region. The TCR β chain constant regions were replaced with a cysteine-substituted murine β chain constant region.

Figure 2L:
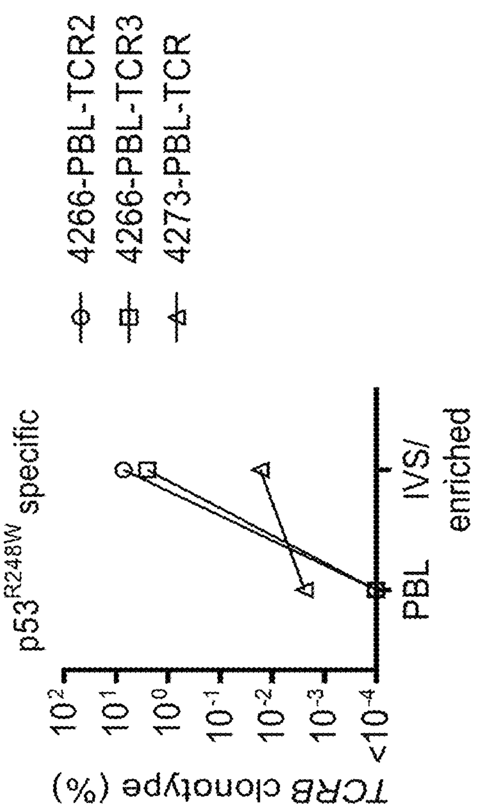
FIGS. 2K-2L are graphs showing the percentage of TCRB clonotypes measured after tracking CDR3B with known specificity to mutated TP53 before (PBL) and after (IVS/enriched) the IVS and 4-1BB enrichment protocol. $P53^{R175H}$-specific clonotypes are shown in K. $P53^{R248W}$-specific clonotypes are shown in L.
Figure 2K:
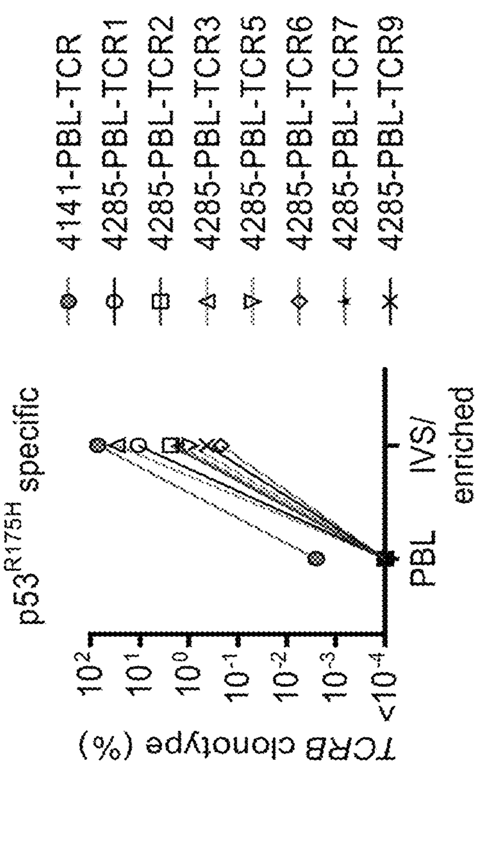

A total of 11 TCRs targeting p53$^{R175H}$ (patients 4141 and 4285) and p53$^{R248W}$ (patients 4266 and 4273) neoantigen were identified (Table 5). The TCR for patient 4149 was unable to be determined due to limited availability of T cells. The same p53 neoantigen-reactive TCRs from TIL (Malekzadeh et al., *J. Clin. Invest.* 129(3):1109-14 (2019)) were identified in PBL after IVS and 4-1BB/OX40 enrichment in patients 4141, 4266 and 4273 targeting p53$^{R175H}$/HLA-A*02:01, p53$^{R248W}$/HLA-A*68:01 and p53$^{R248W}$/HLA-DPB1*02:01, respectively. No additional TP53 mutation-reactive T cells were identified in these patients. In contrast, 7 unique p53$^{R175H}$ neoantigen-specific TCRs from patient 4285 were identified from PBL, which were not present in the TIL study, and the TCR derived from TIL was not found in the PBL populations. The functional avidities of the PBL-derived TCRs (4285-PBL-TCR) were comparable to the TIL-derived TCR (4285-TIL-TCR) with recognition of p53$^{R175H}$ LP to 10 ng/mL and no response to the WT p53$^{R175}$ LP (FIGS. 2C-2J). Tracking of p53$^{R175H}$ neoantigen-specific TCRB clonotypes from patients 4141 and 4285 demonstrated exponential expansion after IVS and 4-1BB/OX40 enrichment compared to the starting PBL (FIG. 2K). Moreover, the CDR3B sequences from patient 4285 were below the limit of detection (<0.001% from $2\times10^5$ reads) in bulk PBL but were of sufficient frequencies following IVS and 4-1BB/OX40 enrichment, including four TCRs in the top 10 total CDR3B clonotypes (Table 5). The p53$^{R248W}$ neoantigen-specific TCRs from patient 4266 were also below the limit of detection in the PBL but were 2.6% (4266-PBL-TCR3) and 7.5% (4266-PBL-TCR2) in the 4266-CD8 TP53-TMG-IVS culture (FIG. 2L). The TCR with specificity to p53$^{R248W}$ neoantigen enriched from 0.002% to 0.017% in the 4273-CD4 p53-LP-IVS culture (FIG. 2L). Collectively, the data demonstrated that PBL can be source of public TP53 mutation-reactive TCRs identical or comparable to intratumoral TCRs.

Example 5

This example demonstrated that the common HLA restriction elements and p53 neoepitopes were immunogenic.

Figure 3A:
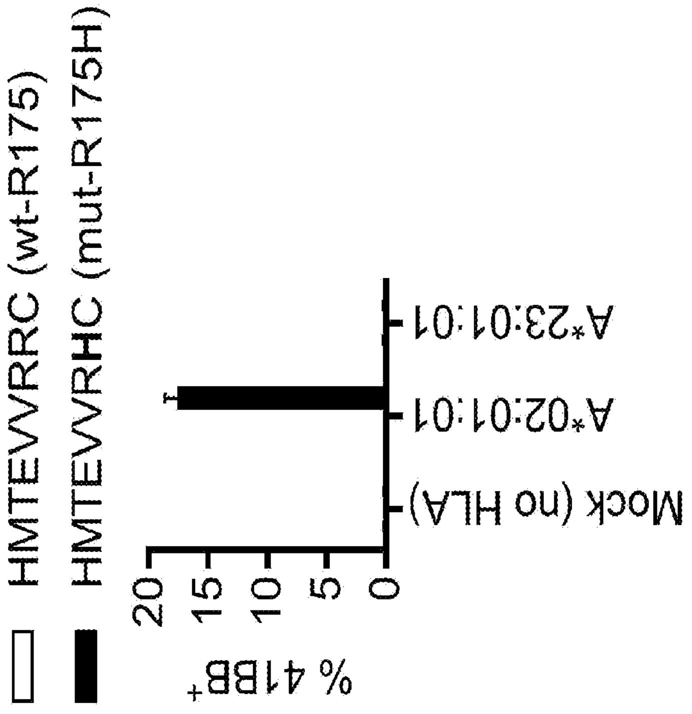
FIG. 3A is a graph showing the percentage of 4-1BB positive cells measured following transfection of a COS 7 monkey cell line with the indicated HLA and pulsed with the indicated minimal p53 peptide (WT (open bars); mutated (closed bars)). Results from the 4141-CD8 TP53-TMG-IVS culture are shown. The TMG-wtR175 had mutated TP53 at all positions except for R175H. The sequence HMTEVVRRC is SEQ ID NO: 95. The sequence HMTEVVRHC is SEQ ID NO: 96.
Figure 3B:
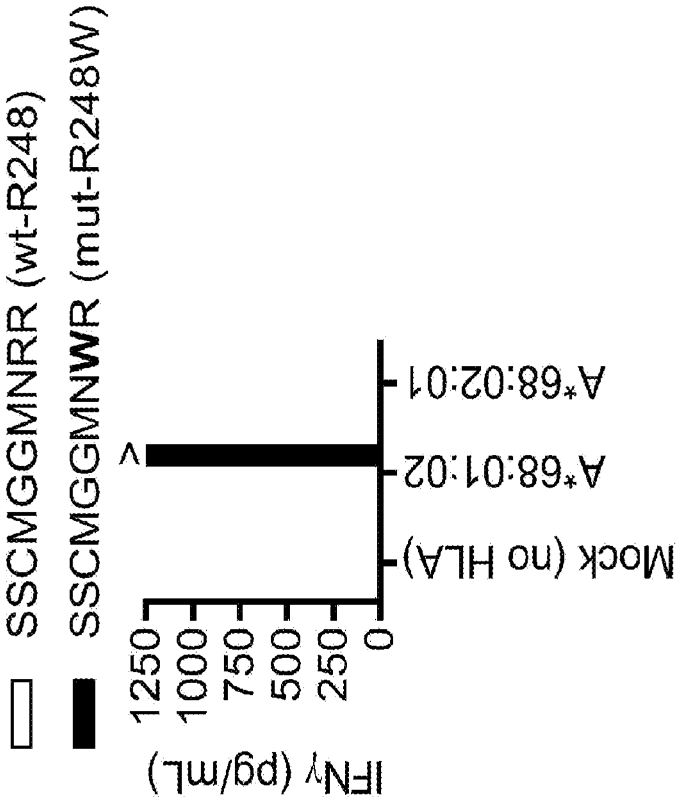
FIG. 3B is a graph showing the amount of IFN-γ measured following transfection of a COS 7 monkey cell line with the indicated HLA and pulsed with the indicated minimal p53 peptide (WT (open bars); mutated (closed bars)). Results from 4266-CD8 TP53-TMG-IVS culture are shown. The sequence SSCMGGMNRR is SEQ ID NO: 97. The sequence SSCMGGMNWR is SEQ ID NO: 98.
Figure 3C:
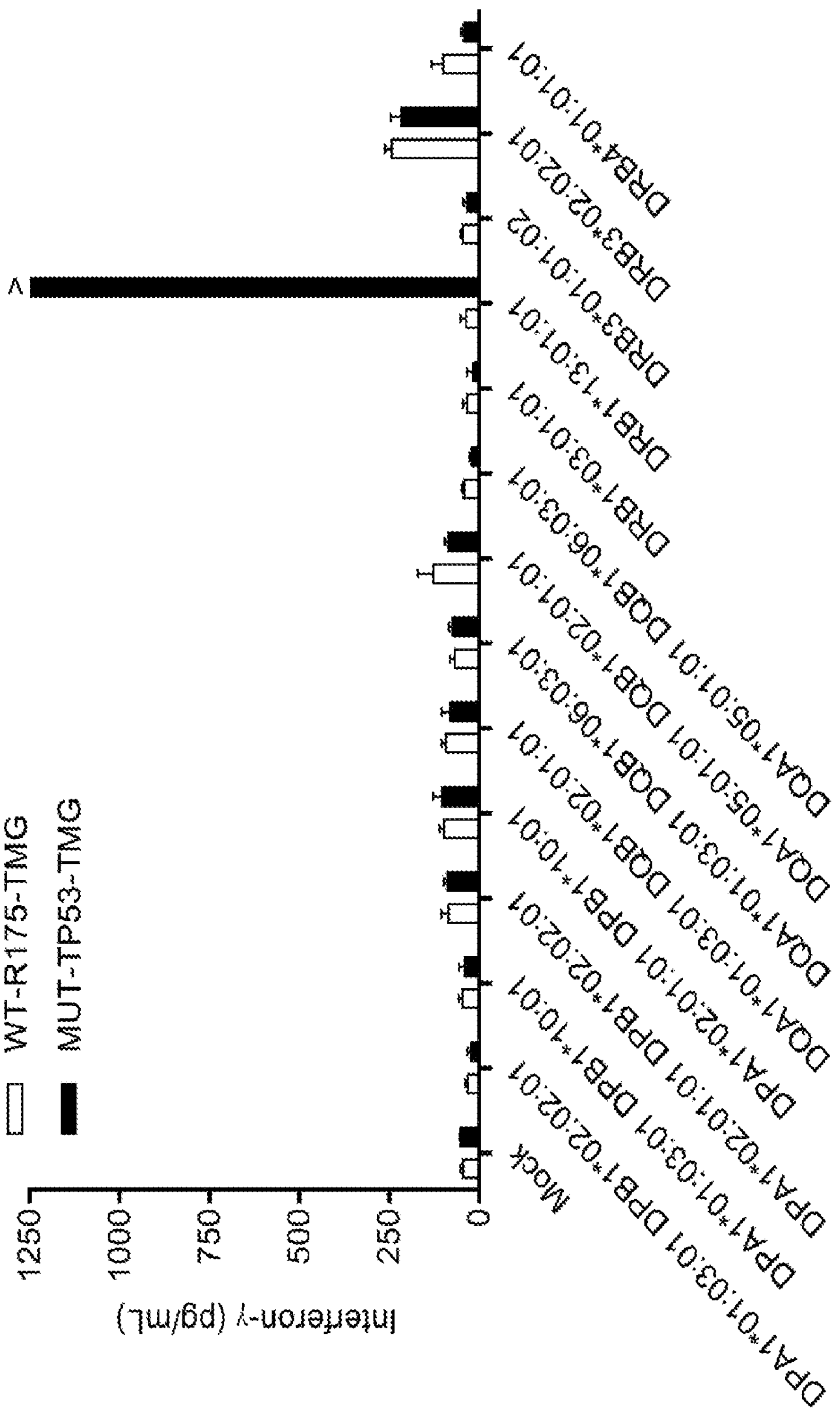
FIG. 3C is a graph showing the results of an experiment in which a COS 7 monkey tumor cell line was transfected with HLA plasmid DNA corresponding to patient 4285's haplotype and either WT TP53 TMG only at R175H position (WT-R175-TMG; open bars) or the mutated TP53-TMG containing the p53-R175H neoantigen (closed bars). The following day, the 4285-CD4 TP53-TMG-IVS culture was added and co-cultured. After overnight incubation, the co-culture supernatants were analyzed by ELISA for interferon-gamma secretion. Data are mean±SEM (n=3).
Figure 4:
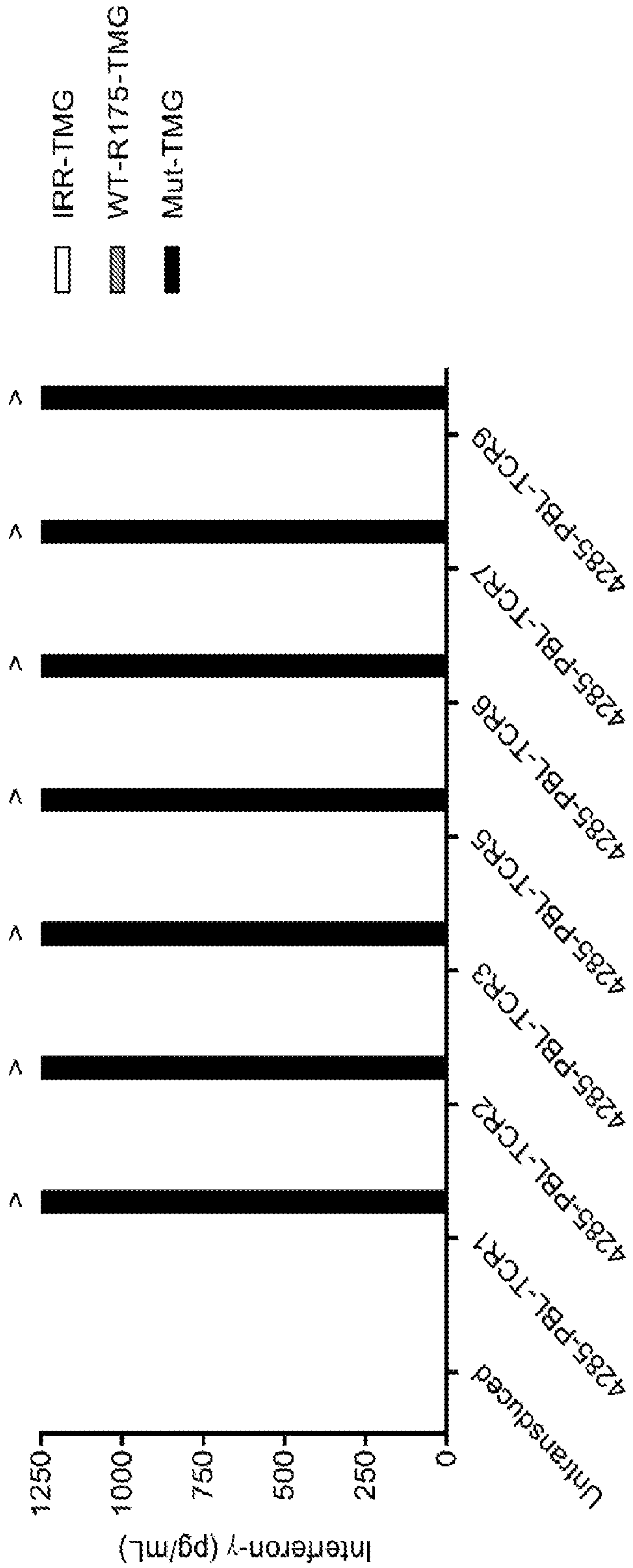
FIG. 4 is a graph showing the results of an experiment in which a COS 7 monkey tumor cell line was transfected with DRA1*01:01:01 and DRB1*13:01:01 and either irrelevant (open bars), WT TP53 TMG only at R175H position (WT-R175-TMG; gray bars) or the mutated TP53-TMG containing the p53-R175H neoantigen (closed bars). The following day, the T cells transduced with 4285-PBL-TCRs or untransduced were added and co-cultured. After overnight incubation, the co-culture supernatants were analyzed by ELISA for interferon-gamma secretion. Data are mean±SEM (n=3).

The recognized minimal p53 neoepitopes and corresponding HLA restrictions were then assessed. HLA mapping was accomplished by transfecting DNA plasmids corresponding to each of the patient's individual HLA alleles into COS 7 monkey cell line (lacking HLA) and pulsing peptides or co-transfecting with TMG, similar to previous reports (Malekzadeh et al., *J Clin. Invest.* 129(3):1109-14 (2019); Deniger et al., *Clin. Cancer Res.*, 24(22):5562-73 (2018)). The 4141-CD8 TP53-TMG-IVS culture was specific for the p53$^{R175H}$ HMTEVVRHC (SEQ ID NO: 96) neoepitope in the context of HLA-A*02:01, a highly frequent HLA in the USA population (Gonzales et al., *Hisp. Health Care Int.*, 15(4):180-8 (2017)), as measured by 4-1BB expression (FIG. 3A). HLA-A*68:01 restricted the p53$^{R248W}$ neoepitope SSCMGGMNWR (SEQ ID NO: 98) recognized by the CD8 TP53-TMG-IVS culture as measured by IFNγ secretion (FIG. 3B). This was expected as the TCRs from TIL in patients 4141 and 4266 were found in these IVS cultures and had already established minimal neoepitopes and HLA restriction elements (Malekzadeh et al., *J. Clin. Invest.* 129(3):1109-14 (2019)). Similarly, the 4273-PBL-TCR was found in the 4273-CD4 p53-LP-IVS culture and had a known p53$^{R248W}$ and HLA-DPB1*02:01 combination from the TIL studies. Even though the TCRs were different between PBL and TIL for patient 4285, the 4285-CD4 TP53-TMG-IVS culture was specific for the same p53$^{R175H}$ and HLA-DBR1*13:01 combination found in the TIL (FIG. 3C). Furthermore, all 4285-PBL-TCRs were specific for p53$^{R175H}$ and HLA-DBR1*13:01 and were all present in the 4285-CD4 TP53-TMG-IVS culture by TCRB sequencing (Table 5; FIG. 4). Fifteen amino acid p53$^{R175H}$ peptides overlapping 14 amino acids were pulsed on DCs from patient 4285 and co-cultured with TCR transduced T cells, and the core peptide EVVRHCPHHER (SEQ ID NO: 2) was determined to be the common sequence recognized by 4285-PBL-TCRs in the context of HLA-DRB1*13:01 (Table 6). In sum, the same TCRs from TIL in PBL that recognized the same HLA and minimal p53 neoepitopes were found in three cases and in one case additional TCRs with the same p53 neoantigen specificity as the intratumoral T cells were found.

TABLE 6

| peptide | UT | 4285-PBL-TCR1 | 4285-PBL-TCR2 | 4285-PBL-TCR3 | 4285-PBL-TCR5 | 4285-PBL-TCR6 | 4285-PBL-TCR7 | 4285-PBL-TCR9 |
|---|---|---|---|---|---|---|---|---|
| YKQSQHMTEVVRHCP (SEQ ID NO: 99) | – | – | – | – | – | – | – | – |
| KQSQHMTEVVRHCPH (SEQ ID NO: 100) | – | – | – | + | – | – | – | + |
| QSQHMTEVVRHCPHH (SEQ ID NO: 101) | – | – | ++ | + | ++ | – | – | + |
| SQHMTEVVRHCPHHE (SEQ ID NO: 102) | | – | ++ | ++ | ++ | – | – | ++ |
| QHMTEVVRHCPHHER (SEQ ID NO: 103) | – | + | ++ | ++ | ++ | + | + | ++ |
| HMTEVVRHCPHHERC (SEQ ID NO: 104) | – | ++ | ++ | ++ | ++ | ++ | ++ | ++ |
| MTEVVRHCPHHERCS (SEQ ID NO: 105) | – | ++ | ++ | ++ | ++ | ++ | ++ | ++ |
| TEVVRHCPHHERCSD (SEQ ID NO: 106) | – | ++ | ++ | ++ | ++ | ++ | ++ | ++ |
| EVVRHCPHHERCSDS (SEQ ID NO: 107) | – | ++ | ++ | ++ | ++ | ++ | ++ | ++ |
| VVRHCPHHERCSDSD (SEQ ID NO: 108) | – | ++ | – | + | – | ++ | ++ | – |
| VRHCPHHERCSDSDG (SEQ ID NO: 109) | – | ++ | – | – | – | + | ++ | – |
| Vehicle (DMSO) | – | – | – | – | – | – | – | – |

Example 6

This example demonstrates that tumor cells process and present p53 neoepitopes on HLA which are recognized by PBL-derived T cells following IVS.

Figure 3D:
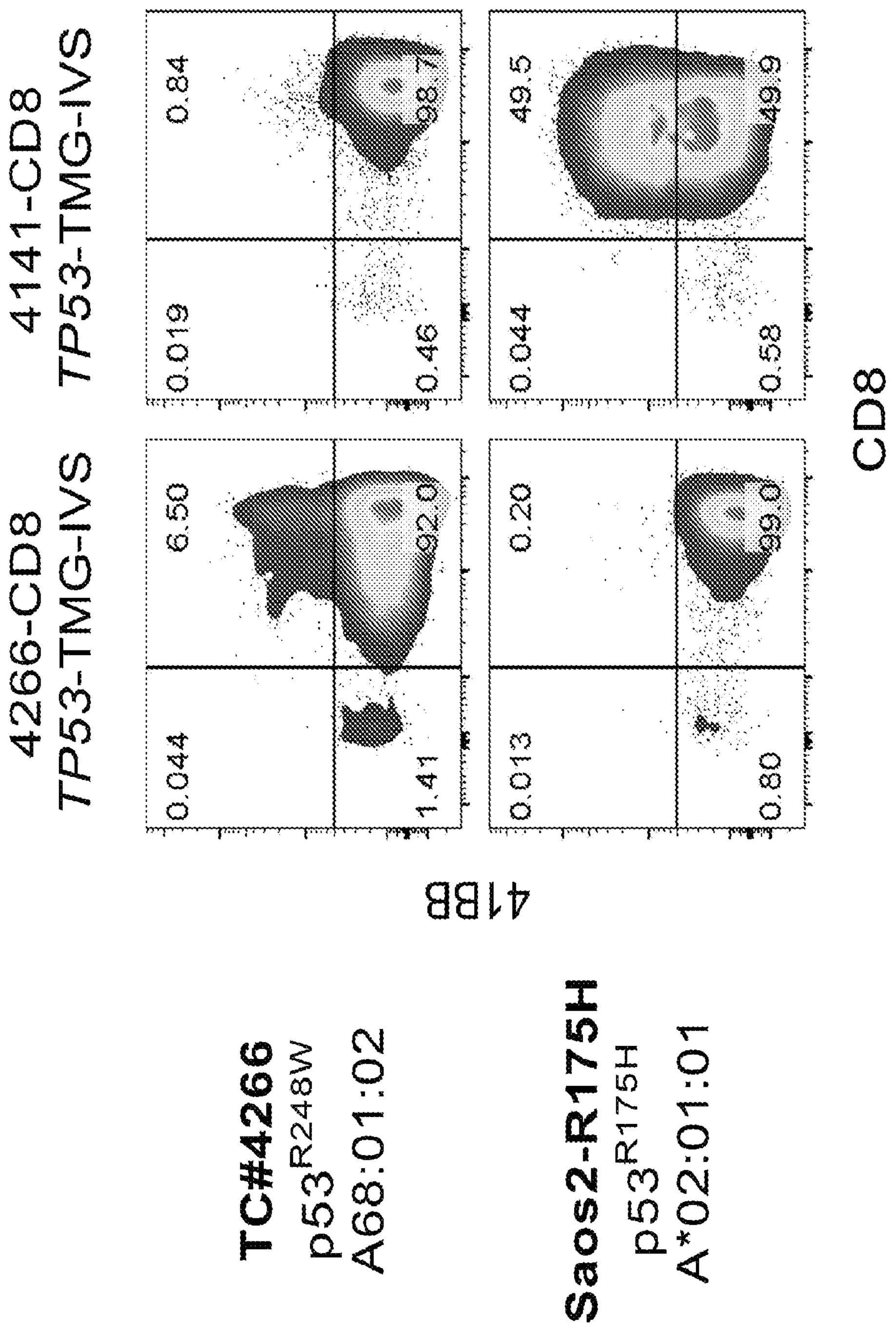
FIG. 3D shows flow cytometry plots showing the upregulation of 4-1BB on $CD8^+$ T cells from TP53-TMG-IVS cultures (4266-CD8 on left and 4141-CD8 on right) following co-culture with TC #4266 (autologous xenograft from patient 4266; A*68:01; $p53^{R248W}$) and Saos2 cells (A*02:01) overexpressing full length $p53^{R175H}$ gene.

TP53 mutation reactive T cells were evaluated for the capacity to recognize naturally processed and presented antigen expressed on the tumor cell surface. Saos2-R175H osteosarcoma tumor cell line (HLA-A*02:01 and overexpressing full length $p53^{R175H}$) and TC #4266 human xenograft tumor cell line ($p53^{R248W}$ and HLA-A*68:01:02 colon cancer) were used as models. Following overnight co-culture, $CD8^+$ T cells from the 4141-CD8 TP53-TMG-IVS and 4266-CD8 TP53-TMG-IVS cultures upregulated 4-1BB in response to Saos2-R175H and TC #4266 cell lines, respectively, with minimal activation the cross-matched cell line (FIG. 3D). Thus, TP53 mutation-specific T cells from PBL could recognize tumor cells with naturally processed and presented p53 neoepitopes.

Example 7

This example demonstrates the amino acid sequences of the TCRs constructed in Example 4 and named in the header of Table 6. The amino acid sequences of the TCR alpha and beta chain variable regions of these TCRs are shown in Table 7. The CDRs are underlined.

TABLE 7

| TCRName | TCR chain | Amino acid sequence |
|---|---|---|
| 4285-PBL-TCR1 | Alpha chain variable region (with N-terminal signal peptide) | MHLVTSITVLLSLGIMGDAKTTQPNSMESNEEEPVHLPCNHSTISGTDYIHWYRQLPSQGPEYVIHGLTSNVNNRMASLAIAEDRKSSTLILHRATLRDAAVYYCILRDNNARLMFGDGTQLVVKP (SEQ ID NO: 9) |
| | Alpha chain variable region (with wild-type N-terminal signal peptide) | MKLVTSITVLLSLGIMGDAKTTQPNSMESNEEEPVHLPCNHSTISGTDYIHWYRQLPSQGPEYVIHGLTSNVNNRMASLAIAEDRKSSTLILHRATLRDAAVYYCILRDNNARLMFGDGTQLVVKP (SEQ ID NO: 178) |
| | Beta chain variable region (with N-terminal signal peptide) | MAPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASGLVGFNQPQHFGDGTRLSIL (SEQ ID NO: 10) |
| | Beta chain variable region (with wild-type N-terminal signal peptide) | MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASGLVGFNQPQHFGDGTRLSIL (SEQ ID NO: 205) |
| | Alpha chain variable region (predicted sequence without N-terminal signal peptide) | KTTQPNSMESNEEEPVHLPCNHSTISGTDYIHWYRQLPSQGPEYVIHGLTSNVNNRMASLAIAEDRKSSTLILHRATLRDAAVYYCILRDNNARLMFGDGTQLVVKP (SEQ ID NO: 142) |

TABLE 7-continued

| TCRName | TCR chain | Amino acid sequence |
|---|---|---|
| | Beta chain variable region (predicted sequence without N-terminal signal peptide) | QVTQNPRYLITVTGKKLTVTCSQNMNHEYMSWYRQDPGLGLRQIYYSMNVEVTDKGDVPEGYKVSRKEKRNFPLILESPSPNQTSLYFCASGLVGFNQPQHFGDGTRLSIL (SEQ ID NO: 143) |
| 4285-PBL-TCR2 | Alpha chain variable region (with N-terminal signal peptide) | MHLVARVTVFLTFGTIIDAKTTQPPSMDCAEGRAANLPCNHSTISGNEYVYWYRQIHSQGPQYIIHGLKNNETNEMASLIITEDRKSSTLILPHATLRDTAVYYCIVRARANAGGTSYGKLTFGQGTILTVHP (SEQ ID NO: 20) |
| | Alpha chain variable region (with wild-type N-terminal signal peptide) | MRLVARVTVFLTFGTIIDAKTTQPPSMDCAEGRAANLPCNHSTISGNEYVYWYRQIHSQGPQYIIHGLKNNETNEMASLIITEDRKSSTLILPHATLRDTAVYYCIVRARANAGGTSYGKLTFGQGTILTVHP (SEQ ID NO: 181) |
| | Beta chain variable region (with N-terminal signal peptide) | MAMSNQVLCCVVLCFLGANTVDGGITQSPKYLFRKEGQNVTLSCEQNLNHDAMYWYRQDPGQGLRLIYYSQIVNDFQKGDIAEGYSVSREKKESFPLTVTSAQKNPTAFYLCASLQFNEQFFGPGTRLTVL (SEQ ID NO: 21) |
| | Beta chain variable region (with N-terminal signal peptide) | MANQVLCCVVLCFLGANTVDGGITQSPKYLFRKEGQNVTLSCEQNLNHDAMYWYRQDPGQGLRLIYYSQIVNDFQKGDIAEGYSVSREKKESFPLTVTSAQKNPTAFYLCASLQFNEQFFGPGTRLTVL (SEQ ID NO: 226) |
| | Beta chain variable region (with wild-type N-terminal signal peptide) | MSNQVLCCVVLCFLGANTVDGGITQSPKYLFRKEGQNVTLSCEQNLNHDAMYWYRQDPGQGLRLIYYSQIVNDFQKGDIAEGYSVSREKKESFPLTVTSAQKNPTAFYLCASLQFNEQFFGPGTRLTVL (SEQ ID NO: 207) |
| | Alpha chain variable region (predicted sequence without N-terminal signal peptide) | KTTQPPSMDCAEGRAANLPCNHSTISGNEYVYWYRQIHSQGPQYIIHGLKNNETNEMASLIITEDRKSSTLILPHATLRDTAVYYCIVRARANAGGTSYGKLTFGQGTILTVHP (SEQ ID NO: 144) |
| | Beta chain variable region (predicted sequence without N-terminal signal peptide) | GITQSPKYLFRKEGQNVTLSCEQNLNHDAMYWYRQDPGQGLRLIYYSQIVNDFQKGDIAEGYSVSREKKESFPLTVTSAQKNPTAFYLCASLQFNEQFFGPGTRLTVL (SEQ ID NO: 145) |
| 4285-PBL-TCR3 | Alpha chain variable region (with N-terminal signal peptide) | MHLQSTLGAVWLGLLLNSLWKVAESKDQVFQPSTVASSEGAVVEIFCNHSVSNAYNFFWYLHFPGCAPRLLVKGSKPSQQGRYNMTYERFSSSLLILQVREADAAVYYCAVEDRRRTALIFGKGTTLSVSS (SEQ ID NO: 31) |
| | Alpha chain variable region (with wild-type N-terminal signal peptide) | MALQSTLGAVWLGLLLNSLWKVAESKDQVFQPSTVASSEGAVVEIFCNHSVSNAYNFFWYLHFPGCAPRLLVKGSKPSQQGRYNMTYERFSSSLLILQVREADAAVYYCAVEDRRRTALIFGKGTTLSVSS (SEQ ID NO: 184) |
| | Beta chain variable region (with N-terminal signal peptide) | MATWLVCWAIFSLLKAGLTEPEVTQTPSHQVTQMGQEVILRCVPISNHLYFYWYRQILGQKVEFLVSFYNNEISEKSEIFDDQFSVERPDGSNFTLKIRSTKLEDSAMYFCASSEYQSQSNEQFFGPGTRLTVL (SEQ ID NO: 32) |
| | Beta chain variable region (with wild-type N-terminal signal peptide) | MDTWLVCWAIFSLLKAGLTEPEVTQTPSHQVTQMGQEVILRCVPISNHLYFYWYRQILGQKVEFLVSFYNNEISEKSEIFDDQFSVERPDGSNFTLKIRSTKLEDSAMYFCASSEYQSQSNEQFFGPGTRLTVL (SEQ ID NO: 209) |
| | Alpha chain variable region (predicted sequence without N-terminal signal peptide) | KDQVFQPSTVASSEGAVVEIFCNHSVSNAYNFFWYLHFPGCAPRLLVKGSKPSQQGRYNMTYERFSSSLLILQVREADAAVYYCAVEDRRRTALIFGKGTTLSVSS (SEQ ID NO: 146) |
| | Beta chain variable region (predicted sequence without N-terminal signal peptide) | EPEVTQTPSHQVTQMGQEVILRCVPISNHLYFYWYRQILGQKVEFLVSFYNNEISEKSEIFDDQFSVERPDGSNFTLKIRSTKLEDSAMYFCASSEYQSQSNEQFFGPGTRLTVL (SEQ ID NO: 147) |
| 4285-PBL-TCR5 | Alpha chain variable region (with N-terminal signal peptide) | MHLVARVTVFLTFGTIIDAKTTQPPSMDCAEGRAANLPCNHSTISGNEYVYWYRQIHSQGPQYIIHGLKNNETNEMASLIITEDRKSSTLILPHATLRDTAVYYCIVRGSPGAGGTSYGKLTFGQGTILTVHP (SEQ ID NO: 42) |
| | Alpha chain | MRLVARVTVFLTFGTIIDAKTTQPPSMDCAEGRAANLPCNHSTISGNE |

TABLE 7-continued

| TCRName | TCR chain | Amino acid sequence |
|---|---|---|
| | variable region (with wild-type N-terminal signal peptide) | YVYWYRQIHSQGPQYIIHGLKNNETNEMASLIITEDRKSSTLILPHATLRDTAVYYCIVRGSPGAGGTSYGKLTFGQGTILTVHP (SEQ ID NO: 187) |
| | Beta chain variable region (with N-terminal signal peptide) | MANQVLCCVVLCFLGANTVDGGITQSPKYLFRKEGQNVTLSCEQNLNHDAMYWYRQDPGQGLRLIYYSQIVNDFQKGDIAEGYSVSREKKESFPLTVTSAQKNPTAFYLCASSIRTEAFFGQGTRLTVV (SEQ ID NO: 43) |
| | Beta chain variable region (with wild-type N-terminal signal peptide) | MSNQVLCCVVLCFLGANTVDGGITQSPKYLFRKEGQNVTLSCEQNLNHDAMYWYRQDPGQGLRLIYYSQIVNDFQKGDIAEGYSVSREKKESFPLTVTSAQKNPTAFYLCASSIRTEAFFGQGTRLTVV (SEQ ID NO: 211) |
| | Alpha chain variable region (predicted sequence without N-terminal signal peptide) | KTTQPPSMDCAEGRAANLPCNHSTISGNEYVYWYRQIHSQGPQYIIHGLKNNETNEMASLIITEDRKSSTLILPHATLRDTAVYYCIVRGSPGAGGTSYGKLTFGQGTILTVHP (SEQ ID NO: 148) |
| | Beta chain variable region (predicted sequence without N-terminal signal peptide) | GITQSPKYLFRKEGQNVTLSCEQNLNHDAMYWYRQDPGQGLRLIYYSQIVNDFQKGDIAEGYSVSREKKESFPLTVTSAQKNPTAFYLCASSIRTEAFFGQGTRLTVV (SEQ ID NO: 149) |
| 4285-PBL-TCR6 | Alpha chain variable region (with N-terminal signal peptide) | MHLITSMLVLWMQLSQVNGQQVMQIPQYQHVQEGEDFTTYCNSSTTLSNIQWYKQRPGGHPVFLIQLVKSGEVKKQKRLTFQFGEAKKNSSLHITATQTTDVGTYFCAGPGGAGSYQLTFGKGTKLSVIP (SEQ ID NO: 53) |
| | Alpha chain variable region (with wild-type N-terminal signal peptide) | MLLITSMLVLWMQLSQVNGQQVMQIPQYQHVQEGEDFTTYCNSSTTLSNIQWYKQRPGGHPVFLIQLVKSGEVKKQKRLTFQFGEAKKNSSLHITATQTTDVGTYFCAGPGGAGSYQLTFGKGTKLSVIP (SEQ ID NO: 190) |
| | Beta chain variable region (with N-terminal signal peptide) | MAPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSPFVVIGQINEQYFGPGTRLTVT (SEQ ID NO: 54) |
| | Beta chain variable region (with wild-type N-terminal signal peptide) | MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSPFVVIGQINEQYFGPGTRLTVT (SEQ ID NO: 213) |
| | Alpha chain variable region (predicted sequence without N-terminal signal peptide) | QQVMQIPQYQHVQEGEDFTTYCNSSTTLSNIQWYKQRPGGHPVFLIQLVKSGEVKKQKRLTEQFGEAKKNSSLHITATQTTDVGTYFCAGPGGAGSYQLTFGKGTKLSVIP (SEQ ID NO: 150) |
| | Beta chain variable region (predicted sequence without N-terminal signal peptide) | QVTQNPRYLITVTGKKLTVTCSQNMNHEYMSWYRQDPGLGLRQIYYSMNVEVTDKGDVPEGYKVSRKEKRNFPLILESPSPNQTSLYFCASSPFVVIGQINEQYFGPGTRLTVT (SEQ ID NO: 151) |
| 4285-PBL-TCR7 | Alpha chain variable region (with N-terminal signal peptide) | MHKLLAMILWLQLDRLSGELKVEQNPLFLSMQEGKNYTIYCNYSTTSDRLYWYRQDPGKSLESLFVLLSNGAVKQEGRLMASLDTKARLSTLHITAAVHDLSATYFCAVAHMDSNYQLIWGAGTKLIIKP (SEQ ID NO: 64) |
| | Alpha chain variable region (with wild-type N-terminal signal peptide) | MKKLLAMILWLQLDRLSGELKVEQNPLFLSMQEGKNYTIYCNYSTTSDRLYWYRQDPGKSLESLFVLLSNGAVKQEGRLMASLDTKARLSTLHITAAVHDLSATYFCAVAHMDSNYQLIWGAGTKLIIKP (SEQ ID NO: 193) |
| | Beta chain variable region (with N-terminal signal peptide) | MALGLLCCGAFSLLWAGPVNAGVTQTPKFRVLKTGQSMTLLCAQDMNHEYMYWYRQDPGMGLRLIHYSVGEGTTAKGEVPDGYNVSRLKKQNFLLGLESAAPSQTSVYFCASSYAGLAAPREQFFGPGTRLTVL (SEQ ID NO: 65) |
| | Beta chain variable region (with wild-type N-terminal signal peptide) | MSLGLLCCGAFSLLWAGPVNAGVTQTPKFRVLKTGQSMTLLCAQDMNHEYMYWYRQDPGMGLRLIHYSVGEGTTAKGEVPDGYNVSRLKKQNFLLGLESAAPSQTSVYFCASSYAGLAAPREQFFGPGTRLTVL (SEQ ID NO: 215) |

TABLE 7-continued

| TCRName | TCR chain | Amino acid sequence |
|---|---|---|
| | Alpha chain variable region (predicted sequence without N-terminal signal peptide) | ELKVEQNPLFLSMQEGKNYTIYCNYSTTSDRLYWYRQDPGKSLESLFVLLSNGAVKQEGRLMASLDTKARLSTLHITAAVHDLSATYFCAVAHMDSNYQLIWGAGTKLIIKP (SEQ ID NO: 152) |
| | Beta chain variable region (predicted sequence without N-terminal signal peptide) | GVTQTPKFRVLKTGQSMTLLCAQDMNHEYMYWYRQDPGMGLRLIHYSVGEGTTAKGEVPDGYNVSRLKKQNFLLGLESAAPSQTSVYFCASSYAGLAAPREQFFGPGTRLTVL (SEQ ID NO: 153) |
| 4285-PBL-TCR9 | Alpha chain variable region (with N-terminal signal peptide) | MHLVARVTVFLTFGTIIDAKTTQPPSMDCAEGRAANLPCNHSTISGNEYVYWYRQIHSQGPQYIIHGLKNNETNEMASLIITEDRKSSTLILPHATLRDTAVYYCIVRARANAGGTSYGKLTFGQGTILTVHP (SEQ ID NO: 75) |
| | Alpha chain variable region (with wild-type N-terminal signal peptide) | MRLVARVTVFLTFGTIIDAKTTQPPSMDCAEGRAANLPCNHSTISGNEYVYWYRQIHSQGPQYIIHGLKNNETNEMASLIITEDRKSSTLILPHATLRDTAVYYCIVRARANAGGTSYGKLTFGQGTILTVHP (SEQ ID NO: 196) |
| | Beta chain variable region (with N-terminal signal peptide) | MANQVLCCVVLCFLGANTVDGGITQSPKYLFRKEGQNVTLSCEQNLNHDAMYWYRQDPGQGLRLIYYSQIVNDFQKGDIAEGYSVSREKKESFPLTVTSAQKNPTAFYLCATRTGNEAFFGQGTRLTVV (SEQ ID NO: 76) |
| | Beta chain variable region (with wild-type N-terminal signal peptide) | MSNQVLCCVVLCFLGANTVDGGITQSPKYLFRKEGQNVTLSCEQNLNHDAMYWYRQDPGQGLRLIYYSQIVNDFQKGDIAEGYSVSREKKESFPLTVTSAQKNPTAFYLCATRTGNEAFFGQGTRLTVV (SEQ ID NO: 217) |
| | Alpha chain variable region (predicted sequence without N-terminal signal peptide) | KTTQPPSMDCAEGRAANLPCNHSTISGNEYVYWYRQIHSQGPQYIIHGLKNNETNEMASLIITEDRKSSTLILPHATLRDTAVYYCIVRARANAGGTSYGKLTFGQGTILTVHP (SEQ ID NO: 154) |
| | Beta chain variable region (predicted sequence without N-terminal signal peptide) | GITQSPKYLFRKEGQNVTLSCEQNLNHDAMYWYRQDPGQGLRLIYYSQIVNDFQKGDIAEGYSVSREKKESFPLTVTSAQKNPTAFYLCATRTGNEAFFGQGTRLTVV (SEQ ID NO: 155) |

TCR name: 4285-PBL-TCR1

(SEQ ID NO: 13)

MAPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASGLVGFNQPQHFGDGTRLSIL*EDLRNVTPPKVSLFEPSKAELANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS*RAKRSGSGATNFSLLKQAGDVEENPGPMHLVTSITVLLSLGIMGDAKTTQPNSMESNEEEPVHLPCNHSTISGTDYIHWYRQLPSQGPEYVIHGLTSNVNNRMASLAIAEDRKSSTLILHRATLRDAAVYYCILRDNNARLMFGDGTQLVVKP*NIQNPEPAVYQLKDPRSQDSTLCLFTDFDSQINVPKTMESGTFITDKCVLDMKAMDSKSNGALAWSNQTSFTCQDIFKETNATYPSSDVPCDATLTEKSFETDMNLNFQNLLVIVLRILLLKVAGFNLLMTLRLWSS*

The sequence of TCR 4285-PBL-TCR1, which was isolated from Patient 4285, is set forth immediately above. Starting from the amino terminus, the first underlined region is the CDR1beta (SEQ ID NO: 6), the second underlined region is the CDR2beta (SEQ ID NO: 7), the third underlined region is the CDR3beta (SEQ ID NO: 8), the fourth underlined region is the CDR1alpha (SEQ ID NO: 3), the fifth underlined region is the CDR2alpha (SEQ ID NO: 4), and the sixth underlined region is the CDR3alpha (SEQ ID NO: 5). The bold region is the linker (SEQ ID NO: 94). Starting from the amino terminus, the first italicized region is the beta chain constant region (SEQ ID NO: 93) and the second italicized region is the alpha chain constant region (SEQ ID NO: 91). The beta chain variable region (SEQ ID NO: 10) includes the sequence starting from the amino terminus and ending immediately prior to the start of the beta chain constant region. The alpha chain variable region (SEQ ID NO: 9) includes the sequence starting immediately after the linker and ending immediately prior to the start of the alpha chain constant region. The full-length beta chain (SEQ ID NO: 12) includes the sequence starting from the amino terminus and ending immediately prior to the start of the linker. The full-length alpha chain (SEQ ID NO: 11) includes the sequence starting immediately after the linker and ending with the carboxyl terminus.

A variant of 4285-PBL-TCR1 comprising a wild-type alpha chain signal peptide is set forth in SEQ ID NO: 180. The variant comprises an alpha chain variable region (with the wild-type signal peptide) as set forth in SEQ ID NO: 178. The full-length alpha chain of the variant is set forth in SEQ ID NO: 179.

Another variant of 4285-PBL-TCR1 comprises a beta chain variable region (with a wild-type signal peptide) as set forth in SEQ ID NO: 205. The full-length beta chain of the variant is set forth in SEQ ID NO: 206.

The predicted 4285-PBL-TCR1 alpha and beta chain variable region mature sequences without N-terminal signal peptides are shown in Table 7. The predicted alpha chain variable region for the mature sequence without the N-terminal signal peptide is shown in SEQ ID NO: 142. The predicted full-length alpha chain (inclusive of the alpha chain variable and constant regions) without the N-terminal signal peptide is shown in SEQ ID NO: 160. The predicted beta chain variable region without the N-terminal signal peptide is shown in SEQ ID NO: 143. The predicted full-length beta chain (inclusive of the beta chain variable and constant regions) without the N-terminal signal peptide is shown in SEQ ID NO: 161.

TCR name: 4285-PBL-TCR2

(SEQ ID NQ: 24)

MAMSNQVLCCVVLCFLGANTVDGGITQSPKYLFRKEGQNVTLSCEQNLN

HDAMYWYRQDPGQGLRLIYYSQIVNDFQKGDIAEGYSVSREKKESFPLT

VTSAQKNPTAFYLCASLQFNEQFFGPGTRLTVL*EDLRNVTPPKVSLFEP*

*SKAEIANKQKATLVCLARGFFPDHVELSWWVNGKEVHSGVCTDPQAYKE*

*SNYSYCLSSRLRVSATFWHNPRNHFRCQVQFHGLSEEDKWPEGSPKPVT*

*QNISAEAWGRADCGITSASYQQGVLSATILYEILLGKATLYAVLVSTLV*

*VMAMVKRKNS*RAKRSGSGATNFSLLKQAGDVEENPGPMHLVARVTVFLT

FGTIIDAKTTQPPSMDCAEGRAANLPCNHSTISGNEYVYWYRQIHSQGP

QYIIHGLKNNETNEMASLIITEDRKSSTLILPHATLRDTAVYYCIVRAR

ANAGGTSYGKLTFGQGTILTVHP*NIQNPEPAVYQLKDPRSQDSTLCLFT*

*DFDSQINVPKTMESGTFITDKCVLDMKAMDSKSNGAIAWSNQTSFTCQD*

*IFKETNATYPSSDVPCDATLTEKSFETDMNLNFQNLLVIVLRILLLKVA*

*GFNLLMTLRLWSS*

The sequence of TCR 4285-PBL-TCR2, which was isolated from Patient 4285, is set forth immediately above. Starting from the amino terminus, the first underlined region is the CDR1beta (SEQ ID NO: 17), the second underlined region is the CDR2beta (SEQ ID NO: 18), the third underlined region is the CDR3beta (SEQ ID NO: 19), the fourth underlined region is the CDR1alpha (SEQ ID NO: 14), the fifth underlined region is the CDR2alpha (SEQ ID NO: 15), and the sixth underlined region is the CDR3alpha (SEQ ID NO: 16). The bold region is the linker (SEQ ID NO: 94). Starting from the amino terminus, the first italicized region is the beta chain constant region (SEQ ID NO: 93) and the second italicized region is the alpha chain constant region (SEQ ID NO: 91). The beta chain variable region (SEQ ID NO: 21) includes the sequence starting from the amino terminus and ending immediately prior to the start of the beta chain constant region. The alpha chain variable region (SEQ ID NO: 20) includes the sequence starting immediately after the linker and ending immediately prior to the start of the alpha chain constant region. The full-length beta chain (SEQ ID NO: 23) includes the sequence starting from the amino terminus and ending immediately prior to the start of the linker. The full-length alpha chain (SEQ ID NO: 22) includes the sequence starting immediately after the linker and ending with the carboxyl terminus.

A variant of 4285-PBL-TCR2 comprising a wild-type alpha chain signal peptide is set forth in SEQ ID NO: 183. The variant comprises an alpha chain variable region (with the wild-type signal peptide) as set forth in SEQ ID NO: 181. The full-length alpha chain of the variant is set forth in SEQ ID NO: 182.

Another variant of 4285-PBL-TCR2 comprises a beta chain variable region (with a wild-type signal peptide) as set forth in SEQ ID NO: 207. The full-length beta chain of the variant is set forth in SEQ ID NO: 208.

The predicted 4285-PBL-TCR2 alpha and beta chain variable region mature sequences without N-terminal signal peptides are shown in Table 7. The predicted alpha chain variable region for the mature sequence without the N-terminal signal peptide is shown in SEQ ID NO: 144. The predicted full-length alpha chain (inclusive of the alpha chain variable and constant regions) without the N-terminal signal peptide is shown in SEQ ID NO: 162. The predicted beta chain variable region without the N-terminal signal peptides is shown in SEQ ID NO: 145. The predicted full-length beta chain (inclusive of the beta chain variable and constant regions) without the N-terminal signal peptide is shown in SEQ ID NO: 163.

TCR name: 4285-PBL-TCR3

(SEQ ID NQ: 35)

MATWLVCWAIFSLLKAGLTEPEVTQTPSHQVTQMGQEVILRCVPISNHL

YFYWYRQILGQKVEFLVSFYNNEISEKSEIFDDQFSVERPDGSNFTLKI

RSTKLEDSAMYFCASSEYQSQSNEQFFGPGTRLTVL*EDLRNVTPPKVSL*

*FEPSKAEIANKQKATLVCLARGFFPDHVELSWWVNGKEVHSGVCTDPQA*

*YKESNYSYCLSSRLRVSATFWHNPRNHFRCQVQFHGLSEEDKWPEGSPK*

*PVTQNISAEAWGRADCGITSASYQQGVLSATILYEILLGKATLYAVLVS*

*TLVVMAMVKRKNS*RAKRSGSGATNFSLLKQAGDVEENPGPMHLQSTLGA

VWLGLLLNSLWKVAESKDQVFQPSTVASSEGAVVEIFCNHSVSNAYNFF

WYLHFPGCAPRLLVKGSKPSQQGRYNMTYERFSSSLLILQVREADAAVY

YCAVEDRRRTALIFGKGTTLSVSS*NIQNPEPAVYQLKDPRSQDSTLCLF*

*TDFDSQINVPKTMESGTFITDKCVLDMKAMDSKSNGAIAWSNQTSFTCQ*

*DIFKETNATYPSSDVPCDATLTEKSFETDMNLNFQNLLVIVLRILLLKV*

*AGFNLLMTLRLWSS*

The sequence of TCR 4285-PBL-TCR3, which was isolated from Patient 4285, is set forth immediately above. Starting from the amino terminus, the first underlined region is the CDR1beta (SEQ ID NO: 28), the second underlined region is the CDR2beta (SEQ ID NO: 29), the third underlined region is the CDR3beta (SEQ ID NO: 30), the fourth underlined region is the CDR1alpha (SEQ ID NO: 25), the fifth underlined region is the CDR2alpha (SEQ ID NO: 26), and the sixth underlined region is the CDR3alpha (SEQ ID NO: 27). The bold region is the linker (SEQ ID NO: 94). Starting from the amino terminus, the first italicized region is the beta chain constant region (SEQ ID NO: 93) and the second italicized region is the alpha chain constant region (SEQ ID NO: 91). The beta chain variable region (SEQ ID NO: 32) includes the sequence starting from the amino terminus and ending immediately prior to the start of the beta chain constant region. The alpha chain variable region (SEQ ID NO: 31) includes the sequence starting immediately after the linker and ending immediately prior to the start of the alpha chain constant region. The full-length beta chain (SEQ ID NO: 34) includes the sequence starting from the amino terminus and ending immediately prior to the start of the linker. The full-length alpha chain (SEQ ID NO: 33) includes the sequence starting immediately after the linker and ending with the carboxyl terminus.

A variant of 4285-PBL-TCR3 comprising a wild-type alpha chain signal peptide is set forth in SEQ ID NO: 186. The variant comprises an alpha chain variable region (with the wild-type signal peptide) as set forth in SEQ ID NO: 184. The full-length alpha chain of the variant is set forth in SEQ ID NO: 185.

Another variant of 4285-PBL-TCR3 comprises a beta chain variable region (with a wild-type signal peptide) as set forth in SEQ ID NO: 209. The full-length beta chain of the variant is set forth in SEQ ID NO: 210.

The predicted 4285-PBL-TCR3 alpha and beta chain variable region mature sequences without N-terminal signal peptides are shown in Table 7. The predicted alpha chain variable region for the mature sequence without the N-terminal signal peptide is shown in SEQ ID NO: 146. The predicted full-length alpha chain (inclusive of the alpha chain variable and constant regions) without the N-terminal signal peptide is shown in SEQ ID NO: 164. The predicted beta chain variable region without the N-terminal signal peptide is shown in SEQ ID NO: 147. The predicted full-length beta chain (inclusive of the beta chain variable and constant regions) without the N-terminal signal peptide is shown in SEQ ID NO: 165.

TCR name: 4285-PBL-TCR5

(SEQ ID NQ: 46)

MANQVLCCVVLCFLGANTVDGGITQSPKYLFRKEGQNVTLSCEQNLNHD
AMYWYRQDPGQGLRLIYYSQIVNDFQKGDIAEGYSVSREKKESFPLTVT
SAQKNPTAFYLCASSIRTEAFFGQGTRLTVV*EDLRNVTPPLVSLFEPSK*
*AEIANKQKATLVCLARGFFPDHVELSWWVNGKEVHSGVCTDPQAYKESN*
*YSYCLSSRLRVSATFWHNPRNHFRCQVQFHGLSEEDKWPEGSPKPVTQN*
*ISAEAWGRADCGITSASYQQGVLSATILYEILLGKATLYAVLVSTLWMA*
*MVKRKNS*RAKRSGSGATNFSLLKQAGDVEENPGPMHLVARVTVFLTFGT
IIDAKTTQPPSMDCAEGRAANLPCNHSTISGNEYVYWYRQIHSQGPQYI
IHGLKNNETNEMASLIITEDRKSSTLILPHATLRDTAVYYCIVRGSPGA
GGTSYGKLTFGQGTILTVHP*NIQNPEPAVYQLKDPRSQDSTLCLFTDFD*
*SQINVPKTMESGTFITDKCVLDMKAMDSKSNGAIAWSNQTSFTCQDIFK*
*ETNATYPSSDVPCDATLTEKSFETDMNLNFQNLLVIVLRILLLKVAGFN*
*LLMTLRLWSS*

The sequence of TCR 4285-PBL-TCR5, which was isolated from Patient 4285, is set forth immediately above. Starting from the amino terminus, the first underlined region is the CDR1beta (SEQ ID NO: 39), the second underlined region is the CDR2beta (SEQ ID NO: 40), the third underlined region is the CDR3beta (SEQ ID NO: 41), the fourth underlined region is the CDR1alpha (SEQ ID NO: 36), the fifth underlined region is the CDR2alpha (SEQ ID NO: 37), and the sixth underlined region is the CDR3alpha (SEQ ID NO: 38). The bold region is the linker (SEQ ID NO: 94). Starting from the amino terminus, the first italicized region is the beta chain constant region (SEQ ID NO: 93) and the second italicized region is the alpha chain constant region (SEQ ID NO: 91). The beta chain variable region (SEQ ID NO: 43) includes the sequence starting from the amino terminus and ending immediately prior to the start of the beta chain constant region. The alpha chain variable region (SEQ ID NO: 42) includes the sequence starting immediately after the linker and ending immediately prior to the start of the alpha chain constant region. The full-length beta chain (SEQ ID NO: 45) includes the sequence starting from the amino terminus and ending immediately prior to the start of the linker. The full-length alpha chain (SEQ ID NO: 44) includes the sequence starting immediately after the linker and ending with the carboxyl terminus.

A variant of 4285-PBL-TCR5 comprising a wild-type alpha chain signal peptide is set forth in SEQ ID NO: 189. The variant comprises an alpha chain variable region (with the wild-type signal peptide) as set forth in SEQ ID NO: 187. The full-length alpha chain of the variant is set forth in SEQ ID NO: 188.

Another variant of 4285-PBL-TCR5 comprises a beta chain variable region (with a wild-type signal peptide) as set forth in SEQ ID NO: 211. The full-length beta chain of the variant is set forth in SEQ ID NO: 212.

The predicted 4285-PBL-TCR5 alpha and beta chain variable region mature sequences without N-terminal signal peptides are shown in Table 7. The predicted alpha chain variable region for the mature sequence without the N-terminal signal peptide is shown in SEQ ID NO: 148. The predicted full-length alpha chain (inclusive of the alpha chain variable and constant regions) without the N-terminal signal peptide is shown in SEQ ID NO: 166. The predicted beta chain variable region without the N-terminal signal peptide is shown in SEQ ID NO: 149. The predicted full-length beta chain (inclusive of the beta chain variable and constant regions) without the N-terminal signal peptide is shown in SEQ ID NO: 167.

TCR name: 4285-PBL-TCR6

(SEQ ID NQ: 57)

MAPQLLGYVVLCLLGAGPLEAQVTQNPRYLITVTGKKLTVTCSQNMNHEY
MSWYRQDPGLGLRQIYYSMNVEVTDKGDVPEGYKVSRKEKRNFPLILESP
SPNQTSLYFCASSPFVVIGQINEQYFGPGTRLTVT*EDLRNVTPPKVSLFE*
*PSKAEIANKQKATLVCLARGFFPDHVELSWWVNGKEVHSGVCTDPQAYKE*
*SNYSYCLSSRLRVSATFWHNPRNHFRCQVQFHGLSEEDKWPEGSPKPVTQ*
*NISAEAWGRADCGITSASYQQGVLSATILYEILLGKATLYAVLVSTLVVM*
*AMVKRKNS*RAKRSGSGATNFSLLKQAGDVEENPGPMHLITSMLVLWMQLS
QVNGQQVMQIPQYQHVQEGEDFTTYCNSSTTLSNIQWYKQRPGGHPVFLI
QLVKSGEVKKQKRLTFQFGEAKKNSSLHITATQTTDVGTYFCAGPGGAGS
YQLTFGKGTKLSVIP*NIQNPEPAVYQLKDPRSQDSTLCLFTDFDSQINVP*
*KTMESGTFITDKCVLDMKAMDSKSNGAIAWSNQTSFTCQDIFKETNATYP*
*SSDVPCDATLTEKSFETDMNLNFQNLLVIVLRILLLKVAGFNLLMTLRLW*
*SS*

The sequence of TCR 4285-PBL-TCR6, which was isolated from Patient 4285, is set forth immediately above. Starting from the amino terminus, the first underlined region is the CDR1beta (SEQ ID NO: 50), the second underlined region is the CDR2beta (SEQ ID NO: 51), the third underlined region is the CDR3beta (SEQ ID NO: 52), the fourth underlined region is the CDR1alpha (SEQ ID NO: 47), the fifth underlined region is the CDR2alpha (SEQ ID NO: 48), and the sixth underlined region is the CDR3alpha (SEQ ID NO: 49). The bold region is the linker (SEQ ID NO: 94). Starting from the amino terminus, the first italicized region is the beta chain constant region (SEQ ID NO: 93) and the second italicized region is the alpha chain constant region (SEQ ID NO: 91). The beta chain variable region (SEQ ID NO: 54) includes the sequence starting from the amino terminus and ending immediately prior to the start of the beta chain constant region. The alpha chain variable region (SEQ ID NO: 53) includes the sequence starting immediately after the linker and ending immediately prior to the start of the alpha chain constant region. The full-length beta chain (SEQ ID NO: 56) includes the sequence starting from the amino terminus and ending immediately prior to the start of the linker. The full-length alpha chain (SEQ ID NO: 55) includes the sequence starting immediately after the linker and ending with the carboxyl terminus.

A variant of 4285-PBL-TCR6 comprising a wild-type alpha chain signal peptide is set forth in SEQ ID NO: 192. The variant comprises an alpha chain variable region (with the wild-type signal peptide) as set forth in SEQ ID NO: 190. The full-length alpha chain of the variant is set forth in SEQ ID NO: 191.

Another variant of 4285-PBL-TCR6 comprises a beta chain variable region (with a wild-type signal peptide) as set forth in SEQ ID NO: 213. The full-length beta chain of the variant is set forth in SEQ ID NO: 214.

The predicted 4285-PBL-TCR6 alpha and beta chain variable region mature sequences without N-terminal signal peptides are shown in Table 7. The predicted alpha chain variable region for the mature sequence without the N-terminal signal peptide is shown in SEQ ID NO: 150. The predicted full-length alpha chain (inclusive of the alpha chain variable and constant regions) without the N-terminal signal peptide is shown in SEQ ID NO: 168. The predicted beta chain variable region without the N-terminal signal peptide is shown in SEQ ID NO: 151. The predicted full-length beta chain (inclusive of the beta chain variable and constant regions) without the N-terminal signal peptide is shown in SEQ ID NO: 169.

TCR name: 4285-PBL-TCR7

(SEQ ID NQ: 68)

MALGLLCCGAFSLLWAGPVNAGVTQTPKFRVLKTGQSMTLLCAQDMNHE

YMYWYRQDPGMGLRLIHYSVGEGTTAKGEVPDGYNVSRLKKQNFLLGLE

SAAPSQTSVYFCASSYAGLAAPREQFFGPGTRLTVL*EDLRNVTPPKVSL*

*FEPSKAEIANKQKATLVCLARGFFPDHVELSWWVNGKEVHSGVCTDPQA*

*YKESNYSYCLSSRLRVSATFWHNPRNHFRCQVQFHGLSEEDKWPEGSPK*

*PVTQNISAEAWGRADCGITSASYQQGVLSATILYEILLGKATLYAVLVS*

*TLVVMAMVKRKNS*RAKRSGSGATNFSLLKQAGDVEENPGPMHKLLAMIL

WLQLDRLSGELKVEQNPLFLSMQEGKNYTIYCNYSTTSDRLYWYRQDPG

KSLESLFVLLSNGAVKQEGRLMASLDTKARLSTLHITAAVHDLSATYFC

AVAHMDSNYQLIWGAGTKLIIKP*NIQNPEPAVYQLKDPRSQDSTLCLFT*

*DFDSQINVPKMESGTFITDKCVLDMKAMDSKSNGAIAWSNQTSFTCQD*

*IFKETNATYPSSDVPCDATLTEKSFETDMNLNFQNLLVIVLRILLLKVA*

*GFNLLMTLRLWSS*

The sequence of TCR 4285-PBL-TCR7, which was isolated from Patient 4285, is set forth immediately above. Starting from the amino terminus, the first underlined region is the CDR1beta (SEQ ID NO: 61), the second underlined region is the CDR2beta (SEQ ID NO: 62), the third underlined region is the CDR3beta (SEQ ID NO: 63), the fourth underlined region is the CDR1alpha (SEQ ID NO: 58), the fifth underlined region is the CDR2alpha (SEQ ID NO: 59), and the sixth underlined region is the CDR3alpha (SEQ ID NO: 60). The bold region is the linker (SEQ ID NO: 94). Starting from the amino terminus, the first italicized region is the beta chain constant region (SEQ ID NO: 93) and the second italicized region is the alpha chain constant region (SEQ ID NO: 91). The beta chain variable region (SEQ ID NO: 65) includes the sequence starting from the amino terminus and ending immediately prior to the start of the beta chain constant region. The alpha chain variable region (SEQ ID NO: 64) includes the sequence starting immediately after the linker and ending immediately prior to the start of the alpha chain constant region. The full-length beta chain (SEQ ID NO: 67) includes the sequence starting from the amino terminus and ending immediately prior to the start of the linker. The full-length alpha chain (SEQ ID NO: 66) includes the sequence starting immediately after the linker and ending with the carboxyl terminus.

A variant of 4285-PBL-TCR7 comprising a wild-type alpha chain signal peptide is set forth in SEQ ID NO: 195. The variant comprises an alpha chain variable region (with the wild-type signal peptide) as set forth in SEQ ID NO: 193. The full-length alpha chain of the variant is set forth in SEQ ID NO: 194.

Another variant of 4285-PBL-TCR7 comprises a beta chain variable region (with a wild-type signal peptide) as set forth in SEQ ID NO: 215. The full-length beta chain of the variant is set forth in SEQ ID NO: 216.

The predicted 4285-PBL-TCR7 alpha and beta chain variable region mature sequences without N-terminal signal peptides are shown in Table 7. The predicted alpha chain variable region for the mature sequence without the N-terminal signal peptide is shown in SEQ ID NO: 152. The predicted full-length alpha chain (inclusive of the alpha chain variable and constant regions) without the N-terminal signal peptide is shown in SEQ ID NO: 170. The predicted beta chain variable region without the N-terminal signal peptide is shown in SEQ ID NO: 153. The predicted full-length beta chain (inclusive of the beta chain variable and constant regions) without the N-terminal signal peptide is shown in SEQ ID NO: 171.

TCR name: 4285-PBL-TCR9

(SEQ ID NQ: 79)

MANQVLCCVVLCFLGANTVDGGITQSPKYLFRKEGQNVTLSCEQNLNHD

AMYWYRQDPGQGLRLIYYSQIVNDFQKGDIAEGYSVSREKKESFPLTVT

SAQKNPTAFYLCATRYGNEAFFGQGYRLYVN*EDLRNVTPPKVSLFEPSK*

*AEIANKQKATLVCLARGFFPDHVELSWWVNGKEVHSGVCTDPQAYKESN*

*YSYCLSSRLRVSATFWHNPRNHFRCQVQFHGLSEEDKWPEGSPKPVTQN*

*ISAEAWGRADCGITSASYQQGVLSATILYEILLGKATLYAVLVSTLWMA*

*MVKRKNS*RAKRSGSGATNFSLLKQAGDVEENPGPMHLVARVTVFLTFGT

IIDAKTTQPPSMDCAEGRAANLPCNHSTISGNEYVYWYRQIHSQGPQYI

IHGLKNNETNEMASLIITEDRKSSTLILPHATLRDTAVYYCIVRARANA

-continued

GGTSYGKLTFGQGTILTVHP*NIQNPEPAVYQLKDPRSQDSTLCLFTDFD*

*SQINVPKTMESGTFITDKCVLDMKAMDSKSNGAIAWSNQTSFTCQDIFK*

*ETNATYPSSDVPCDATLTEKSFETDMNLNFQNLLVIVLRILLLKVAGFN*

*LLMTLRLWSS*

The sequence of TCR 4285-PBL-TCR9, which was isolated from Patient 4285, is set forth immediately above. Starting from the amino terminus, the first underlined region is the CDR1beta (SEQ ID NO: 72), the second underlined region is the CDR2beta (SEQ ID NO: 73), the third underlined region is the CDR3beta (SEQ ID NO: 74), the fourth underlined region is the CDR1alpha (SEQ ID NO: 69), the fifth underlined region is the CDR2alpha (SEQ ID NO: 70), and the sixth underlined region is the CDR3alpha (SEQ ID NO: 71). The bold region is the linker (SEQ ID NO: 94). Starting from the amino terminus, the first italicized region is the beta chain constant region (SEQ ID NO: 93) and the second italicized region is the alpha chain constant region (SEQ ID NO: 91). The beta chain variable region (SEQ ID NO: 76) includes the sequence starting from the amino terminus and ending immediately prior to the start of the beta chain constant region. The alpha chain variable region (SEQ ID NO: 75) includes the sequence starting immediately after the linker and ending immediately prior to the start of the alpha chain constant region. The full-length beta chain (SEQ ID NO: 78) includes the sequence starting from the amino terminus and ending immediately prior to the start of the linker. The full-length alpha chain (SEQ ID NO: 77) includes the sequence starting immediately after the linker and ending with the carboxyl terminus.

A variant of 4285-PBL-TCR9 comprising a wild-type alpha chain signal peptide is set forth in SEQ ID NO: 198. The variant comprises an alpha chain variable region (with the wild-type signal peptide) as set forth in SEQ ID NO: 196. The full-length alpha chain of the variant is set forth in SEQ ID NO: 197.

Another variant of 4285-PBL-TCR9 comprises a beta chain variable region (with a wild-type signal peptide) as set forth in SEQ ID NO: 217. The full-length beta chain of the variant is set forth in SEQ ID NO: 218.

The predicted 4285-PBL-TCR9 alpha and beta chain variable region mature sequences without N-terminal signal peptides are shown in Table 7. The predicted alpha chain variable region for the mature sequence without the N-terminal signal peptide is shown in SEQ ID NO: 154. The predicted full-length alpha chain (inclusive of the alpha chain variable and constant regions) without the N-terminal signal peptide is shown in SEQ ID NO: 172. The predicted beta chain variable region without the N-terminal signal peptide is shown in SEQ ID NO: 155. The predicted full-length beta chain (inclusive of the beta chain variable and constant regions) without the N-terminal signal peptide is shown in SEQ ID NO: 173.

Example 8

This example demonstrates the frequencies of CD8$^+$4-1BB$^+$ T cells detected following co-culture of T cells from a tumor sample from Patient 4259 with mutated p53-Y220C peptide.

Figure 5:
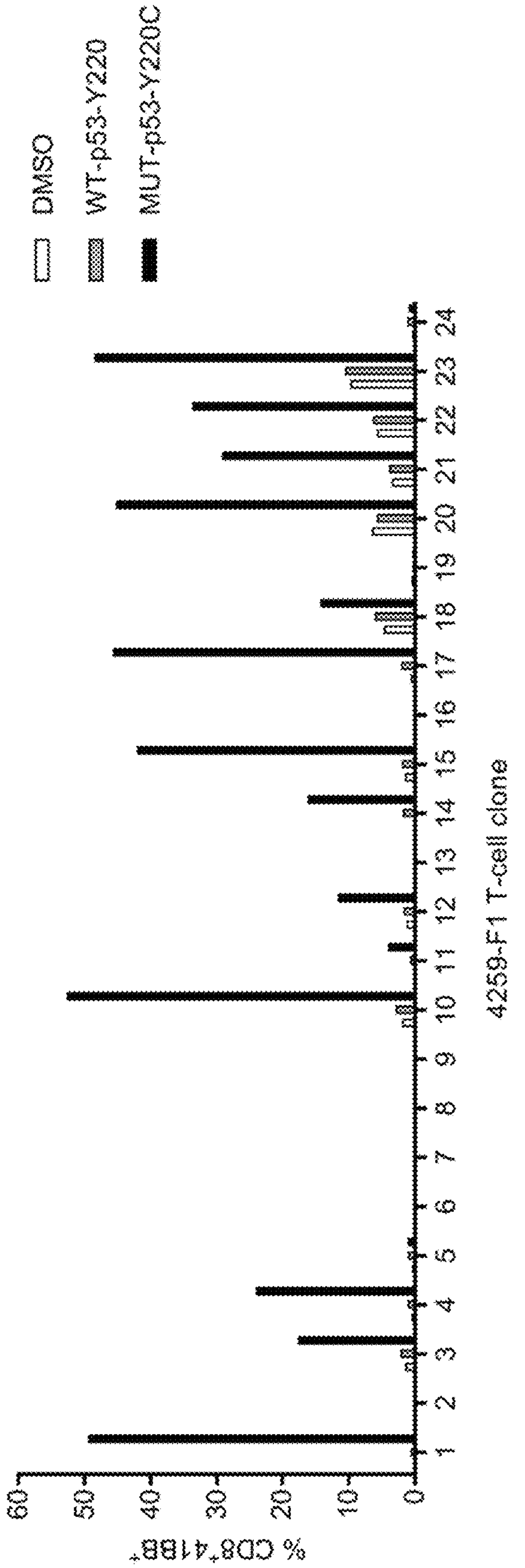
FIG. 5 is a graph showing the results of an experiment in which T-cell clones were prepared by limiting dilution after sorting $CD8^+$ T cells from the 4259-F1 tumor fragment culture. The 24 cultures were co-cultured with T2 tumor cells (HLA-A*02:01) pulsed with DMSO (peptide vehicle), WT p53-Y220 peptide or MUT p53-Y220C peptide. After overnight incubation, the cells were stained for CD3, CD8 and 4-1BB then analyzed by flow cytometry. The frequencies of $CD8^+$4-$1BB^+$ T cells are displayed from the cultures.

T-cell clones were prepared by limiting dilution after sorting CD8$^+$ T cells from 4259-F1 tumor fragment culture. The 24 cultures were co-cultured with T2 tumor cells (HLA-A*02:01) pulsed with DMSO (peptide vehicle), WT p53-Y220 peptide (VVPYEPPEV) (SEQ ID NO: 112) or MUT p53-Y220C peptide (VVPCEPPEV) (SEQ ID NO: 113). After overnight incubation, the cells were stained for CD3, CD8 and 4-1BB then analyzed by flow cytometry. The frequencies of CD8$^+$4-1BB$^+$ T cells from the cultures are shown in FIG. 5. As shown in FIG. 5, reactive T-cell clones were obtained.

Example 9

This example demonstrates the isolation of the p53-Y220C neoantigen-reactive T-cell receptor 4259-F1-TCR.

The sequence of the TCR with specificity to p53-Y220C and HLA-A*02:01 (from the fragment culture F1 of patient 4259 of Example 8) was difficult to determine. The sequence was unable to be determined using the classical single cell PCR technique. Two limitations of the single cell PCR technique are that (1) it only sequences a short part of the TCR gene surrounding the hypervariable CDR3 region leading the investigator to infer the rest of the TCR using less polymorphic regions of the TCR, e.g., the variable family, and (2) only one sequence can be present to have a functional sequencing readout by Sanger sequencing method. These issues were circumvented by making T-cell clones by limiting dilution and then sequencing the full length TCRalpha and TCRbeta genes as expressed mRNA transcripts by 5'RACE. It was then determined that the T-cell clonotype with specificity for p53-Y220C and HLA-A*02:01 expressed two TCRalpha and two TCRbeta chains. This is in contrast with most T cells which only express one TCRalpha and one TCRbeta. Only one of the TCRbeta chains was functional because the other one had a frameshift that resulted in a premature stop codon. Moreover, this TCRbeta chain was of the TRBV7-9*03 family instead of the TRBV7-9*01 family that was reported by single cell PCR and TRBV7-9 family (low resolution) Adaptive Biotechnologies TCRB survey sequencing. There is a non-conserved amino acid substitution between the two variable chains (N or D at position 26) indicating that the choice of TRBV7-9*03 was useful (see FIG. 9). There were two identified functional TCRalpha chains and only one of them was paired correctly with the functional TCRbeta to confer specificity to p53-Y220C and HLA-A*02:01.

TCR pairs were reconstructed and cloned into retroviral vectors. The second amino acid residue was changed to alanine (A) to have a stronger kozak sequence for highly efficient translation. The TCR α chain constant regions were replaced with a cysteine-substituted, LVL-modified murine α chain constant region. The TCR β chain constant regions were replaced with a cysteine-substituted murine β chain constant region.

TCR name: 4259-F1-TCR (SEQ ID NO: 90)

MATSLLCWMALCLLGADHADTGVSQDPRHKITKRGQNVTFRCDPISEHN

RLYWYRQTLGQGPEFLTYFQNEAQLEKSRLLSDRFSAERPKGSFSTLEI

QRTEQGDSAMYLCASSPGLAYEQYFGPGTRLTVT*EDLRNVTPPKVSLFE*

*PSKAEIANKQKATLVCLARGFFPDHVELSWWVNGKEVHSGVCTDPQAYK*

*ESNYSYCLSSRLRVSATFWHNPRNHFRCQVQFHGLSEEDKWPEGSPKPV*

*TQNISAEAWGRADCGITSASYQQGVLSATILYEILLGKATLYAVLVSTL*

*VVMAMVKRKNS*RAKRSGSGATNFSLLKQAGDVEENPGPMHSAPISMLAM

-continued

LFTLSGLRAQSVAQPEDQVNVAEGNPLTVKCTYSVSGNPYLFWYVQYPN

RGLQFLLKYITGDNLVKGSYGFEAEFNKSQTSFHLKKPSALVSDSALYF

CAVRDGSATSGTYKYIFGTGTRLKVLA*NIQNPEPAVYQLKDPRSQDSTL*

*CLFTDFDSQINVPKTMESGTFITDKCVLDMKAMDSKSNGAIAWSNQTSF*

*TCQDIFKETNATYPSSDVPCDATLTEKSFETDMNLNFQNLLVIVLRILL*

*LKVAGFNLLMTLRLWSS*

The sequence of the p53-Y220C neoantigen-reactive TCR 4259-F1-TCR, which was isolated from Patient 4259, is set forth immediately above. Starting from the amino terminus, the first underlined region is the CDR1beta (SEQ ID NO: 83), the second underlined region is the CDR2beta (SEQ ID NO: 84), the third underlined region is the CDR3beta (SEQ ID NO: 85), the fourth underlined region is the CDR1alpha (SEQ ID NO: 80), the fifth underlined region is the CDR2alpha (SEQ ID NO: 81), and the sixth underlined region is the CDR3alpha (SEQ ID NO: 82). The bold region is the linker (SEQ ID NO: 94). Starting from the amino terminus, the first italicized region is the beta chain constant region (SEQ ID NO: 93) and the second italicized region is the alpha chain constant region (SEQ ID NO: 91). The beta chain variable region (SEQ ID NO: 87) includes the sequence starting from the amino terminus and ending immediately prior to the start of the beta chain constant region. The alpha chain variable region (SEQ ID NO: 86) includes the sequence starting immediately after the linker and ending immediately prior to the start of the alpha chain constant region. The full-length beta chain (SEQ ID NO: 89) includes the sequence starting from the amino terminus and ending immediately prior to the start of the linker. The full-length alpha chain (SEQ ID NO: 88) includes the sequence starting immediately after the linker and ending with the carboxyl terminus.

A variant of 4259-F1-TCR comprising an alpha chain with a wild-type signal peptide is set forth in SEQ ID NO: 201. The variant comprises an alpha chain variable region (with the wild-type signal peptide) as set forth in SEQ ID NO: 199. The full-length alpha chain of the variant is set forth in SEQ ID NO: 200.

Another variant of 4259-F1-TCR comprises a beta chain variable region (with a wild-type signal peptide) as set forth in SEQ ID NO: 219. The full-length beta chain of the variant is set forth in SEQ ID NO: 220.

The amino acid sequences of the 4259-F1-TCR alpha and beta chain variable regions are shown in Table 8. The CDRs are underlined. The predicted full-length alpha chain (inclusive of the alpha chain variable and constant regions) without the N-terminal signal peptide is shown in SEQ ID NO: 174. The predicted full-length beta chain (inclusive of the beta chain variable and constant regions) without the N-terminal signal peptide is shown in SEQ ID NO: 175.

TABLE 8

| TCR Name | TCR chain | Amino acid sequence |
|---|---|---|
| 4259-F1-TCR | Alpha chain variable region (with N-terminal signal peptide) | MHSAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDGSATSGTYKYIFGTGTRLKVLA (SEQ ID NO: 86) |
| | Alpha chain variable region (with wild-type N-terminal signal peptide) | MASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDGSATSGTYKYIFGTGTRLKVLA (SEQ ID NO: 199) |
| | Beta chain variable region (with N-terminal signal peptide) | MATSLLCWMALCLLGADHADTGVSQDPRHKITKRGQNVTFRCDPISEHNRLYWYRQTLGQGPEFLTYFQNEAQLEKSRLLSDRFSAERPKGSFSTLEIQRTEQGDSAMYLCASSPGLAYEQYFGPGTRLTVT (SEQ ID NO: 87) |
| | Beta chain variable region (with wild-type N-terminal signal peptide) | MGTSLLCWMALCLLGADHADTGVSQDPRHKITKRGQNVTFRCDPISEHNRLYWYRQTLGQGPEFLTYFQNEAQLEKSRLLSDRFSAERPKGSFSTLEIQRTEQGDSAMYLCASSPGLAYEQYFGPGTRLTVT (SEQ ID NO: 219) |
| | Alpha chain variable region (predicted sequence without N-terminal signal peptide) | QSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDGSATSGTYKYIFGTGTRLKVLA (SEQ ID NO: 156) |
| | Beta chain variable region (predicted sequence without N-terminal signal peptide) | DTGVSQDPRHKITKRGQNVTFRCDPISEHNRLYWYRQTLGQGPEFLTYFQNEAQLEKSRLLSDRFSAERPKGSFSTLEIQRTEQGDSAMYLCASSPGLAYEQYFGPGTRLTVT (SEQ ID NO: 157) |

Example 10

This example demonstrates that the 4259-F1-TCR of Example 9 specifically recognizes mutated p53-Y220C peptide and not the corresponding WT peptide.

Figure 6:
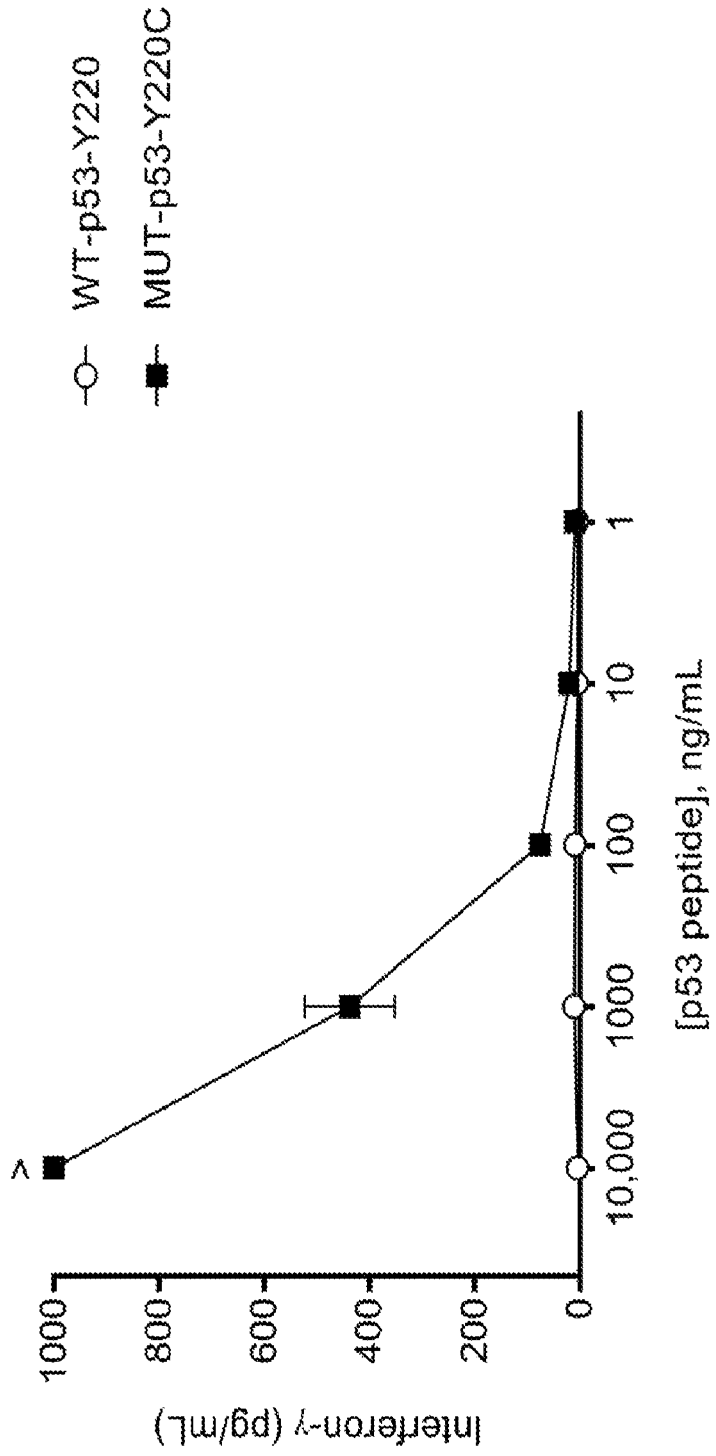
FIG. 6 is a graph showing the results of an experiment in which the 4259-F1-TCR was transduced into donor peripheral blood T cells then co-cultured with T2 tumor cells (HLA-A*02:01) pulsed with decreasing concentrations of either WT p53-Y220 peptide (VVPYEPPEV) (SEQ ID NO: 112) or MUT p53-Y220C peptide (VVPCEPPEV) (SEQ ID NO: 113). After overnight incubation, the co-culture supernatants were analyzed by ELISA for interferon-gamma secretion. Data are mean±SEM (n=3).

The 4259-F1-TCR of Example 9 was transduced into donor peripheral blood T cells then co-cultured with T2 tumor cells (HLA-A*02:01) pulsed with decreasing concentrations of either WT p53-Y220 peptide (VVPYEPPEV) (SEQ ID NO: 112) or MUT p53-Y220C peptide (VVP- CEPPEV) (SEQ ID NO: 113). After overnight incubation, the co-culture supernatants were analyzed by ELISA for interferon-gamma secretion. The results are shown in FIG. 6.

Example 11

This example demonstrates that the 4259-F1-TCR specifically recognizes tumor cells expressing p53-Y220C presented by HLA-A*02:01.

Figure 7:
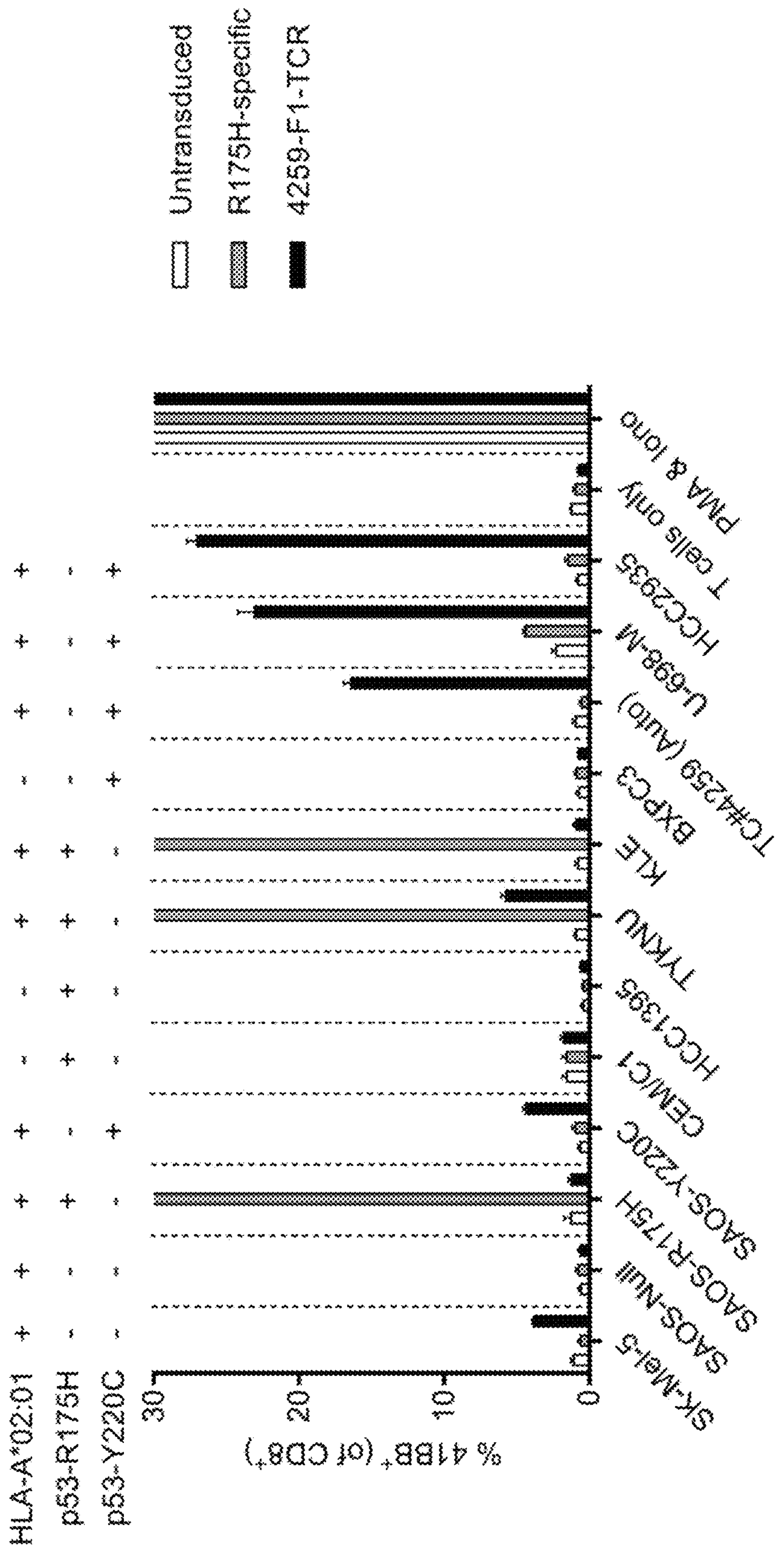
FIG. 7 is a graph showing the results of an experiment in which T cells either expressing no TCR (untransduced), a p53-R175H specific TCR or the 4259-F1-TCR were co-cultured with tumor cells, which either with or without expression of HLA-A*02:01, p53-R175H or p53-Y220C. After overnight incubation, the cells were stained for CD3, CD8 and 4-1BB then analyzed by flow cytometry. The frequencies of $CD8^+$4-$1BB^+$ T cells are displayed from the cultures. Data are mean±SEM (n=3).

T cells either expressing no TCR (untransduced), a p53-R175H specific TCR or the 4259-F1-TCR of Example 9 were co-cultured with tumor cells, either with or without expression of HLA-A*02:01, p53-R175H or p53-Y220C. After overnight incubation, the cells were stained for CD3, CD8 and 4-1BB then analyzed by flow cytometry. The frequencies of $CD8^{+}4\text{-}1BB^{+}$ T cells from the cultures are shown in FIG. 7.

Example 12

This example demonstrates the isolation and specific reactivity of a TCR from patient 4141.

A summary of the treatment of patients with p53 mutation-reactive TIL is provided in Table 9.

TABLE 9

| Tumor Type | Patient | p53 mut | Infusion bag screening | Total # of Cells ($\times10^9$) | % of p53 reactive TIL | # of p53 reactive TIL ($\times10^9$) | Response | Duration (months) |
|---|---|---|---|---|---|---|---|---|
| Colon | 4141 | R175H | Y | 69 | 0.8 | 0.6 | N.R. | — |

Figure 10:
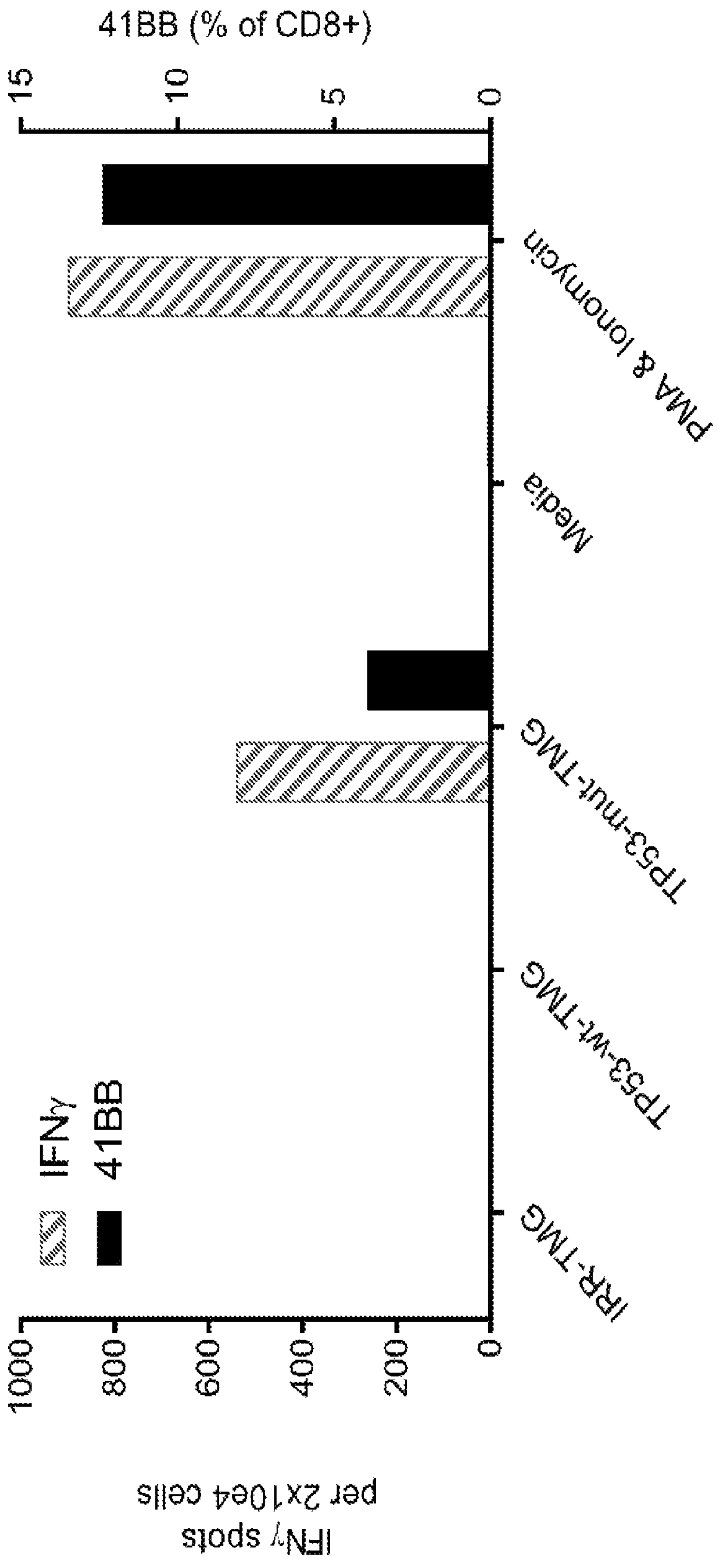
FIG. 10 is a graph showing the percentage of 4-1BB positive cells (% of CD8+) (right y-axis; black bars) and IFN-γ (spots per 2×104 cells) (left y-axis; hatched bars) measured following co-culture of TIL from Patient 4141 (fragment culture 12) with autologous APCs transfected with TMG encoding irrelevant mutations (TMG-IRR), WT p53 sequence (TP53-wt-TMG) or mutated p53 sequence including R175H (TP53-mut-TMG). Media alone and PMA and ionomycin were negative and positive controls, respectively.

Autologous APCs were transfected with TMG encoding irrelevant mutations, WT p53 sequence, or mutated p53 sequence including R175H. Media alone and PMA and ionomycin were negative and positive controls, respectively. The following day, TIL from patient 4141 (fragment culture 12) were co-cultured overnight at 37° C. with TMG-transfected APCs. Secretion of IFN-γ was evaluated by ELISPOT. Expression of 4-1BB was evaluated by flow cytometry after gating for lymphocytes→living cells (PI negative)→CD3+ (T cells)→CD4-CD8+. The results are shown in FIG. 10.

Figure 11:
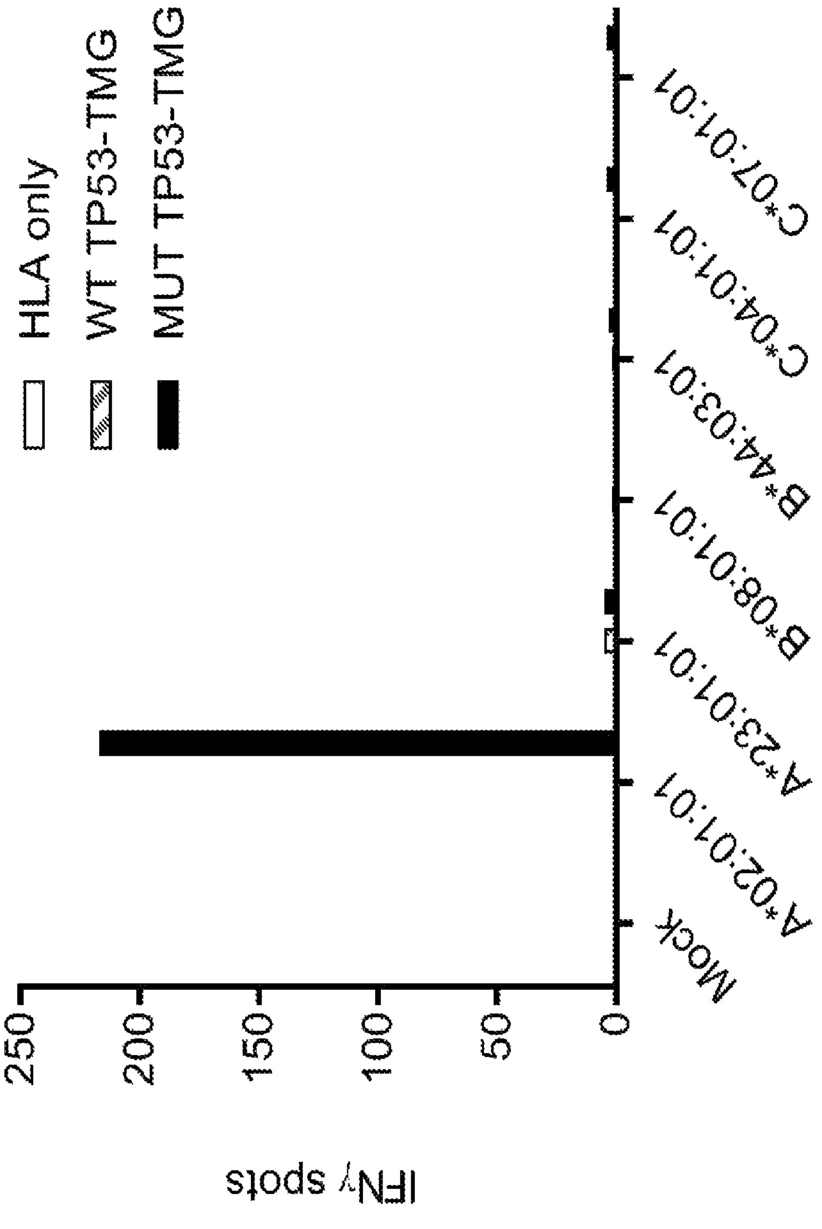
FIG. 11 is a graph showing the number of IFN-γ-positive spots per 2×104 effector cells measured following co-culture of TIL from Patient 4141 (fragment culture 12) with Cos7 cells co-transfected with the indicated HLA alleles and either no extra gene (HLA only; open bars), WT TP53 TMG (gray hatched bars), or mutated (black bars) TP53 TMG containing the p53-R175H sequence.

Cos7 cells ($2.5\times10^4$ per well) were plated on wells of flat-bottom 96 well plates. The following day, cells were co-transfected with individual HLA alleles from patient 4141 and either no extra gene, WT TP53 TMG, or mutated TP53 TMG containing the p53-R175H sequence. TIL with specificity to p53-R175H from Patient 4141 (fragment culture 12) were co-cultured the following day with transfected Cos7 cells and were incubated overnight at 37° C. Secretion of IFN-γ was evaluated by ELISPOT. The results are shown in FIG. 11.

Figure 12:
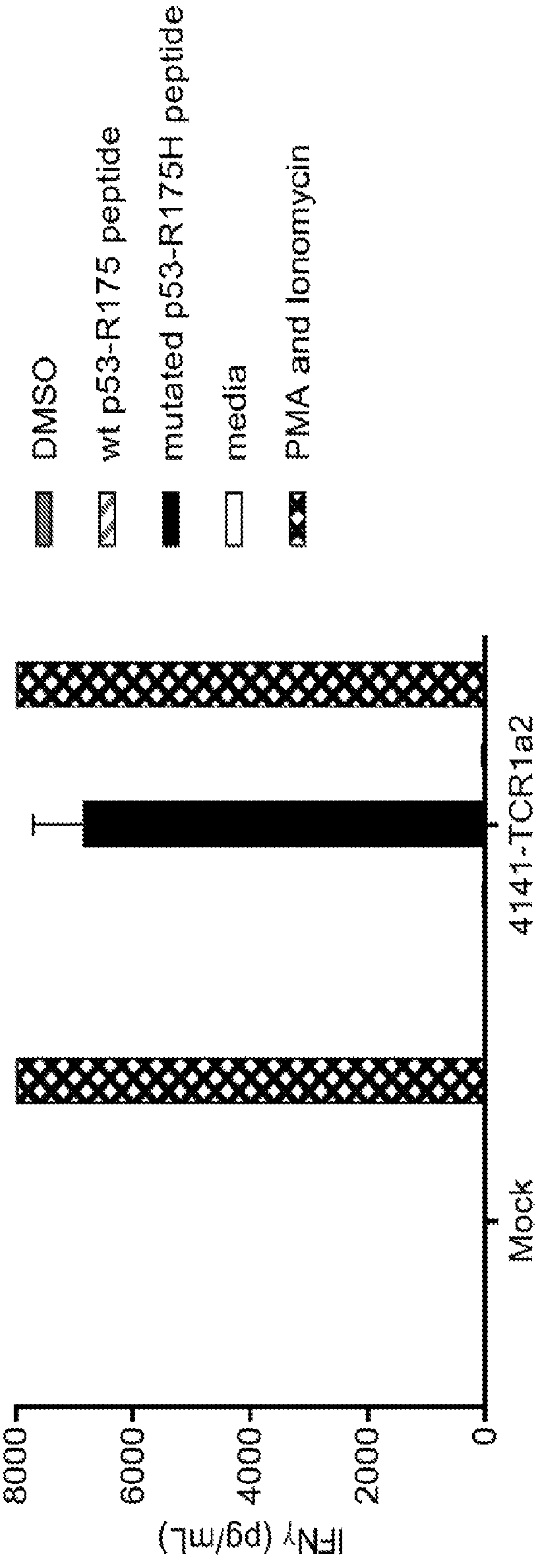
FIG. 12 is a graph showing the concentration of IFN-γ (pg/mL) measured following co-culture of T cells expressing mock (no TCR) or 4141-TCR1a2 with T2 tumor cells (expressing HLA-A*02:01). T2 cells were pulsed with peptide vehicle (DMSO; gray bars) or purified (>95% by HPLC) peptides composed of WT p53-R175 peptide (hatched gray bars) or mutated p53-R175H peptide (black bars). Media alone (open bars) and PMA and Ionomycin (lattice bars) were negative and positive controls, respectively. Data are mean±SEM (n=3).

T cells expressing mock (no TCR) or 4141-TCR1a2 were co-cultured with T2 tumor cells (expressing HLA-A*02:01). T2 cells were pulsed for 2 hours at 37° C. with peptide vehicle (DMSO) or purified (>95% by HPLC) peptides composed of WT p53-R175 peptide HMTEVVRRC (SEQ ID NO: 95) or mutated p53-R175H peptide HMTEVVRHC (SEQ ID NO: 96). Media alone and PMA and Ionomycin were negative and positive controls, respectively. Co-cultures were performed overnight at 37° C. Secretion of IFN-γ was evaluated by ELISA. The results are shown in FIG. 12.

Figure 13:
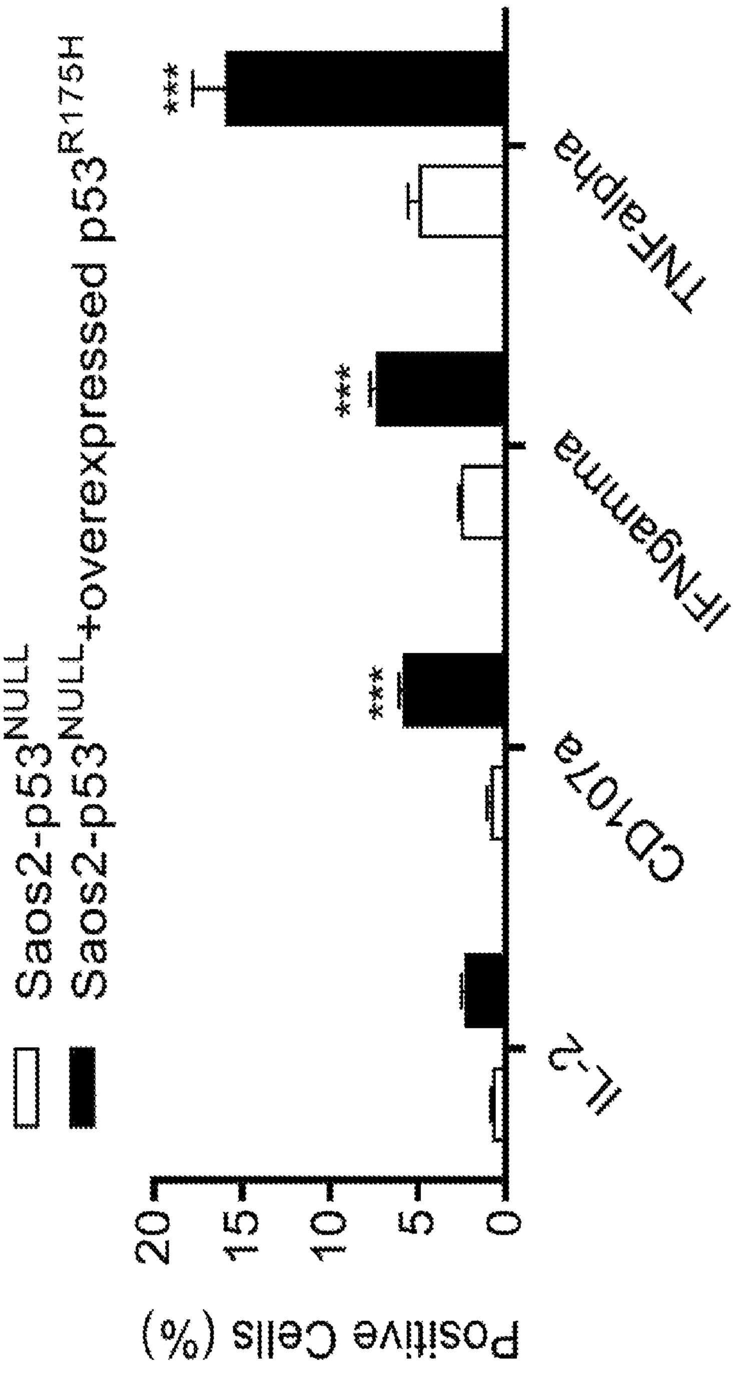
FIG. 13 is a graph showing the percentage of cells positive for expression of one of the indicated markers following co-culture of T cells expressing 4141-TCR1a2 with Saos2 cells (p53-NULL and HLA-A*02:01+), which were either unmanipulated (unshaded bars) or made to overexpress full length p53-R175H protein (shaded bars). Data are mean±SEM (n=3). Student's two-tailed t-tests were performed for each cytokine between the two cell lines for statistical analyses (***p<0.001).

T cells expressing 4141-TCR1a2 were co-cultured overnight at 37° C. with Saos2 cells (p53-NULL and HLA-A*02:01+), which were either unmanipulated or made to overexpress full length p53-R175H protein. Inhibitors of secretion (monensin and brefeldin A) were added to co-cultures to trap cytokines within T cells. After 6 hours of co-culture, cells were fixed and permeabilized then stained for IL-2, CD107a, IFN-γ and tumor necrosis factor-alpha (TNFα). Flow cytometry was used to analyze co-cultures based on a lymphocyte gate. The results are shown in FIG. 13.

The sequence of TCR 4141-TCR1a2, which was isolated from Patient 4141, is set forth below. Starting from the amino terminus, the first underlined region is the CDR1alpha (SEQ ID NO: 131), the second underlined region is the CDR2alpha (SEQ ID NO: 132), the third underlined region is the CDR3alpha (SEQ ID NO: 133), the fourth underlined region is the CDR1beta (SEQ ID NO: 134), the fifth underlined region is the CDR2beta (SEQ ID NO: 135), and the sixth underlined region is the CDR3beta (SEQ ID NO: 136). The bold region is the linker (SEQ ID NO: 94). Starting from the amino terminus, the first italicized region is the alpha chain constant region (SEQ ID NO: 91) and the second italicized region is the beta chain constant region (SEQ ID NO: 93). The alpha chain variable region (SEQ ID NO: 137) includes the sequence starting from the amino terminus and ending immediately prior to the start of the alpha chain constant region. The beta chain variable region (SEQ ID NO: 138) includes the sequence starting immediately after the linker and ending immediately prior to the start of the beta chain constant region. The full-length alpha chain (SEQ ID NO: 139) includes the sequence starting from the amino terminus and ending immediately prior to the start of the linker. The full-length beta chain (SEQ ID NO: 140) includes the sequence starting immediately after the linker and ending with the carboxyl terminus.

Cancer reactive T cells were identified as described below. The TCR was isolated as described below.

TCR name: 4141-TCR1a2
Recognition of p53 mutation: R175H
Screening method: p53 "hotspot" mutation universal screening
Co-culture to identify TCR: Co-culture 4141 infusion bag TIL with p53mutTMG and sorted CD8+41BB+ T cells
Method to identify TCR: single-cell RT-PCR then TA TQPQ cloning kit (Thermo Fisher Scientific, Waltham, MA) for alpha chain
TCR orientation: alpha-beta
Expression vector: SB transposon (SEQ ID NO: 141)

MAKSLRVLLVILWLQLSWVWSQQKEVEQDPGPLSVPEGAIVSLNCTYSNSAFQYFM

WYRQYSRKGPELLMYTYSSGNKEDGRFTAQVDKSSKYISLFIRDSQPSDSATYLCAM

SGLKEDSSYKLIFGSGTRLLVRP*NIQNPEPAVYQLKDPRSQDSTLCLFTDFDSQINVPKT*

*MESGTFITDKCVLDMKAMDSKSNGAIAWSNQTSFTCQDIFKETNATYPSSDVPCDATLTE*

*KSFETDMNLNFQNLLVIVLRILLLKVAGFNLLMTLRLWSS*RAKRSGSGATNFSLLKQAG

DVEENPGPMHPQLLGYVVLCLLGAGPLEAQVTQNPRYLITVTGKKLTVTCSQNMN

HEYMSWYRQDPGLGLRQIYYSMNVEVTDKGDVPEGYKVSRKEKRNFPLILESPSPN

QTSLYFCASSIQQGADTQYFGPGTRLTVL*EDLRNVTPPKVSLFEPSKAEIANKQKATLVC*

*LARGFFPDHVELSWWVNGKEVHSGVCTDPQAYKESNYSYCLSSRLRVSATFWHNPRNHFR*

*CQVQFHGLSEEDKWPEGSPKPVTQNISAEAWGRADCGITSASYQQGVLSATILYEILLGKA*

*TLYAVLVSTLVVMAMVKRKNS*

A variant of 4141-TCR1a2 comprising a beta chain with a wild-type signal peptide is set forth in SEQ ID NO: 204. The variant comprises a beta chain variable region (with the wild-type signal peptide) as set forth in SEQ ID NO: 202. The full-length beta chain of the variant is set forth in SEQ ID NO: 203.

Another variant of 4141-TCR1a2 comprising an alpha chain with a wild-type signal peptide is set forth in SEQ ID NO: 225. The variant comprises a beta chain variable region as set forth in SEQ ID NO: 221. The full-length beta chain of the variant is set forth in SEQ ID NO: 222. The variant comprises an alpha chain variable region (with the wild-type signal peptide) as set forth in SEQ ID NO: 223. The full-length alpha chain of the variant is set forth in SEQ ID NO: 224.

The amino acid sequences of the 4141-TCR1a2 alpha and beta chain variable regions are shown in Table 10. The CDRs are underlined. The predicted full-length alpha chain (inclusive of the alpha chain variable and constant regions) without the N-terminal signal peptide is shown in SEQ ID NO: 176. The predicted full-length beta chain (inclusive of the beta chain variable and constant regions) without the N-terminal signal peptide is shown in SEQ ID NO: 177.

TABLE 10

| TCRName | TCR chain | Amino acid sequence |
|---|---|---|
| 4141-TCR1a2 | Alpha chain variable region (with N-terminal signal peptide) | MAKSLRVLLVILWLQLSWVWSQQKEVEQDPGPLSVPEGAIVSLNCTYSNSAFQYFMWYRQYSRKGPELLMYTYSSGNKEDGRFTAQVDKSSKYISLFIRDSQPSDSATYLCAMSGLKEDSSYKLIFGSGTRLLVRP (SEQ ID NQ: 137) |
| | Alpha chain variable region (with wild-type N-terminal signal peptide) | MMKSLRVLLVILWLQLSWVWSQQKEVEQDPGPLSVPEGAIVSLNCTYSNSAFQYFMWYRQYSRKGPELLMYTYSSGNKEDGRFTAQVDKSSKYISLFIRDSQPSDSATYLCAMSGLKEDSSYKLIFGSGTRLLVRP (SEQ ID NQ: 223) |
| | Beta chain variable region (with N-terminal signal peptide) | MHPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSIQQGADTQYFGPGTRLTVL (SEQ ID NQ: 138) |
| | Beta chain variable region (with N-terminal signal peptide) | MAPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSIQQGADTQYFGPGTRLTVL (SEQ ID NQ: 221) |
| | Beta chain variable region (with wild-type N-terminal signal peptide) | MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSIQQGADTQYFGPGTRLTVL (SEQ ID NQ: 202) |

TABLE 10-continued

| TCRName | TCR chain | Amino acid sequence |
|---|---|---|
| | Alpha chain variable region (predicted sequence without N-terminal signal peptide) | QQKEVEQDPGPLSVPEGAIVSLNCTYSNSAFQYFMWYRQYSRKGPELLMYTYSSGNKEDGRFTAQVDKSSKYISLFIRDSQPSDSATYLCAMSGLKEDSSYKLIFGSGTRLLVRP (SEQ ID NO: 159) |
| | Beta chain variable region (predicted sequence without N-terminal signal peptide) | QVTQNPRYLITVTGKKLTVTCSQNMNHEYMSWYRQDPGLGLRQIYYSMNVEVTDKGDVPEGYKVSRKEKRNFPLILESPSPNQTSLYFCASSIQQGADTQYFGPGTRLTVL (SEQ ID NO: 158) |

The statistics for 4141-TCR1a2 from patient 4141 are set forth in Table 11 below.

TABLE 11

| Parameter | # | Frequency |
|---|---|---|
| Total wells | 96 | 100% |
| CDR3alpha | Unknown (TA TOPO cloning) | Not applicable |
| CDR3beta | 58 | 60.4% |

The TCR 4141-TCR1a2 was isolated, expressed in T cells and tested against the relevant antigen. A summary of the results is shown in Table 12.

TABLE 12

| TCR name | p53 a.a. substitution | TCR tested? | p53 mutation reactive? |
|---|---|---|---|
| 4141-TCR1a2 | R175H | yes | yes |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified T cell receptor (TCR) having antigenic specificity for a human p53$^{Y220C}$ amino acid sequence, wherein the TCR comprises the amino acid sequences of all of SEQ ID NOs: 80-85.

2. The TCR of claim 1, wherein the TCR comprises the amino acid sequences of:

(1) both of SEQ ID NOs: 86 and 87;

(2) both of SEQ ID NOs: 156 and 157;

(3) both of SEQ ID NOs: 199 and 87; or (4) both of SEQ ID NOs: 86 and 219.

3. The TCR of claim 1, wherein the TCR comprises the amino acid sequences of:

(1) both of SEQ ID NOs: 88 and 89;

(2) both of SEQ ID NOs: 174 and 175;

(3) both of SEQ ID NOs: 200 and 89; or (4) both of SEQ ID NOs: 88 and 220.

4. The TCR of claim 1, wherein the human p53$^{Y220C}$ amino acid sequence is SEQ ID NO: 113.

5. The TCR of claim 1, wherein the TCR does not have antigenic specificity for the wild-type human p53 amino acid sequence of SEQ ID NO: 112.

6. An isolated or purified polypeptide comprising a functional portion of the TCR of claim 1, wherein the polypeptide comprises the amino acid sequences of all of SEQ ID NOs: 80-85.

7. The polypeptide of claim 6, wherein the polypeptide comprises the amino acid sequences of:

(1) both of SEQ ID NOs: 86 and 87;

(2) both of SEQ ID NOs: 156 and 157;

(3) both of SEQ ID NOs: 199 and 87; or (4) both of SEQ ID NOs: 86 and 219.

8. The polypeptide of claim 6, wherein the polypeptide comprises the amino acid sequences of:

(1) both of SEQ ID NOs: 88 and 89;

(2) both of SEQ ID NOs: 174 and 175;

(3) both of SEQ ID NOs: 200 and 89; or (4) both of SEQ ID NOs: 88 and 220.

9. An isolated or purified nucleic acid comprising a nucleotide sequence encoding the TCR of claim 1.

10. A recombinant expression vector comprising the nucleic acid of claim 9.

11. The recombinant expression vector of claim 10, which is a transposon or a lentiviral vector.

12. A method of producing a host cell expressing a TCR that has antigenic specificity for the peptide of SEQ ID NO: 113, the method comprising contacting a cell with the vector of claim 10 under conditions that allow introduction of the vector into the cell.

13. An isolated or purified TCR encoded by the nucleic acid of claim 9.

14. An isolated or purified TCR that results from expression of the nucleic acid of claim 9.

15. An isolated or purified host cell comprising the nucleic acid of claim 9.

16. The host cell of claim 15, wherein the cell is a human lymphocyte.

17. The host cell of claim 15, wherein the cell is selected from the group consisting of a T cell, a natural killer T (NKT) cell, an invariant natural killer T (iNKT) cell, and a natural killer (NK) cell.

18. An isolated or purified population of cells comprising the host cell of claim 15.

19. A method of treating cancer in a mammal, comprising administering to the mammal the population of cells of claim 18 in an amount effective to treat cancer in the mammal.

20. The method according to claim 19, wherein the population of cells is autologous to the mammal.

21. The method according to claim 19, wherein the population of cells is allogeneic to the mammal.

22. The method according to claim 19, wherein the cancer is an epithelial cancer.

23. The method according to claim 19, wherein the cancer is cholangiocarcinoma, melanoma, colon cancer, rectal cancer, ovarian cancer, endometrial cancer, non-small cell lung cancer (NSCLC), glioblastoma, uterine cervical cancer, head and neck cancer, breast cancer, pancreatic cancer, or bladder cancer.

24. The method according to claim 19, wherein the cancer is known to comprise a Y220C mutation in human p53.

25. A method of inducing an immune response against a cancer in a mammal, comprising administering to the mammal the population of cells of claim 18 in an amount effective to induce an immune response against the cancer in the mammal.

26. A method of producing a TCR, the method comprising culturing the host cell of claim 15 so that the TCR is produced.

27. A pharmaceutical composition comprising (a) the TCR of claim 1 and (b) a pharmaceutically acceptable carrier.

28. A method of detecting the presence of cancer in mammal, the method comprising:

(a) contacting a sample comprising cells of the cancer with the TCR of claim 1, thereby forming a complex; and (b) detecting the complex, wherein detection of the complex is indicative of the presence of cancer in the mammal.

29. An isolated or purified protein comprising:

a first polypeptide chain comprising the amino acid sequences of all of SEQ ID NOS: 80-82 and a second polypeptide chain comprising the amino acid sequences of all of SEQ ID NOs: 83-85.

30. The protein of claim 29, wherein the protein comprises:

(1) a first polypeptide chain comprising the amino acid sequence of SEQ ID NO: 86 and a second polypeptide chain comprising the amino acid sequence of SEQ ID NO: 87;

(2) a first polypeptide chain comprising the amino acid sequence of SEQ ID NO: 156 and a second polypeptide chain comprising the amino acid sequence of SEQ ID NO: 157;

(3) a first polypeptide chain comprising the amino acid sequence of SEQ ID NO: 199 and a second polypeptide chain comprising the amino acid sequence of SEQ ID NO: 87; or (4) a first polypeptide chain comprising the amino acid sequence of SEQ ID NO: 86 and a second polypeptide chain comprising the amino acid sequence of SEQ ID NO: 219.

31. The protein of claim 29, wherein the protein comprises:

(1) a first polypeptide chain comprising the amino acid sequence of SEQ ID NO: 88 and a second polypeptide chain comprising the amino acid sequence of SEQ ID NO: 89;

(2) a first polypeptide chain comprising the amino acid sequence of SEQ ID NO: 174 and a second polypeptide chain comprising the amino acid sequence of SEQ ID NO: 175;

(3) a first polypeptide chain comprising the amino acid sequence of SEQ ID NO: 200 and a second polypeptide chain comprising the amino acid sequence of SEQ ID NO: 89;

(4) a first polypeptide chain comprising the amino acid sequence of SEQ ID NO: 88 and a second polypeptide chain comprising the amino acid sequence of SEQ ID NO: 220.

32. An isolated or purified nucleic acid comprising, from 5' to 3', a first nucleotide sequence and a second nucleotide sequence, wherein the first and second nucleotide sequence, respectively, encode the amino sequences of SEQ ID NOs: 86 and 87; 87 and 86; 156 and 157; 157 and 156; 199 and 87; 87 and 199; 86 and 219; or 219 and 86.

33. The isolated or purified nucleic acid of claim 32, further comprising a third nucleotide acid sequence interposed between the first and second nucleotide sequence, wherein the third nucleotide sequence encodes a cleavable linker peptide.

34. The isolated or purified nucleic acid of claim 33, wherein the cleavable linker peptide comprises the amino acid sequence of SEQ ID NO: 94.

35. The isolated or purified nucleic acid of claim 34, which encodes an amino acid sequence selected from the group consisting of: SEQ ID NO: 90 or 201.

* * * * *

SEQUENCE LISTING

```
<160> NUMBER OF SEQ ID NOS: 230

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30
```

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 2
<211> LENGTH: 11
<212> TYPE: PRT
<213> ORGANISM: Homo sapiens

<400> SEQUENCE: 2

Glu Val Val Arg His Cys Pro His His Glu Arg 1 5 10

<210> SEQ ID NO 3
<211> LENGTH: 7
<212> TYPE: PRT
<213> ORGANISM: Homo sapiens

<400> SEQUENCE: 3

Thr Ile Ser Gly Thr Asp Tyr
1 5

<210> SEQ ID NO 4
<211> LENGTH: 5
<212> TYPE: PRT
<213> ORGANISM: Homo sapiens

<400> SEQUENCE: 4

Gly Leu Thr Ser Asn
1 5

<210> SEQ ID NO 5
<211> LENGTH: 12
<212> TYPE: PRT
<213> ORGANISM: Homo sapiens

<400> SEQUENCE: 5

Cys Ile Leu Arg Asp Asn Asn Ala Arg Leu Met Phe
1 5 10

<210> SEQ ID NO 6
<211> LENGTH: 5
<212> TYPE: PRT
<213> ORGANISM: Homo sapiens

<400> SEQUENCE: 6

Met Asn His Glu Tyr
1 5

<210> SEQ ID NO 7
<211> LENGTH: 6
<212> TYPE: PRT
<213> ORGANISM: Homo sapiens

<400> SEQUENCE: 7

Ser Met Asn Val Glu Val
1 5

<210> SEQ ID NO 8
<211> LENGTH: 14
<212> TYPE: PRT
<213> ORGANISM: Homo sapiens

<400> SEQUENCE: 8

Cys Ala Ser Gly Leu Val Gly Phe Asn Gln Pro Gln His Phe
1 5 10

<210> SEQ ID NO 9
<211> LENGTH: 126
<212> TYPE: PRT
<213> ORGANISM: Homo sapiens

<400> SEQUENCE: 9

Met His Leu Val Thr Ser Ile Thr Val Leu Leu Ser Leu Gly Ile Met
1 5 10 15

```
Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Arg Asp Asn Asn Ala
            100                 105                 110

Arg Leu Met Phe Gly Asp Gly Thr Gln Leu Val Val Lys Pro
        115                 120                 125


<210> SEQ ID NO 10
<211> LENGTH: 132
<212> TYPE: PRT
<213> ORGANISM: Homo sapiens

<400> SEQUENCE: 10

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Gly Leu Val Gly Phe Asn Gln Pro Gln His Phe Gly Asp Gly Thr Arg
        115                 120                 125

Leu Ser Ile Leu
    130


<210> SEQ ID NO 11
<211> LENGTH: 263
<212> TYPE: PRT
<213> ORGANISM: Artificial Sequence
<220> FEATURE:
<223> OTHER INFORMATION: Synthetic

<400> SEQUENCE: 11

Met His Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
```

65 70 75 80

Ile Ala Glu Asp Arg Lys Ser Ser Thr Leu Ile Leu His Arg Ala Thr
85 90 95

Leu Arg Asp Ala Ala Val Tyr Tyr Cys Ile Leu Arg Asp Asn Asn Ala
100 105 110

Arg Leu Met Phe Gly Asp Gly Thr Gln Leu Val Val Lys Pro Asn Ile
115 120 125

Gln Asn Pro Glu Pro Ala Val Tyr Gln Leu Lys Asp Pro Arg Ser Gln
130 135 140

Asp Ser Thr Leu Cys Leu Phe Thr Asp Phe Asp Ser Gln Ile Asn Val
145 150 155 160

Pro Lys Thr Met Glu Ser Gly Thr Phe Ile Thr Asp Lys Cys Val Leu
165 170 175

Asp Met Lys Ala Met Asp Ser Lys Ser Asn Gly Ala Ile Ala Trp Ser
180 185 190

Asn Gln Thr Ser Phe Thr Cys Gln Asp Ile Phe Lys Glu Thr Asn Ala
195 200 205

Thr Tyr Pro Ser Ser Asp Val Pro Cys Asp Ala Thr Leu Thr Glu Lys
210 215 220

Ser Phe Glu Thr Asp Met Asn Leu Asn Phe Gln Asn Leu Leu Val Ile
225 230 235 240

Val Leu Arg Ile Leu Leu Leu Lys Val Ala Gly Phe Asn Leu Leu Met
245 250 255

Thr Leu Arg Leu Trp Ser Ser
260

<210> SEQ ID NO 12
<211> LENGTH: 305
<212> TYPE: PRT
<213> ORGANISM: Artificial Sequence
<220> FEATURE:
<223> OTHER INFORMATION: Synthetic

<400> SEQUENCE: 12

Met Ala Pro Gln Leu Leu Gly Tyr Val Val Leu Cys Leu Leu Gly Ala
1 5 10 15

Gly Pro Leu Glu Ala Gln Val Thr Gln Asn Pro Arg Tyr Leu Ile Thr
20 25 30

Val Thr Gly Lys Lys Leu Thr Val Thr Cys Ser Gln Asn Met Asn His
35 40 45

Glu Tyr Met Ser Trp Tyr Arg Gln Asp Pro Gly Leu Gly Leu Arg Gln
50 55 60

Ile Tyr Tyr Ser Met Asn Val Glu Val Thr Asp Lys Gly Asp Val Pro
65 70 75 80

Glu Gly Tyr Lys Val Ser Arg Lys Glu Lys Arg Asn Phe Pro Leu Ile
85 90 95

Leu Glu Ser Pro Ser Pro Asn Gln Thr Ser Leu Tyr Phe Cys Ala Ser
100 105 110

Gly Leu Val Gly Phe Asn Gln Pro Gln His Phe Gly Asp Gly Thr Arg
115 120 125

Leu Ser Ile Leu Glu Asp Leu Arg Asn Val Thr Pro Pro Lys Val Ser
130 135 140

Leu Phe Glu Pro Ser Lys Ala Glu Ile Ala Asn Lys Gln Lys Ala Thr
145 150 155 160

Leu Val Cys Leu Ala Arg Gly Phe Phe Pro Asp His Val Glu Leu Ser

```
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305


<210> SEQ ID NO 13
<211> LENGTH: 595
<212> TYPE: PRT
<213> ORGANISM: Artificial Sequence
<220> FEATURE:
<223> OTHER INFORMATION: Synthetic

<400> SEQUENCE: 13

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Gly Leu Val Gly Phe Asn Gln Pro Gln His Phe Gly Asp Gly Thr Arg
        115                 120                 125

Leu Ser Ile Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
```

```
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met His Leu Val
                325                 330                 335

Thr Ser Ile Thr Val Leu Leu Ser Leu Gly Ile Met Gly Asp Ala Lys
            340                 345                 350

Thr Thr Gln Pro Asn Ser Met Glu Ser Asn Glu Glu Glu Pro Val His
        355                 360                 365

Leu Pro Cys Asn His Ser Thr Ile Ser Gly Thr Asp Tyr Ile His Trp
    370                 375                 380

Tyr Arg Gln Leu Pro Ser Gln Gly Pro Glu Tyr Val Ile His Gly Leu
385                 390                 395                 400

Thr Ser Asn Val Asn Asn Arg Met Ala Ser Leu Ala Ile Ala Glu Asp
                405                 410                 415

Arg Lys Ser Ser Thr Leu Ile Leu His Arg Ala Thr Leu Arg Asp Ala
            420                 425                 430

Ala Val Tyr Tyr Cys Ile Leu Arg Asp Asn Asn Ala Arg Leu Met Phe
        435                 440                 445

Gly Asp Gly Thr Gln Leu Val Val Lys Pro Asn Ile Gln Asn Pro Glu
    450                 455                 460

Pro Ala Val Tyr Gln Leu Lys Asp Pro Arg Ser Gln Asp Ser Thr Leu
465                 470                 475                 480

Cys Leu Phe Thr Asp Phe Asp Ser Gln Ile Asn Val Pro Lys Thr Met
                485                 490                 495

Glu Ser Gly Thr Phe Ile Thr Asp Lys Cys Val Leu Asp Met Lys Ala
            500                 505                 510

Met Asp Ser Lys Ser Asn Gly Ala Ile Ala Trp Ser Asn Gln Thr Ser
        515                 520                 525

Phe Thr Cys Gln Asp Ile Phe Lys Glu Thr Asn Ala Thr Tyr Pro Ser
    530                 535                 540

Ser Asp Val Pro Cys Asp Ala Thr Leu Thr Glu Lys Ser Phe Glu Thr
545                 550                 555                 560

Asp Met Asn Leu Asn Phe Gln Asn Leu Leu Val Ile Val Leu Arg Ile
                565                 570                 575

Leu Leu Leu Lys Val Ala Gly Phe Asn Leu Leu Met Thr Leu Arg Leu
            580                 585                 590

Trp Ser Ser
        595
```

<210> SEQ ID NO 14
<211> LENGTH: 7
<212> TYPE: PRT
<213> ORGANISM: Homo sapiens

<400> SEQUENCE: 14

Thr Ile Ser Gly Asn Glu Tyr
1 5

<210> SEQ ID NO 15
<211> LENGTH: 5
<212> TYPE: PRT
<213> ORGANISM: Homo sapiens

<400> SEQUENCE: 15

Gly Leu Lys Asn Asn
1 5

<210> SEQ ID NO 16
<211> LENGTH: 19
<212> TYPE: PRT
<213> ORGANISM: Homo sapiens

<400> SEQUENCE: 16

Cys Ile Val Arg Ala Arg Ala Asn Ala Gly Gly Thr Ser Tyr Gly Lys
1 5 10 15

Leu Thr Phe

<210> SEQ ID NO 17
<211> LENGTH: 5
<212> TYPE: PRT
<213> ORGANISM: Homo sapiens

<400> SEQUENCE: 17

Leu Asn His Asp Ala
1 5

<210> SEQ ID NO 18
<211> LENGTH: 6
<212> TYPE: PRT
<213> ORGANISM: Homo sapiens

<400> SEQUENCE: 18

Ser Gln Ile Val Asn Asp
1 5

<210> SEQ ID NO 19
<211> LENGTH: 11
<212> TYPE: PRT
<213> ORGANISM: Homo sapiens

<400> SEQUENCE: 19

Cys Ala Ser Leu Gln Phe Asn Glu Gln Phe Phe
1 5 10

<210> SEQ ID NO 20
<211> LENGTH: 133
<212> TYPE: PRT
<213> ORGANISM: Homo sapiens

<400> SEQUENCE: 20

Met His Leu Val Ala Arg Val Thr Val Phe Leu Thr Phe Gly Thr Ile
1 5 10 15

Ile Asp Ala Lys Thr Thr Gln Pro Pro Ser Met Asp Cys Ala Glu Gly
20 25 30

Arg Ala Ala Asn Leu Pro Cys Asn His Ser Thr Ile Ser Gly Asn Glu
35 40 45

Tyr Val Tyr Trp Tyr Arg Gln Ile His Ser Gln Gly Pro Gln Tyr Ile
50 55 60

Ile His Gly Leu Lys Asn Asn Glu Thr Asn Glu Met Ala Ser Leu Ile
65 70 75 80

Ile Thr Glu Asp Arg Lys Ser Ser Thr Leu Ile Leu Pro His Ala Thr
85 90 95

Leu Arg Asp Thr Ala Val Tyr Tyr Cys Ile Val Arg Ala Arg Ala Asn
100 105 110

Ala Gly Gly Thr Ser Tyr Gly Lys Leu Thr Phe Gly Gln Gly Thr Ile
115 120 125

Leu Thr Val His Pro
130

<210> SEQ ID NO 21
<211> LENGTH: 131
<212> TYPE: PRT
<213> ORGANISM: Homo sapiens

<400> SEQUENCE: 21

Met Ala Met Ser Asn Gln Val Leu Cys Cys Val Val Leu Cys Phe Leu
1 5 10 15

Gly Ala Asn Thr Val Asp Gly Gly Ile Thr Gln Ser Pro Lys Tyr Leu
20 25 30

Phe Arg Lys Glu Gly Gln Asn Val Thr Leu Ser Cys Glu Gln Asn Leu
35 40 45

Asn His Asp Ala Met Tyr Trp Tyr Arg Gln Asp Pro Gly Gln Gly Leu
50 55 60

Arg Leu Ile Tyr Tyr Ser Gln Ile Val Asn Asp Phe Gln Lys Gly Asp
65 70 75 80

Ile Ala Glu Gly Tyr Ser Val Ser Arg Glu Lys Lys Glu Ser Phe Pro
85 90 95

Leu Thr Val Thr Ser Ala Gln Lys Asn Pro Thr Ala Phe Tyr Leu Cys
100 105 110

Ala Ser Leu Gln Phe Asn Glu Gln Phe Phe Gly Pro Gly Thr Arg Leu
115 120 125

Thr Val Leu
130

<210> SEQ ID NO 22
<211> LENGTH: 270
<212> TYPE: PRT
<213> ORGANISM: Artificial Sequence
<220> FEATURE:
<223> OTHER INFORMATION: Synthetic

<400> SEQUENCE: 22

Met His Leu Val Ala Arg Val Thr Val Phe Leu Thr Phe Gly Thr Ile
1 5 10 15

Ile Asp Ala Lys Thr Thr Gln Pro Pro Ser Met Asp Cys Ala Glu Gly
20 25 30

Arg Ala Ala Asn Leu Pro Cys Asn His Ser Thr Ile Ser Gly Asn Glu
35 40 45

Tyr Val Tyr Trp Tyr Arg Gln Ile His Ser Gln Gly Pro Gln Tyr Ile
50 55 60

Ile His Gly Leu Lys Asn Asn Glu Thr Asn Glu Met Ala Ser Leu Ile
65 70 75 80

```
Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Arg Ala Asn
            100                 105                 110

Ala Gly Gly Thr Ser Tyr Gly Lys Leu Thr Phe Gly Gln Gly Thr Ile
        115                 120                 125

Leu Thr Val His Pro Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 23
<211> LENGTH: 304
<212> TYPE: PRT
<213> ORGANISM: Artificial Sequence
<220> FEATURE:
<223> OTHER INFORMATION: Synthetic

<400> SEQUENCE: 23

Met Ala Met Ser Asn Gln Val Leu Cys Cys Val Val Leu Cys Phe Leu
1               5                   10                  15

Gly Ala Asn Thr Val Asp Gly Gly Ile Thr Gln Ser Pro Lys Tyr Leu
            20                  25                  30

Phe Arg Lys Glu Gly Gln Asn Val Thr Leu Ser Cys Glu Gln Asn Leu
        35                  40                  45

Asn His Asp Ala Met Tyr Trp Tyr Arg Gln Asp Pro Gly Gln Gly Leu
    50                  55                  60

Arg Leu Ile Tyr Tyr Ser Gln Ile Val Asn Asp Phe Gln Lys Gly Asp
65                  70                  75                  80

Ile Ala Glu Gly Tyr Ser Val Ser Arg Glu Lys Lys Glu Ser Phe Pro
                85                  90                  95

Leu Thr Val Thr Ser Ala Gln Lys Asn Pro Thr Ala Phe Tyr Leu Cys
            100                 105                 110

Ala Ser Leu Gln Phe Asn Glu Gln Phe Phe Gly Pro Gly Thr Arg Leu
        115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175
```

```
Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300


<210> SEQ ID NO 24
<211> LENGTH: 601
<212> TYPE: PRT
<213> ORGANISM: Artificial Sequence
<220> FEATURE:
<223> OTHER INFORMATION: Synthetic

<400> SEQUENCE: 24

Met Ala Met Ser Asn Gln Val Leu Cys Cys Val Val Leu Cys Phe Leu
1               5                   10                  15

Gly Ala Asn Thr Val Asp Gly Gly Ile Thr Gln Ser Pro Lys Tyr Leu
            20                  25                  30

Phe Arg Lys Glu Gly Gln Asn Val Thr Leu Ser Cys Glu Gln Asn Leu
        35                  40                  45

Asn His Asp Ala Met Tyr Trp Tyr Arg Gln Asp Pro Gly Gln Gly Leu
    50                  55                  60

Arg Leu Ile Tyr Tyr Ser Gln Ile Val Asn Asp Phe Gln Lys Gly Asp
65                  70                  75                  80

Ile Ala Glu Gly Tyr Ser Val Ser Arg Glu Lys Lys Glu Ser Phe Pro
                85                  90                  95

Leu Thr Val Thr Ser Ala Gln Lys Asn Pro Thr Ala Phe Tyr Leu Cys
            100                 105                 110

Ala Ser Leu Gln Phe Asn Glu Gln Phe Phe Gly Pro Gly Thr Arg Leu
        115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240
```

```
Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met His Leu Val Ala
                325                 330                 335

Arg Val Thr Val Phe Leu Thr Phe Gly Thr Ile Ile Asp Ala Lys Thr
            340                 345                 350

Thr Gln Pro Pro Ser Met Asp Cys Ala Glu Gly Arg Ala Ala Asn Leu
        355                 360                 365

Pro Cys Asn His Ser Thr Ile Ser Gly Asn Glu Tyr Val Tyr Trp Tyr
    370                 375                 380

Arg Gln Ile His Ser Gln Gly Pro Gln Tyr Ile Ile His Gly Leu Lys
385                 390                 395                 400

Asn Asn Glu Thr Asn Glu Met Ala Ser Leu Ile Ile Thr Glu Asp Arg
                405                 410                 415

Lys Ser Ser Thr Leu Ile Leu Pro His Ala Thr Leu Arg Asp Thr Ala
            420                 425                 430

Val Tyr Tyr Cys Ile Val Arg Ala Arg Ala Asn Ala Gly Gly Thr Ser
        435                 440                 445

Tyr Gly Lys Leu Thr Phe Gly Gln Gly Thr Ile Leu Thr Val His Pro
    450                 455                 460

Asn Ile Gln Asn Pro Glu Pro Ala Val Tyr Gln Leu Lys Asp Pro Arg
465                 470                 475                 480

Ser Gln Asp Ser Thr Leu Cys Leu Phe Thr Asp Phe Asp Ser Gln Ile
                485                 490                 495

Asn Val Pro Lys Thr Met Glu Ser Gly Thr Phe Ile Thr Asp Lys Cys
            500                 505                 510

Val Leu Asp Met Lys Ala Met Asp Ser Lys Ser Asn Gly Ala Ile Ala
        515                 520                 525

Trp Ser Asn Gln Thr Ser Phe Thr Cys Gln Asp Ile Phe Lys Glu Thr
    530                 535                 540

Asn Ala Thr Tyr Pro Ser Ser Asp Val Pro Cys Asp Ala Thr Leu Thr
545                 550                 555                 560

Glu Lys Ser Phe Glu Thr Asp Met Asn Leu Asn Phe Gln Asn Leu Leu
                565                 570                 575

Val Ile Val Leu Arg Ile Leu Leu Leu Lys Val Ala Gly Phe Asn Leu
            580                 585                 590

Leu Met Thr Leu Arg Leu Trp Ser Ser
        595                 600


<210> SEQ ID NO 25
<211> LENGTH: 6
<212> TYPE: PRT
<213> ORGANISM: Homo sapiens

<400> SEQUENCE: 25

Val Ser Asn Ala Tyr Asn
1               5
```

<210> SEQ ID NO 26
<211> LENGTH: 4
<212> TYPE: PRT
<213> ORGANISM: Homo sapiens

<400> SEQUENCE: 26

Gly Ser Lys Pro
1

<210> SEQ ID NO 27
<211> LENGTH: 13
<212> TYPE: PRT
<213> ORGANISM: Homo sapiens

<400> SEQUENCE: 27

Cys Ala Val Glu Asp Arg Arg Arg Thr Ala Leu Ile Phe
1 5 10

<210> SEQ ID NO 28
<211> LENGTH: 5
<212> TYPE: PRT
<213> ORGANISM: Homo sapiens

<400> SEQUENCE: 28

Ser Asn His Leu Tyr
1 5

<210> SEQ ID NO 29
<211> LENGTH: 6
<212> TYPE: PRT
<213> ORGANISM: Homo sapiens

<400> SEQUENCE: 29

Phe Tyr Asn Asn Glu Ile
1 5

<210> SEQ ID NO 30
<211> LENGTH: 15
<212> TYPE: PRT
<213> ORGANISM: Homo sapiens

<400> SEQUENCE: 30

Cys Ala Ser Ser Glu Tyr Gln Ser Gln Ser Asn Glu Gln Phe Phe
1 5 10 15

<210> SEQ ID NO 31
<211> LENGTH: 131
<212> TYPE: PRT
<213> ORGANISM: Homo sapiens

<400> SEQUENCE: 31

Met His Leu Gln Ser Thr Leu Gly Ala Val Trp Leu Gly Leu Leu Leu
1 5 10 15

Asn Ser Leu Trp Lys Val Ala Glu Ser Lys Asp Gln Val Phe Gln Pro
20 25 30

Ser Thr Val Ala Ser Ser Glu Gly Ala Val Val Glu Ile Phe Cys Asn
35 40 45

His Ser Val Ser Asn Ala Tyr Asn Phe Phe Trp Tyr Leu His Phe Pro
50 55 60

Gly Cys Ala Pro Arg Leu Leu Val Lys Gly Ser Lys Pro Ser Gln Gln
65 70 75 80

```
Gly Arg Tyr Asn Met Thr Tyr Glu Arg Phe Ser Ser Ser Leu Leu Ile
                85                  90                  95

Leu Gln Val Arg Glu Ala Asp Ala Ala Val Tyr Tyr Cys Ala Val Glu
            100                 105                 110

Asp Arg Arg Arg Thr Ala Leu Ile Phe Gly Lys Gly Thr Thr Leu Ser
        115                 120                 125

Val Ser Ser
    130


<210> SEQ ID NO 32
<211> LENGTH: 134
<212> TYPE: PRT
<213> ORGANISM: Homo sapiens

<400> SEQUENCE: 32

Met Ala Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Tyr Gln Ser Gln Ser Asn Glu Gln Phe Phe Gly Pro Gly
        115                 120                 125

Thr Arg Leu Thr Val Leu
    130


<210> SEQ ID NO 33
<211> LENGTH: 268
<212> TYPE: PRT
<213> ORGANISM: Artificial Sequence
<220> FEATURE:
<223> OTHER INFORMATION: Synthetic

<400> SEQUENCE: 33

Met His Leu Gln Ser Thr Leu Gly Ala Val Trp Leu Gly Leu Leu Leu
1               5                   10                  15

Asn Ser Leu Trp Lys Val Ala Glu Ser Lys Asp Gln Val Phe Gln Pro
            20                  25                  30

Ser Thr Val Ala Ser Ser Glu Gly Ala Val Val Glu Ile Phe Cys Asn
        35                  40                  45

His Ser Val Ser Asn Ala Tyr Asn Phe Phe Trp Tyr Leu His Phe Pro
    50                  55                  60

Gly Cys Ala Pro Arg Leu Leu Val Lys Gly Ser Lys Pro Ser Gln Gln
65                  70                  75                  80

Gly Arg Tyr Asn Met Thr Tyr Glu Arg Phe Ser Ser Ser Leu Leu Ile
                85                  90                  95

Leu Gln Val Arg Glu Ala Asp Ala Ala Val Tyr Tyr Cys Ala Val Glu
            100                 105                 110

Asp Arg Arg Arg Thr Ala Leu Ile Phe Gly Lys Gly Thr Thr Leu Ser
```

```
        115                 120                 125

Val Ser Ser Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Cys Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Leu Val Ile Val Leu Arg Ile Leu Leu Leu Lys Val Ala Gly
                245                 250                 255

Phe Asn Leu Leu Met Thr Leu Arg Leu Trp Ser Ser
            260                 265


<210> SEQ ID NO 34
<211> LENGTH: 307
<212> TYPE: PRT
<213> ORGANISM: Artificial Sequence
<220> FEATURE:
<223> OTHER INFORMATION: Synthetic

<400> SEQUENCE: 34

Met Ala Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Tyr Gln Ser Gln Ser Asn Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
```

```
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser
305
```

<210> SEQ ID NO 35
<211> LENGTH: 602
<212> TYPE: PRT
<213> ORGANISM: Artificial Sequence
<220> FEATURE:
<223> OTHER INFORMATION: Synthetic

<400> SEQUENCE: 35

```
Met Ala Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Tyr Gln Ser Gln Ser Asn Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
```

```
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met His
                325                 330                 335

Leu Gln Ser Thr Leu Gly Ala Val Trp Leu Gly Leu Leu Leu Asn Ser
            340                 345                 350

Leu Trp Lys Val Ala Glu Ser Lys Asp Gln Val Phe Gln Pro Ser Thr
        355                 360                 365

Val Ala Ser Ser Glu Gly Ala Val Val Glu Ile Phe Cys Asn His Ser
    370                 375                 380

Val Ser Asn Ala Tyr Asn Phe Phe Trp Tyr Leu His Phe Pro Gly Cys
385                 390                 395                 400

Ala Pro Arg Leu Leu Val Lys Gly Ser Lys Pro Ser Gln Gln Gly Arg
                405                 410                 415

Tyr Asn Met Thr Tyr Glu Arg Phe Ser Ser Ser Leu Leu Ile Leu Gln
            420                 425                 430

Val Arg Glu Ala Asp Ala Ala Val Tyr Tyr Cys Ala Val Glu Asp Arg
        435                 440                 445

Arg Arg Thr Ala Leu Ile Phe Gly Lys Gly Thr Thr Leu Ser Val Ser
    450                 455                 460

Ser Asn Ile Gln Asn Pro Glu Pro Ala Val Tyr Gln Leu Lys Asp Pro
465                 470                 475                 480

Arg Ser Gln Asp Ser Thr Leu Cys Leu Phe Thr Asp Phe Asp Ser Gln
                485                 490                 495

Ile Asn Val Pro Lys Thr Met Glu Ser Gly Thr Phe Ile Thr Asp Lys
            500                 505                 510

Cys Val Leu Asp Met Lys Ala Met Asp Ser Lys Ser Asn Gly Ala Ile
        515                 520                 525

Ala Trp Ser Asn Gln Thr Ser Phe Thr Cys Gln Asp Ile Phe Lys Glu
    530                 535                 540

Thr Asn Ala Thr Tyr Pro Ser Ser Asp Val Pro Cys Asp Ala Thr Leu
545                 550                 555                 560

Thr Glu Lys Ser Phe Glu Thr Asp Met Asn Leu Asn Phe Gln Asn Leu
                565                 570                 575

Leu Val Ile Val Leu Arg Ile Leu Leu Leu Lys Val Ala Gly Phe Asn
            580                 585                 590

Leu Leu Met Thr Leu Arg Leu Trp Ser Ser
        595                 600


<210> SEQ ID NO 36
<211> LENGTH: 7
<212> TYPE: PRT
<213> ORGANISM: Homo sapiens

<400> SEQUENCE: 36

Thr Ile Ser Gly Asn Glu Tyr
1               5


<210> SEQ ID NO 37
<211> LENGTH: 5
```

<212> TYPE: PRT
<213> ORGANISM: Homo sapiens

<400> SEQUENCE: 37

Gly Leu Lys Asn Asn
1               5

<210> SEQ ID NO 38
<211> LENGTH: 19
<212> TYPE: PRT
<213> ORGANISM: Homo sapiens

<400> SEQUENCE: 38

Cys Ile Val Arg Gly Ser Pro Gly Ala Gly Gly Thr Ser Tyr Gly Lys
1               5                   10                  15

Leu Thr Phe

<210> SEQ ID NO 39
<211> LENGTH: 5
<212> TYPE: PRT
<213> ORGANISM: Homo sapiens

<400> SEQUENCE: 39

Leu Asn His Asp Ala
1               5

<210> SEQ ID NO 40
<211> LENGTH: 6
<212> TYPE: PRT
<213> ORGANISM: Homo sapiens

<400> SEQUENCE: 40

Ser Gln Ile Val Asn Asp
1               5

<210> SEQ ID NO 41
<211> LENGTH: 11
<212> TYPE: PRT
<213> ORGANISM: Homo sapiens

<400> SEQUENCE: 41

Cys Ala Ser Ser Ile Arg Thr Glu Ala Phe Phe
1               5                   10

<210> SEQ ID NO 42
<211> LENGTH: 133
<212> TYPE: PRT
<213> ORGANISM: Homo sapiens

<400> SEQUENCE: 42

Met His Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

```
Leu Arg Asp Thr Ala Val Tyr Tyr Cys Ile Val Arg Gly Ser Pro Gly
            100                 105                 110

Ala Gly Gly Thr Ser Tyr Gly Lys Leu Thr Phe Gly Gln Gly Thr Ile
        115                 120                 125

Leu Thr Val His Pro
    130
```

<210> SEQ ID NO 43
<211> LENGTH: 129
<212> TYPE: PRT
<213> ORGANISM: Homo sapiens

<400> SEQUENCE: 43

```
Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Arg Thr Glu Ala Phe Phe Gly Gln Gly Thr Arg Leu Thr Val
        115                 120                 125

Val
```

<210> SEQ ID NO 44
<211> LENGTH: 270
<212> TYPE: PRT
<213> ORGANISM: Artificial Sequence
<220> FEATURE:
<223> OTHER INFORMATION: Synthetic

<400> SEQUENCE: 44

```
Met His Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Gly Ser Pro Gly
            100                 105                 110

Ala Gly Gly Thr Ser Tyr Gly Lys Leu Thr Phe Gly Gln Gly Thr Ile
        115                 120                 125

Leu Thr Val His Pro Asn Ile Gln Asn Pro Glu Pro Ala Val Tyr Gln
```

```
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 45
<211> LENGTH: 302
<212> TYPE: PRT
<213> ORGANISM: Artificial Sequence
<220> FEATURE:
<223> OTHER INFORMATION: Synthetic

<400> SEQUENCE: 45

Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Arg Thr Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
```

```
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser
    290                 295                 300


<210> SEQ ID NO 46
<211> LENGTH: 599
<212> TYPE: PRT
<213> ORGANISM: Artificial Sequence
<220> FEATURE:
<223> OTHER INFORMATION: Synthetic

<400> SEQUENCE: 46

Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Arg Thr Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser Arg Ala
```

```
    290                 295                 300

Lys Arg Ser Gly Ser Gly Ala Thr Asn Phe Ser Leu Leu Lys Gln Ala
305                 310                 315                 320

Gly Asp Val Glu Glu Asn Pro Gly Pro Met His Leu Val Ala Arg Val
                325                 330                 335

Thr Val Phe Leu Thr Phe Gly Thr Ile Ile Asp Ala Lys Thr Thr Gln
            340                 345                 350

Pro Pro Ser Met Asp Cys Ala Glu Gly Arg Ala Ala Asn Leu Pro Cys
        355                 360                 365

Asn His Ser Thr Ile Ser Gly Asn Glu Tyr Val Tyr Trp Tyr Arg Gln
    370                 375                 380

Ile His Ser Gln Gly Pro Gln Tyr Ile Ile His Gly Leu Lys Asn Asn
385                 390                 395                 400

Glu Thr Asn Glu Met Ala Ser Leu Ile Ile Thr Glu Asp Arg Lys Ser
                405                 410                 415

Ser Thr Leu Ile Leu Pro His Ala Thr Leu Arg Asp Thr Ala Val Tyr
            420                 425                 430

Tyr Cys Ile Val Arg Gly Ser Pro Gly Ala Gly Gly Thr Ser Tyr Gly
        435                 440                 445

Lys Leu Thr Phe Gly Gln Gly Thr Ile Leu Thr Val His Pro Asn Ile
    450                 455                 460

Gln Asn Pro Glu Pro Ala Val Tyr Gln Leu Lys Asp Pro Arg Ser Gln
465                 470                 475                 480

Asp Ser Thr Leu Cys Leu Phe Thr Asp Phe Asp Ser Gln Ile Asn Val
                485                 490                 495

Pro Lys Thr Met Glu Ser Gly Thr Phe Ile Thr Asp Lys Cys Val Leu
            500                 505                 510

Asp Met Lys Ala Met Asp Ser Lys Ser Asn Gly Ala Ile Ala Trp Ser
        515                 520                 525

Asn Gln Thr Ser Phe Thr Cys Gln Asp Ile Phe Lys Glu Thr Asn Ala
    530                 535                 540

Thr Tyr Pro Ser Ser Asp Val Pro Cys Asp Ala Thr Leu Thr Glu Lys
545                 550                 555                 560

Ser Phe Glu Thr Asp Met Asn Leu Asn Phe Gln Asn Leu Leu Val Ile
                565                 570                 575

Val Leu Arg Ile Leu Leu Leu Lys Val Ala Gly Phe Asn Leu Leu Met
            580                 585                 590

Thr Leu Arg Leu Trp Ser Ser
        595


<210> SEQ ID NO 47
<211> LENGTH: 5
<212> TYPE: PRT
<213> ORGANISM: Homo sapiens

<400> SEQUENCE: 47

Thr Thr Leu Ser Asn
1               5


<210> SEQ ID NO 48
<211> LENGTH: 7
<212> TYPE: PRT
<213> ORGANISM: Homo sapiens

<400> SEQUENCE: 48

Leu Val Lys Ser Gly Glu Val
```

1 5

<210> SEQ ID NO 49
<211> LENGTH: 14
<212> TYPE: PRT
<213> ORGANISM: Homo sapiens

<400> SEQUENCE: 49

Cys Ala Gly Pro Gly Gly Ala Gly Ser Tyr Gln Leu Thr Phe
1 5 10

<210> SEQ ID NO 50
<211> LENGTH: 5
<212> TYPE: PRT
<213> ORGANISM: Homo sapiens

<400> SEQUENCE: 50

Met Asn His Glu Tyr
1 5

<210> SEQ ID NO 51
<211> LENGTH: 6
<212> TYPE: PRT
<213> ORGANISM: Homo sapiens

<400> SEQUENCE: 51

Ser Met Asn Val Glu Val
1 5

<210> SEQ ID NO 52
<211> LENGTH: 17
<212> TYPE: PRT
<213> ORGANISM: Homo sapiens

<400> SEQUENCE: 52

Cys Ala Ser Ser Pro Phe Val Val Ile Gly Gln Ile Asn Glu Gln Tyr
1 5 10 15

Phe

<210> SEQ ID NO 53
<211> LENGTH: 130
<212> TYPE: PRT
<213> ORGANISM: Homo sapiens

<400> SEQUENCE: 53

Met His Leu Ile Thr Ser Met Leu Val Leu Trp Met Gln Leu Ser Gln
1 5 10 15

Val Asn Gly Gln Gln Val Met Gln Ile Pro Gln Tyr Gln His Val Gln
20 25 30

Glu Gly Glu Asp Phe Thr Thr Tyr Cys Asn Ser Ser Thr Thr Leu Ser
35 40 45

Asn Ile Gln Trp Tyr Lys Gln Arg Pro Gly Gly His Pro Val Phe Leu
50 55 60

Ile Gln Leu Val Lys Ser Gly Glu Val Lys Lys Gln Lys Arg Leu Thr
65 70 75 80

Phe Gln Phe Gly Glu Ala Lys Lys Asn Ser Ser Leu His Ile Thr Ala
85 90 95

Thr Gln Thr Thr Asp Val Gly Thr Tyr Phe Cys Ala Gly Pro Gly Gly
100 105 110

Ala Gly Ser Tyr Gln Leu Thr Phe Gly Lys Gly Thr Lys Leu Ser Val
115 120 125

```
Ile Pro
    130


<210> SEQ ID NO 54
<211> LENGTH: 135
<212> TYPE: PRT
<213> ORGANISM: Homo sapiens

<400> SEQUENCE: 54

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Phe Val Val Ile Gly Gln Ile Asn Glu Gln Tyr Phe Gly Pro
        115                 120                 125

Gly Thr Arg Leu Thr Val Thr
    130                 135


<210> SEQ ID NO 55
<211> LENGTH: 267
<212> TYPE: PRT
<213> ORGANISM: Artificial Sequence
<220> FEATURE:
<223> OTHER INFORMATION: Synthetic

<400> SEQUENCE: 55

Met His Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Pro Gly Gly
            100                 105                 110

Ala Gly Ser Tyr Gln Leu Thr Phe Gly Lys Gly Thr Lys Leu Ser Val
        115                 120                 125

Ile Pro Asn Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160
```

```
Gln Ile Asn Val Pro Lys Thr Met Glu Ser Gly Thr Phe Ile Thr Asp
                165                 170                 175

Lys Cys Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Leu Val Ile Val Leu Arg Ile Leu Leu Leu Lys Val Ala Gly Phe
                245                 250                 255

Asn Leu Leu Met Thr Leu Arg Leu Trp Ser Ser
            260                 265


<210> SEQ ID NO 56
<211> LENGTH: 308
<212> TYPE: PRT
<213> ORGANISM: Artificial Sequence
<220> FEATURE:
<223> OTHER INFORMATION: Synthetic

<400> SEQUENCE: 56

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Phe Val Val Ile Gly Gln Ile Asn Glu Gln Tyr Phe Gly Pro
        115                 120                 125

Gly Thr Arg Leu Thr Val Thr Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255
```

```
Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300

Arg Lys Asn Ser
305


<210> SEQ ID NO 57
<211> LENGTH: 602
<212> TYPE: PRT
<213> ORGANISM: Artificial Sequence
<220> FEATURE:
<223> OTHER INFORMATION: Synthetic

<400> SEQUENCE: 57

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Phe Val Val Ile Gly Gln Ile Asn Glu Gln Tyr Phe Gly Pro
        115                 120                 125

Gly Thr Arg Leu Thr Val Thr Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300
```

```
Arg Lys Asn Ser Arg Ala Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

His Leu Ile Thr Ser Met Leu Val Leu Trp Met Gln Leu Ser Gln Val
            340                 345                 350

Asn Gly Gln Gln Val Met Gln Ile Pro Gln Tyr Gln His Val Gln Glu
        355                 360                 365

Gly Glu Asp Phe Thr Thr Tyr Cys Asn Ser Ser Thr Thr Leu Ser Asn
    370                 375                 380

Ile Gln Trp Tyr Lys Gln Arg Pro Gly Gly His Pro Val Phe Leu Ile
385                 390                 395                 400

Gln Leu Val Lys Ser Gly Glu Val Lys Lys Gln Lys Arg Leu Thr Phe
                405                 410                 415

Gln Phe Gly Glu Ala Lys Lys Asn Ser Ser Leu His Ile Thr Ala Thr
            420                 425                 430

Gln Thr Thr Asp Val Gly Thr Tyr Phe Cys Ala Gly Pro Gly Gly Ala
        435                 440                 445

Gly Ser Tyr Gln Leu Thr Phe Gly Lys Gly Thr Lys Leu Ser Val Ile
    450                 455                 460

Pro Asn Ile Gln Asn Pro Glu Pro Ala Val Tyr Gln Leu Lys Asp Pro
465                 470                 475                 480

Arg Ser Gln Asp Ser Thr Leu Cys Leu Phe Thr Asp Phe Asp Ser Gln
                485                 490                 495

Ile Asn Val Pro Lys Thr Met Glu Ser Gly Thr Phe Ile Thr Asp Lys
            500                 505                 510

Cys Val Leu Asp Met Lys Ala Met Asp Ser Lys Ser Asn Gly Ala Ile
        515                 520                 525

Ala Trp Ser Asn Gln Thr Ser Phe Thr Cys Gln Asp Ile Phe Lys Glu
    530                 535                 540

Thr Asn Ala Thr Tyr Pro Ser Ser Asp Val Pro Cys Asp Ala Thr Leu
545                 550                 555                 560

Thr Glu Lys Ser Phe Glu Thr Asp Met Asn Leu Asn Phe Gln Asn Leu
                565                 570                 575

Leu Val Ile Val Leu Arg Ile Leu Leu Leu Lys Val Ala Gly Phe Asn
            580                 585                 590

Leu Leu Met Thr Leu Arg Leu Trp Ser Ser
        595                 600


<210> SEQ ID NO 58
<211> LENGTH: 5
<212> TYPE: PRT
<213> ORGANISM: Homo sapiens

<400> SEQUENCE: 58

Thr Thr Ser Asp Arg
1               5


<210> SEQ ID NO 59
<211> LENGTH: 7
<212> TYPE: PRT
<213> ORGANISM: Homo sapiens

<400> SEQUENCE: 59

Leu Leu Ser Asn Gly Ala Val
1               5
```

<210> SEQ ID NO 60
<211> LENGTH: 14
<212> TYPE: PRT
<213> ORGANISM: Homo sapiens

<400> SEQUENCE: 60

```
Cys Ala Val Ala His Met Asp Ser Asn Tyr Gln Leu Ile Trp
1               5                   10
```

<210> SEQ ID NO 61
<211> LENGTH: 5
<212> TYPE: PRT
<213> ORGANISM: Homo sapiens

<400> SEQUENCE: 61

```
Met Asn His Glu Tyr
1               5
```

<210> SEQ ID NO 62
<211> LENGTH: 6
<212> TYPE: PRT
<213> ORGANISM: Homo sapiens

<400> SEQUENCE: 62

```
Ser Val Gly Glu Gly Thr
1               5
```

<210> SEQ ID NO 63
<211> LENGTH: 16
<212> TYPE: PRT
<213> ORGANISM: Homo sapiens

<400> SEQUENCE: 63

```
Cys Ala Ser Ser Tyr Ala Gly Leu Ala Ala Pro Arg Glu Gln Phe Phe
1               5                   10                  15
```

<210> SEQ ID NO 64
<211> LENGTH: 130
<212> TYPE: PRT
<213> ORGANISM: Homo sapiens

<400> SEQUENCE: 64

```
Met His Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Ala His Met
            100                 105                 110

Asp Ser Asn Tyr Gln Leu Ile Trp Gly Ala Gly Thr Lys Leu Ile Ile
        115                 120                 125

Lys Pro
    130
```

<210> SEQ ID NO 65
<211> LENGTH: 134
<212> TYPE: PRT
<213> ORGANISM: Homo sapiens

<400> SEQUENCE: 65

```
Met Ala Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Tyr Ala Gly Leu Ala Ala Pro Arg Glu Gln Phe Phe Gly Pro Gly
        115                 120                 125

Thr Arg Leu Thr Val Leu
    130
```

<210> SEQ ID NO 66
<211> LENGTH: 267
<212> TYPE: PRT
<213> ORGANISM: Artificial Sequence
<220> FEATURE:
<223> OTHER INFORMATION: Synthetic

<400> SEQUENCE: 66

```
Met His Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Ala His Met
            100                 105                 110

Asp Ser Asn Tyr Gln Leu Ile Trp Gly Ala Gly Thr Lys Leu Ile Ile
        115                 120                 125

Lys Pro Asn Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Cys Val Leu Asp Met Lys Ala Met Asp Ser Lys Ser Asn Gly Ala
```

```
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Leu Val Ile Val Leu Arg Ile Leu Leu Leu Lys Val Ala Gly Phe
                245                 250                 255

Asn Leu Leu Met Thr Leu Arg Leu Trp Ser Ser
            260                 265


<210> SEQ ID NO 67
<211> LENGTH: 307
<212> TYPE: PRT
<213> ORGANISM: Artificial Sequence
<220> FEATURE:
<223> OTHER INFORMATION: Synthetic

<400> SEQUENCE: 67

Met Ala Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Tyr Ala Gly Leu Ala Ala Pro Arg Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
```

```
        275                 280                 285

Tyr Ala Val Leu Val Ser Thr Leu Val Val Met Ala Met Val Lys Arg
    290                 295                 300

Lys Asn Ser
305


<210> SEQ ID NO 68
<211> LENGTH: 601
<212> TYPE: PRT
<213> ORGANISM: Artificial Sequence
<220> FEATURE:
<223> OTHER INFORMATION: Synthetic

<400> SEQUENCE: 68

Met Ala Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Tyr Ala Gly Leu Ala Ala Pro Arg Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met His
```

```
                325                 330                 335

Lys Leu Leu Ala Met Ile Leu Trp Leu Gln Leu Asp Arg Leu Ser Gly
            340                 345                 350

Glu Leu Lys Val Glu Gln Asn Pro Leu Phe Leu Ser Met Gln Glu Gly
        355                 360                 365

Lys Asn Tyr Thr Ile Tyr Cys Asn Tyr Ser Thr Thr Ser Asp Arg Leu
    370                 375                 380

Tyr Trp Tyr Arg Gln Asp Pro Gly Lys Ser Leu Glu Ser Leu Phe Val
385                 390                 395                 400

Leu Leu Ser Asn Gly Ala Val Lys Gln Glu Gly Arg Leu Met Ala Ser
                405                 410                 415

Leu Asp Thr Lys Ala Arg Leu Ser Thr Leu His Ile Thr Ala Ala Val
            420                 425                 430

His Asp Leu Ser Ala Thr Tyr Phe Cys Ala Val Ala His Met Asp Ser
        435                 440                 445

Asn Tyr Gln Leu Ile Trp Gly Ala Gly Thr Lys Leu Ile Ile Lys Pro
    450                 455                 460

Asn Ile Gln Asn Pro Glu Pro Ala Val Tyr Gln Leu Lys Asp Pro Arg
465                 470                 475                 480

Ser Gln Asp Ser Thr Leu Cys Leu Phe Thr Asp Phe Asp Ser Gln Ile
                485                 490                 495

Asn Val Pro Lys Thr Met Glu Ser Gly Thr Phe Ile Thr Asp Lys Cys
            500                 505                 510

Val Leu Asp Met Lys Ala Met Asp Ser Lys Ser Asn Gly Ala Ile Ala
        515                 520                 525

Trp Ser Asn Gln Thr Ser Phe Thr Cys Gln Asp Ile Phe Lys Glu Thr
    530                 535                 540

Asn Ala Thr Tyr Pro Ser Ser Asp Val Pro Cys Asp Ala Thr Leu Thr
545                 550                 555                 560

Glu Lys Ser Phe Glu Thr Asp Met Asn Leu Asn Phe Gln Asn Leu Leu
                565                 570                 575

Val Ile Val Leu Arg Ile Leu Leu Leu Lys Val Ala Gly Phe Asn Leu
            580                 585                 590

Leu Met Thr Leu Arg Leu Trp Ser Ser
        595                 600
```

<210> SEQ ID NO 69
<211> LENGTH: 7
<212> TYPE: PRT
<213> ORGANISM: Homo sapiens

<400> SEQUENCE: 69

```
Thr Ile Ser Gly Asn Glu Tyr
1               5
```

<210> SEQ ID NO 70
<211> LENGTH: 5
<212> TYPE: PRT
<213> ORGANISM: Homo sapiens

<400> SEQUENCE: 70

```
Gly Leu Lys Asn Asn
1               5
```

<210> SEQ ID NO 71
<211> LENGTH: 19
<212> TYPE: PRT

<213> ORGANISM: Homo sapiens

<400> SEQUENCE: 71

Cys Ile Val Arg Ala Arg Ala Asn Ala Gly Gly Thr Ser Tyr Gly Lys
1 5 10 15

Leu Thr Phe

<210> SEQ ID NO 72
<211> LENGTH: 5
<212> TYPE: PRT
<213> ORGANISM: Homo sapiens

<400> SEQUENCE: 72

Leu Asn His Asp Ala
1 5

<210> SEQ ID NO 73
<211> LENGTH: 6
<212> TYPE: PRT
<213> ORGANISM: Homo sapiens

<400> SEQUENCE: 73

Ser Gln Ile Val Asn Asp
1 5

<210> SEQ ID NO 74
<211> LENGTH: 11
<212> TYPE: PRT
<213> ORGANISM: Homo sapiens

<400> SEQUENCE: 74

Cys Ala Thr Arg Thr Gly Asn Glu Ala Phe Phe
1 5 10

<210> SEQ ID NO 75
<211> LENGTH: 133
<212> TYPE: PRT
<213> ORGANISM: Homo sapiens

<400> SEQUENCE: 75

Met His Leu Val Ala Arg Val Thr Val Phe Leu Thr Phe Gly Thr Ile
1 5 10 15

Ile Asp Ala Lys Thr Thr Gln Pro Pro Ser Met Asp Cys Ala Glu Gly
20 25 30

Arg Ala Ala Asn Leu Pro Cys Asn His Ser Thr Ile Ser Gly Asn Glu
35 40 45

Tyr Val Tyr Trp Tyr Arg Gln Ile His Ser Gln Gly Pro Gln Tyr Ile
50 55 60

Ile His Gly Leu Lys Asn Asn Glu Thr Asn Glu Met Ala Ser Leu Ile
65 70 75 80

Ile Thr Glu Asp Arg Lys Ser Ser Thr Leu Ile Leu Pro His Ala Thr
85 90 95

Leu Arg Asp Thr Ala Val Tyr Tyr Cys Ile Val Arg Ala Arg Ala Asn
100 105 110

Ala Gly Gly Thr Ser Tyr Gly Lys Leu Thr Phe Gly Gln Gly Thr Ile
115 120 125

Leu Thr Val His Pro
130

<210> SEQ ID NO 76

<211> LENGTH: 129
<212> TYPE: PRT
<213> ORGANISM: Homo sapiens

<400> SEQUENCE: 76

Met Ala Asn Gln Val Leu Cys Cys Val Val Leu Cys Phe Leu Gly Ala
1 5 10 15

Asn Thr Val Asp Gly Gly Ile Thr Gln Ser Pro Lys Tyr Leu Phe Arg
20 25 30

Lys Glu Gly Gln Asn Val Thr Leu Ser Cys Glu Gln Asn Leu Asn His
35 40 45

Asp Ala Met Tyr Trp Tyr Arg Gln Asp Pro Gly Gln Gly Leu Arg Leu
50 55 60

Ile Tyr Tyr Ser Gln Ile Val Asn Asp Phe Gln Lys Gly Asp Ile Ala
65 70 75 80

Glu Gly Tyr Ser Val Ser Arg Glu Lys Lys Glu Ser Phe Pro Leu Thr
85 90 95

Val Thr Ser Ala Gln Lys Asn Pro Thr Ala Phe Tyr Leu Cys Ala Thr
100 105 110

Arg Thr Gly Asn Glu Ala Phe Phe Gly Gln Gly Thr Arg Leu Thr Val
115 120 125

Val

<210> SEQ ID NO 77
<211> LENGTH: 270
<212> TYPE: PRT
<213> ORGANISM: Artificial Sequence
<220> FEATURE:
<223> OTHER INFORMATION: Synthetic

<400> SEQUENCE: 77

Met His Leu Val Ala Arg Val Thr Val Phe Leu Thr Phe Gly Thr Ile
1 5 10 15

Ile Asp Ala Lys Thr Thr Gln Pro Pro Ser Met Asp Cys Ala Glu Gly
20 25 30

Arg Ala Ala Asn Leu Pro Cys Asn His Ser Thr Ile Ser Gly Asn Glu
35 40 45

Tyr Val Tyr Trp Tyr Arg Gln Ile His Ser Gln Gly Pro Gln Tyr Ile
50 55 60

Ile His Gly Leu Lys Asn Asn Glu Thr Asn Glu Met Ala Ser Leu Ile
65 70 75 80

Ile Thr Glu Asp Arg Lys Ser Ser Thr Leu Ile Leu Pro His Ala Thr
85 90 95

Leu Arg Asp Thr Ala Val Tyr Tyr Cys Ile Val Arg Ala Arg Ala Asn
100 105 110

Ala Gly Gly Thr Ser Tyr Gly Lys Leu Thr Phe Gly Gln Gly Thr Ile
115 120 125

Leu Thr Val His Pro Asn Ile Gln Asn Pro Glu Pro Ala Val Tyr Gln
130 135 140

Leu Lys Asp Pro Arg Ser Gln Asp Ser Thr Leu Cys Leu Phe Thr Asp
145 150 155 160

Phe Asp Ser Gln Ile Asn Val Pro Lys Thr Met Glu Ser Gly Thr Phe
165 170 175

Ile Thr Asp Lys Cys Val Leu Asp Met Lys Ala Met Asp Ser Lys Ser
180 185 190

Asn Gly Ala Ile Ala Trp Ser Asn Gln Thr Ser Phe Thr Cys Gln Asp

```
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 78
<211> LENGTH: 302
<212> TYPE: PRT
<213> ORGANISM: Artificial Sequence
<220> FEATURE:
<223> OTHER INFORMATION: Synthetic

<400> SEQUENCE: 78

Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Thr
            100                 105                 110

Arg Thr Gly Asn Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser
```

290 295 300

<210> SEQ ID NO 79
<211> LENGTH: 599
<212> TYPE: PRT
<213> ORGANISM: Artificial Sequence
<220> FEATURE:
<223> OTHER INFORMATION: Synthetic

<400> SEQUENCE: 79

```
Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Thr
            100                 105                 110

Arg Thr Gly Asn Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser Arg Ala
    290                 295                 300

Lys Arg Ser Gly Ser Gly Ala Thr Asn Phe Ser Leu Leu Lys Gln Ala
305                 310                 315                 320

Gly Asp Val Glu Glu Asn Pro Gly Pro Met His Leu Val Ala Arg Val
                325                 330                 335

Thr Val Phe Leu Thr Phe Gly Thr Ile Ile Asp Ala Lys Thr Thr Gln
            340                 345                 350

Pro Pro Ser Met Asp Cys Ala Glu Gly Arg Ala Ala Asn Leu Pro Cys
```

355 360 365

Asn His Ser Thr Ile Ser Gly Asn Glu Tyr Val Tyr Trp Tyr Arg Gln
370 375 380

Ile His Ser Gln Gly Pro Gln Tyr Ile Ile His Gly Leu Lys Asn Asn
385 390 395 400

Glu Thr Asn Glu Met Ala Ser Leu Ile Ile Thr Glu Asp Arg Lys Ser
405 410 415

Ser Thr Leu Ile Leu Pro His Ala Thr Leu Arg Asp Thr Ala Val Tyr
420 425 430

Tyr Cys Ile Val Arg Ala Arg Ala Asn Ala Gly Gly Thr Ser Tyr Gly
435 440 445

Lys Leu Thr Phe Gly Gln Gly Thr Ile Leu Thr Val His Pro Asn Ile
450 455 460

Gln Asn Pro Glu Pro Ala Val Tyr Gln Leu Lys Asp Pro Arg Ser Gln
465 470 475 480

Asp Ser Thr Leu Cys Leu Phe Thr Asp Phe Asp Ser Gln Ile Asn Val
485 490 495

Pro Lys Thr Met Glu Ser Gly Thr Phe Ile Thr Asp Lys Cys Val Leu
500 505 510

Asp Met Lys Ala Met Asp Ser Lys Ser Asn Gly Ala Ile Ala Trp Ser
515 520 525

Asn Gln Thr Ser Phe Thr Cys Gln Asp Ile Phe Lys Glu Thr Asn Ala
530 535 540

Thr Tyr Pro Ser Ser Asp Val Pro Cys Asp Ala Thr Leu Thr Glu Lys
545 550 555 560

Ser Phe Glu Thr Asp Met Asn Leu Asn Phe Gln Asn Leu Leu Val Ile
565 570 575

Val Leu Arg Ile Leu Leu Leu Lys Val Ala Gly Phe Asn Leu Leu Met
580 585 590

Thr Leu Arg Leu Trp Ser Ser
595

<210> SEQ ID NO 80
<211> LENGTH: 6
<212> TYPE: PRT
<213> ORGANISM: Homo sapiens

<400> SEQUENCE: 80

Val Ser Gly Asn Pro Tyr
1 5

<210> SEQ ID NO 81
<211> LENGTH: 8
<212> TYPE: PRT
<213> ORGANISM: Homo sapiens

<400> SEQUENCE: 81

Tyr Ile Thr Gly Asp Asn Leu Val
1 5

<210> SEQ ID NO 82
<211> LENGTH: 17
<212> TYPE: PRT
<213> ORGANISM: Homo sapiens

<400> SEQUENCE: 82

Cys Ala Val Arg Asp Gly Ser Ala Thr Ser Gly Thr Tyr Lys Tyr Ile
1 5 10 15

Phe

<210> SEQ ID NO 83
<211> LENGTH: 5
<212> TYPE: PRT
<213> ORGANISM: Homo sapiens

<400> SEQUENCE: 83

Ser Glu His Asn Arg
1               5

<210> SEQ ID NO 84
<211> LENGTH: 6
<212> TYPE: PRT
<213> ORGANISM: Homo sapiens

<400> SEQUENCE: 84

Phe Gln Asn Glu Ala Gln
1               5

<210> SEQ ID NO 85
<211> LENGTH: 13
<212> TYPE: PRT
<213> ORGANISM: Homo sapiens

<400> SEQUENCE: 85

Cys Ala Ser Ser Pro Gly Leu Ala Tyr Glu Gln Tyr Phe
1               5                   10

<210> SEQ ID NO 86
<211> LENGTH: 136
<212> TYPE: PRT
<213> ORGANISM: Homo sapiens

<400> SEQUENCE: 86

Met His Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Gly Ser Ala Thr Ser Gly Thr Tyr Lys Tyr Ile Phe Gly Thr
        115                 120                 125

Gly Thr Arg Leu Lys Val Leu Ala
    130                 135

<210> SEQ ID NO 87
<211> LENGTH: 132
<212> TYPE: PRT
<213> ORGANISM: Homo sapiens

<400> SEQUENCE: 87

```
Met Ala Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Pro Gly Leu Ala Tyr Glu Gln Tyr Phe Gly Pro Gly Thr Arg
        115                 120                 125

Leu Thr Val Thr
    130


<210> SEQ ID NO 88
<211> LENGTH: 273
<212> TYPE: PRT
<213> ORGANISM: Artificial Sequence
<220> FEATURE:
<223> OTHER INFORMATION: Synthetic

<400> SEQUENCE: 88

Met His Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Gly Ser Ala Thr Ser Gly Thr Tyr Lys Tyr Ile Phe Gly Thr
        115                 120                 125

Gly Thr Arg Leu Lys Val Leu Ala Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220
```

```
Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
            260                 265                 270

Ser


<210> SEQ ID NO 89
<211> LENGTH: 305
<212> TYPE: PRT
<213> ORGANISM: Artificial Sequence
<220> FEATURE:
<223> OTHER INFORMATION: Synthetic

<400> SEQUENCE: 89

Met Ala Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Pro Gly Leu Ala Tyr Glu Gln Tyr Phe Gly Pro Gly Thr Arg
        115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
```

305

<210> SEQ ID NO 90
<211> LENGTH: 605
<212> TYPE: PRT
<213> ORGANISM: Artificial Sequence
<220> FEATURE:
<223> OTHER INFORMATION: Synthetic

<400> SEQUENCE: 90

Met Ala Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Pro Gly Leu Ala Tyr Glu Gln Tyr Phe Gly Pro Gly Thr Arg
        115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met His Ser Ala
                325                 330                 335

Pro Ile Ser Met Leu Ala Met Leu Phe Thr Leu Ser Gly Leu Arg Ala
            340                 345                 350

Gln Ser Val Ala Gln Pro Glu Asp Gln Val Asn Val Ala Glu Gly Asn

```
        355                 360                 365

Pro Leu Thr Val Lys Cys Thr Tyr Ser Val Ser Gly Asn Pro Tyr Leu
    370                 375                 380

Phe Trp Tyr Val Gln Tyr Pro Asn Arg Gly Leu Gln Phe Leu Leu Lys
385                 390                 395                 400

Tyr Ile Thr Gly Asp Asn Leu Val Lys Gly Ser Tyr Gly Phe Glu Ala
                405                 410                 415

Glu Phe Asn Lys Ser Gln Thr Ser Phe His Leu Lys Lys Pro Ser Ala
            420                 425                 430

Leu Val Ser Asp Ser Ala Leu Tyr Phe Cys Ala Val Arg Asp Gly Ser
        435                 440                 445

Ala Thr Ser Gly Thr Tyr Lys Tyr Ile Phe Gly Thr Gly Thr Arg Leu
    450                 455                 460

Lys Val Leu Ala Asn Ile Gln Asn Pro Glu Pro Ala Val Tyr Gln Leu
465                 470                 475                 480

Lys Asp Pro Arg Ser Gln Asp Ser Thr Leu Cys Leu Phe Thr Asp Phe
                485                 490                 495

Asp Ser Gln Ile Asn Val Pro Lys Thr Met Glu Ser Gly Thr Phe Ile
            500                 505                 510

Thr Asp Lys Cys Val Leu Asp Met Lys Ala Met Asp Ser Lys Ser Asn
        515                 520                 525

Gly Ala Ile Ala Trp Ser Asn Gln Thr Ser Phe Thr Cys Gln Asp Ile
    530                 535                 540

Phe Lys Glu Thr Asn Ala Thr Tyr Pro Ser Ser Asp Val Pro Cys Asp
545                 550                 555                 560

Ala Thr Leu Thr Glu Lys Ser Phe Glu Thr Asp Met Asn Leu Asn Phe
                565                 570                 575

Gln Asn Leu Leu Val Ile Val Leu Arg Ile Leu Leu Leu Lys Val Ala
            580                 585                 590

Gly Phe Asn Leu Leu Met Thr Leu Arg Leu Trp Ser Ser
        595                 600                 605


<210> SEQ ID NO 91
<211> LENGTH: 137
<212> TYPE: PRT
<213> ORGANISM: Artificial Sequence
<220> FEATURE:
<223> OTHER INFORMATION: Synthetic

<400> SEQUENCE: 91

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
```

```
        115                 120                 125

Leu Met Thr Leu Arg Leu Trp Ser Ser
    130                 135


<210> SEQ ID NO 92
<211> LENGTH: 137
<212> TYPE: PRT
<213> ORGANISM: Artificial Sequence
<220> FEATURE:
<223> OTHER INFORMATION: Synthetic

<400> SEQUENCE: 92

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 93
<211> LENGTH: 173
<212> TYPE: PRT
<213> ORGANISM: Artificial Sequence
<220> FEATURE:
<223> OTHER INFORMATION: Synthetic

<400> SEQUENCE: 93

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140
```

```
Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170


<210> SEQ ID NO 94
<211> LENGTH: 27
<212> TYPE: PRT
<213> ORGANISM: Artificial Sequence
<220> FEATURE:
<223> OTHER INFORMATION: Synthetic

<400> SEQUENCE: 94

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25


<210> SEQ ID NO 95
<211> LENGTH: 9
<212> TYPE: PRT
<213> ORGANISM: Homo sapiens

<400> SEQUENCE: 95

His Met Thr Glu Val Val Arg Arg Cys
1               5


<210> SEQ ID NO 96
<211> LENGTH: 9
<212> TYPE: PRT
<213> ORGANISM: Homo sapiens

<400> SEQUENCE: 96

His Met Thr Glu Val Val Arg His Cys
1               5


<210> SEQ ID NO 97
<211> LENGTH: 10
<212> TYPE: PRT
<213> ORGANISM: Homo sapiens

<400> SEQUENCE: 97

Ser Ser Cys Met Gly Gly Met Asn Arg Arg
1               5                   10


<210> SEQ ID NO 98
<211> LENGTH: 10
<212> TYPE: PRT
<213> ORGANISM: Homo sapiens

<400> SEQUENCE: 98

Ser Ser Cys Met Gly Gly Met Asn Trp Arg
1               5                   10


<210> SEQ ID NO 99
<211> LENGTH: 15
<212> TYPE: PRT
<213> ORGANISM: Homo sapiens

<400> SEQUENCE: 99

Tyr Lys Gln Ser Gln His Met Thr Glu Val Val Arg His Cys Pro
1               5                   10                  15


<210> SEQ ID NO 100
```

<211> LENGTH: 15
<212> TYPE: PRT
<213> ORGANISM: Homo sapiens

<400> SEQUENCE: 100

Lys Gln Ser Gln His Met Thr Glu Val Val Arg His Cys Pro His
1 5 10 15

<210> SEQ ID NO 101
<211> LENGTH: 15
<212> TYPE: PRT
<213> ORGANISM: Homo sapiens

<400> SEQUENCE: 101

Gln Ser Gln His Met Thr Glu Val Val Arg His Cys Pro His His
1 5 10 15

<210> SEQ ID NO 102
<211> LENGTH: 15
<212> TYPE: PRT
<213> ORGANISM: Homo sapiens

<400> SEQUENCE: 102

Ser Gln His Met Thr Glu Val Val Arg His Cys Pro His His Glu
1 5 10 15

<210> SEQ ID NO 103
<211> LENGTH: 15
<212> TYPE: PRT
<213> ORGANISM: Homo sapiens

<400> SEQUENCE: 103

Gln His Met Thr Glu Val Val Arg His Cys Pro His His Glu Arg
1 5 10 15

<210> SEQ ID NO 104
<211> LENGTH: 15
<212> TYPE: PRT
<213> ORGANISM: Homo sapiens

<400> SEQUENCE: 104

His Met Thr Glu Val Val Arg His Cys Pro His His Glu Arg Cys
1 5 10 15

<210> SEQ ID NO 105
<211> LENGTH: 15
<212> TYPE: PRT
<213> ORGANISM: Homo sapiens

<400> SEQUENCE: 105

Met Thr Glu Val Val Arg His Cys Pro His His Glu Arg Cys Ser
1 5 10 15

<210> SEQ ID NO 106
<211> LENGTH: 15
<212> TYPE: PRT
<213> ORGANISM: Homo sapiens

<400> SEQUENCE: 106

Thr Glu Val Val Arg His Cys Pro His His Glu Arg Cys Ser Asp
1 5 10 15

<210> SEQ ID NO 107
<211> LENGTH: 15
<212> TYPE: PRT

<213> ORGANISM: Homo sapiens

<400> SEQUENCE: 107

Glu Val Val Arg His Cys Pro His His Glu Arg Cys Ser Asp Ser
1 5 10 15

<210> SEQ ID NO 108
<211> LENGTH: 15
<212> TYPE: PRT
<213> ORGANISM: Homo sapiens

<400> SEQUENCE: 108

Val Val Arg His Cys Pro His His Glu Arg Cys Ser Asp Ser Asp
1 5 10 15

<210> SEQ ID NO 109
<211> LENGTH: 15
<212> TYPE: PRT
<213> ORGANISM: Homo sapiens

<400> SEQUENCE: 109

Val Arg His Cys Pro His His Glu Arg Cys Ser Asp Ser Asp Gly
1 5 10 15

<210> SEQ ID NO 110
<211> LENGTH: 25
<212> TYPE: PRT
<213> ORGANISM: Homo sapiens

<400> SEQUENCE: 110

Tyr Lys Gln Ser Gln His Met Thr Glu Val Val Arg Arg Cys Pro His
1 5 10 15

His Glu Arg Cys Ser Asp Ser Asp Gly
20 25

<210> SEQ ID NO 111
<211> LENGTH: 25
<212> TYPE: PRT
<213> ORGANISM: Homo sapiens

<400> SEQUENCE: 111

Tyr Lys Gln Ser Gln His Met Thr Glu Val Val Arg His Cys Pro His
1 5 10 15

His Glu Arg Cys Ser Asp Ser Asp Gly
20 25

<210> SEQ ID NO 112
<211> LENGTH: 9
<212> TYPE: PRT
<213> ORGANISM: Homo sapiens

<400> SEQUENCE: 112

Val Val Pro Tyr Glu Pro Pro Glu Val
1 5

<210> SEQ ID NO 113
<211> LENGTH: 9
<212> TYPE: PRT
<213> ORGANISM: Homo sapiens

<400> SEQUENCE: 113

Val Val Pro Cys Glu Pro Pro Glu Val
1 5

<210> SEQ ID NO 114
<211> LENGTH: 341
<212> TYPE: PRT
<213> ORGANISM: Homo sapiens

<400> SEQUENCE: 114

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Asp Gln Thr Ser Phe
                325                 330                 335

Gln Lys Glu Asn Cys
            340
```

<210> SEQ ID NO 115
<211> LENGTH: 346
<212> TYPE: PRT
<213> ORGANISM: Homo sapiens

<400> SEQUENCE: 115

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Met Leu Leu Asp Leu
                325                 330                 335

Arg Trp Cys Tyr Phe Leu Ile Asn Ser Ser
            340                 345

<210> SEQ ID NO 116
<211> LENGTH: 354
<212> TYPE: PRT
<213> ORGANISM: Homo sapiens

<400> SEQUENCE: 116

Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
20 25 30

Pro Val Ala Pro Ala Pro Ala Ala Pro Thr Pro Ala Ala Pro Ala Pro
35 40 45

Ala Pro Ser Trp Pro Leu Ser Ser Ser Val Pro Ser Gln Lys Thr Tyr
50 55 60

Gln Gly Ser Tyr Gly Phe Arg Leu Gly Phe Leu His Ser Gly Thr Ala
65 70 75 80

Lys Ser Val Thr Cys Thr Tyr Ser Pro Ala Leu Asn Lys Met Phe Cys
85 90 95

Gln Leu Ala Lys Thr Cys Pro Val Gln Leu Trp Val Asp Ser Thr Pro
100 105 110

Pro Pro Gly Thr Arg Val Arg Ala Met Ala Ile Tyr Lys Gln Ser Gln
115 120 125

His Met Thr Glu Val Val Arg Arg Cys Pro His His Glu Arg Cys Ser
130 135 140

Asp Ser Asp Gly Leu Ala Pro Pro Gln His Leu Ile Arg Val Glu Gly
145 150 155 160

Asn Leu Arg Val Glu Tyr Leu Asp Asp Arg Asn Thr Phe Arg His Ser
165 170 175

Val Val Val Pro Tyr Glu Pro Pro Glu Val Gly Ser Asp Cys Thr Thr
180 185 190

Ile His Tyr Asn Tyr Met Cys Asn Ser Ser Cys Met Gly Gly Met Asn
195 200 205

Arg Arg Pro Ile Leu Thr Ile Ile Thr Leu Glu Asp Ser Ser Gly Asn
210 215 220

Leu Leu Gly Arg Asn Ser Phe Glu Val Arg Val Cys Ala Cys Pro Gly
225 230 235 240

Arg Asp Arg Arg Thr Glu Glu Glu Asn Leu Arg Lys Lys Gly Glu Pro
245 250 255

His His Glu Leu Pro Pro Gly Ser Thr Lys Arg Ala Leu Pro Asn Asn
260 265 270

Thr Ser Ser Ser Pro Gln Pro Lys Lys Lys Pro Leu Asp Gly Glu Tyr
275 280 285

Phe Thr Leu Gln Ile Arg Gly Arg Glu Arg Phe Glu Met Phe Arg Glu
290 295 300

Leu Asn Glu Ala Leu Glu Leu Lys Asp Ala Gln Ala Gly Lys Glu Pro
305 310 315 320

Gly Gly Ser Arg Ala His Ser Ser His Leu Lys Ser Lys Lys Gly Gln
325 330 335

Ser Thr Ser Arg His Lys Lys Leu Met Phe Lys Thr Glu Gly Pro Asp
340 345 350

Ser Asp

<210> SEQ ID NO 117
<211> LENGTH: 302
<212> TYPE: PRT
<213> ORGANISM: Homo sapiens

<400> SEQUENCE: 117

Met Asp Asp Leu Met Leu Ser Pro Asp Asp Ile Glu Gln Trp Phe Thr
1 5 10 15

Glu Asp Pro Gly Pro Asp Glu Ala Pro Arg Met Pro Glu Ala Ala Pro
20 25 30

```
Pro Val Ala Pro Ala Pro Ala Ala Pro Thr Pro Ala Ala Pro Ala Pro
        35                  40                  45

Ala Pro Ser Trp Pro Leu Ser Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
        275                 280                 285

Phe Thr Leu Gln Asp Gln Thr Ser Phe Gln Lys Glu Asn Cys
    290                 295                 300


<210> SEQ ID NO 118
<211> LENGTH: 307
<212> TYPE: PRT
<213> ORGANISM: Homo sapiens

<400> SEQUENCE: 118

Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
            20                  25                  30

Pro Val Ala Pro Ala Pro Ala Ala Pro Thr Pro Ala Ala Pro Ala Pro
        35                  40                  45

Ala Pro Ser Trp Pro Leu Ser Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
```

```
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
        275                 280                 285

Phe Thr Leu Gln Met Leu Leu Asp Leu Arg Trp Cys Tyr Phe Leu Ile
    290                 295                 300

Asn Ser Ser
305


<210> SEQ ID NO 119
<211> LENGTH: 261
<212> TYPE: PRT
<213> ORGANISM: Homo sapiens

<400> SEQUENCE: 119

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160
```

```
Gly Glu Pro His His Glu Leu Pro Pro Gly Ser Thr Lys Arg Ala Leu
            165                 170                 175

Pro Asn Asn Thr Ser Ser Ser Pro Gln Pro Lys Lys Lys Pro Leu Asp
            180                 185                 190

Gly Glu Tyr Phe Thr Leu Gln Ile Arg Gly Arg Glu Arg Phe Glu Met
        195                 200                 205

Phe Arg Glu Leu Asn Glu Ala Leu Glu Leu Lys Asp Ala Gln Ala Gly
    210                 215                 220

Lys Glu Pro Gly Gly Ser Arg Ala His Ser Ser His Leu Lys Ser Lys
225                 230                 235                 240

Lys Gly Gln Ser Thr Ser Arg His Lys Lys Leu Met Phe Lys Thr Glu
            245                 250                 255

Gly Pro Asp Ser Asp
            260


<210> SEQ ID NO 120
<211> LENGTH: 209
<212> TYPE: PRT
<213> ORGANISM: Homo sapiens

<400> SEQUENCE: 120

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
            165                 170                 175

Pro Asn Asn Thr Ser Ser Ser Pro Gln Pro Lys Lys Lys Pro Leu Asp
            180                 185                 190

Gly Glu Tyr Phe Thr Leu Gln Asp Gln Thr Ser Phe Gln Lys Glu Asn
        195                 200                 205

Cys


<210> SEQ ID NO 121
<211> LENGTH: 214
<212> TYPE: PRT
<213> ORGANISM: Homo sapiens

<400> SEQUENCE: 121

Met Phe Cys Gln Leu Ala Lys Thr Cys Pro Val Gln Leu Trp Val Asp
```

```
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Met Leu Leu Asp Leu Arg Trp Cys Tyr
        195                 200                 205

Phe Leu Ile Asn Ser Ser
    210


<210> SEQ ID NO 122
<211> LENGTH: 14
<212> TYPE: PRT
<213> ORGANISM: Homo sapiens

<400> SEQUENCE: 122

Cys Ala Ser Ser Ile Gln Gln Gly Ala Asp Thr Gln Tyr Phe
1               5                   10


<210> SEQ ID NO 123
<211> LENGTH: 13
<212> TYPE: PRT
<213> ORGANISM: Homo sapiens

<400> SEQUENCE: 123

Cys Ala Ser Ser Ile Asn Arg Tyr Thr Glu Ala Phe Phe
1               5                   10


<210> SEQ ID NO 124
<211> LENGTH: 17
<212> TYPE: PRT
<213> ORGANISM: Homo sapiens

<400> SEQUENCE: 124

Cys Ala Ser Ser Tyr Pro Ser Met Asp Arg Asp Arg Tyr Gly Tyr Thr
1               5                   10                  15

Phe


<210> SEQ ID NO 125
<211> LENGTH: 15
```

<212> TYPE: PRT
<213> ORGANISM: Homo sapiens

<400> SEQUENCE: 125

Cys Ala Ser Asn Leu Gly Gly Gly Ser Thr Asp Thr Gln Tyr Phe
1 5 10 15

<210> SEQ ID NO 126
<211> LENGTH: 15
<212> TYPE: PRT
<213> ORGANISM: Homo sapiens

<400> SEQUENCE: 126

Cys Ala Ser Ser Phe Gly Ser Gly Ser Thr Asp Thr Gln Tyr Phe
1 5 10 15

<210> SEQ ID NO 127
<211> LENGTH: 12
<212> TYPE: PRT
<213> ORGANISM: Homo sapiens

<400> SEQUENCE: 127

Cys Ala Ser Ser Ser Arg Asp Tyr Glu Gln Tyr Phe
1 5 10

<210> SEQ ID NO 128
<211> LENGTH: 8
<212> TYPE: PRT
<213> ORGANISM: Artificial Sequence
<220> FEATURE:
<223> OTHER INFORMATION: Synthetic

<400> SEQUENCE: 128

Arg Ala Lys Arg Ser Gly Ser Gly
1 5

<210> SEQ ID NO 129
<211> LENGTH: 115
<212> TYPE: PRT
<213> ORGANISM: Homo sapiens

<400> SEQUENCE: 129

Met Gly Thr Ser Leu Leu Cys Trp Met Ala Leu Cys Leu Leu Gly Ala
1 5 10 15

Asp His Ala Asp Thr Gly Val Ser Gln Asn Pro Arg His Lys Ile Thr
20 25 30

Lys Arg Gly Gln Asn Val Thr Phe Arg Cys Asp Pro Ile Ser Glu His
35 40 45

Asn Arg Leu Tyr Trp Tyr Arg Gln Thr Leu Gly Gln Gly Pro Glu Phe
50 55 60

Leu Thr Tyr Phe Gln Asn Glu Ala Gln Leu Glu Lys Ser Arg Leu Leu
65 70 75 80

Ser Asp Arg Phe Ser Ala Glu Arg Pro Lys Gly Ser Phe Ser Thr Leu
85 90 95

Glu Ile Gln Arg Thr Glu Gln Gly Asp Ser Ala Met Tyr Leu Cys Ala
100 105 110

Ser Ser Leu
115

<210> SEQ ID NO 130
<211> LENGTH: 115
<212> TYPE: PRT

<213> ORGANISM: Homo sapiens

<400> SEQUENCE: 130

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu
        115

<210> SEQ ID NO 131
<211> LENGTH: 6
<212> TYPE: PRT
<213> ORGANISM: Homo sapiens

<400> SEQUENCE: 131

Asn Ser Ala Phe Gln Tyr
1               5

<210> SEQ ID NO 132
<211> LENGTH: 6
<212> TYPE: PRT
<213> ORGANISM: Homo sapiens

<400> SEQUENCE: 132

Thr Tyr Ser Ser Gly Asn
1               5

<210> SEQ ID NO 133
<211> LENGTH: 16
<212> TYPE: PRT
<213> ORGANISM: Homo sapiens

<400> SEQUENCE: 133

Cys Ala Met Ser Gly Leu Lys Glu Asp Ser Ser Tyr Lys Leu Ile Phe
1               5                   10                  15

<210> SEQ ID NO 134
<211> LENGTH: 5
<212> TYPE: PRT
<213> ORGANISM: Homo sapiens

<400> SEQUENCE: 134

Met Asn His Glu Tyr
1               5

<210> SEQ ID NO 135
<211> LENGTH: 6
<212> TYPE: PRT
<213> ORGANISM: Homo sapiens

<400> SEQUENCE: 135

Ser Met Asn Val Glu Val
1 5

<210> SEQ ID NO 136
<211> LENGTH: 14
<212> TYPE: PRT
<213> ORGANISM: Homo sapiens

<400> SEQUENCE: 136

Cys Ala Ser Ser Ile Gln Gln Gly Ala Asp Thr Gln Tyr Phe
1 5 10

<210> SEQ ID NO 137
<211> LENGTH: 136
<212> TYPE: PRT
<213> ORGANISM: Homo sapiens

<400> SEQUENCE: 137

Met Ala Lys Ser Leu Arg Val Leu Leu Val Ile Leu Trp Leu Gln Leu
1 5 10 15

Ser Trp Val Trp Ser Gln Gln Lys Glu Val Glu Gln Asp Pro Gly Pro
20 25 30

Leu Ser Val Pro Glu Gly Ala Ile Val Ser Leu Asn Cys Thr Tyr Ser
35 40 45

Asn Ser Ala Phe Gln Tyr Phe Met Trp Tyr Arg Gln Tyr Ser Arg Lys
50 55 60

Gly Pro Glu Leu Leu Met Tyr Thr Tyr Ser Ser Gly Asn Lys Glu Asp
65 70 75 80

Gly Arg Phe Thr Ala Gln Val Asp Lys Ser Ser Lys Tyr Ile Ser Leu
85 90 95

Phe Ile Arg Asp Ser Gln Pro Ser Asp Ser Ala Thr Tyr Leu Cys Ala
100 105 110

Met Ser Gly Leu Lys Glu Asp Ser Ser Tyr Lys Leu Ile Phe Gly Ser
115 120 125

Gly Thr Arg Leu Leu Val Arg Pro
130 135

<210> SEQ ID NO 138
<211> LENGTH: 132
<212> TYPE: PRT
<213> ORGANISM: Homo sapiens

<400> SEQUENCE: 138

Met His Pro Gln Leu Leu Gly Tyr Val Val Leu Cys Leu Leu Gly Ala
1 5 10 15

Gly Pro Leu Glu Ala Gln Val Thr Gln Asn Pro Arg Tyr Leu Ile Thr
20 25 30

Val Thr Gly Lys Lys Leu Thr Val Thr Cys Ser Gln Asn Met Asn His
35 40 45

Glu Tyr Met Ser Trp Tyr Arg Gln Asp Pro Gly Leu Gly Leu Arg Gln
50 55 60

Ile Tyr Tyr Ser Met Asn Val Glu Val Thr Asp Lys Gly Asp Val Pro
65 70 75 80

Glu Gly Tyr Lys Val Ser Arg Lys Glu Lys Arg Asn Phe Pro Leu Ile
85 90 95

Leu Glu Ser Pro Ser Pro Asn Gln Thr Ser Leu Tyr Phe Cys Ala Ser
100 105 110

```
Ser Ile Gln Gln Gly Ala Asp Thr Gln Tyr Phe Gly Pro Gly Thr Arg
        115                 120                 125

Leu Thr Val Leu
    130


<210> SEQ ID NO 139
<211> LENGTH: 273
<212> TYPE: PRT
<213> ORGANISM: Artificial Sequence
<220> FEATURE:
<223> OTHER INFORMATION: Synthetic

<400> SEQUENCE: 139

Met Ala Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Gly Leu Lys Glu Asp Ser Ser Tyr Lys Leu Ile Phe Gly Ser
        115                 120                 125

Gly Thr Arg Leu Leu Val Arg Pro Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
            260                 265                 270

Ser


<210> SEQ ID NO 140
<211> LENGTH: 305
<212> TYPE: PRT
<213> ORGANISM: Artificial Sequence
<220> FEATURE:
<223> OTHER INFORMATION: Synthetic

<400> SEQUENCE: 140
```

Met His Pro Gln Leu Leu Gly Tyr Val Val Leu Cys Leu Leu Gly Ala
1 5 10 15

Gly Pro Leu Glu Ala Gln Val Thr Gln Asn Pro Arg Tyr Leu Ile Thr
20 25 30

Val Thr Gly Lys Lys Leu Thr Val Thr Cys Ser Gln Asn Met Asn His
35 40 45

Glu Tyr Met Ser Trp Tyr Arg Gln Asp Pro Gly Leu Gly Leu Arg Gln
50 55 60

Ile Tyr Tyr Ser Met Asn Val Glu Val Thr Asp Lys Gly Asp Val Pro
65 70 75 80

Glu Gly Tyr Lys Val Ser Arg Lys Glu Lys Arg Asn Phe Pro Leu Ile
85 90 95

Leu Glu Ser Pro Ser Pro Asn Gln Thr Ser Leu Tyr Phe Cys Ala Ser
100 105 110

Ser Ile Gln Gln Gly Ala Asp Thr Gln Tyr Phe Gly Pro Gly Thr Arg
115 120 125

Leu Thr Val Leu Glu Asp Leu Arg Asn Val Thr Pro Pro Lys Val Ser
130 135 140

Leu Phe Glu Pro Ser Lys Ala Glu Ile Ala Asn Lys Gln Lys Ala Thr
145 150 155 160

Leu Val Cys Leu Ala Arg Gly Phe Phe Pro Asp His Val Glu Leu Ser
165 170 175

Trp Trp Val Asn Gly Lys Glu Val His Ser Gly Val Cys Thr Asp Pro
180 185 190

Gln Ala Tyr Lys Glu Ser Asn Tyr Ser Tyr Cys Leu Ser Ser Arg Leu
195 200 205

Arg Val Ser Ala Thr Phe Trp His Asn Pro Arg Asn His Phe Arg Cys
210 215 220

Gln Val Gln Phe His Gly Leu Ser Glu Glu Asp Lys Trp Pro Glu Gly
225 230 235 240

Ser Pro Lys Pro Val Thr Gln Asn Ile Ser Ala Glu Ala Trp Gly Arg
245 250 255

Ala Asp Cys Gly Ile Thr Ser Ala Ser Tyr Gln Gln Gly Val Leu Ser
260 265 270

Ala Thr Ile Leu Tyr Glu Ile Leu Leu Gly Lys Ala Thr Leu Tyr Ala
275 280 285

Val Leu Val Ser Thr Leu Val Val Met Ala Met Val Lys Arg Lys Asn
290 295 300

Ser
305

<210> SEQ ID NO 141
<211> LENGTH: 605
<212> TYPE: PRT
<213> ORGANISM: Artificial Sequence
<220> FEATURE:
<223> OTHER INFORMATION: Synthetic

<400> SEQUENCE: 141

Met Ala Lys Ser Leu Arg Val Leu Leu Val Ile Leu Trp Leu Gln Leu
1 5 10 15

Ser Trp Val Trp Ser Gln Gln Lys Glu Val Glu Gln Asp Pro Gly Pro
20 25 30

Leu Ser Val Pro Glu Gly Ala Ile Val Ser Leu Asn Cys Thr Tyr Ser
35 40 45

```
Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Gly Leu Lys Glu Asp Ser Ser Tyr Lys Leu Ile Phe Gly Ser
        115                 120                 125

Gly Thr Arg Leu Leu Val Arg Pro Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
            260                 265                 270

Ser Arg Ala Lys Arg Ser Gly Ser Gly Ala Thr Asn Phe Ser Leu Leu
        275                 280                 285

Lys Gln Ala Gly Asp Val Glu Glu Asn Pro Gly Pro Met His Pro Gln
    290                 295                 300

Leu Leu Gly Tyr Val Val Leu Cys Leu Leu Gly Ala Gly Pro Leu Glu
305                 310                 315                 320

Ala Gln Val Thr Gln Asn Pro Arg Tyr Leu Ile Thr Val Thr Gly Lys
                325                 330                 335

Lys Leu Thr Val Thr Cys Ser Gln Asn Met Asn His Glu Tyr Met Ser
            340                 345                 350

Trp Tyr Arg Gln Asp Pro Gly Leu Gly Leu Arg Gln Ile Tyr Tyr Ser
        355                 360                 365

Met Asn Val Glu Val Thr Asp Lys Gly Asp Val Pro Glu Gly Tyr Lys
    370                 375                 380

Val Ser Arg Lys Glu Lys Arg Asn Phe Pro Leu Ile Leu Glu Ser Pro
385                 390                 395                 400

Ser Pro Asn Gln Thr Ser Leu Tyr Phe Cys Ala Ser Ser Ile Gln Gln
                405                 410                 415

Gly Ala Asp Thr Gln Tyr Phe Gly Pro Gly Thr Arg Leu Thr Val Leu
            420                 425                 430

Glu Asp Leu Arg Asn Val Thr Pro Pro Lys Val Ser Leu Phe Glu Pro
        435                 440                 445

Ser Lys Ala Glu Ile Ala Asn Lys Gln Lys Ala Thr Leu Val Cys Leu
    450                 455                 460

Ala Arg Gly Phe Phe Pro Asp His Val Glu Leu Ser Trp Trp Val Asn
```

```
465                 470                 475                 480

Gly Lys Glu Val His Ser Gly Val Cys Thr Asp Pro Gln Ala Tyr Lys
                485                 490                 495

Glu Ser Asn Tyr Ser Tyr Cys Leu Ser Ser Arg Leu Arg Val Ser Ala
            500                 505                 510

Thr Phe Trp His Asn Pro Arg Asn His Phe Arg Cys Gln Val Gln Phe
        515                 520                 525

His Gly Leu Ser Glu Glu Asp Lys Trp Pro Glu Gly Ser Pro Lys Pro
    530                 535                 540

Val Thr Gln Asn Ile Ser Ala Glu Ala Trp Gly Arg Ala Asp Cys Gly
545                 550                 555                 560

Ile Thr Ser Ala Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Thr Leu Val Val Met Ala Met Val Lys Arg Lys Asn Ser
        595                 600                 605


<210> SEQ ID NO 142
<211> LENGTH: 107
<212> TYPE: PRT
<213> ORGANISM: Homo sapiens

<400> SEQUENCE: 142

Lys Thr Thr Gln Pro Asn Ser Met Glu Ser Asn Glu Glu Glu Pro Val
1               5                   10                  15

His Leu Pro Cys Asn His Ser Thr Ile Ser Gly Thr Asp Tyr Ile His
            20                  25                  30

Trp Tyr Arg Gln Leu Pro Ser Gln Gly Pro Glu Tyr Val Ile His Gly
        35                  40                  45

Leu Thr Ser Asn Val Asn Asn Arg Met Ala Ser Leu Ala Ile Ala Glu
    50                  55                  60

Asp Arg Lys Ser Ser Thr Leu Ile Leu His Arg Ala Thr Leu Arg Asp
65                  70                  75                  80

Ala Ala Val Tyr Tyr Cys Ile Leu Arg Asp Asn Asn Ala Arg Leu Met
                85                  90                  95

Phe Gly Asp Gly Thr Gln Leu Val Val Lys Pro
            100                 105


<210> SEQ ID NO 143
<211> LENGTH: 111
<212> TYPE: PRT
<213> ORGANISM: Homo sapiens

<400> SEQUENCE: 143

Gln Val Thr Gln Asn Pro Arg Tyr Leu Ile Thr Val Thr Gly Lys Lys
1               5                   10                  15

Leu Thr Val Thr Cys Ser Gln Asn Met Asn His Glu Tyr Met Ser Trp
            20                  25                  30

Tyr Arg Gln Asp Pro Gly Leu Gly Leu Arg Gln Ile Tyr Tyr Ser Met
        35                  40                  45

Asn Val Glu Val Thr Asp Lys Gly Asp Val Pro Glu Gly Tyr Lys Val
    50                  55                  60

Ser Arg Lys Glu Lys Arg Asn Phe Pro Leu Ile Leu Glu Ser Pro Ser
65                  70                  75                  80

Pro Asn Gln Thr Ser Leu Tyr Phe Cys Ala Ser Gly Leu Val Gly Phe
```

```
                85                  90                  95

Asn Gln Pro Gln His Phe Gly Asp Gly Thr Arg Leu Ser Ile Leu
            100                 105                 110


<210> SEQ ID NO 144
<211> LENGTH: 114
<212> TYPE: PRT
<213> ORGANISM: Homo sapiens

<400> SEQUENCE: 144

Lys Thr Thr Gln Pro Pro Ser Met Asp Cys Ala Glu Gly Arg Ala Ala
1               5                   10                  15

Asn Leu Pro Cys Asn His Ser Thr Ile Ser Gly Asn Glu Tyr Val Tyr
            20                  25                  30

Trp Tyr Arg Gln Ile His Ser Gln Gly Pro Gln Tyr Ile Ile His Gly
        35                  40                  45

Leu Lys Asn Asn Glu Thr Asn Glu Met Ala Ser Leu Ile Ile Thr Glu
    50                  55                  60

Asp Arg Lys Ser Ser Thr Leu Ile Leu Pro His Ala Thr Leu Arg Asp
65                  70                  75                  80

Thr Ala Val Tyr Tyr Cys Ile Val Arg Ala Arg Ala Asn Ala Gly Gly
                85                  90                  95

Thr Ser Tyr Gly Lys Leu Thr Phe Gly Gln Gly Thr Ile Leu Thr Val
            100                 105                 110

His Pro


<210> SEQ ID NO 145
<211> LENGTH: 108
<212> TYPE: PRT
<213> ORGANISM: Homo sapiens

<400> SEQUENCE: 145

Gly Ile Thr Gln Ser Pro Lys Tyr Leu Phe Arg Lys Glu Gly Gln Asn
1               5                   10                  15

Val Thr Leu Ser Cys Glu Gln Asn Leu Asn His Asp Ala Met Tyr Trp
            20                  25                  30

Tyr Arg Gln Asp Pro Gly Gln Gly Leu Arg Leu Ile Tyr Tyr Ser Gln
        35                  40                  45

Ile Val Asn Asp Phe Gln Lys Gly Asp Ile Ala Glu Gly Tyr Ser Val
    50                  55                  60

Ser Arg Glu Lys Lys Glu Ser Phe Pro Leu Thr Val Thr Ser Ala Gln
65                  70                  75                  80

Lys Asn Pro Thr Ala Phe Tyr Leu Cys Ala Ser Leu Gln Phe Asn Glu
                85                  90                  95

Gln Phe Phe Gly Pro Gly Thr Arg Leu Thr Val Leu
            100                 105


<210> SEQ ID NO 146
<211> LENGTH: 106
<212> TYPE: PRT
<213> ORGANISM: Homo sapiens

<400> SEQUENCE: 146

Lys Asp Gln Val Phe Gln Pro Ser Thr Val Ala Ser Ser Glu Gly Ala
1               5                   10                  15

Val Val Glu Ile Phe Cys Asn His Ser Val Ser Asn Ala Tyr Asn Phe
            20                  25                  30
```

```
Phe Trp Tyr Leu His Phe Pro Gly Cys Ala Pro Arg Leu Leu Val Lys
        35                  40                  45

Gly Ser Lys Pro Ser Gln Gln Gly Arg Tyr Asn Met Thr Tyr Glu Arg
    50                  55                  60

Phe Ser Ser Ser Leu Leu Ile Leu Gln Val Arg Glu Ala Asp Ala Ala
65                  70                  75                  80

Val Tyr Tyr Cys Ala Val Glu Asp Arg Arg Arg Thr Ala Leu Ile Phe
                85                  90                  95

Gly Lys Gly Thr Thr Leu Ser Val Ser Ser
            100                 105


<210> SEQ ID NO 147
<211> LENGTH: 115
<212> TYPE: PRT
<213> ORGANISM: Homo sapiens

<400> SEQUENCE: 147

Glu Pro Glu Val Thr Gln Thr Pro Ser His Gln Val Thr Gln Met Gly
1               5                   10                  15

Gln Glu Val Ile Leu Arg Cys Val Pro Ile Ser Asn His Leu Tyr Phe
            20                  25                  30

Tyr Trp Tyr Arg Gln Ile Leu Gly Gln Lys Val Glu Phe Leu Val Ser
        35                  40                  45

Phe Tyr Asn Asn Glu Ile Ser Glu Lys Ser Glu Ile Phe Asp Asp Gln
    50                  55                  60

Phe Ser Val Glu Arg Pro Asp Gly Ser Asn Phe Thr Leu Lys Ile Arg
65                  70                  75                  80

Ser Thr Lys Leu Glu Asp Ser Ala Met Tyr Phe Cys Ala Ser Ser Glu
                85                  90                  95

Tyr Gln Ser Gln Ser Asn Glu Gln Phe Phe Gly Pro Gly Thr Arg Leu
            100                 105                 110

Thr Val Leu
        115


<210> SEQ ID NO 148
<211> LENGTH: 114
<212> TYPE: PRT
<213> ORGANISM: Homo sapiens

<400> SEQUENCE: 148

Lys Thr Thr Gln Pro Pro Ser Met Asp Cys Ala Glu Gly Arg Ala Ala
1               5                   10                  15

Asn Leu Pro Cys Asn His Ser Thr Ile Ser Gly Asn Glu Tyr Val Tyr
            20                  25                  30

Trp Tyr Arg Gln Ile His Ser Gln Gly Pro Gln Tyr Ile Ile His Gly
        35                  40                  45

Leu Lys Asn Asn Glu Thr Asn Glu Met Ala Ser Leu Ile Ile Thr Glu
    50                  55                  60

Asp Arg Lys Ser Ser Thr Leu Ile Leu Pro His Ala Thr Leu Arg Asp
65                  70                  75                  80

Thr Ala Val Tyr Tyr Cys Ile Val Arg Gly Ser Pro Gly Ala Gly Gly
                85                  90                  95

Thr Ser Tyr Gly Lys Leu Thr Phe Gly Gln Gly Thr Ile Leu Thr Val
            100                 105                 110

His Pro
```

<210> SEQ ID NO 149
<211> LENGTH: 108
<212> TYPE: PRT
<213> ORGANISM: Homo sapiens

<400> SEQUENCE: 149

```
Gly Ile Thr Gln Ser Pro Lys Tyr Leu Phe Arg Lys Glu Gly Gln Asn
1               5                   10                  15

Val Thr Leu Ser Cys Glu Gln Asn Leu Asn His Asp Ala Met Tyr Trp
            20                  25                  30

Tyr Arg Gln Asp Pro Gly Gln Gly Leu Arg Leu Ile Tyr Tyr Ser Gln
        35                  40                  45

Ile Val Asn Asp Phe Gln Lys Gly Asp Ile Ala Glu Gly Tyr Ser Val
    50                  55                  60

Ser Arg Glu Lys Lys Glu Ser Phe Pro Leu Thr Val Thr Ser Ala Gln
65                  70                  75                  80

Lys Asn Pro Thr Ala Phe Tyr Leu Cys Ala Ser Ser Ile Arg Thr Glu
                85                  90                  95

Ala Phe Phe Gly Gln Gly Thr Arg Leu Thr Val Val
            100                 105
```

<210> SEQ ID NO 150
<211> LENGTH: 111
<212> TYPE: PRT
<213> ORGANISM: Homo sapiens

<400> SEQUENCE: 150

```
Gln Gln Val Met Gln Ile Pro Gln Tyr Gln His Val Gln Glu Gly Glu
1               5                   10                  15

Asp Phe Thr Thr Tyr Cys Asn Ser Ser Thr Thr Leu Ser Asn Ile Gln
            20                  25                  30

Trp Tyr Lys Gln Arg Pro Gly Gly His Pro Val Phe Leu Ile Gln Leu
        35                  40                  45

Val Lys Ser Gly Glu Val Lys Lys Gln Lys Arg Leu Thr Phe Gln Phe
    50                  55                  60

Gly Glu Ala Lys Lys Asn Ser Ser Leu His Ile Thr Ala Thr Gln Thr
65                  70                  75                  80

Thr Asp Val Gly Thr Tyr Phe Cys Ala Gly Pro Gly Gly Ala Gly Ser
                85                  90                  95

Tyr Gln Leu Thr Phe Gly Lys Gly Thr Lys Leu Ser Val Ile Pro
            100                 105                 110
```

<210> SEQ ID NO 151
<211> LENGTH: 114
<212> TYPE: PRT
<213> ORGANISM: Homo sapiens

<400> SEQUENCE: 151

```
Gln Val Thr Gln Asn Pro Arg Tyr Leu Ile Thr Val Thr Gly Lys Lys
1               5                   10                  15

Leu Thr Val Thr Cys Ser Gln Asn Met Asn His Glu Tyr Met Ser Trp
            20                  25                  30

Tyr Arg Gln Asp Pro Gly Leu Gly Leu Arg Gln Ile Tyr Tyr Ser Met
        35                  40                  45

Asn Val Glu Val Thr Asp Lys Gly Asp Val Pro Glu Gly Tyr Lys Val
    50                  55                  60

Ser Arg Lys Glu Lys Arg Asn Phe Pro Leu Ile Leu Glu Ser Pro Ser
65                  70                  75                  80
```

Pro Asn Gln Thr Ser Leu Tyr Phe Cys Ala Ser Ser Pro Phe Val Val
85 90 95

Ile Gly Gln Ile Asn Glu Gln Tyr Phe Gly Pro Gly Thr Arg Leu Thr
100 105 110

Val Thr

<210> SEQ ID NO 152
<211> LENGTH: 112
<212> TYPE: PRT
<213> ORGANISM: Homo sapiens

<400> SEQUENCE: 152

Glu Leu Lys Val Glu Gln Asn Pro Leu Phe Leu Ser Met Gln Glu Gly
1 5 10 15

Lys Asn Tyr Thr Ile Tyr Cys Asn Tyr Ser Thr Thr Ser Asp Arg Leu
20 25 30

Tyr Trp Tyr Arg Gln Asp Pro Gly Lys Ser Leu Glu Ser Leu Phe Val
35 40 45

Leu Leu Ser Asn Gly Ala Val Lys Gln Glu Gly Arg Leu Met Ala Ser
50 55 60

Leu Asp Thr Lys Ala Arg Leu Ser Thr Leu His Ile Thr Ala Ala Val
65 70 75 80

His Asp Leu Ser Ala Thr Tyr Phe Cys Ala Val Ala His Met Asp Ser
85 90 95

Asn Tyr Gln Leu Ile Trp Gly Ala Gly Thr Lys Leu Ile Ile Lys Pro
100 105 110

<210> SEQ ID NO 153
<211> LENGTH: 113
<212> TYPE: PRT
<213> ORGANISM: Homo sapiens

<400> SEQUENCE: 153

Gly Val Thr Gln Thr Pro Lys Phe Arg Val Leu Lys Thr Gly Gln Ser
1 5 10 15

Met Thr Leu Leu Cys Ala Gln Asp Met Asn His Glu Tyr Met Tyr Trp
20 25 30

Tyr Arg Gln Asp Pro Gly Met Gly Leu Arg Leu Ile His Tyr Ser Val
35 40 45

Gly Glu Gly Thr Thr Ala Lys Gly Glu Val Pro Asp Gly Tyr Asn Val
50 55 60

Ser Arg Leu Lys Lys Gln Asn Phe Leu Leu Gly Leu Glu Ser Ala Ala
65 70 75 80

Pro Ser Gln Thr Ser Val Tyr Phe Cys Ala Ser Ser Tyr Ala Gly Leu
85 90 95

Ala Ala Pro Arg Glu Gln Phe Phe Gly Pro Gly Thr Arg Leu Thr Val
100 105 110

Leu

<210> SEQ ID NO 154
<211> LENGTH: 114
<212> TYPE: PRT
<213> ORGANISM: Homo sapiens

<400> SEQUENCE: 154

Lys Thr Thr Gln Pro Pro Ser Met Asp Cys Ala Glu Gly Arg Ala Ala
1 5 10 15

Asn Leu Pro Cys Asn His Ser Thr Ile Ser Gly Asn Glu Tyr Val Tyr
20 25 30

Trp Tyr Arg Gln Ile His Ser Gln Gly Pro Gln Tyr Ile Ile His Gly
35 40 45

Leu Lys Asn Asn Glu Thr Asn Glu Met Ala Ser Leu Ile Ile Thr Glu
50 55 60

Asp Arg Lys Ser Ser Thr Leu Ile Leu Pro His Ala Thr Leu Arg Asp
65 70 75 80

Thr Ala Val Tyr Tyr Cys Ile Val Arg Ala Arg Ala Asn Ala Gly Gly
85 90 95

Thr Ser Tyr Gly Lys Leu Thr Phe Gly Gln Gly Thr Ile Leu Thr Val
100 105 110

His Pro

<210> SEQ ID NO 155
<211> LENGTH: 108
<212> TYPE: PRT
<213> ORGANISM: Homo sapiens

<400> SEQUENCE: 155

Gly Ile Thr Gln Ser Pro Lys Tyr Leu Phe Arg Lys Glu Gly Gln Asn
1 5 10 15

Val Thr Leu Ser Cys Glu Gln Asn Leu Asn His Asp Ala Met Tyr Trp
20 25 30

Tyr Arg Gln Asp Pro Gly Gln Gly Leu Arg Leu Ile Tyr Tyr Ser Gln
35 40 45

Ile Val Asn Asp Phe Gln Lys Gly Asp Ile Ala Glu Gly Tyr Ser Val
50 55 60

Ser Arg Glu Lys Lys Glu Ser Phe Pro Leu Thr Val Thr Ser Ala Gln
65 70 75 80

Lys Asn Pro Thr Ala Phe Tyr Leu Cys Ala Thr Arg Thr Gly Asn Glu
85 90 95

Ala Phe Phe Gly Gln Gly Thr Arg Leu Thr Val Val
100 105

<210> SEQ ID NO 156
<211> LENGTH: 116
<212> TYPE: PRT
<213> ORGANISM: Homo sapiens

<400> SEQUENCE: 156

Gln Ser Val Ala Gln Pro Glu Asp Gln Val Asn Val Ala Glu Gly Asn
1 5 10 15

Pro Leu Thr Val Lys Cys Thr Tyr Ser Val Ser Gly Asn Pro Tyr Leu
20 25 30

Phe Trp Tyr Val Gln Tyr Pro Asn Arg Gly Leu Gln Phe Leu Leu Lys
35 40 45

Tyr Ile Thr Gly Asp Asn Leu Val Lys Gly Ser Tyr Gly Phe Glu Ala
50 55 60

Glu Phe Asn Lys Ser Gln Thr Ser Phe His Leu Lys Lys Pro Ser Ala
65 70 75 80

Leu Val Ser Asp Ser Ala Leu Tyr Phe Cys Ala Val Arg Asp Gly Ser
85 90 95

Ala Thr Ser Gly Thr Tyr Lys Tyr Ile Phe Gly Thr Gly Thr Arg Leu
100 105 110

```
Lys Val Leu Ala
        115


<210> SEQ ID NO 157
<211> LENGTH: 113
<212> TYPE: PRT
<213> ORGANISM: Homo sapiens

<400> SEQUENCE: 157

Asp Thr Gly Val Ser Gln Asp Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Pro
                85                  90                  95

Gly Leu Ala Tyr Glu Gln Tyr Phe Gly Pro Gly Thr Arg Leu Thr Val
            100                 105                 110

Thr


<210> SEQ ID NO 158
<211> LENGTH: 111
<212> TYPE: PRT
<213> ORGANISM: Homo sapiens

<400> SEQUENCE: 158

Gln Val Thr Gln Asn Pro Arg Tyr Leu Ile Thr Val Thr Gly Lys Lys
1               5                   10                  15

Leu Thr Val Thr Cys Ser Gln Asn Met Asn His Glu Tyr Met Ser Trp
            20                  25                  30

Tyr Arg Gln Asp Pro Gly Leu Gly Leu Arg Gln Ile Tyr Tyr Ser Met
        35                  40                  45

Asn Val Glu Val Thr Asp Lys Gly Asp Val Pro Glu Gly Tyr Lys Val
    50                  55                  60

Ser Arg Lys Glu Lys Arg Asn Phe Pro Leu Ile Leu Glu Ser Pro Ser
65                  70                  75                  80

Pro Asn Gln Thr Ser Leu Tyr Phe Cys Ala Ser Ser Ile Gln Gln Gly
                85                  90                  95

Ala Asp Thr Gln Tyr Phe Gly Pro Gly Thr Arg Leu Thr Val Leu
            100                 105                 110


<210> SEQ ID NO 159
<211> LENGTH: 115
<212> TYPE: PRT
<213> ORGANISM: Homo sapiens

<400> SEQUENCE: 159

Gln Gln Lys Glu Val Glu Gln Asp Pro Gly Pro Leu Ser Val Pro Glu
1               5                   10                  15

Gly Ala Ile Val Ser Leu Asn Cys Thr Tyr Ser Asn Ser Ala Phe Gln
            20                  25                  30

Tyr Phe Met Trp Tyr Arg Gln Tyr Ser Arg Lys Gly Pro Glu Leu Leu
        35                  40                  45
```

```
Met Tyr Thr Tyr Ser Ser Gly Asn Lys Glu Asp Gly Arg Phe Thr Ala
    50                  55                  60

Gln Val Asp Lys Ser Ser Lys Tyr Ile Ser Leu Phe Ile Arg Asp Ser
65                  70                  75                  80

Gln Pro Ser Asp Ser Ala Thr Tyr Leu Cys Ala Met Ser Gly Leu Lys
                85                  90                  95

Glu Asp Ser Ser Tyr Lys Leu Ile Phe Gly Ser Gly Thr Arg Leu Leu
            100                 105                 110

Val Arg Pro
        115
```

<210> SEQ ID NO 160
<211> LENGTH: 244
<212> TYPE: PRT
<213> ORGANISM: Artificial Sequence
<220> FEATURE:
<223> OTHER INFORMATION: Synthetic

<400> SEQUENCE: 160

```
Lys Thr Thr Gln Pro Asn Ser Met Glu Ser Asn Glu Glu Glu Pro Val
1               5                   10                  15

His Leu Pro Cys Asn His Ser Thr Ile Ser Gly Thr Asp Tyr Ile His
            20                  25                  30

Trp Tyr Arg Gln Leu Pro Ser Gln Gly Pro Glu Tyr Val Ile His Gly
        35                  40                  45

Leu Thr Ser Asn Val Asn Asn Arg Met Ala Ser Leu Ala Ile Ala Glu
    50                  55                  60

Asp Arg Lys Ser Ser Thr Leu Ile Leu His Arg Ala Thr Leu Arg Asp
65                  70                  75                  80

Ala Ala Val Tyr Tyr Cys Ile Leu Arg Asp Asn Asn Ala Arg Leu Met
                85                  90                  95

Phe Gly Asp Gly Thr Gln Leu Val Val Lys Pro Asn Ile Gln Asn Pro
            100                 105                 110

Glu Pro Ala Val Tyr Gln Leu Lys Asp Pro Arg Ser Gln Asp Ser Thr
        115                 120                 125

Leu Cys Leu Phe Thr Asp Phe Asp Ser Gln Ile Asn Val Pro Lys Thr
    130                 135                 140

Met Glu Ser Gly Thr Phe Ile Thr Asp Lys Cys Val Leu Asp Met Lys
145                 150                 155                 160

Ala Met Asp Ser Lys Ser Asn Gly Ala Ile Ala Trp Ser Asn Gln Thr
                165                 170                 175

Ser Phe Thr Cys Gln Asp Ile Phe Lys Glu Thr Asn Ala Thr Tyr Pro
            180                 185                 190

Ser Ser Asp Val Pro Cys Asp Ala Thr Leu Thr Glu Lys Ser Phe Glu
        195                 200                 205

Thr Asp Met Asn Leu Asn Phe Gln Asn Leu Leu Val Ile Val Leu Arg
    210                 215                 220

Ile Leu Leu Leu Lys Val Ala Gly Phe Asn Leu Leu Met Thr Leu Arg
225                 230                 235                 240

Leu Trp Ser Ser
```

<210> SEQ ID NO 161
<211> LENGTH: 284
<212> TYPE: PRT
<213> ORGANISM: Artificial Sequence
<220> FEATURE:

<223> OTHER INFORMATION: Synthetic

<400> SEQUENCE: 161

Gln Val Thr Gln Asn Pro Arg Tyr Leu Ile Thr Val Thr Gly Lys Lys
1 5 10 15

Leu Thr Val Thr Cys Ser Gln Asn Met Asn His Glu Tyr Met Ser Trp
20 25 30

Tyr Arg Gln Asp Pro Gly Leu Gly Leu Arg Gln Ile Tyr Tyr Ser Met
35 40 45

Asn Val Glu Val Thr Asp Lys Gly Asp Val Pro Glu Gly Tyr Lys Val
50 55 60

Ser Arg Lys Glu Lys Arg Asn Phe Pro Leu Ile Leu Glu Ser Pro Ser
65 70 75 80

Pro Asn Gln Thr Ser Leu Tyr Phe Cys Ala Ser Gly Leu Val Gly Phe
85 90 95

Asn Gln Pro Gln His Phe Gly Asp Gly Thr Arg Leu Ser Ile Leu Glu
100 105 110

Asp Leu Arg Asn Val Thr Pro Pro Lys Val Ser Leu Phe Glu Pro Ser
115 120 125

Lys Ala Glu Ile Ala Asn Lys Gln Lys Ala Thr Leu Val Cys Leu Ala
130 135 140

Arg Gly Phe Phe Pro Asp His Val Glu Leu Ser Trp Trp Val Asn Gly
145 150 155 160

Lys Glu Val His Ser Gly Val Cys Thr Asp Pro Gln Ala Tyr Lys Glu
165 170 175

Ser Asn Tyr Ser Tyr Cys Leu Ser Ser Arg Leu Arg Val Ser Ala Thr
180 185 190

Phe Trp His Asn Pro Arg Asn His Phe Arg Cys Gln Val Gln Phe His
195 200 205

Gly Leu Ser Glu Glu Asp Lys Trp Pro Glu Gly Ser Pro Lys Pro Val
210 215 220

Thr Gln Asn Ile Ser Ala Glu Ala Trp Gly Arg Ala Asp Cys Gly Ile
225 230 235 240

Thr Ser Ala Ser Tyr Gln Gln Gly Val Leu Ser Ala Thr Ile Leu Tyr
245 250 255

Glu Ile Leu Leu Gly Lys Ala Thr Leu Tyr Ala Val Leu Val Ser Thr
260 265 270

Leu Val Val Met Ala Met Val Lys Arg Lys Asn Ser
275 280

<210> SEQ ID NO 162
<211> LENGTH: 251
<212> TYPE: PRT
<213> ORGANISM: Artificial Sequence
<220> FEATURE:
<223> OTHER INFORMATION: Synthetic

<400> SEQUENCE: 162

Lys Thr Thr Gln Pro Pro Ser Met Asp Cys Ala Glu Gly Arg Ala Ala
1 5 10 15

Asn Leu Pro Cys Asn His Ser Thr Ile Ser Gly Asn Glu Tyr Val Tyr
20 25 30

Trp Tyr Arg Gln Ile His Ser Gln Gly Pro Gln Tyr Ile Ile His Gly
35 40 45

Leu Lys Asn Asn Glu Thr Asn Glu Met Ala Ser Leu Ile Ile Thr Glu
50 55 60

```
Asp Arg Lys Ser Ser Thr Leu Ile Leu Pro His Ala Thr Leu Arg Asp
65                  70                  75                  80

Thr Ala Val Tyr Tyr Cys Ile Val Arg Ala Arg Ala Asn Ala Gly Gly
                85                  90                  95

Thr Ser Tyr Gly Lys Leu Thr Phe Gly Gln Gly Thr Ile Leu Thr Val
            100                 105                 110

His Pro Asn Ile Gln Asn Pro Glu Pro Ala Val Tyr Gln Leu Lys Asp
        115                 120                 125

Pro Arg Ser Gln Asp Ser Thr Leu Cys Leu Phe Thr Asp Phe Asp Ser
    130                 135                 140

Gln Ile Asn Val Pro Lys Thr Met Glu Ser Gly Thr Phe Ile Thr Asp
145                 150                 155                 160

Lys Cys Val Leu Asp Met Lys Ala Met Asp Ser Lys Ser Asn Gly Ala
                165                 170                 175

Ile Ala Trp Ser Asn Gln Thr Ser Phe Thr Cys Gln Asp Ile Phe Lys
            180                 185                 190

Glu Thr Asn Ala Thr Tyr Pro Ser Ser Asp Val Pro Cys Asp Ala Thr
        195                 200                 205

Leu Thr Glu Lys Ser Phe Glu Thr Asp Met Asn Leu Asn Phe Gln Asn
    210                 215                 220

Leu Leu Val Ile Val Leu Arg Ile Leu Leu Leu Lys Val Ala Gly Phe
225                 230                 235                 240

Asn Leu Leu Met Thr Leu Arg Leu Trp Ser Ser
                245                 250


<210> SEQ ID NO 163
<211> LENGTH: 281
<212> TYPE: PRT
<213> ORGANISM: Artificial Sequence
<220> FEATURE:
<223> OTHER INFORMATION: Synthetic

<400> SEQUENCE: 163

Gly Ile Thr Gln Ser Pro Lys Tyr Leu Phe Arg Lys Glu Gly Gln Asn
1               5                   10                  15

Val Thr Leu Ser Cys Glu Gln Asn Leu Asn His Asp Ala Met Tyr Trp
            20                  25                  30

Tyr Arg Gln Asp Pro Gly Gln Gly Leu Arg Leu Ile Tyr Tyr Ser Gln
        35                  40                  45

Ile Val Asn Asp Phe Gln Lys Gly Asp Ile Ala Glu Gly Tyr Ser Val
    50                  55                  60

Ser Arg Glu Lys Lys Glu Ser Phe Pro Leu Thr Val Thr Ser Ala Gln
65                  70                  75                  80

Lys Asn Pro Thr Ala Phe Tyr Leu Cys Ala Ser Leu Gln Phe Asn Glu
                85                  90                  95

Gln Phe Phe Gly Pro Gly Thr Arg Leu Thr Val Leu Glu Asp Leu Arg
            100                 105                 110

Asn Val Thr Pro Pro Lys Val Ser Leu Phe Glu Pro Ser Lys Ala Glu
        115                 120                 125

Ile Ala Asn Lys Gln Lys Ala Thr Leu Val Cys Leu Ala Arg Gly Phe
    130                 135                 140

Phe Pro Asp His Val Glu Leu Ser Trp Trp Val Asn Gly Lys Glu Val
145                 150                 155                 160

His Ser Gly Val Cys Thr Asp Pro Gln Ala Tyr Lys Glu Ser Asn Tyr
                165                 170                 175
```

```
Ser Tyr Cys Leu Ser Ser Arg Leu Arg Val Ser Ala Thr Phe Trp His
            180                 185                 190

Asn Pro Arg Asn His Phe Arg Cys Gln Val Gln Phe His Gly Leu Ser
        195                 200                 205

Glu Glu Asp Lys Trp Pro Glu Gly Ser Pro Lys Pro Val Thr Gln Asn
    210                 215                 220

Ile Ser Ala Glu Ala Trp Gly Arg Ala Asp Cys Gly Ile Thr Ser Ala
225                 230                 235                 240

Ser Tyr Gln Gln Gly Val Leu Ser Ala Thr Ile Leu Tyr Glu Ile Leu
                245                 250                 255

Leu Gly Lys Ala Thr Leu Tyr Ala Val Leu Val Ser Thr Leu Val Val
            260                 265                 270

Met Ala Met Val Lys Arg Lys Asn Ser
        275                 280


<210> SEQ ID NO 164
<211> LENGTH: 243
<212> TYPE: PRT
<213> ORGANISM: Artificial Sequence
<220> FEATURE:
<223> OTHER INFORMATION: Synthetic

<400> SEQUENCE: 164

Lys Asp Gln Val Phe Gln Pro Ser Thr Val Ala Ser Ser Glu Gly Ala
1               5                   10                  15

Val Val Glu Ile Phe Cys Asn His Ser Val Ser Asn Ala Tyr Asn Phe
            20                  25                  30

Phe Trp Tyr Leu His Phe Pro Gly Cys Ala Pro Arg Leu Leu Val Lys
        35                  40                  45

Gly Ser Lys Pro Ser Gln Gln Gly Arg Tyr Asn Met Thr Tyr Glu Arg
    50                  55                  60

Phe Ser Ser Ser Leu Leu Ile Leu Gln Val Arg Glu Ala Asp Ala Ala
65                  70                  75                  80

Val Tyr Tyr Cys Ala Val Glu Asp Arg Arg Arg Thr Ala Leu Ile Phe
                85                  90                  95

Gly Lys Gly Thr Thr Leu Ser Val Ser Ser Asn Ile Gln Asn Pro Glu
            100                 105                 110

Pro Ala Val Tyr Gln Leu Lys Asp Pro Arg Ser Gln Asp Ser Thr Leu
        115                 120                 125

Cys Leu Phe Thr Asp Phe Asp Ser Gln Ile Asn Val Pro Lys Thr Met
    130                 135                 140

Glu Ser Gly Thr Phe Ile Thr Asp Lys Cys Val Leu Asp Met Lys Ala
145                 150                 155                 160

Met Asp Ser Lys Ser Asn Gly Ala Ile Ala Trp Ser Asn Gln Thr Ser
                165                 170                 175

Phe Thr Cys Gln Asp Ile Phe Lys Glu Thr Asn Ala Thr Tyr Pro Ser
            180                 185                 190

Ser Asp Val Pro Cys Asp Ala Thr Leu Thr Glu Lys Ser Phe Glu Thr
        195                 200                 205

Asp Met Asn Leu Asn Phe Gln Asn Leu Leu Val Ile Val Leu Arg Ile
    210                 215                 220

Leu Leu Leu Lys Val Ala Gly Phe Asn Leu Leu Met Thr Leu Arg Leu
225                 230                 235                 240

Trp Ser Ser
```

<210> SEQ ID NO 165
<211> LENGTH: 288
<212> TYPE: PRT
<213> ORGANISM: Artificial Sequence
<220> FEATURE:
<223> OTHER INFORMATION: Synthetic

<400> SEQUENCE: 165

```
Glu Pro Glu Val Thr Gln Thr Pro Ser His Gln Val Thr Gln Met Gly
1               5                   10                  15

Gln Glu Val Ile Leu Arg Cys Val Pro Ile Ser Asn His Leu Tyr Phe
            20                  25                  30

Tyr Trp Tyr Arg Gln Ile Leu Gly Gln Lys Val Glu Phe Leu Val Ser
        35                  40                  45

Phe Tyr Asn Asn Glu Ile Ser Glu Lys Ser Glu Ile Phe Asp Asp Gln
    50                  55                  60

Phe Ser Val Glu Arg Pro Asp Gly Ser Asn Phe Thr Leu Lys Ile Arg
65                  70                  75                  80

Ser Thr Lys Leu Glu Asp Ser Ala Met Tyr Phe Cys Ala Ser Ser Glu
                85                  90                  95

Tyr Gln Ser Gln Ser Asn Glu Gln Phe Phe Gly Pro Gly Thr Arg Leu
            100                 105                 110

Thr Val Leu Glu Asp Leu Arg Asn Val Thr Pro Pro Lys Val Ser Leu
        115                 120                 125

Phe Glu Pro Ser Lys Ala Glu Ile Ala Asn Lys Gln Lys Ala Thr Leu
    130                 135                 140

Val Cys Leu Ala Arg Gly Phe Phe Pro Asp His Val Glu Leu Ser Trp
145                 150                 155                 160

Trp Val Asn Gly Lys Glu Val His Ser Gly Val Cys Thr Asp Pro Gln
                165                 170                 175

Ala Tyr Lys Glu Ser Asn Tyr Ser Tyr Cys Leu Ser Ser Arg Leu Arg
            180                 185                 190

Val Ser Ala Thr Phe Trp His Asn Pro Arg Asn His Phe Arg Cys Gln
        195                 200                 205

Val Gln Phe His Gly Leu Ser Glu Glu Asp Lys Trp Pro Glu Gly Ser
    210                 215                 220

Pro Lys Pro Val Thr Gln Asn Ile Ser Ala Glu Ala Trp Gly Arg Ala
225                 230                 235                 240

Asp Cys Gly Ile Thr Ser Ala Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Thr Leu Val Val Met Ala Met Val Lys Arg Lys Asn Ser
        275                 280                 285
```

<210> SEQ ID NO 166
<211> LENGTH: 251
<212> TYPE: PRT
<213> ORGANISM: Artificial Sequence
<220> FEATURE:
<223> OTHER INFORMATION: Synthetic

<400> SEQUENCE: 166

```
Lys Thr Thr Gln Pro Pro Ser Met Asp Cys Ala Glu Gly Arg Ala Ala
1               5                   10                  15

Asn Leu Pro Cys Asn His Ser Thr Ile Ser Gly Asn Glu Tyr Val Tyr
            20                  25                  30
```

```
Trp Tyr Arg Gln Ile His Ser Gln Gly Pro Gln Tyr Ile Ile His Gly
        35                  40                  45

Leu Lys Asn Asn Glu Thr Asn Glu Met Ala Ser Leu Ile Ile Thr Glu
    50                  55                  60

Asp Arg Lys Ser Ser Thr Leu Ile Leu Pro His Ala Thr Leu Arg Asp
65                  70                  75                  80

Thr Ala Val Tyr Tyr Cys Ile Val Arg Gly Ser Pro Gly Ala Gly Gly
                85                  90                  95

Thr Ser Tyr Gly Lys Leu Thr Phe Gly Gln Gly Thr Ile Leu Thr Val
            100                 105                 110

His Pro Asn Ile Gln Asn Pro Glu Pro Ala Val Tyr Gln Leu Lys Asp
        115                 120                 125

Pro Arg Ser Gln Asp Ser Thr Leu Cys Leu Phe Thr Asp Phe Asp Ser
    130                 135                 140

Gln Ile Asn Val Pro Lys Thr Met Glu Ser Gly Thr Phe Ile Thr Asp
145                 150                 155                 160

Lys Cys Val Leu Asp Met Lys Ala Met Asp Ser Lys Ser Asn Gly Ala
                165                 170                 175

Ile Ala Trp Ser Asn Gln Thr Ser Phe Thr Cys Gln Asp Ile Phe Lys
            180                 185                 190

Glu Thr Asn Ala Thr Tyr Pro Ser Ser Asp Val Pro Cys Asp Ala Thr
        195                 200                 205

Leu Thr Glu Lys Ser Phe Glu Thr Asp Met Asn Leu Asn Phe Gln Asn
    210                 215                 220

Leu Leu Val Ile Val Leu Arg Ile Leu Leu Leu Lys Val Ala Gly Phe
225                 230                 235                 240

Asn Leu Leu Met Thr Leu Arg Leu Trp Ser Ser
                245                 250
```

<210> SEQ ID NO 167
<211> LENGTH: 281
<212> TYPE: PRT
<213> ORGANISM: Artificial Sequence
<220> FEATURE:
<223> OTHER INFORMATION: Synthetic

<400> SEQUENCE: 167

```
Gly Ile Thr Gln Ser Pro Lys Tyr Leu Phe Arg Lys Glu Gly Gln Asn
1               5                   10                  15

Val Thr Leu Ser Cys Glu Gln Asn Leu Asn His Asp Ala Met Tyr Trp
            20                  25                  30

Tyr Arg Gln Asp Pro Gly Gln Gly Leu Arg Leu Ile Tyr Tyr Ser Gln
        35                  40                  45

Ile Val Asn Asp Phe Gln Lys Gly Asp Ile Ala Glu Gly Tyr Ser Val
    50                  55                  60

Ser Arg Glu Lys Lys Glu Ser Phe Pro Leu Thr Val Thr Ser Ala Gln
65                  70                  75                  80

Lys Asn Pro Thr Ala Phe Tyr Leu Cys Ala Ser Ser Ile Arg Thr Glu
                85                  90                  95

Ala Phe Phe Gly Gln Gly Thr Arg Leu Thr Val Val Glu Asp Leu Arg
            100                 105                 110

Asn Val Thr Pro Pro Lys Val Ser Leu Phe Glu Pro Ser Lys Ala Glu
        115                 120                 125

Ile Ala Asn Lys Gln Lys Ala Thr Leu Val Cys Leu Ala Arg Gly Phe
    130                 135                 140
```

```
Phe Pro Asp His Val Glu Leu Ser Trp Trp Val Asn Gly Lys Glu Val
145                 150                 155                 160

His Ser Gly Val Cys Thr Asp Pro Gln Ala Tyr Lys Glu Ser Asn Tyr
                165                 170                 175

Ser Tyr Cys Leu Ser Ser Arg Leu Arg Val Ser Ala Thr Phe Trp His
            180                 185                 190

Asn Pro Arg Asn His Phe Arg Cys Gln Val Gln Phe His Gly Leu Ser
        195                 200                 205

Glu Glu Asp Lys Trp Pro Glu Gly Ser Pro Lys Pro Val Thr Gln Asn
    210                 215                 220

Ile Ser Ala Glu Ala Trp Gly Arg Ala Asp Cys Gly Ile Thr Ser Ala
225                 230                 235                 240

Ser Tyr Gln Gln Gly Val Leu Ser Ala Thr Ile Leu Tyr Glu Ile Leu
                245                 250                 255

Leu Gly Lys Ala Thr Leu Tyr Ala Val Leu Val Ser Thr Leu Val Val
            260                 265                 270

Met Ala Met Val Lys Arg Lys Asn Ser
        275                 280


<210> SEQ ID NO 168
<211> LENGTH: 248
<212> TYPE: PRT
<213> ORGANISM: Artificial Sequence
<220> FEATURE:
<223> OTHER INFORMATION: Synthetic

<400> SEQUENCE: 168

Gln Gln Val Met Gln Ile Pro Gln Tyr Gln His Val Gln Glu Gly Glu
1               5                   10                  15

Asp Phe Thr Thr Tyr Cys Asn Ser Ser Thr Thr Leu Ser Asn Ile Gln
            20                  25                  30

Trp Tyr Lys Gln Arg Pro Gly Gly His Pro Val Phe Leu Ile Gln Leu
        35                  40                  45

Val Lys Ser Gly Glu Val Lys Lys Gln Lys Arg Leu Thr Phe Gln Phe
    50                  55                  60

Gly Glu Ala Lys Lys Asn Ser Ser Leu His Ile Thr Ala Thr Gln Thr
65                  70                  75                  80

Thr Asp Val Gly Thr Tyr Phe Cys Ala Gly Pro Gly Gly Ala Gly Ser
                85                  90                  95

Tyr Gln Leu Thr Phe Gly Lys Gly Thr Lys Leu Ser Val Ile Pro Asn
            100                 105                 110

Ile Gln Asn Pro Glu Pro Ala Val Tyr Gln Leu Lys Asp Pro Arg Ser
        115                 120                 125

Gln Asp Ser Thr Leu Cys Leu Phe Thr Asp Phe Asp Ser Gln Ile Asn
    130                 135                 140

Val Pro Lys Thr Met Glu Ser Gly Thr Phe Ile Thr Asp Lys Cys Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
        195                 200                 205

Lys Ser Phe Glu Thr Asp Met Asn Leu Asn Phe Gln Asn Leu Leu Val
    210                 215                 220
```

Ile Val Leu Arg Ile Leu Leu Leu Lys Val Ala Gly Phe Asn Leu Leu
225 230 235 240

Met Thr Leu Arg Leu Trp Ser Ser
245

<210> SEQ ID NO 169
<211> LENGTH: 287
<212> TYPE: PRT
<213> ORGANISM: Artificial Sequence
<220> FEATURE:
<223> OTHER INFORMATION: Synthetic

<400> SEQUENCE: 169

Gln Val Thr Gln Asn Pro Arg Tyr Leu Ile Thr Val Thr Gly Lys Lys
1 5 10 15

Leu Thr Val Thr Cys Ser Gln Asn Met Asn His Glu Tyr Met Ser Trp
20 25 30

Tyr Arg Gln Asp Pro Gly Leu Gly Leu Arg Gln Ile Tyr Tyr Ser Met
35 40 45

Asn Val Glu Val Thr Asp Lys Gly Asp Val Pro Glu Gly Tyr Lys Val
50 55 60

Ser Arg Lys Glu Lys Arg Asn Phe Pro Leu Ile Leu Glu Ser Pro Ser
65 70 75 80

Pro Asn Gln Thr Ser Leu Tyr Phe Cys Ala Ser Ser Pro Phe Val Val
85 90 95

Ile Gly Gln Ile Asn Glu Gln Tyr Phe Gly Pro Gly Thr Arg Leu Thr
100 105 110

Val Thr Glu Asp Leu Arg Asn Val Thr Pro Pro Lys Val Ser Leu Phe
115 120 125

Glu Pro Ser Lys Ala Glu Ile Ala Asn Lys Gln Lys Ala Thr Leu Val
130 135 140

Cys Leu Ala Arg Gly Phe Phe Pro Asp His Val Glu Leu Ser Trp Trp
145 150 155 160

Val Asn Gly Lys Glu Val His Ser Gly Val Cys Thr Asp Pro Gln Ala
165 170 175

Tyr Lys Glu Ser Asn Tyr Ser Tyr Cys Leu Ser Ser Arg Leu Arg Val
180 185 190

Ser Ala Thr Phe Trp His Asn Pro Arg Asn His Phe Arg Cys Gln Val
195 200 205

Gln Phe His Gly Leu Ser Glu Glu Asp Lys Trp Pro Glu Gly Ser Pro
210 215 220

Lys Pro Val Thr Gln Asn Ile Ser Ala Glu Ala Trp Gly Arg Ala Asp
225 230 235 240

Cys Gly Ile Thr Ser Ala Ser Tyr Gln Gln Gly Val Leu Ser Ala Thr
245 250 255

Ile Leu Tyr Glu Ile Leu Leu Gly Lys Ala Thr Leu Tyr Ala Val Leu
260 265 270

Val Ser Thr Leu Val Val Met Ala Met Val Lys Arg Lys Asn Ser
275 280 285

<210> SEQ ID NO 170
<211> LENGTH: 249
<212> TYPE: PRT
<213> ORGANISM: Artificial Sequence
<220> FEATURE:
<223> OTHER INFORMATION: Synthetic

<400> SEQUENCE: 170

Glu Leu Lys Val Glu Gln Asn Pro Leu Phe Leu Ser Met Gln Glu Gly
1               5                   10                  15

Lys Asn Tyr Thr Ile Tyr Cys Asn Tyr Ser Thr Thr Ser Asp Arg Leu
            20                  25                  30

Tyr Trp Tyr Arg Gln Asp Pro Gly Lys Ser Leu Glu Ser Leu Phe Val
        35                  40                  45

Leu Leu Ser Asn Gly Ala Val Lys Gln Glu Gly Arg Leu Met Ala Ser
    50                  55                  60

Leu Asp Thr Lys Ala Arg Leu Ser Thr Leu His Ile Thr Ala Ala Val
65                  70                  75                  80

His Asp Leu Ser Ala Thr Tyr Phe Cys Ala Val Ala His Met Asp Ser
                85                  90                  95

Asn Tyr Gln Leu Ile Trp Gly Ala Gly Thr Lys Leu Ile Ile Lys Pro
            100                 105                 110

Asn Ile Gln Asn Pro Glu Pro Ala Val Tyr Gln Leu Lys Asp Pro Arg
        115                 120                 125

Ser Gln Asp Ser Thr Leu Cys Leu Phe Thr Asp Phe Asp Ser Gln Ile
    130                 135                 140

Asn Val Pro Lys Thr Met Glu Ser Gly Thr Phe Ile Thr Asp Lys Cys
145                 150                 155                 160

Val Leu Asp Met Lys Ala Met Asp Ser Lys Ser Asn Gly Ala Ile Ala
                165                 170                 175

Trp Ser Asn Gln Thr Ser Phe Thr Cys Gln Asp Ile Phe Lys Glu Thr
            180                 185                 190

Asn Ala Thr Tyr Pro Ser Ser Asp Val Pro Cys Asp Ala Thr Leu Thr
        195                 200                 205

Glu Lys Ser Phe Glu Thr Asp Met Asn Leu Asn Phe Gln Asn Leu Leu
    210                 215                 220

Val Ile Val Leu Arg Ile Leu Leu Leu Lys Val Ala Gly Phe Asn Leu
225                 230                 235                 240

Leu Met Thr Leu Arg Leu Trp Ser Ser
                245

<210> SEQ ID NO 171
<211> LENGTH: 286
<212> TYPE: PRT
<213> ORGANISM: Artificial Sequence
<220> FEATURE:
<223> OTHER INFORMATION: Synthetic

<400> SEQUENCE: 171

Gly Val Thr Gln Thr Pro Lys Phe Arg Val Leu Lys Thr Gly Gln Ser
1               5                   10                  15

Met Thr Leu Leu Cys Ala Gln Asp Met Asn His Glu Tyr Met Tyr Trp
            20                  25                  30

Tyr Arg Gln Asp Pro Gly Met Gly Leu Arg Leu Ile His Tyr Ser Val
        35                  40                  45

Gly Glu Gly Thr Thr Ala Lys Gly Glu Val Pro Asp Gly Tyr Asn Val
    50                  55                  60

Ser Arg Leu Lys Lys Gln Asn Phe Leu Leu Gly Leu Glu Ser Ala Ala
65                  70                  75                  80

Pro Ser Gln Thr Ser Val Tyr Phe Cys Ala Ser Ser Tyr Ala Gly Leu
                85                  90                  95

Ala Ala Pro Arg Glu Gln Phe Phe Gly Pro Gly Thr Arg Leu Thr Val

```
            100                 105                 110

Leu Glu Asp Leu Arg Asn Val Thr Pro Pro Lys Val Ser Leu Phe Glu
        115                 120                 125

Pro Ser Lys Ala Glu Ile Ala Asn Lys Gln Lys Ala Thr Leu Val Cys
    130                 135                 140

Leu Ala Arg Gly Phe Phe Pro Asp His Val Glu Leu Ser Trp Trp Val
145                 150                 155                 160

Asn Gly Lys Glu Val His Ser Gly Val Cys Thr Asp Pro Gln Ala Tyr
                165                 170                 175

Lys Glu Ser Asn Tyr Ser Tyr Cys Leu Ser Ser Arg Leu Arg Val Ser
            180                 185                 190

Ala Thr Phe Trp His Asn Pro Arg Asn His Phe Arg Cys Gln Val Gln
        195                 200                 205

Phe His Gly Leu Ser Glu Glu Asp Lys Trp Pro Glu Gly Ser Pro Lys
    210                 215                 220

Pro Val Thr Gln Asn Ile Ser Ala Glu Ala Trp Gly Arg Ala Asp Cys
225                 230                 235                 240

Gly Ile Thr Ser Ala Ser Tyr Gln Gln Gly Val Leu Ser Ala Thr Ile
                245                 250                 255

Leu Tyr Glu Ile Leu Leu Gly Lys Ala Thr Leu Tyr Ala Val Leu Val
            260                 265                 270

Ser Thr Leu Val Val Met Ala Met Val Lys Arg Lys Asn Ser
        275                 280                 285


<210> SEQ ID NO 172
<211> LENGTH: 251
<212> TYPE: PRT
<213> ORGANISM: Artificial Sequence
<220> FEATURE:
<223> OTHER INFORMATION: Synthetic

<400> SEQUENCE: 172

Lys Thr Thr Gln Pro Pro Ser Met Asp Cys Ala Glu Gly Arg Ala Ala
1               5                   10                  15

Asn Leu Pro Cys Asn His Ser Thr Ile Ser Gly Asn Glu Tyr Val Tyr
            20                  25                  30

Trp Tyr Arg Gln Ile His Ser Gln Gly Pro Gln Tyr Ile Ile His Gly
        35                  40                  45

Leu Lys Asn Asn Glu Thr Asn Glu Met Ala Ser Leu Ile Ile Thr Glu
    50                  55                  60

Asp Arg Lys Ser Ser Thr Leu Ile Leu Pro His Ala Thr Leu Arg Asp
65                  70                  75                  80

Thr Ala Val Tyr Tyr Cys Ile Val Arg Ala Arg Ala Asn Ala Gly Gly
                85                  90                  95

Thr Ser Tyr Gly Lys Leu Thr Phe Gly Gln Gly Thr Ile Leu Thr Val
            100                 105                 110

His Pro Asn Ile Gln Asn Pro Glu Pro Ala Val Tyr Gln Leu Lys Asp
        115                 120                 125

Pro Arg Ser Gln Asp Ser Thr Leu Cys Leu Phe Thr Asp Phe Asp Ser
    130                 135                 140

Gln Ile Asn Val Pro Lys Thr Met Glu Ser Gly Thr Phe Ile Thr Asp
145                 150                 155                 160

Lys Cys Val Leu Asp Met Lys Ala Met Asp Ser Lys Ser Asn Gly Ala
                165                 170                 175

Ile Ala Trp Ser Asn Gln Thr Ser Phe Thr Cys Gln Asp Ile Phe Lys
```

```
            180                 185                 190

Glu Thr Asn Ala Thr Tyr Pro Ser Ser Asp Val Pro Cys Asp Ala Thr
        195                 200                 205

Leu Thr Glu Lys Ser Phe Glu Thr Asp Met Asn Leu Asn Phe Gln Asn
    210                 215                 220

Leu Leu Val Ile Val Leu Arg Ile Leu Leu Leu Lys Val Ala Gly Phe
225                 230                 235                 240

Asn Leu Leu Met Thr Leu Arg Leu Trp Ser Ser
                245                 250


<210> SEQ ID NO 173
<211> LENGTH: 281
<212> TYPE: PRT
<213> ORGANISM: Artificial Sequence
<220> FEATURE:
<223> OTHER INFORMATION: Synthetic

<400> SEQUENCE: 173

Gly Ile Thr Gln Ser Pro Lys Tyr Leu Phe Arg Lys Glu Gly Gln Asn
1               5                   10                  15

Val Thr Leu Ser Cys Glu Gln Asn Leu Asn His Asp Ala Met Tyr Trp
            20                  25                  30

Tyr Arg Gln Asp Pro Gly Gln Gly Leu Arg Leu Ile Tyr Tyr Ser Gln
        35                  40                  45

Ile Val Asn Asp Phe Gln Lys Gly Asp Ile Ala Glu Gly Tyr Ser Val
    50                  55                  60

Ser Arg Glu Lys Lys Glu Ser Phe Pro Leu Thr Val Thr Ser Ala Gln
65                  70                  75                  80

Lys Asn Pro Thr Ala Phe Tyr Leu Cys Ala Thr Arg Thr Gly Asn Glu
                85                  90                  95

Ala Phe Phe Gly Gln Gly Thr Arg Leu Thr Val Val Glu Asp Leu Arg
            100                 105                 110

Asn Val Thr Pro Pro Lys Val Ser Leu Phe Glu Pro Ser Lys Ala Glu
        115                 120                 125

Ile Ala Asn Lys Gln Lys Ala Thr Leu Val Cys Leu Ala Arg Gly Phe
    130                 135                 140

Phe Pro Asp His Val Glu Leu Ser Trp Trp Val Asn Gly Lys Glu Val
145                 150                 155                 160

His Ser Gly Val Cys Thr Asp Pro Gln Ala Tyr Lys Glu Ser Asn Tyr
                165                 170                 175

Ser Tyr Cys Leu Ser Ser Arg Leu Arg Val Ser Ala Thr Phe Trp His
            180                 185                 190

Asn Pro Arg Asn His Phe Arg Cys Gln Val Gln Phe His Gly Leu Ser
        195                 200                 205

Glu Glu Asp Lys Trp Pro Glu Gly Ser Pro Lys Pro Val Thr Gln Asn
    210                 215                 220

Ile Ser Ala Glu Ala Trp Gly Arg Ala Asp Cys Gly Ile Thr Ser Ala
225                 230                 235                 240

Ser Tyr Gln Gln Gly Val Leu Ser Ala Thr Ile Leu Tyr Glu Ile Leu
                245                 250                 255

Leu Gly Lys Ala Thr Leu Tyr Ala Val Leu Val Ser Thr Leu Val Val
            260                 265                 270

Met Ala Met Val Lys Arg Lys Asn Ser
        275                 280
```

<210> SEQ ID NO 174
<211> LENGTH: 253
<212> TYPE: PRT
<213> ORGANISM: Artificial Sequence
<220> FEATURE:
<223> OTHER INFORMATION: Synthetic

<400> SEQUENCE: 174

```
Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Gly Ser
                85                  90                  95

Ala Thr Ser Gly Thr Tyr Lys Tyr Ile Phe Gly Thr Gly Thr Arg Leu
            100                 105                 110

Lys Val Leu Ala Asn Ile Gln Asn Pro Glu Pro Ala Val Tyr Gln Leu
        115                 120                 125

Lys Asp Pro Arg Ser Gln Asp Ser Thr Leu Cys Leu Phe Thr Asp Phe
    130                 135                 140

Asp Ser Gln Ile Asn Val Pro Lys Thr Met Glu Ser Gly Thr Phe Ile
145                 150                 155                 160

Thr Asp Lys Cys Val Leu Asp Met Lys Ala Met Asp Ser Lys Ser Asn
                165                 170                 175

Gly Ala Ile Ala Trp Ser Asn Gln Thr Ser Phe Thr Cys Gln Asp Ile
            180                 185                 190

Phe Lys Glu Thr Asn Ala Thr Tyr Pro Ser Ser Asp Val Pro Cys Asp
        195                 200                 205

Ala Thr Leu Thr Glu Lys Ser Phe Glu Thr Asp Met Asn Leu Asn Phe
    210                 215                 220

Gln Asn Leu Leu Val Ile Val Leu Arg Ile Leu Leu Leu Lys Val Ala
225                 230                 235                 240

Gly Phe Asn Leu Leu Met Thr Leu Arg Leu Trp Ser Ser
                245                 250
```

<210> SEQ ID NO 175
<211> LENGTH: 286
<212> TYPE: PRT
<213> ORGANISM: Artificial Sequence
<220> FEATURE:
<223> OTHER INFORMATION: Synthetic

<400> SEQUENCE: 175

```
Asp Thr Gly Val Ser Gln Asp Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60
```

Phe Ser Ala Glu Arg Pro Lys Gly Ser Phe Ser Thr Leu Glu Ile Gln
65 70 75 80

Arg Thr Glu Gln Gly Asp Ser Ala Met Tyr Leu Cys Ala Ser Ser Pro
85 90 95

Gly Leu Ala Tyr Glu Gln Tyr Phe Gly Pro Gly Thr Arg Leu Thr Val
100 105 110

Thr Glu Asp Leu Arg Asn Val Thr Pro Pro Lys Val Ser Leu Phe Glu
115 120 125

Pro Ser Lys Ala Glu Ile Ala Asn Lys Gln Lys Ala Thr Leu Val Cys
130 135 140

Leu Ala Arg Gly Phe Phe Pro Asp His Val Glu Leu Ser Trp Trp Val
145 150 155 160

Asn Gly Lys Glu Val His Ser Gly Val Cys Thr Asp Pro Gln Ala Tyr
165 170 175

Lys Glu Ser Asn Tyr Ser Tyr Cys Leu Ser Ser Arg Leu Arg Val Ser
180 185 190

Ala Thr Phe Trp His Asn Pro Arg Asn His Phe Arg Cys Gln Val Gln
195 200 205

Phe His Gly Leu Ser Glu Glu Asp Lys Trp Pro Glu Gly Ser Pro Lys
210 215 220

Pro Val Thr Gln Asn Ile Ser Ala Glu Ala Trp Gly Arg Ala Asp Cys
225 230 235 240

Gly Ile Thr Ser Ala Ser Tyr Gln Gln Gly Val Leu Ser Ala Thr Ile
245 250 255

Leu Tyr Glu Ile Leu Leu Gly Lys Ala Thr Leu Tyr Ala Val Leu Val
260 265 270

Ser Thr Leu Val Val Met Ala Met Val Lys Arg Lys Asn Ser
275 280 285

<210> SEQ ID NO 176
<211> LENGTH: 252
<212> TYPE: PRT
<213> ORGANISM: Artificial Sequence
<220> FEATURE:
<223> OTHER INFORMATION: Synthetic

<400> SEQUENCE: 176

Gln Gln Lys Glu Val Glu Gln Asp Pro Gly Pro Leu Ser Val Pro Glu
1 5 10 15

Gly Ala Ile Val Ser Leu Asn Cys Thr Tyr Ser Asn Ser Ala Phe Gln
20 25 30

Tyr Phe Met Trp Tyr Arg Gln Tyr Ser Arg Lys Gly Pro Glu Leu Leu
35 40 45

Met Tyr Thr Tyr Ser Ser Gly Asn Lys Glu Asp Gly Arg Phe Thr Ala
50 55 60

Gln Val Asp Lys Ser Ser Lys Tyr Ile Ser Leu Phe Ile Arg Asp Ser
65 70 75 80

Gln Pro Ser Asp Ser Ala Thr Tyr Leu Cys Ala Met Ser Gly Leu Lys
85 90 95

Glu Asp Ser Ser Tyr Lys Leu Ile Phe Gly Ser Gly Thr Arg Leu Leu
100 105 110

Val Arg Pro Asn Ile Gln Asn Pro Glu Pro Ala Val Tyr Gln Leu Lys
115 120 125

Asp Pro Arg Ser Gln Asp Ser Thr Leu Cys Leu Phe Thr Asp Phe Asp
130 135 140

```
Ser Gln Ile Asn Val Pro Lys Thr Met Glu Ser Gly Thr Phe Ile Thr
145                 150                 155                 160

Asp Lys Cys Val Leu Asp Met Lys Ala Met Asp Ser Lys Ser Asn Gly
                165                 170                 175

Ala Ile Ala Trp Ser Asn Gln Thr Ser Phe Thr Cys Gln Asp Ile Phe
            180                 185                 190

Lys Glu Thr Asn Ala Thr Tyr Pro Ser Ser Asp Val Pro Cys Asp Ala
        195                 200                 205

Thr Leu Thr Glu Lys Ser Phe Glu Thr Asp Met Asn Leu Asn Phe Gln
    210                 215                 220

Asn Leu Leu Val Ile Val Leu Arg Ile Leu Leu Leu Lys Val Ala Gly
225                 230                 235                 240

Phe Asn Leu Leu Met Thr Leu Arg Leu Trp Ser Ser
                245                 250


<210> SEQ ID NO 177
<211> LENGTH: 284
<212> TYPE: PRT
<213> ORGANISM: Artificial Sequence
<220> FEATURE:
<223> OTHER INFORMATION: Synthetic

<400> SEQUENCE: 177

Gln Val Thr Gln Asn Pro Arg Tyr Leu Ile Thr Val Thr Gly Lys Lys
1               5                   10                  15

Leu Thr Val Thr Cys Ser Gln Asn Met Asn His Glu Tyr Met Ser Trp
            20                  25                  30

Tyr Arg Gln Asp Pro Gly Leu Gly Leu Arg Gln Ile Tyr Tyr Ser Met
        35                  40                  45

Asn Val Glu Val Thr Asp Lys Gly Asp Val Pro Glu Gly Tyr Lys Val
    50                  55                  60

Ser Arg Lys Glu Lys Arg Asn Phe Pro Leu Ile Leu Glu Ser Pro Ser
65                  70                  75                  80

Pro Asn Gln Thr Ser Leu Tyr Phe Cys Ala Ser Ser Ile Gln Gln Gly
                85                  90                  95

Ala Asp Thr Gln Tyr Phe Gly Pro Gly Thr Arg Leu Thr Val Leu Glu
            100                 105                 110

Asp Leu Arg Asn Val Thr Pro Pro Lys Val Ser Leu Phe Glu Pro Ser
        115                 120                 125

Lys Ala Glu Ile Ala Asn Lys Gln Lys Ala Thr Leu Val Cys Leu Ala
    130                 135                 140

Arg Gly Phe Phe Pro Asp His Val Glu Leu Ser Trp Trp Val Asn Gly
145                 150                 155                 160

Lys Glu Val His Ser Gly Val Cys Thr Asp Pro Gln Ala Tyr Lys Glu
                165                 170                 175

Ser Asn Tyr Ser Tyr Cys Leu Ser Ser Arg Leu Arg Val Ser Ala Thr
            180                 185                 190

Phe Trp His Asn Pro Arg Asn His Phe Arg Cys Gln Val Gln Phe His
        195                 200                 205

Gly Leu Ser Glu Glu Asp Lys Trp Pro Glu Gly Ser Pro Lys Pro Val
    210                 215                 220

Thr Gln Asn Ile Ser Ala Glu Ala Trp Gly Arg Ala Asp Cys Gly Ile
225                 230                 235                 240

Thr Ser Ala Ser Tyr Gln Gln Gly Val Leu Ser Ala Thr Ile Leu Tyr
                245                 250                 255
```

```
Glu Ile Leu Leu Gly Lys Ala Thr Leu Tyr Ala Val Leu Val Ser Thr
            260                 265                 270

Leu Val Val Met Ala Met Val Lys Arg Lys Asn Ser
        275                 280


<210> SEQ ID NO 178
<211> LENGTH: 126
<212> TYPE: PRT
<213> ORGANISM: Homo sapiens

<400> SEQUENCE: 178

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Arg Asp Asn Asn Ala
            100                 105                 110

Arg Leu Met Phe Gly Asp Gly Thr Gln Leu Val Val Lys Pro
        115                 120                 125


<210> SEQ ID NO 179
<211> LENGTH: 263
<212> TYPE: PRT
<213> ORGANISM: Artificial Sequence
<220> FEATURE:
<223> OTHER INFORMATION: Synthetic

<400> SEQUENCE: 179

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Arg Asp Asn Asn Ala
            100                 105                 110

Arg Leu Met Phe Gly Asp Gly Thr Gln Leu Val Val Lys Pro Asn Ile
        115                 120                 125

Gln Asn Pro Glu Pro Ala Val Tyr Gln Leu Lys Asp Pro Arg Ser Gln
    130                 135                 140

Asp Ser Thr Leu Cys Leu Phe Thr Asp Phe Asp Ser Gln Ile Asn Val
145                 150                 155                 160

Pro Lys Thr Met Glu Ser Gly Thr Phe Ile Thr Asp Lys Cys Val Leu
```

```
            165                 170                 175

Asp Met Lys Ala Met Asp Ser Lys Ser Asn Gly Ala Ile Ala Trp Ser
        180                 185                 190

Asn Gln Thr Ser Phe Thr Cys Gln Asp Ile Phe Lys Glu Thr Asn Ala
    195                 200                 205

Thr Tyr Pro Ser Ser Asp Val Pro Cys Asp Ala Thr Leu Thr Glu Lys
210                 215                 220

Ser Phe Glu Thr Asp Met Asn Leu Asn Phe Gln Asn Leu Leu Val Ile
225                 230                 235                 240

Val Leu Arg Ile Leu Leu Leu Lys Val Ala Gly Phe Asn Leu Leu Met
                245                 250                 255

Thr Leu Arg Leu Trp Ser Ser
            260


<210> SEQ ID NO 180
<211> LENGTH: 595
<212> TYPE: PRT
<213> ORGANISM: Artificial Sequence
<220> FEATURE:
<223> OTHER INFORMATION: Synthetic

<400> SEQUENCE: 180

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Gly Leu Val Gly Phe Asn Gln Pro Gln His Phe Gly Asp Gly Thr Arg
        115                 120                 125

Leu Ser Ile Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
```

```
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met Lys Leu Val
                325                 330                 335

Thr Ser Ile Thr Val Leu Leu Ser Leu Gly Ile Met Gly Asp Ala Lys
            340                 345                 350

Thr Thr Gln Pro Asn Ser Met Glu Ser Asn Glu Glu Glu Pro Val His
        355                 360                 365

Leu Pro Cys Asn His Ser Thr Ile Ser Gly Thr Asp Tyr Ile His Trp
    370                 375                 380

Tyr Arg Gln Leu Pro Ser Gln Gly Pro Glu Tyr Val Ile His Gly Leu
385                 390                 395                 400

Thr Ser Asn Val Asn Asn Arg Met Ala Ser Leu Ala Ile Ala Glu Asp
                405                 410                 415

Arg Lys Ser Ser Thr Leu Ile Leu His Arg Ala Thr Leu Arg Asp Ala
            420                 425                 430

Ala Val Tyr Tyr Cys Ile Leu Arg Asp Asn Asn Ala Arg Leu Met Phe
        435                 440                 445

Gly Asp Gly Thr Gln Leu Val Val Lys Pro Asn Ile Gln Asn Pro Glu
    450                 455                 460

Pro Ala Val Tyr Gln Leu Lys Asp Pro Arg Ser Gln Asp Ser Thr Leu
465                 470                 475                 480

Cys Leu Phe Thr Asp Phe Asp Ser Gln Ile Asn Val Pro Lys Thr Met
                485                 490                 495

Glu Ser Gly Thr Phe Ile Thr Asp Lys Cys Val Leu Asp Met Lys Ala
            500                 505                 510

Met Asp Ser Lys Ser Asn Gly Ala Ile Ala Trp Ser Asn Gln Thr Ser
        515                 520                 525

Phe Thr Cys Gln Asp Ile Phe Lys Glu Thr Asn Ala Thr Tyr Pro Ser
    530                 535                 540

Ser Asp Val Pro Cys Asp Ala Thr Leu Thr Glu Lys Ser Phe Glu Thr
545                 550                 555                 560

Asp Met Asn Leu Asn Phe Gln Asn Leu Leu Val Ile Val Leu Arg Ile
                565                 570                 575

Leu Leu Leu Lys Val Ala Gly Phe Asn Leu Leu Met Thr Leu Arg Leu
            580                 585                 590

Trp Ser Ser
        595


<210> SEQ ID NO 181
<211> LENGTH: 133
<212> TYPE: PRT
<213> ORGANISM: Homo sapiens

<400> SEQUENCE: 181

Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30
```

```
Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Arg Ala Asn
            100                 105                 110

Ala Gly Gly Thr Ser Tyr Gly Lys Leu Thr Phe Gly Gln Gly Thr Ile
        115                 120                 125

Leu Thr Val His Pro
    130


<210> SEQ ID NO 182
<211> LENGTH: 270
<212> TYPE: PRT
<213> ORGANISM: Artificial Sequence
<220> FEATURE:
<223> OTHER INFORMATION: Synthetic

<400> SEQUENCE: 182

Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Arg Ala Asn
            100                 105                 110

Ala Gly Gly Thr Ser Tyr Gly Lys Leu Thr Phe Gly Gln Gly Thr Ile
        115                 120                 125

Leu Thr Val His Pro Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255
```

```
Ala Gly Phe Asn Leu Leu Met Thr Leu Arg Leu Trp Ser Ser
            260                 265                 270


<210> SEQ ID NO 183
<211> LENGTH: 601
<212> TYPE: PRT
<213> ORGANISM: Artificial Sequence
<220> FEATURE:
<223> OTHER INFORMATION: Synthetic

<400> SEQUENCE: 183

Met Ala Met Ser Asn Gln Val Leu Cys Cys Val Val Leu Cys Phe Leu
1               5                   10                  15

Gly Ala Asn Thr Val Asp Gly Gly Ile Thr Gln Ser Pro Lys Tyr Leu
            20                  25                  30

Phe Arg Lys Glu Gly Gln Asn Val Thr Leu Ser Cys Glu Gln Asn Leu
        35                  40                  45

Asn His Asp Ala Met Tyr Trp Tyr Arg Gln Asp Pro Gly Gln Gly Leu
    50                  55                  60

Arg Leu Ile Tyr Tyr Ser Gln Ile Val Asn Asp Phe Gln Lys Gly Asp
65                  70                  75                  80

Ile Ala Glu Gly Tyr Ser Val Ser Arg Glu Lys Lys Glu Ser Phe Pro
                85                  90                  95

Leu Thr Val Thr Ser Ala Gln Lys Asn Pro Thr Ala Phe Tyr Leu Cys
            100                 105                 110

Ala Ser Leu Gln Phe Asn Glu Gln Phe Phe Gly Pro Gly Thr Arg Leu
        115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met Arg Leu Val Ala
                325                 330                 335

Arg Val Thr Val Phe Leu Thr Phe Gly Thr Ile Ile Asp Ala Lys Thr
            340                 345                 350
```

```
Thr Gln Pro Pro Ser Met Asp Cys Ala Glu Gly Arg Ala Ala Asn Leu
        355                 360                 365

Pro Cys Asn His Ser Thr Ile Ser Gly Asn Glu Tyr Val Tyr Trp Tyr
    370                 375                 380

Arg Gln Ile His Ser Gln Gly Pro Gln Tyr Ile Ile His Gly Leu Lys
385                 390                 395                 400

Asn Asn Glu Thr Asn Glu Met Ala Ser Leu Ile Ile Thr Glu Asp Arg
                405                 410                 415

Lys Ser Ser Thr Leu Ile Leu Pro His Ala Thr Leu Arg Asp Thr Ala
            420                 425                 430

Val Tyr Tyr Cys Ile Val Arg Ala Arg Ala Asn Ala Gly Gly Thr Ser
        435                 440                 445

Tyr Gly Lys Leu Thr Phe Gly Gln Gly Thr Ile Leu Thr Val His Pro
    450                 455                 460

Asn Ile Gln Asn Pro Glu Pro Ala Val Tyr Gln Leu Lys Asp Pro Arg
465                 470                 475                 480

Ser Gln Asp Ser Thr Leu Cys Leu Phe Thr Asp Phe Asp Ser Gln Ile
                485                 490                 495

Asn Val Pro Lys Thr Met Glu Ser Gly Thr Phe Ile Thr Asp Lys Cys
            500                 505                 510

Val Leu Asp Met Lys Ala Met Asp Ser Lys Ser Asn Gly Ala Ile Ala
        515                 520                 525

Trp Ser Asn Gln Thr Ser Phe Thr Cys Gln Asp Ile Phe Lys Glu Thr
    530                 535                 540

Asn Ala Thr Tyr Pro Ser Ser Asp Val Pro Cys Asp Ala Thr Leu Thr
545                 550                 555                 560

Glu Lys Ser Phe Glu Thr Asp Met Asn Leu Asn Phe Gln Asn Leu Leu
                565                 570                 575

Val Ile Val Leu Arg Ile Leu Leu Leu Lys Val Ala Gly Phe Asn Leu
            580                 585                 590

Leu Met Thr Leu Arg Leu Trp Ser Ser
        595                 600


<210> SEQ ID NO 184
<211> LENGTH: 131
<212> TYPE: PRT
<213> ORGANISM: Homo sapiens

<400> SEQUENCE: 184

Met Ala Leu Gln Ser Thr Leu Gly Ala Val Trp Leu Gly Leu Leu Leu
1               5                   10                  15

Asn Ser Leu Trp Lys Val Ala Glu Ser Lys Asp Gln Val Phe Gln Pro
            20                  25                  30

Ser Thr Val Ala Ser Ser Glu Gly Ala Val Val Glu Ile Phe Cys Asn
        35                  40                  45

His Ser Val Ser Asn Ala Tyr Asn Phe Phe Trp Tyr Leu His Phe Pro
    50                  55                  60

Gly Cys Ala Pro Arg Leu Leu Val Lys Gly Ser Lys Pro Ser Gln Gln
65                  70                  75                  80

Gly Arg Tyr Asn Met Thr Tyr Glu Arg Phe Ser Ser Ser Leu Leu Ile
                85                  90                  95

Leu Gln Val Arg Glu Ala Asp Ala Ala Val Tyr Tyr Cys Ala Val Glu
            100                 105                 110

Asp Arg Arg Arg Thr Ala Leu Ile Phe Gly Lys Gly Thr Thr Leu Ser
        115                 120                 125
```

Val Ser Ser
130

<210> SEQ ID NO 185
<211> LENGTH: 268
<212> TYPE: PRT
<213> ORGANISM: Artificial Sequence
<220> FEATURE:
<223> OTHER INFORMATION: Synthetic

<400> SEQUENCE: 185

Met Ala Leu Gln Ser Thr Leu Gly Ala Val Trp Leu Gly Leu Leu Leu
1 5 10 15

Asn Ser Leu Trp Lys Val Ala Glu Ser Lys Asp Gln Val Phe Gln Pro
20 25 30

Ser Thr Val Ala Ser Ser Glu Gly Ala Val Val Glu Ile Phe Cys Asn
35 40 45

His Ser Val Ser Asn Ala Tyr Asn Phe Phe Trp Tyr Leu His Phe Pro
50 55 60

Gly Cys Ala Pro Arg Leu Leu Val Lys Gly Ser Lys Pro Ser Gln Gln
65 70 75 80

Gly Arg Tyr Asn Met Thr Tyr Glu Arg Phe Ser Ser Ser Leu Leu Ile
85 90 95

Leu Gln Val Arg Glu Ala Asp Ala Ala Val Tyr Tyr Cys Ala Val Glu
100 105 110

Asp Arg Arg Arg Thr Ala Leu Ile Phe Gly Lys Gly Thr Thr Leu Ser
115 120 125

Val Ser Ser Asn Ile Gln Asn Pro Glu Pro Ala Val Tyr Gln Leu Lys
130 135 140

Asp Pro Arg Ser Gln Asp Ser Thr Leu Cys Leu Phe Thr Asp Phe Asp
145 150 155 160

Ser Gln Ile Asn Val Pro Lys Thr Met Glu Ser Gly Thr Phe Ile Thr
165 170 175

Asp Lys Cys Val Leu Asp Met Lys Ala Met Asp Ser Lys Ser Asn Gly
180 185 190

Ala Ile Ala Trp Ser Asn Gln Thr Ser Phe Thr Cys Gln Asp Ile Phe
195 200 205

Lys Glu Thr Asn Ala Thr Tyr Pro Ser Ser Asp Val Pro Cys Asp Ala
210 215 220

Thr Leu Thr Glu Lys Ser Phe Glu Thr Asp Met Asn Leu Asn Phe Gln
225 230 235 240

Asn Leu Leu Val Ile Val Leu Arg Ile Leu Leu Leu Lys Val Ala Gly
245 250 255

Phe Asn Leu Leu Met Thr Leu Arg Leu Trp Ser Ser
260 265

<210> SEQ ID NO 186
<211> LENGTH: 602
<212> TYPE: PRT
<213> ORGANISM: Artificial Sequence
<220> FEATURE:
<223> OTHER INFORMATION: Synthetic

<400> SEQUENCE: 186

Met Ala Thr Trp Leu Val Cys Trp Ala Ile Phe Ser Leu Leu Lys Ala
1 5 10 15

Gly Leu Thr Glu Pro Glu Val Thr Gln Thr Pro Ser His Gln Val Thr

-continued

```
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Tyr Gln Ser Gln Ser Asn Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Ala
                325                 330                 335

Leu Gln Ser Thr Leu Gly Ala Val Trp Leu Gly Leu Leu Leu Asn Ser
            340                 345                 350

Leu Trp Lys Val Ala Glu Ser Lys Asp Gln Val Phe Gln Pro Ser Thr
        355                 360                 365

Val Ala Ser Ser Glu Gly Ala Val Val Glu Ile Phe Cys Asn His Ser
    370                 375                 380

Val Ser Asn Ala Tyr Asn Phe Phe Trp Tyr Leu His Phe Pro Gly Cys
385                 390                 395                 400

Ala Pro Arg Leu Leu Val Lys Gly Ser Lys Pro Ser Gln Gln Gly Arg
                405                 410                 415

Tyr Asn Met Thr Tyr Glu Arg Phe Ser Ser Ser Leu Leu Ile Leu Gln
            420                 425                 430

Val Arg Glu Ala Asp Ala Ala Val Tyr Tyr Cys Ala Val Glu Asp Arg
        435                 440                 445
```

```
Arg Arg Thr Ala Leu Ile Phe Gly Lys Gly Thr Thr Leu Ser Val Ser
    450                 455                 460

Ser Asn Ile Gln Asn Pro Glu Pro Ala Val Tyr Gln Leu Lys Asp Pro
465                 470                 475                 480

Arg Ser Gln Asp Ser Thr Leu Cys Leu Phe Thr Asp Phe Asp Ser Gln
                485                 490                 495

Ile Asn Val Pro Lys Thr Met Glu Ser Gly Thr Phe Ile Thr Asp Lys
            500                 505                 510

Cys Val Leu Asp Met Lys Ala Met Asp Ser Lys Ser Asn Gly Ala Ile
        515                 520                 525

Ala Trp Ser Asn Gln Thr Ser Phe Thr Cys Gln Asp Ile Phe Lys Glu
    530                 535                 540

Thr Asn Ala Thr Tyr Pro Ser Ser Asp Val Pro Cys Asp Ala Thr Leu
545                 550                 555                 560

Thr Glu Lys Ser Phe Glu Thr Asp Met Asn Leu Asn Phe Gln Asn Leu
                565                 570                 575

Leu Val Ile Val Leu Arg Ile Leu Leu Leu Lys Val Ala Gly Phe Asn
            580                 585                 590

Leu Leu Met Thr Leu Arg Leu Trp Ser Ser
        595                 600
```

<210> SEQ ID NO 187
<211> LENGTH: 133
<212> TYPE: PRT
<213> ORGANISM: Homo sapiens

<400> SEQUENCE: 187

```
Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Gly Ser Pro Gly
            100                 105                 110

Ala Gly Gly Thr Ser Tyr Gly Lys Leu Thr Phe Gly Gln Gly Thr Ile
        115                 120                 125

Leu Thr Val His Pro
    130
```

<210> SEQ ID NO 188
<211> LENGTH: 270
<212> TYPE: PRT
<213> ORGANISM: Artificial Sequence
<220> FEATURE:
<223> OTHER INFORMATION: Synthetic

<400> SEQUENCE: 188

```
Met Arg Leu Val Ala Arg Val Thr Val Phe Leu Thr Phe Gly Thr Ile
1               5                   10                  15
```

```
Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Gly Ser Pro Gly
            100                 105                 110

Ala Gly Gly Thr Ser Tyr Gly Lys Leu Thr Phe Gly Gln Gly Thr Ile
        115                 120                 125

Leu Thr Val His Pro Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 189
<211> LENGTH: 599
<212> TYPE: PRT
<213> ORGANISM: Artificial Sequence
<220> FEATURE:
<223> OTHER INFORMATION: Synthetic

<400> SEQUENCE: 189

```
Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110
```

```
Ser Ile Arg Thr Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser Arg Ala
    290                 295                 300

Lys Arg Ser Gly Ser Gly Ala Thr Asn Phe Ser Leu Leu Lys Gln Ala
305                 310                 315                 320

Gly Asp Val Glu Glu Asn Pro Gly Pro Met Arg Leu Val Ala Arg Val
                325                 330                 335

Thr Val Phe Leu Thr Phe Gly Thr Ile Ile Asp Ala Lys Thr Thr Gln
            340                 345                 350

Pro Pro Ser Met Asp Cys Ala Glu Gly Arg Ala Ala Asn Leu Pro Cys
        355                 360                 365

Asn His Ser Thr Ile Ser Gly Asn Glu Tyr Val Tyr Trp Tyr Arg Gln
    370                 375                 380

Ile His Ser Gln Gly Pro Gln Tyr Ile Ile His Gly Leu Lys Asn Asn
385                 390                 395                 400

Glu Thr Asn Glu Met Ala Ser Leu Ile Ile Thr Glu Asp Arg Lys Ser
                405                 410                 415

Ser Thr Leu Ile Leu Pro His Ala Thr Leu Arg Asp Thr Ala Val Tyr
            420                 425                 430

Tyr Cys Ile Val Arg Gly Ser Pro Gly Ala Gly Gly Thr Ser Tyr Gly
        435                 440                 445

Lys Leu Thr Phe Gly Gln Gly Thr Ile Leu Thr Val His Pro Asn Ile
    450                 455                 460

Gln Asn Pro Glu Pro Ala Val Tyr Gln Leu Lys Asp Pro Arg Ser Gln
465                 470                 475                 480

Asp Ser Thr Leu Cys Leu Phe Thr Asp Phe Asp Ser Gln Ile Asn Val
                485                 490                 495

Pro Lys Thr Met Glu Ser Gly Thr Phe Ile Thr Asp Lys Cys Val Leu
            500                 505                 510

Asp Met Lys Ala Met Asp Ser Lys Ser Asn Gly Ala Ile Ala Trp Ser
        515                 520                 525

Asn Gln Thr Ser Phe Thr Cys Gln Asp Ile Phe Lys Glu Thr Asn Ala
```

```
    530                 535                 540

Thr Tyr Pro Ser Ser Asp Val Pro Cys Asp Ala Thr Leu Thr Glu Lys
545                 550                 555                 560

Ser Phe Glu Thr Asp Met Asn Leu Asn Phe Gln Asn Leu Leu Val Ile
                565                 570                 575

Val Leu Arg Ile Leu Leu Leu Lys Val Ala Gly Phe Asn Leu Leu Met
            580                 585                 590

Thr Leu Arg Leu Trp Ser Ser
        595


<210> SEQ ID NO 190
<211> LENGTH: 130
<212> TYPE: PRT
<213> ORGANISM: Homo sapiens

<400> SEQUENCE: 190

Met Leu Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Pro Gly Gly
            100                 105                 110

Ala Gly Ser Tyr Gln Leu Thr Phe Gly Lys Gly Thr Lys Leu Ser Val
        115                 120                 125

Ile Pro
    130


<210> SEQ ID NO 191
<211> LENGTH: 267
<212> TYPE: PRT
<213> ORGANISM: Artificial Sequence
<220> FEATURE:
<223> OTHER INFORMATION: Synthetic

<400> SEQUENCE: 191

Met Leu Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Pro Gly Gly
            100                 105                 110
```

```
Ala Gly Ser Tyr Gln Leu Thr Phe Gly Lys Gly Thr Lys Leu Ser Val
        115                 120                 125

Ile Pro Asn Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Cys Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Leu Val Ile Val Leu Arg Ile Leu Leu Leu Lys Val Ala Gly Phe
                245                 250                 255

Asn Leu Leu Met Thr Leu Arg Leu Trp Ser Ser
            260                 265


<210> SEQ ID NO 192
<211> LENGTH: 602
<212> TYPE: PRT
<213> ORGANISM: Artificial Sequence
<220> FEATURE:
<223> OTHER INFORMATION: Synthetic

<400> SEQUENCE: 192

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Phe Val Val Ile Gly Gln Ile Asn Glu Gln Tyr Phe Gly Pro
        115                 120                 125

Gly Thr Arg Leu Thr Val Thr Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205
```

```
Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300

Arg Lys Asn Ser Arg Ala Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

Leu Leu Ile Thr Ser Met Leu Val Leu Trp Met Gln Leu Ser Gln Val
            340                 345                 350

Asn Gly Gln Gln Val Met Gln Ile Pro Gln Tyr Gln His Val Gln Glu
        355                 360                 365

Gly Glu Asp Phe Thr Thr Tyr Cys Asn Ser Ser Thr Thr Leu Ser Asn
    370                 375                 380

Ile Gln Trp Tyr Lys Gln Arg Pro Gly Gly His Pro Val Phe Leu Ile
385                 390                 395                 400

Gln Leu Val Lys Ser Gly Glu Val Lys Lys Gln Lys Arg Leu Thr Phe
                405                 410                 415

Gln Phe Gly Glu Ala Lys Lys Asn Ser Ser Leu His Ile Thr Ala Thr
            420                 425                 430

Gln Thr Thr Asp Val Gly Thr Tyr Phe Cys Ala Gly Pro Gly Gly Ala
        435                 440                 445

Gly Ser Tyr Gln Leu Thr Phe Gly Lys Gly Thr Lys Leu Ser Val Ile
    450                 455                 460

Pro Asn Ile Gln Asn Pro Glu Pro Ala Val Tyr Gln Leu Lys Asp Pro
465                 470                 475                 480

Arg Ser Gln Asp Ser Thr Leu Cys Leu Phe Thr Asp Phe Asp Ser Gln
                485                 490                 495

Ile Asn Val Pro Lys Thr Met Glu Ser Gly Thr Phe Ile Thr Asp Lys
            500                 505                 510

Cys Val Leu Asp Met Lys Ala Met Asp Ser Lys Ser Asn Gly Ala Ile
        515                 520                 525

Ala Trp Ser Asn Gln Thr Ser Phe Thr Cys Gln Asp Ile Phe Lys Glu
    530                 535                 540

Thr Asn Ala Thr Tyr Pro Ser Ser Asp Val Pro Cys Asp Ala Thr Leu
545                 550                 555                 560

Thr Glu Lys Ser Phe Glu Thr Asp Met Asn Leu Asn Phe Gln Asn Leu
                565                 570                 575

Leu Val Ile Val Leu Arg Ile Leu Leu Leu Lys Val Ala Gly Phe Asn
            580                 585                 590

Leu Leu Met Thr Leu Arg Leu Trp Ser Ser
        595                 600
```

<210> SEQ ID NO 193
<211> LENGTH: 130

<212> TYPE: PRT
<213> ORGANISM: Homo sapiens

<400> SEQUENCE: 193

```
Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Ala His Met
            100                 105                 110

Asp Ser Asn Tyr Gln Leu Ile Trp Gly Ala Gly Thr Lys Leu Ile Ile
        115                 120                 125

Lys Pro
    130
```

<210> SEQ ID NO 194
<211> LENGTH: 267
<212> TYPE: PRT
<213> ORGANISM: Artificial Sequence
<220> FEATURE:
<223> OTHER INFORMATION: Synthetic

<400> SEQUENCE: 194

```
Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Ala His Met
            100                 105                 110

Asp Ser Asn Tyr Gln Leu Ile Trp Gly Ala Gly Thr Lys Leu Ile Ile
        115                 120                 125

Lys Pro Asn Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Cys Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
```

```
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Leu Val Ile Val Leu Arg Ile Leu Leu Leu Lys Val Ala Gly Phe
                245                 250                 255

Asn Leu Leu Met Thr Leu Arg Leu Trp Ser Ser
            260                 265


<210> SEQ ID NO 195
<211> LENGTH: 601
<212> TYPE: PRT
<213> ORGANISM: Artificial Sequence
<220> FEATURE:
<223> OTHER INFORMATION: Synthetic

<400> SEQUENCE: 195

Met Ala Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Tyr Ala Gly Leu Ala Ala Pro Arg Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
```

```
    290                 295                 300

Lys Asn Ser Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Lys
                325                 330                 335

Lys Leu Leu Ala Met Ile Leu Trp Leu Gln Leu Asp Arg Leu Ser Gly
            340                 345                 350

Glu Leu Lys Val Glu Gln Asn Pro Leu Phe Leu Ser Met Gln Glu Gly
        355                 360                 365

Lys Asn Tyr Thr Ile Tyr Cys Asn Tyr Ser Thr Thr Ser Asp Arg Leu
    370                 375                 380

Tyr Trp Tyr Arg Gln Asp Pro Gly Lys Ser Leu Glu Ser Leu Phe Val
385                 390                 395                 400

Leu Leu Ser Asn Gly Ala Val Lys Gln Glu Gly Arg Leu Met Ala Ser
                405                 410                 415

Leu Asp Thr Lys Ala Arg Leu Ser Thr Leu His Ile Thr Ala Ala Val
            420                 425                 430

His Asp Leu Ser Ala Thr Tyr Phe Cys Ala Val Ala His Met Asp Ser
        435                 440                 445

Asn Tyr Gln Leu Ile Trp Gly Ala Gly Thr Lys Leu Ile Ile Lys Pro
    450                 455                 460

Asn Ile Gln Asn Pro Glu Pro Ala Val Tyr Gln Leu Lys Asp Pro Arg
465                 470                 475                 480

Ser Gln Asp Ser Thr Leu Cys Leu Phe Thr Asp Phe Asp Ser Gln Ile
                485                 490                 495

Asn Val Pro Lys Thr Met Glu Ser Gly Thr Phe Ile Thr Asp Lys Cys
            500                 505                 510

Val Leu Asp Met Lys Ala Met Asp Ser Lys Ser Asn Gly Ala Ile Ala
        515                 520                 525

Trp Ser Asn Gln Thr Ser Phe Thr Cys Gln Asp Ile Phe Lys Glu Thr
    530                 535                 540

Asn Ala Thr Tyr Pro Ser Ser Asp Val Pro Cys Asp Ala Thr Leu Thr
545                 550                 555                 560

Glu Lys Ser Phe Glu Thr Asp Met Asn Leu Asn Phe Gln Asn Leu Leu
                565                 570                 575

Val Ile Val Leu Arg Ile Leu Leu Leu Lys Val Ala Gly Phe Asn Leu
            580                 585                 590

Leu Met Thr Leu Arg Leu Trp Ser Ser
        595                 600
```

<210> SEQ ID NO 196
<211> LENGTH: 133
<212> TYPE: PRT
<213> ORGANISM: Homo sapiens

<400> SEQUENCE: 196

```
Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60
```

```
Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Arg Ala Asn
            100                 105                 110

Ala Gly Gly Thr Ser Tyr Gly Lys Leu Thr Phe Gly Gln Gly Thr Ile
        115                 120                 125

Leu Thr Val His Pro
    130


<210> SEQ ID NO 197
<211> LENGTH: 270
<212> TYPE: PRT
<213> ORGANISM: Artificial Sequence
<220> FEATURE:
<223> OTHER INFORMATION: Synthetic

<400> SEQUENCE: 197

Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Arg Ala Asn
            100                 105                 110

Ala Gly Gly Thr Ser Tyr Gly Lys Leu Thr Phe Gly Gln Gly Thr Ile
        115                 120                 125

Leu Thr Val His Pro Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 198
<211> LENGTH: 599
```

<212> TYPE: PRT
<213> ORGANISM: Artificial Sequence
<220> FEATURE:
<223> OTHER INFORMATION: Synthetic

<400> SEQUENCE: 198

```
Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Thr
            100                 105                 110

Arg Thr Gly Asn Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser Arg Ala
    290                 295                 300

Lys Arg Ser Gly Ser Gly Ala Thr Asn Phe Ser Leu Leu Lys Gln Ala
305                 310                 315                 320

Gly Asp Val Glu Glu Asn Pro Gly Pro Met Arg Leu Val Ala Arg Val
                325                 330                 335

Thr Val Phe Leu Thr Phe Gly Thr Ile Ile Asp Ala Lys Thr Thr Gln
            340                 345                 350

Pro Pro Ser Met Asp Cys Ala Glu Gly Arg Ala Ala Asn Leu Pro Cys
        355                 360                 365

Asn His Ser Thr Ile Ser Gly Asn Glu Tyr Val Tyr Trp Tyr Arg Gln
    370                 375                 380
```

Ile His Ser Gln Gly Pro Gln Tyr Ile Ile His Gly Leu Lys Asn Asn
385 390 395 400

Glu Thr Asn Glu Met Ala Ser Leu Ile Ile Thr Glu Asp Arg Lys Ser
405 410 415

Ser Thr Leu Ile Leu Pro His Ala Thr Leu Arg Asp Thr Ala Val Tyr
420 425 430

Tyr Cys Ile Val Arg Ala Arg Ala Asn Ala Gly Gly Thr Ser Tyr Gly
435 440 445

Lys Leu Thr Phe Gly Gln Gly Thr Ile Leu Thr Val His Pro Asn Ile
450 455 460

Gln Asn Pro Glu Pro Ala Val Tyr Gln Leu Lys Asp Pro Arg Ser Gln
465 470 475 480

Asp Ser Thr Leu Cys Leu Phe Thr Asp Phe Asp Ser Gln Ile Asn Val
485 490 495

Pro Lys Thr Met Glu Ser Gly Thr Phe Ile Thr Asp Lys Cys Val Leu
500 505 510

Asp Met Lys Ala Met Asp Ser Lys Ser Asn Gly Ala Ile Ala Trp Ser
515 520 525

Asn Gln Thr Ser Phe Thr Cys Gln Asp Ile Phe Lys Glu Thr Asn Ala
530 535 540

Thr Tyr Pro Ser Ser Asp Val Pro Cys Asp Ala Thr Leu Thr Glu Lys
545 550 555 560

Ser Phe Glu Thr Asp Met Asn Leu Asn Phe Gln Asn Leu Leu Val Ile
565 570 575

Val Leu Arg Ile Leu Leu Leu Lys Val Ala Gly Phe Asn Leu Leu Met
580 585 590

Thr Leu Arg Leu Trp Ser Ser
595

<210> SEQ ID NO 199
<211> LENGTH: 136
<212> TYPE: PRT
<213> ORGANISM: Homo sapiens

<400> SEQUENCE: 199

Met Ala Ser Ala Pro Ile Ser Met Leu Ala Met Leu Phe Thr Leu Ser
1 5 10 15

Gly Leu Arg Ala Gln Ser Val Ala Gln Pro Glu Asp Gln Val Asn Val
20 25 30

Ala Glu Gly Asn Pro Leu Thr Val Lys Cys Thr Tyr Ser Val Ser Gly
35 40 45

Asn Pro Tyr Leu Phe Trp Tyr Val Gln Tyr Pro Asn Arg Gly Leu Gln
50 55 60

Phe Leu Leu Lys Tyr Ile Thr Gly Asp Asn Leu Val Lys Gly Ser Tyr
65 70 75 80

Gly Phe Glu Ala Glu Phe Asn Lys Ser Gln Thr Ser Phe His Leu Lys
85 90 95

Lys Pro Ser Ala Leu Val Ser Asp Ser Ala Leu Tyr Phe Cys Ala Val
100 105 110

Arg Asp Gly Ser Ala Thr Ser Gly Thr Tyr Lys Tyr Ile Phe Gly Thr
115 120 125

Gly Thr Arg Leu Lys Val Leu Ala
130 135

<210> SEQ ID NO 200

<211> LENGTH: 273
<212> TYPE: PRT
<213> ORGANISM: Artificial Sequence
<220> FEATURE:
<223> OTHER INFORMATION: Synthetic

<400> SEQUENCE: 200

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Gly Ser Ala Thr Ser Gly Thr Tyr Lys Tyr Ile Phe Gly Thr
        115                 120                 125

Gly Thr Arg Leu Lys Val Leu Ala Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
            260                 265                 270

Ser
```

<210> SEQ ID NO 201
<211> LENGTH: 605
<212> TYPE: PRT
<213> ORGANISM: Artificial Sequence
<220> FEATURE:
<223> OTHER INFORMATION: Synthetic

<400> SEQUENCE: 201

```
Met Ala Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45
```

```
Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Pro Gly Leu Ala Tyr Glu Gln Tyr Phe Gly Pro Gly Thr Arg
        115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met Ala Ser Ala
                325                 330                 335

Pro Ile Ser Met Leu Ala Met Leu Phe Thr Leu Ser Gly Leu Arg Ala
            340                 345                 350

Gln Ser Val Ala Gln Pro Glu Asp Gln Val Asn Val Ala Glu Gly Asn
        355                 360                 365

Pro Leu Thr Val Lys Cys Thr Tyr Ser Val Ser Gly Asn Pro Tyr Leu
    370                 375                 380

Phe Trp Tyr Val Gln Tyr Pro Asn Arg Gly Leu Gln Phe Leu Leu Lys
385                 390                 395                 400

Tyr Ile Thr Gly Asp Asn Leu Val Lys Gly Ser Tyr Gly Phe Glu Ala
                405                 410                 415

Glu Phe Asn Lys Ser Gln Thr Ser Phe His Leu Lys Lys Pro Ser Ala
            420                 425                 430

Leu Val Ser Asp Ser Ala Leu Tyr Phe Cys Ala Val Arg Asp Gly Ser
        435                 440                 445

Ala Thr Ser Gly Thr Tyr Lys Tyr Ile Phe Gly Thr Gly Thr Arg Leu
    450                 455                 460
```

```
Lys Val Leu Ala Asn Ile Gln Asn Pro Glu Pro Ala Val Tyr Gln Leu
465                 470                 475                 480

Lys Asp Pro Arg Ser Gln Asp Ser Thr Leu Cys Leu Phe Thr Asp Phe
                485                 490                 495

Asp Ser Gln Ile Asn Val Pro Lys Thr Met Glu Ser Gly Thr Phe Ile
            500                 505                 510

Thr Asp Lys Cys Val Leu Asp Met Lys Ala Met Asp Ser Lys Ser Asn
        515                 520                 525

Gly Ala Ile Ala Trp Ser Asn Gln Thr Ser Phe Thr Cys Gln Asp Ile
    530                 535                 540

Phe Lys Glu Thr Asn Ala Thr Tyr Pro Ser Ser Asp Val Pro Cys Asp
545                 550                 555                 560

Ala Thr Leu Thr Glu Lys Ser Phe Glu Thr Asp Met Asn Leu Asn Phe
                565                 570                 575

Gln Asn Leu Leu Val Ile Val Leu Arg Ile Leu Leu Leu Lys Val Ala
            580                 585                 590

Gly Phe Asn Leu Leu Met Thr Leu Arg Leu Trp Ser Ser
        595                 600                 605


<210> SEQ ID NO 202
<211> LENGTH: 132
<212> TYPE: PRT
<213> ORGANISM: Homo sapiens

<400> SEQUENCE: 202

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ile Gln Gln Gly Ala Asp Thr Gln Tyr Phe Gly Pro Gly Thr Arg
        115                 120                 125

Leu Thr Val Leu
    130


<210> SEQ ID NO 203
<211> LENGTH: 305
<212> TYPE: PRT
<213> ORGANISM: Artificial Sequence
<220> FEATURE:
<223> OTHER INFORMATION: Synthetic

<400> SEQUENCE: 203

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
```

```
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ile Gln Gln Gly Ala Asp Thr Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305


<210> SEQ ID NO 204
<211> LENGTH: 605
<212> TYPE: PRT
<213> ORGANISM: Artificial Sequence
<220> FEATURE:
<223> OTHER INFORMATION: Synthetic

<400> SEQUENCE: 204

Met Ala Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
```

```
                85                  90                  95

Phe Ile Arg Asp Ser Gln Pro Ser Asp Ser Ala Thr Tyr Leu Cys Ala
            100                 105                 110

Met Ser Gly Leu Lys Glu Asp Ser Ser Tyr Lys Leu Ile Phe Gly Ser
        115                 120                 125

Gly Thr Arg Leu Leu Val Arg Pro Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
            260                 265                 270

Ser Arg Ala Lys Arg Ser Gly Ser Gly Ala Thr Asn Phe Ser Leu Leu
        275                 280                 285

Lys Gln Ala Gly Asp Val Glu Glu Asn Pro Gly Pro Met Gly Pro Gln
    290                 295                 300

Leu Leu Gly Tyr Val Val Leu Cys Leu Leu Gly Ala Gly Pro Leu Glu
305                 310                 315                 320

Ala Gln Val Thr Gln Asn Pro Arg Tyr Leu Ile Thr Val Thr Gly Lys
                325                 330                 335

Lys Leu Thr Val Thr Cys Ser Gln Asn Met Asn His Glu Tyr Met Ser
            340                 345                 350

Trp Tyr Arg Gln Asp Pro Gly Leu Gly Leu Arg Gln Ile Tyr Tyr Ser
        355                 360                 365

Met Asn Val Glu Val Thr Asp Lys Gly Asp Val Pro Glu Gly Tyr Lys
    370                 375                 380

Val Ser Arg Lys Glu Lys Arg Asn Phe Pro Leu Ile Leu Glu Ser Pro
385                 390                 395                 400

Ser Pro Asn Gln Thr Ser Leu Tyr Phe Cys Ala Ser Ser Ile Gln Gln
                405                 410                 415

Gly Ala Asp Thr Gln Tyr Phe Gly Pro Gly Thr Arg Leu Thr Val Leu
            420                 425                 430

Glu Asp Leu Arg Asn Val Thr Pro Pro Lys Val Ser Leu Phe Glu Pro
        435                 440                 445

Ser Lys Ala Glu Ile Ala Asn Lys Gln Lys Ala Thr Leu Val Cys Leu
    450                 455                 460

Ala Arg Gly Phe Phe Pro Asp His Val Glu Leu Ser Trp Trp Val Asn
465                 470                 475                 480

Gly Lys Glu Val His Ser Gly Val Cys Thr Asp Pro Gln Ala Tyr Lys
                485                 490                 495

Glu Ser Asn Tyr Ser Tyr Cys Leu Ser Ser Arg Leu Arg Val Ser Ala
            500                 505                 510
```

```
Thr Phe Trp His Asn Pro Arg Asn His Phe Arg Cys Gln Val Gln Phe
        515                 520                 525

His Gly Leu Ser Glu Glu Asp Lys Trp Pro Glu Gly Ser Pro Lys Pro
    530                 535                 540

Val Thr Gln Asn Ile Ser Ala Glu Ala Trp Gly Arg Ala Asp Cys Gly
545                 550                 555                 560

Ile Thr Ser Ala Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Thr Leu Val Val Met Ala Met Val Lys Arg Lys Asn Ser
        595                 600                 605


<210> SEQ ID NO 205
<211> LENGTH: 132
<212> TYPE: PRT
<213> ORGANISM: Homo sapiens

<400> SEQUENCE: 205

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Gly Leu Val Gly Phe Asn Gln Pro Gln His Phe Gly Asp Gly Thr Arg
        115                 120                 125

Leu Ser Ile Leu
    130


<210> SEQ ID NO 206
<211> LENGTH: 305
<212> TYPE: PRT
<213> ORGANISM: Artificial Sequence
<220> FEATURE:
<223> OTHER INFORMATION: Synthetic

<400> SEQUENCE: 206

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80
```

```
Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Gly Leu Val Gly Phe Asn Gln Pro Gln His Phe Gly Asp Gly Thr Arg
        115                 120                 125

Leu Ser Ile Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305


<210> SEQ ID NO 207
<211> LENGTH: 129
<212> TYPE: PRT
<213> ORGANISM: Homo sapiens

<400> SEQUENCE: 207

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Leu Gln Phe Asn Glu Gln Phe Phe Gly Pro Gly Thr Arg Leu Thr Val
        115                 120                 125

Leu
```

<210> SEQ ID NO 208
<211> LENGTH: 302
<212> TYPE: PRT
<213> ORGANISM: Artificial Sequence
<220> FEATURE:
<223> OTHER INFORMATION: Synthetic

<400> SEQUENCE: 208

Met Ser Asn Gln Val Leu Cys Cys Val Val Leu Cys Phe Leu Gly Ala
1 5 10 15

Asn Thr Val Asp Gly Gly Ile Thr Gln Ser Pro Lys Tyr Leu Phe Arg
20 25 30

Lys Glu Gly Gln Asn Val Thr Leu Ser Cys Glu Gln Asn Leu Asn His
35 40 45

Asp Ala Met Tyr Trp Tyr Arg Gln Asp Pro Gly Gln Gly Leu Arg Leu
50 55 60

Ile Tyr Tyr Ser Gln Ile Val Asn Asp Phe Gln Lys Gly Asp Ile Ala
65 70 75 80

Glu Gly Tyr Ser Val Ser Arg Glu Lys Lys Glu Ser Phe Pro Leu Thr
85 90 95

Val Thr Ser Ala Gln Lys Asn Pro Thr Ala Phe Tyr Leu Cys Ala Ser
100 105 110

Leu Gln Phe Asn Glu Gln Phe Phe Gly Pro Gly Thr Arg Leu Thr Val
115 120 125

Leu Glu Asp Leu Arg Asn Val Thr Pro Pro Lys Val Ser Leu Phe Glu
130 135 140

Pro Ser Lys Ala Glu Ile Ala Asn Lys Gln Lys Ala Thr Leu Val Cys
145 150 155 160

Leu Ala Arg Gly Phe Phe Pro Asp His Val Glu Leu Ser Trp Trp Val
165 170 175

Asn Gly Lys Glu Val His Ser Gly Val Cys Thr Asp Pro Gln Ala Tyr
180 185 190

Lys Glu Ser Asn Tyr Ser Tyr Cys Leu Ser Ser Arg Leu Arg Val Ser
195 200 205

Ala Thr Phe Trp His Asn Pro Arg Asn His Phe Arg Cys Gln Val Gln
210 215 220

Phe His Gly Leu Ser Glu Glu Asp Lys Trp Pro Glu Gly Ser Pro Lys
225 230 235 240

Pro Val Thr Gln Asn Ile Ser Ala Glu Ala Trp Gly Arg Ala Asp Cys
245 250 255

Gly Ile Thr Ser Ala Ser Tyr Gln Gln Gly Val Leu Ser Ala Thr Ile
260 265 270

Leu Tyr Glu Ile Leu Leu Gly Lys Ala Thr Leu Tyr Ala Val Leu Val
275 280 285

Ser Thr Leu Val Val Met Ala Met Val Lys Arg Lys Asn Ser
290 295 300

<210> SEQ ID NO 209
<211> LENGTH: 134
<212> TYPE: PRT
<213> ORGANISM: Homo sapiens

<400> SEQUENCE: 209

Met Asp Thr Trp Leu Val Cys Trp Ala Ile Phe Ser Leu Leu Lys Ala
1 5 10 15

Gly Leu Thr Glu Pro Glu Val Thr Gln Thr Pro Ser His Gln Val Thr

```
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Tyr Gln Ser Gln Ser Asn Glu Gln Phe Phe Gly Pro Gly
        115                 120                 125

Thr Arg Leu Thr Val Leu
    130


<210> SEQ ID NO 210
<211> LENGTH: 307
<212> TYPE: PRT
<213> ORGANISM: Artificial Sequence
<220> FEATURE:
<223> OTHER INFORMATION: Synthetic

<400> SEQUENCE: 210

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Tyr Gln Ser Gln Ser Asn Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
```

```
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser
305


<210> SEQ ID NO 211
<211> LENGTH: 129
<212> TYPE: PRT
<213> ORGANISM: Homo sapiens

<400> SEQUENCE: 211

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Arg Thr Glu Ala Phe Phe Gly Gln Gly Thr Arg Leu Thr Val
        115                 120                 125

Val


<210> SEQ ID NO 212
<211> LENGTH: 302
<212> TYPE: PRT
<213> ORGANISM: Artificial Sequence
<220> FEATURE:
<223> OTHER INFORMATION: Synthetic

<400> SEQUENCE: 212

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110
```

```
Ser Ile Arg Thr Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser
    290                 295                 300


<210> SEQ ID NO 213
<211> LENGTH: 135
<212> TYPE: PRT
<213> ORGANISM: Homo sapiens

<400> SEQUENCE: 213

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Phe Val Val Ile Gly Gln Ile Asn Glu Gln Tyr Phe Gly Pro
        115                 120                 125

Gly Thr Arg Leu Thr Val Thr
    130                 135


<210> SEQ ID NO 214
<211> LENGTH: 308
<212> TYPE: PRT
<213> ORGANISM: Artificial Sequence
<220> FEATURE:
<223> OTHER INFORMATION: Synthetic
```

<400> SEQUENCE: 214

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Phe Val Val Ile Gly Gln Ile Asn Glu Gln Tyr Phe Gly Pro
        115                 120                 125

Gly Thr Arg Leu Thr Val Thr Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300

Arg Lys Asn Ser
305
```

<210> SEQ ID NO 215
<211> LENGTH: 134
<212> TYPE: PRT
<213> ORGANISM: Homo sapiens

<400> SEQUENCE: 215

```
Met Ser Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45
```

```
Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Tyr Ala Gly Leu Ala Ala Pro Arg Glu Gln Phe Phe Gly Pro Gly
        115                 120                 125

Thr Arg Leu Thr Val Leu
    130
```

<210> SEQ ID NO 216
<211> LENGTH: 307
<212> TYPE: PRT
<213> ORGANISM: Artificial Sequence
<220> FEATURE:
<223> OTHER INFORMATION: Synthetic

<400> SEQUENCE: 216

```
Met Ser Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Tyr Ala Gly Leu Ala Ala Pro Arg Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270
```

```
Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser
305


<210> SEQ ID NO 217
<211> LENGTH: 129
<212> TYPE: PRT
<213> ORGANISM: Homo sapiens

<400> SEQUENCE: 217

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Thr
            100                 105                 110

Arg Thr Gly Asn Glu Ala Phe Phe Gly Gln Gly Thr Arg Leu Thr Val
        115                 120                 125

Val


<210> SEQ ID NO 218
<211> LENGTH: 302
<212> TYPE: PRT
<213> ORGANISM: Artificial Sequence
<220> FEATURE:
<223> OTHER INFORMATION: Synthetic

<400> SEQUENCE: 218

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Thr
            100                 105                 110

Arg Thr Gly Asn Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140
```

Pro Ser Lys Ala Glu Ile Ala Asn Lys Gln Lys Ala Thr Leu Val Cys
145 150 155 160

Leu Ala Arg Gly Phe Phe Pro Asp His Val Glu Leu Ser Trp Trp Val
165 170 175

Asn Gly Lys Glu Val His Ser Gly Val Cys Thr Asp Pro Gln Ala Tyr
180 185 190

Lys Glu Ser Asn Tyr Ser Tyr Cys Leu Ser Ser Arg Leu Arg Val Ser
195 200 205

Ala Thr Phe Trp His Asn Pro Arg Asn His Phe Arg Cys Gln Val Gln
210 215 220

Phe His Gly Leu Ser Glu Glu Asp Lys Trp Pro Glu Gly Ser Pro Lys
225 230 235 240

Pro Val Thr Gln Asn Ile Ser Ala Glu Ala Trp Gly Arg Ala Asp Cys
245 250 255

Gly Ile Thr Ser Ala Ser Tyr Gln Gln Gly Val Leu Ser Ala Thr Ile
260 265 270

Leu Tyr Glu Ile Leu Leu Gly Lys Ala Thr Leu Tyr Ala Val Leu Val
275 280 285

Ser Thr Leu Val Val Met Ala Met Val Lys Arg Lys Asn Ser
290 295 300

<210> SEQ ID NO 219
<211> LENGTH: 132
<212> TYPE: PRT
<213> ORGANISM: Homo sapiens

<400> SEQUENCE: 219

Met Gly Thr Ser Leu Leu Cys Trp Met Ala Leu Cys Leu Leu Gly Ala
1 5 10 15

Asp His Ala Asp Thr Gly Val Ser Gln Asp Pro Arg His Lys Ile Thr
20 25 30

Lys Arg Gly Gln Asn Val Thr Phe Arg Cys Asp Pro Ile Ser Glu His
35 40 45

Asn Arg Leu Tyr Trp Tyr Arg Gln Thr Leu Gly Gln Gly Pro Glu Phe
50 55 60

Leu Thr Tyr Phe Gln Asn Glu Ala Gln Leu Glu Lys Ser Arg Leu Leu
65 70 75 80

Ser Asp Arg Phe Ser Ala Glu Arg Pro Lys Gly Ser Phe Ser Thr Leu
85 90 95

Glu Ile Gln Arg Thr Glu Gln Gly Asp Ser Ala Met Tyr Leu Cys Ala
100 105 110

Ser Ser Pro Gly Leu Ala Tyr Glu Gln Tyr Phe Gly Pro Gly Thr Arg
115 120 125

Leu Thr Val Thr
130

<210> SEQ ID NO 220
<211> LENGTH: 305
<212> TYPE: PRT
<213> ORGANISM: Artificial Sequence
<220> FEATURE:
<223> OTHER INFORMATION: Synthetic

<400> SEQUENCE: 220

Met Gly Thr Ser Leu Leu Cys Trp Met Ala Leu Cys Leu Leu Gly Ala
1 5 10 15

```
Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Pro Gly Leu Ala Tyr Glu Gln Tyr Phe Gly Pro Gly Thr Arg
        115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305


<210> SEQ ID NO 221
<211> LENGTH: 132
<212> TYPE: PRT
<213> ORGANISM: Artificial Sequence
<220> FEATURE:
<223> OTHER INFORMATION: Synthetic

<400> SEQUENCE: 221

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60
```

```
Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ile Gln Gln Gly Ala Asp Thr Gln Tyr Phe Gly Pro Gly Thr Arg
        115                 120                 125

Leu Thr Val Leu
    130


<210> SEQ ID NO 222
<211> LENGTH: 305
<212> TYPE: PRT
<213> ORGANISM: Artificial Sequence
<220> FEATURE:
<223> OTHER INFORMATION: Synthetic

<400> SEQUENCE: 222

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ile Gln Gln Gly Ala Asp Thr Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285
```

```
Val Leu Val Ser Thr Leu Val Val Met Ala Met Val Lys Arg Lys Asn
    290                 295                 300

Ser
305


<210> SEQ ID NO 223
<211> LENGTH: 136
<212> TYPE: PRT
<213> ORGANISM: Artificial Sequence
<220> FEATURE:
<223> OTHER INFORMATION: Synthetic

<400> SEQUENCE: 223

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Gly Leu Lys Glu Asp Ser Ser Tyr Lys Leu Ile Phe Gly Ser
        115                 120                 125

Gly Thr Arg Leu Leu Val Arg Pro
    130                 135


<210> SEQ ID NO 224
<211> LENGTH: 273
<212> TYPE: PRT
<213> ORGANISM: Artificial Sequence
<220> FEATURE:
<223> OTHER INFORMATION: Synthetic

<400> SEQUENCE: 224

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Gly Leu Lys Glu Asp Ser Ser Tyr Lys Leu Ile Phe Gly Ser
        115                 120                 125

Gly Thr Arg Leu Leu Val Arg Pro Asn Ile Gln Asn Pro Glu Pro Ala
    130                 135                 140
```

```
Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
            260                 265                 270

Ser


<210> SEQ ID NO 225
<211> LENGTH: 605
<212> TYPE: PRT
<213> ORGANISM: Artificial Sequence
<220> FEATURE:
<223> OTHER INFORMATION: Synthetic

<400> SEQUENCE: 225

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ile Gln Gln Gly Ala Asp Thr Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220
```

```
Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met Met Lys Ser
                325                 330                 335

Leu Arg Val Leu Leu Val Ile Leu Trp Leu Gln Leu Ser Trp Val Trp
            340                 345                 350

Ser Gln Gln Lys Glu Val Glu Gln Asp Pro Gly Pro Leu Ser Val Pro
        355                 360                 365

Glu Gly Ala Ile Val Ser Leu Asn Cys Thr Tyr Ser Asn Ser Ala Phe
    370                 375                 380

Gln Tyr Phe Met Trp Tyr Arg Gln Tyr Ser Arg Lys Gly Pro Glu Leu
385                 390                 395                 400

Leu Met Tyr Thr Tyr Ser Ser Gly Asn Lys Glu Asp Gly Arg Phe Thr
                405                 410                 415

Ala Gln Val Asp Lys Ser Ser Lys Tyr Ile Ser Leu Phe Ile Arg Asp
            420                 425                 430

Ser Gln Pro Ser Asp Ser Ala Thr Tyr Leu Cys Ala Met Ser Gly Leu
        435                 440                 445

Lys Glu Asp Ser Ser Tyr Lys Leu Ile Phe Gly Ser Gly Thr Arg Leu
    450                 455                 460

Leu Val Arg Pro Asn Ile Gln Asn Pro Glu Pro Ala Val Tyr Gln Leu
465                 470                 475                 480

Lys Asp Pro Arg Ser Gln Asp Ser Thr Leu Cys Leu Phe Thr Asp Phe
                485                 490                 495

Asp Ser Gln Ile Asn Val Pro Lys Thr Met Glu Ser Gly Thr Phe Ile
            500                 505                 510

Thr Asp Lys Cys Val Leu Asp Met Lys Ala Met Asp Ser Lys Ser Asn
        515                 520                 525

Gly Ala Ile Ala Trp Ser Asn Gln Thr Ser Phe Thr Cys Gln Asp Ile
    530                 535                 540

Phe Lys Glu Thr Asn Ala Thr Tyr Pro Ser Ser Asp Val Pro Cys Asp
545                 550                 555                 560

Ala Thr Leu Thr Glu Lys Ser Phe Glu Thr Asp Met Asn Leu Asn Phe
                565                 570                 575

Gln Asn Leu Leu Val Ile Val Leu Arg Ile Leu Leu Leu Lys Val Ala
            580                 585                 590

Gly Phe Asn Leu Leu Met Thr Leu Arg Leu Trp Ser Ser
        595                 600                 605
```

<210> SEQ ID NO 226
<211> LENGTH: 129
<212> TYPE: PRT
<213> ORGANISM: Artificial Sequence
<220> FEATURE:
<223> OTHER INFORMATION: Synthetic

<400> SEQUENCE: 226

Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Leu Gln Phe Asn Glu Gln Phe Phe Gly Pro Gly Thr Arg Leu Thr Val
        115                 120                 125

Leu

<210> SEQ ID NO 227
<211> LENGTH: 302
<212> TYPE: PRT
<213> ORGANISM: Artificial Sequence
<220> FEATURE:
<223> OTHER INFORMATION: Synthetic

<400> SEQUENCE: 227

Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Leu Gln Phe Asn Glu Gln Phe Phe Gly Pro Gly Thr Arg Leu Thr Val
        115                 120                 125

Leu Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln

```
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser
    290                 295                 300


<210> SEQ ID NO 228
<211> LENGTH: 599
<212> TYPE: PRT
<213> ORGANISM: Artificial Sequence
<220> FEATURE:
<223> OTHER INFORMATION: Synthetic

<400> SEQUENCE: 228

Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Leu Gln Phe Asn Glu Gln Phe Phe Gly Pro Gly Thr Arg Leu Thr Val
        115                 120                 125

Leu Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
```

```
        275                 280                 285

Ser Thr Leu Val Val Met Ala Met Val Lys Arg Lys Asn Ser Arg Ala
    290                 295                 300

Lys Arg Ser Gly Ser Gly Ala Thr Asn Phe Ser Leu Leu Lys Gln Ala
305                 310                 315                 320

Gly Asp Val Glu Glu Asn Pro Gly Pro Met His Leu Val Ala Arg Val
                325                 330                 335

Thr Val Phe Leu Thr Phe Gly Thr Ile Ile Asp Ala Lys Thr Thr Gln
            340                 345                 350

Pro Pro Ser Met Asp Cys Ala Glu Gly Arg Ala Ala Asn Leu Pro Cys
        355                 360                 365

Asn His Ser Thr Ile Ser Gly Asn Glu Tyr Val Tyr Trp Tyr Arg Gln
    370                 375                 380

Ile His Ser Gln Gly Pro Gln Tyr Ile Ile His Gly Leu Lys Asn Asn
385                 390                 395                 400

Glu Thr Asn Glu Met Ala Ser Leu Ile Ile Thr Glu Asp Arg Lys Ser
                405                 410                 415

Ser Thr Leu Ile Leu Pro His Ala Thr Leu Arg Asp Thr Ala Val Tyr
            420                 425                 430

Tyr Cys Ile Val Arg Ala Arg Ala Asn Ala Gly Gly Thr Ser Tyr Gly
        435                 440                 445

Lys Leu Thr Phe Gly Gln Gly Thr Ile Leu Thr Val His Pro Asn Ile
    450                 455                 460

Gln Asn Pro Glu Pro Ala Val Tyr Gln Leu Lys Asp Pro Arg Ser Gln
465                 470                 475                 480

Asp Ser Thr Leu Cys Leu Phe Thr Asp Phe Asp Ser Gln Ile Asn Val
                485                 490                 495

Pro Lys Thr Met Glu Ser Gly Thr Phe Ile Thr Asp Lys Cys Val Leu
            500                 505                 510

Asp Met Lys Ala Met Asp Ser Lys Ser Asn Gly Ala Ile Ala Trp Ser
        515                 520                 525

Asn Gln Thr Ser Phe Thr Cys Gln Asp Ile Phe Lys Glu Thr Asn Ala
    530                 535                 540

Thr Tyr Pro Ser Ser Asp Val Pro Cys Asp Ala Thr Leu Thr Glu Lys
545                 550                 555                 560

Ser Phe Glu Thr Asp Met Asn Leu Asn Phe Gln Asn Leu Leu Val Ile
                565                 570                 575

Val Leu Arg Ile Leu Leu Leu Lys Val Ala Gly Phe Asn Leu Leu Met
            580                 585                 590

Thr Leu Arg Leu Trp Ser Ser
        595
```

<210> SEQ ID NO 229
<211> LENGTH: 599
<212> TYPE: PRT
<213> ORGANISM: Artificial Sequence
<220> FEATURE:
<223> OTHER INFORMATION: Synthetic

<400> SEQUENCE: 229

```
Met Ala Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
```

```
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Leu Gln Phe Asn Glu Gln Phe Phe Gly Pro Gly Thr Arg Leu Thr Val
        115                 120                 125

Leu Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser Arg Ala
    290                 295                 300

Lys Arg Ser Gly Ser Gly Ala Thr Asn Phe Ser Leu Leu Lys Gln Ala
305                 310                 315                 320

Gly Asp Val Glu Glu Asn Pro Gly Pro Met Arg Leu Val Ala Arg Val
                325                 330                 335

Thr Val Phe Leu Thr Phe Gly Thr Ile Ile Asp Ala Lys Thr Thr Gln
            340                 345                 350

Pro Pro Ser Met Asp Cys Ala Glu Gly Arg Ala Ala Asn Leu Pro Cys
        355                 360                 365

Asn His Ser Thr Ile Ser Gly Asn Glu Tyr Val Tyr Trp Tyr Arg Gln
    370                 375                 380

Ile His Ser Gln Gly Pro Gln Tyr Ile Ile His Gly Leu Lys Asn Asn
385                 390                 395                 400

Glu Thr Asn Glu Met Ala Ser Leu Ile Ile Thr Glu Asp Arg Lys Ser
                405                 410                 415

Ser Thr Leu Ile Leu Pro His Ala Thr Leu Arg Asp Thr Ala Val Tyr
            420                 425                 430

Tyr Cys Ile Val Arg Ala Arg Ala Asn Ala Gly Gly Thr Ser Tyr Gly
        435                 440                 445

Lys Leu Thr Phe Gly Gln Gly Thr Ile Leu Thr Val His Pro Asn Ile
    450                 455                 460
```

```
Gln Asn Pro Glu Pro Ala Val Tyr Gln Leu Lys Asp Pro Arg Ser Gln
465                 470                 475                 480

Asp Ser Thr Leu Cys Leu Phe Thr Asp Phe Asp Ser Gln Ile Asn Val
                485                 490                 495

Pro Lys Thr Met Glu Ser Gly Thr Phe Ile Thr Asp Lys Cys Val Leu
            500                 505                 510

Asp Met Lys Ala Met Asp Ser Lys Ser Asn Gly Ala Ile Ala Trp Ser
        515                 520                 525

Asn Gln Thr Ser Phe Thr Cys Gln Asp Ile Phe Lys Glu Thr Asn Ala
    530                 535                 540

Thr Tyr Pro Ser Ser Asp Val Pro Cys Asp Ala Thr Leu Thr Glu Lys
545                 550                 555                 560

Ser Phe Glu Thr Asp Met Asn Leu Asn Phe Gln Asn Leu Leu Val Ile
                565                 570                 575

Val Leu Arg Ile Leu Leu Leu Lys Val Ala Gly Phe Asn Leu Leu Met
            580                 585                 590

Thr Leu Arg Leu Trp Ser Ser
        595


<210> SEQ ID NO 230
<211> LENGTH: 4
<212> TYPE: PRT
<213> ORGANISM: Artificial Sequence
<220> FEATURE:
<223> OTHER INFORMATION: Synthetic

<400> SEQUENCE: 230

Arg Ala Lys Arg
1
```